US009493526B2

(12) United States Patent
Cary et al.

(10) Patent No.: US 9,493,526 B2
(45) **Date of Patent: *Nov. 15, 2016**

(54) COMPOSITIONS AND METHODS FOR THE DELIVERY OF OXYGEN

(71) Applicant: THE REGENTS OF THE UNIVERSITY OF CALIFORNIA, Oakland, CA (US)

(72) Inventors: Stephen P. L. Cary, San Mateo, CA (US); Elizabeth M. Boon, Stony Brook, NY (US); Emily Weinert, Berkeley, CA (US); Jonathan A. Winger, Oakland, CA (US); Michael A. Marletta, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/489,395

(22) Filed: Sep. 17, 2014

(65) Prior Publication Data

US 2015/0376250 A1 Dec. 31, 2015

Related U.S. Application Data

(63) Continuation of application No. 13/772,281, filed on Feb. 20, 2013, now abandoned, which is a continuation of application No. 12/302,002, filed as application No. PCT/US2007/012184 on May 21, 2007, now Pat. No. 8,404,631.

(60) Provisional application No. 60/921,505, filed on May 22, 2006.

(51) Int. Cl.

| | |
|---|---|
| ***C07K 14/195*** | (2006.01) |
| ***A61K 38/41*** | (2006.01) |
| ***C07K 14/47*** | (2006.01) |
| ***C07K 14/435*** | (2006.01) |
| ***C07K 14/33*** | (2006.01) |
| *A61K 38/00* | (2006.01) |

(52) U.S. Cl.

CPC ............ *C07K 14/47* (2013.01); *C07K 14/195* (2013.01); *C07K 14/33* (2013.01); *C07K 14/435* (2013.01); *C07K 14/43545* (2013.01); *C07K 14/43563* (2013.01); *C07K 14/43581* (2013.01); *A61K 38/00* (2013.01); *Y10T 436/102499* (2015.01)

(58) Field of Classification Search

CPC ..... C07K 14/195; A61K 38/00; A61K 38/41

See application file for complete search history.

(56) References Cited

U.S. PATENT DOCUMENTS

| | | | |
|---|---|---|---|
| 4,873,192 | A | 10/1989 | Kunkel |
| 5,731,454 | A | 3/1998 | Abraham et al. |
| 6,022,849 | A | 2/2000 | Olson et al. |
| 6,054,427 | A | 4/2000 | Winslow |
| 6,432,918 | B1 | 8/2002 | Winslow |
| 6,455,676 | B1 | 9/2002 | Weickert et al. |
| 6,773,613 | B1 | 8/2004 | Winslow et al. |
| 6,844,317 | B2 | 1/2005 | Winslow et al. |
| 6,849,438 | B1 | 2/2005 | Schmidt et al. |
| 6,974,795 | B2 | 12/2005 | Winslow et al. |
| 8,404,631 | B2 | 3/2013 | Cary et al. |
| 8,404,632 | B2 | 3/2013 | Cary et al. |
| 2003/0096240 | A1 | 5/2003 | Murad et al. |
| 2010/0266673 | A1 | 10/2010 | Cary et al. |
| 2010/0285104 | A1 | 11/2010 | Cary et al. |
| 2013/0288970 | A1 | 10/2013 | Cary et al. |
| 2013/0289252 | A1 | 10/2013 | Cary et al. |

FOREIGN PATENT DOCUMENTS

| | | | |
|---|---|---|---|
| WO | WO-95/27040 | A1 | 10/1995 |
| WO | WO-02/02757 | A2 | 1/2002 |
| WO | WO-02/02757 | A3 | 1/2002 |
| WO | WO-2007/139767 | A2 | 12/2007 |
| WO | WO-2007/139767 | A3 | 12/2007 |
| WO | WO-2007/139791 | A2 | 12/2007 |
| WO | WO-2007/139791 | A3 | 12/2007 |

OTHER PUBLICATIONS

Zhao et al. 1997: Localization of heme binding region in soluble guanylate cyclase. Biochemistry, 36: 15959-15964.*

Gray et al. Jul. 2004; Oxygen sensation and social feeling mediated by a C. elegans guanylate cyclase homologue. Nature. 430: 317-322.*

Anderson, R.F. et al. (2006, e-published Dec. 13, 2005). “Potentiation of the Cytotoxicity of the Anticancer Agent Tirapazamine by Benzotriazine N-Oxides: The Role of Redox Equilibria,” *J. Am. Chem Soc.* 128(1):245-249.

Anonymous. (2006). “Engineering H-NOX Proteins for Therapeutic Nitric Oxide and Oxygen Delivery,” Abstract, UCB Case No. B06-084, University of California, Berkeley Office of Technology Licensing: Berkeley, CA, one page.

Anonymous. (2006). “Marletta Wins Grant to Develop Blood Substitute,” College of Chemistry, University of California, Berkley, Press Release, located at: <http://chemistry.berkeley.edu/publications/news/2006/marlatta_blood.php>, last visited on Oct. 2, 2009, two pages.

Anonymous. (Aug. 10, 2006). “Dreyer's CEO Gives Bridge Funding,” California Institute for Quantitative Bioscience, located at <http://gb3.org/060810rogers.htm,> last visited on Oct. 5, 2009, two pages.

(Continued)

*Primary Examiner* — Karen Cochrane Carlson

(74) *Attorney, Agent, or Firm* — Morrison & Foerster LLP

(57) ABSTRACT

H-NOX proteins are mutated to exhibit improved or optimal kinetic and thermodynamic properties for blood gas $O_2$ delivery. The engineered H-NOX proteins comprise mutations that impart altered $O_2$ or NO ligand-binding relative to the corresponding wild-type H-NOX domain, and are operative as physiologically compatible mammalian blood $O_2$ gas carriers. The invention also provides pharmaceutical compositions, kits, and methods that use wild-type or mutant H-NOX proteins for the treatment of any condition for which delivery of $O_2$ is beneficial.

16 Claims, 46 Drawing Sheets

(56) References Cited

OTHER PUBLICATIONS

Anonymous. (Jan. 1, 2012). "Crystal Screen-User Guide," retrieved from <http://hamptonresearch.com/documents/product/hr003380_2-110_user_guide.pdf>, 3 pages.
Antonini, E. et al. (1971). *Hemoglobin and Myoglobin in Their Reactions with Ligands*, North-Holland Publ.: Amsterdam , four pages. (Table of Volumes Only.).
Aono, S. et. al. (Apr. 19, 2002) "Resonance Raman and Ligand Binding Studies of the Oxygen-Sensing Signal Transducer Protein HemAT from *Bacillus subtilis*," *J. Biol. Chem.* 277(16):13528-13538.
Artz, J.D. et al. (Dec. 1998). "NO Release from NO Donors and Nitrovasodilators: Comparisons Between Oxyhemoglobin and Potentiometric Assays," *Chem. Res. Toxicology* 11(12):1393-1397.
Bobofchak, K.M. et al. (Aug. 2003, e-published Apr. 10, 2003). "A Recombinant Polymeric Hemoglobin With Conformational, Functional, and Physiological Characteristics of an in Vivo $O_2$ Transporter," *Am. J. Physiol. Heart Circ. Physiol.* 285(2):H549-H561.
Boon, E.M. et al. (Aug. 4, 2006; e-pub. May 25, 2006). "Nitric Oxide Binding to Prokaryotic Homologs of the Soluble Guanylate Cyclase β1 H-NOX Domain," *J. Biol. Chem.* 281(31):21892-21902.
Boon, E.M. et al. (2006, e-published on Jul. 13, 2006). "Sensitive and Selective Detection of Nitric Oxide Using an H-NOX Domain," *J. Am. Chem. Soc.* 128:10022-10023.
Boon, E.M. et al. (Apr. 2005, e-published on Feb. 16, 2005). "Ligand Specificity of H-NOX Domains: From sGC to Bacterial NO Sensors," *J. Inorg. Biochem.* 99(4):892-902.
Boon, E.M. et al. (Jun. 2005, e-published on May 24, 2005). "A Molecular Basis for NO Selectivity in Soluble Guanylate Cyclase," *Nature Chemical Biology* 1(1):53-59.
Boon, E.M. et al. (Oct. 5, 2005; e-pub. Aug. 24, 2005). "Ligand Discrimination in Soluble Guanylate Cyclase and the H-NOX Family of Heme Sensor Proteins," *Curr. Opin. Chem. Biol.* 9(5):441-446.
Burgaud, J.L. et al. (2002). "Nitric-Oxide Releasing Molecules: A New Class of Drugs with Several Major Indications," *Current Pharmaceutical Design* 8:201-213.
Cary, S.P.L. et al. (Sep. 13, 2005). "Tonic and Acute Nitric Oxide Signaling Through Soluble Guanylate Cyclase is Mediated by Nonheme Nitric Oxide, ATP, and GTP," *Proc. Natl. Acad. Sci. USA.* 102(37):13064-13069.
Cary, S.P.L. et al. (Apr. 2006; e-pub. Mar. 10, 2006). "Nitric Oxide Signaling: No Longer Simply On or Off," *Trends Bio. Sci.* . . . 31(4):231-239.
Cary, S.P.L. (2005). "Tonic and Acute Nitric Oxide Signaling Through Soluble Guanylate Cyclase: Roles of Non-Heme NO, ATP and GLOBINS," Doctor of Philosophy Thesis submitted to the Department Biological Chemistry, Graduate School at the University of Michigan, pp. i-xvi, 1-203.
Corpet, F. (1988). "Multiple Sequence Alignment with Hierarchical Clustering." *Nucleic Acids Res.* 16(22):10881-10890.
Dente, L. et al. (1985). "The pEMBL Family of Single-Stranded Vectors," in Chapter 5 in *DNA Cloning*, vol. 1 Glover, D.M. ed., IRL Press: Oxford, England, pp. 101-107.
Dings, R.P.M. et al. (Jun. 1, 2007). "Scheduling of Radiation with Angiogenesis Inhibitors Anginex and Avastin Improves Therapeutic Outcome via Vessel Normalization," *Clin. Cancer Res.* 13(11):3395-3402.
Dmochowski, I. J. et al. (Aug. 31, 2000). "Enantiomeric Discrimination of Ru-Substrates by Cytochrome P450cam," *J. Inorg. Biochem.* 81(3):221-228.
Doherty, D.H. et al. (Jul. 1998). "Rate of Reaction with Nitric Oxide Determines the Hypertensive Effect of Cell-Free Hemoglobin," *Nat. Biotechnology* 16:672-676.
Doiron, A. et al. (Aug. 1, 1999). "Tumor Radiosensitization by Sustained Intratumoral Release of Bromodeoxyuridine," *Cancer Res.* 59(15):3677-3681.
Dorie, M.J. et al. (Jan. 1, 1994). "Comparison of the Enhancement of Tumor Responses to Fractionated Irradiation by SR 4233 (Tirapazamine) and by Nicotinamide with Carbogen." *Int. J. Radiat. Oncol. Biol. Phys.* 28(1):145-150.
Eich, R.F. et al. (1996). "Mechanism of NO-Induced Oxidation of Myoglobin and Hemoglobin," *Biochemistry* 35(22):6976-6983.
El-Said, A. et al. (1999). "Comparison of the Effectiveness of Tirapazamine and Carbogen with Nicotinamide in Enhancing the Response of a Human Tumor Xenograft to Fractionated Irradiation." *Radiat. Oncol. Investig.* 7(3):163-169.
Extended European Search Report mailed May 15, 2012 for EP Application No. 11189808.6, filed on Nov. 18, 2011, 9 pages.
Extended European Search Report mailed May 15, 2012 for EP Application No. 11189812.8, filed on Nov. 18, 2011, 9 pages.
Extended European Search Report mailed May 15, 2012 for EP Application No. 11189814.4 filed on Nov. 18, 2011, 10 pages.
Extended European Search Report mailed May 15, 2012 for EP Application No. 11189807.8 filed on Nov. 18, 2011, 9 pages.
Extended European Search Report mailed Aug. 31, 2012 for EP Application No. 11189818.5, filed on Nov. 18, 2011, 11 pages.
Frey, A.D. et. al. (Feb. 2001). "Dissection of Central Carbon Metabolism of Hemoglobin-Expressing *Escherichia coli* by 13C Nuclear Magnetic Resonance Flux Distribution Analysis in Microaerobic Bioprocesses," *Applied and EnvironmentalMicro Biology* 67(2):680-687.
Gatzemeier, U. (2001). "Main Session III. Indications for Chemotherapy in Stage IV Non-Small Cell Lung Cancer," *Lung Cancer* 33(Suppl. 1):S109-S113.
George, I. et al. (Apr. 14, 2006). "A Polymerized Bovine Hemoglobin Oxygen Carrier Preserves Regional Myocardial Function and Reduces InFarct Size After Acute Myocardial Ischemia," *Am J Physiol Heart Circ Physiol* 291:H1126-H1137.
Gilles-Gonzalez, M.A. et al. (1994, e-published on May 1, 2002) "Heme-Based Sensors, Exemplified by the Kinase FixL, Are a New Class of Heme Protein with Distinctive Ligand Binding and Autoxidation," *Biochemistry* 33(26):8067-8073.
Gouet, P. et al. (Apr. 1999). "ESPript: Analysis of Multiple Sequence Alignments in PostScript," *Bioinformatics* 15(4):305-308.
Guarnone, R. et al. (Sep./Oct. 1995). "Performance Characteristics of Hemox-Analyzer for Assessment of the Hemoglobin Dissociation Curve," *Haematologica* 80(5):426-430.
Harrison, L.B. et al. (2002). "Impact of Tumor Hypoxia and Anemia on Radiation Therapy Outcomes," *The Oncologist* 7(6):492-508.
Hefti, M.H. et al. (2004). "The PAS Fold. A Redefinition of the PAS Domain Based Upon Structural Prediction," *Eur. J. Biochem.* 271:1198-1208.
Henning, T. (Jun. 2002). "Polyethylene Glycols (PEGs) and the Pharmaceutical Industry," *Fine, Speciality & Performance Chemicals* pp. 57-59.
International Search Report mailed on Mar. 11, 2008, for PCT Application No. PCT/US07/12184, filed on May 21, 2007, four pages.
International Search Report mailed on Dec. 6, 2007, for PCT Application No. PCT/US07/12133, filed on May 21, 2007, four pages.
Inayat, M.S. et al. (2006). "Oxygen Carriers: A Selected Review," *Transfusion and Apheresis Science* 34(1):25-32.
Iyer, L.M. et al. (Feb. 3, 2003). "Ancient Conserved Domains Shared by Animal Soluble Guanylyl Cyclases and Bacterial Signaling Proteins," *BMC Genomics* 4(1):1-8.
Jain, R.K. et al. (Jan. 2006). "Lessons from Phase III Clinical Trials on Anti-VEGF Therapy for Cancer," *Nat. Clin. Pract. Oncol.* 3(1):24-40.
Jones, D.H. et al. (Jan. 1990). "A Rapid Method for Site-Specific Mutagenesis and Directional Subcloning by Using the Polymerase Chain Reaction to Generate Recombinant Circles," *Biotechniques* 8(2):178-183.
Jones, D.H. et al. (Jan. 1991). "A Rapid Method for Recombination and Site-Specific Mutagenesis by Placing Homologous Ends on DNA Using Polymerase Chain Reaction," *Biotechniques* 10(1):62-66.
Jugdutt, B.I. et al. (May 1994). "Effect of Prolonged Nitrate Therapy on Left Ventricular Remodeling After Canine Acute Myocardial Infarction," *Circulation* 89(5):2297-2307.

(56) References Cited

OTHER PUBLICATIONS

Kaanders, J.H.A.M. et al. (Dec. 2002). "ARCON: a Novel Biology-Based Approach in Radiotherapy," *Lancet Oncol.* 3(12):728-737.
Kaanders, J.H.A.M. et al. (Jul. 2004). "Clinical Studies of Hypoxia Modification in Radiotherapy," *Semin. Radiat. Oncol.* 14(3):233-240.
Karow, D.S. et al. (Aug. 10, 2004; e-published Jul. 13, 2004). "Spectroscopic Characterization of the Soluble Guanylate Cyclase-Like Heme Domains From *Vibrio cholerae* and *Thermoanaerobacter tengcongensis*," *Biochemistry* 43(31):10203-10211.
Karow, D.S. et al. (Dec. 13, 2005, e-published on Nov. 17, 2005). "Characterization of Functional Heme Domains from Soluble Guanylate cyclase," *Biochemistry.* 44(49):16266-16274.
Kavanagh, B.D. et al. (2001). "A Phase I Study of RSR13, a Radiation-Enhancing Hemoglobin Modifier: Tolerance of Repeated Intravenous Doses and Correlation of Pharmacokinetics with Pharmacodynamics," *Int. J. Radiat. Oncol. Biol. Phys.* 49(4):1133-1139.
Kavdia, M. et al. (Feb. 14, 2002). "Model of Nitric Oxide Diffusion in an Arteriole: Impact of Hemoglobin-Based Blood Substitutes," *Am J Physiol Heart Circ Physiol* 282:2245-2253.
Khandelwal, S.R. et al. (1999). "RSR13, an Allosteric Effector of Haemoglobin, and Carbogen Radiosensitize FSAII and SCCVII Tumours in C3H Mice," *Br. J. Cancer* 79(5-6):814-820.
Kharitonov, V.G. et al. (1997). "Kinetics of Nitric Oxide Dissociation from Five- and Six-Coordinate Nitrosyl Hemes and Heme Proteins, Including Soluble Guanylate Cyclase," *Biochemistry* 36(22):6814-6818.
Kramer, G.C. et. al. (2006). "Hemoglobin Based Oxygen Carriers as Resuscitative Solutions for Trauma and Combat Casualty Care," Chapter 12 in *Blood Substitutes*, Winslow, R.M. ed., Academic Press, Inc.: Amsterdam, NL, pp. v-vii, 139-151.
Kunkel, T.A. (Jan. 1985). "Rapid and Efficient Site-Specific Mutagenesis Without Phenotypic Selection," *Proc. Natl. Acad. Sci. USA* 82(2):488-492.
Kunkel, T.A. (1987). "Rapid and Efficient Site-Specific Mutagenesis Without Phenotypic Selection" Chapter 19 in *Methods Enzymology, vol. 154: Recombinant DNA, Part E*, Wu, R. ed. et al., Academic Press, Inc., San Diego, CA, pp. 367-382.
Lawrence, T.S. et al. (Jan. 2003). "The Mechanism of Action of Radiosensitization of Conventional Chemotherapeutic Agents," *Semin. Radiat. Oncol.* 13(1):13-21.
Lee, D-J. et al. (1995). "Results of an RTOG Phase III Trial (RTOG 85-27) Comparing Radiotherapy Plus Etanidazole with Radiotherapy Alone for Locally Advanced Head and Neck Carcinomas," *Int. J. Radiat. Oncol. Biol. Phys.* 32(3):567-576.
Li, Q. et al. (Dec. 2001). "Advances in Bio-Organic Chemical Research on Nitric Oxide," *Chem. J. Chin. Univ.* 22(12):2026-2031.
Maes, E.M. et al. (2004, e-published on May 6, 2004). "Role of Binding Site Loops in Controlling Nitric Oxide Release: Structure and Kinetics of Mutant Forms of Nitrophorin 4," *Biochemistry* 43(21):6679-6690.
Martin, E. et al. (Sep. 22, 2006, e-published on Jul. 24, 2006). "Ligand Selectivity of Soluble Guanylyl Cyclase," *The Journal of Biological Chemistry* 281(38):27836-27845.
Migita, R. et al. (Jun. 1997). "Blood Volume and Cardiac Index in Rats After Exchange Transfusion With Hemoglobin-Based Oxygen Carriers," *J. Appl. Physiol.* 82(6):1995-2002.
Moore, E.G. et al. (May 10, 1976). "Cooperativity in the Dissociation of Nitric Oxide from Hemoglobin," *J. Biol. Chem.* 251(9):2788-2794.
Morris, R.J. et al. (Sep. 10, 1980). "The Role of Diffusion in Limiting the Rate of Ligand Binding to Hemoglobin," *J. Biol. Chem.* 255(17):8050-8053.
Nakamaye, K.L. et al. (Dec. 22, 1986). "Inhibition of Restriction Endonuclease Nci I Cleavage by Phosphorothioate Groups and its Application to Oligonucleotide-Directed Mutagenesis," *Nucleic Acids Res.*14(24):9679-9698.
Nioche, P. et al. (Nov. 26, 2004, e-published on Oct. 7, 2004). "Femtomolar Sensitivity of a NO Sensor From *Clostridium botulinum*," *Science* 306(5701):1550-1553.
Non-Final Office Action mailed Jul. 2, 2012, for U.S. Appl. No. 12/302,002, filed Jun. 26, 2010, 7 pages.
Non-Final Office Action mailed Jul. 5, 2012, for U.S. Appl. No. 12/302,004, filed Jun. 24, 2010, 9 pages.
Olson, J. et al. (Mar. 15, 2004). "No Scavenging and the Hypertensive Effect of Hemoglobin-Based Blood Substitutes," *Free Radical Biology & Medicine* 36(6):685-697.
Ouellet, H. et al. (Apr. 30, 2002). "Truncated Hemoglobin HbN Protects *Mycobacterium bovis* from Nitric Oxide," *Proc. Natl. Acad. Sci. USA* 99(9):5902-5907.
Overgaard, J. et al. (Feb. 1998). "A Randomized Double-Blind Phase III Study of Nimorazole as a Hypoxic Radiosensitizer of Primary Radiotherapy in Supraglottic Larynx and Pharynx Carcinoma. Results of the Danish Head and Neck Cancer Study (DAHANCA) Protocol 5-85." *Radiother. Oncol.* 46(2):135-146.
Partial European Search Report, mailed on May 4, 2012, for EP Patent Application EP 11 18 9818, filed on Nov. 18, 2011, 6 pages.
Pellicena, P. et al. (Aug. 31, 2004). "Crystal Structure of an Oxygen-Binding Heme Domain Related to Soluble Guanylate Cyclases," *Proc. Natl. Acad. Sci. USA* 101(35):12854-12859. Partial.
Pifarré, P. et al. (Feb. 10, 2007, e-published on Dec. 11, 2006). "Species Differences in the Localization of Soluble Guanylyl Cyclase Subunits in Monkey and Rat Brain," *J. Comparative Neurology* 500(5):942-957.
Raat, N.J.H. et al. (Jan. 2005). "Effects of Recombinant-Hemoglobin Solutions rHb2.0 and rHb1.1 on Blood Pressure, Intestinal Blood Flow, and Gut Oxygenation in a Rat Model of Hemorrhagic Shock," *J. Lab. Clin. Med.* 145(1):21-32.
Rockwell, S. et al. (1998). "RSR13, a Synthetic Allosteric Modifier of Hemoglobin, as an Adjunct to Radiotherapy: *Preliminary Studies with EMT6 Cells and Tumors and Normal Tissues in Mice*," *Radiat. Oncol. Investig.* 6(5):199-208.
Rohlfs, R.J. et al. (May 15, 1998). "Arterial Blood Pressure Responses to Cell-Free Hemoglobin Solutions and the Reaction With Nitric Oxide," *J. Biol. Chem.* 273(20):12128-12134.
Rothkegel, C. et al. (2006, e-published on Jul. 5, 2006). "Identification of Residues Crucially Involved in Soluble Guanylate Cyclase Activation," *FEBS Letters* 580:4205-4213.
Shaw, E. et al. (Jun. 15, 2003). "RSR13 Plus Cranial Radiation Therapy in Patients with Brain Metastases: Comparison with the Radiation Therapy Oncology Group Recursive Partitioning Analysis Brain Metastases Database," *J. Clin. Oncol.* 21(12):2364-2371.
Shimamura, S. et al. (2006). "Effect of Intermittent Administration of Sustained Release Isosorbide Dinitrate (sr-ISND) in Rats with Pressure-Overload Heart," *J. Vet. Med. Sci.* 68(3):213-217.
Spahn, D.R. et al. (2005). "Artificial $O_2$ Carriers: Status in 2005," *Curr. Pharm. Des.* 11(31):4099-4114.
Springer, B.A. et al. (1994, e-published on May 1, 2002) "Mechanisms of Ligand Recognition in Myoglobin," *Chem. Rev.* 94(3):699-714.
Stuben, G. et al. (Aug. 1998). "The Effect of Combined Nicotinamide and Carbogen Treatments in Human Tumour Xenografts: Oxygenation and Tumour Control Studies," *Radiother. Oncol.* 48(2):143-148.
Sullivan, J.P. et. al. (Sep./Oct. 2006, e-published on Jul. 22, 2006). "Targeted Oxygen Delivery within Hepatic Hollow Fiber Bioreactors via Supplementation of Hemoglobin-Based Oxygen Carriers," *Biotechnol. Prog.* 22(5):1374-1387.
Sun, L-Q. et al. (Jan. 2001). "Fractionated Irradiation Combined with Carbogen Breathing and Nicotinamide of Two Human Glioblastomas Grafted in Nude Mice." *Radiat Res.* 155(1 Pt. 1):26-31.
Taguchi, S. et al. (Jan. 30, 2004, e-published on Nov. 11, 2003). "Binding of Oxygen and Carbon Monoxide to a Heme-regulated Phosphodiesterase from *Escherichia coli*," *J. Bio. Chem.* 279(5):3340-3347.

(56) References Cited

OTHER PUBLICATIONS

Taylor, J.W. et al. (Dec. 20, 1985). "The Rapid Generation of Oligonucleotide-Directed Mutations at High Frequency Using Phosphorothioate-Modified DNA," *Nucleic Acids Res.* 13(24):8765-8785.

Taylor, J.W. et al. (Dec. 20, 1985). "The Use of Phosphorothioate-Modified DNA in Restriction Enzyme Reactions to Prepare Nicked DNA," *Nucleic Acids Res.* 13(24):8749-8764.

Tsai, A.G. et al. (Oct. 2003, e-published on Jun. 12, 2003). "Targeted $O_2$ Delivery by Low-$P_{50}$ Hemoglobin: A New Basis for $O_2$ Therapeutics," *Am. J. Physiol. Heart Circ. Physiol.* 285:H1411-H1419.

Vandegriff, K.D. et al. (Nov. 1997). "Colloid Osmotic Properties of Modified Hemoglobins: Chemically Cross-Linked Versus Polyethylene Glycol Surface-Conjugated," *Biophys. Chem.* 69(1):23-30.

Vandegriff, K.D. et al. (Aug. 15, 2004, e-published on Jun. 3, 2004). "Kinetics of NO and $O_2$ Binding to a Maleimide Poly(ethylene glycol)-Conjugated Human Haemoglobin," *Biochem J.* 382(Pt 1):183-189.

Vanderkooi, J.M. et al. (Apr. 25, 1987). "An Optical Method for Measurement of Dioxygen Concentration Based Upon Quenching of Phosphorescence," *J. Biol. Chem.* 262(12):5476-5482.

Varlotto, J. et al. (2005). "Anemia, Tumor Hypoxemia, and the Cancer Patient," *Int. J. Radiat. Oncol. Biol. Phys.* 63(1):25-36.

Villard, J.W. et al. (Apr. 16, 2002, e-published on Apr. 1, 2002). "Use of a Blood Substitute to Determine Instantaneous Murine Right Ventricular Thickening with Optical Coherence Tomography," *Circulation* 105:1843-1849.

Von Dobschuetz, E. et al. (Jun. 2004). "Recombinant Human Hemoglobin with Reduced Nitric Oxide-scavenging Capacity Restores Effectively Pancreatic Microcirculatory Disorders in Hemorrhagic Shock," *Anesthesiology* 100(6):1484-1490.

Von Pawel, J. et al. (Mar. 2000). "Tirapazamine Plus Cisplatin Versus Cisplatin in Advanced Non-Small-Cell Lung Cancer: A Report of the International Catapult I Study Group," *J. Clin. Oncol.* 18(6):1351-1359.

Wikipedia (2007). "Nitric Oxide Synthase," Wikipedia, located at <http://web.archieve.org/web/20071104080615/http://en.wikipedia.org/wiki/Nitric_oxide_s . . . >, last visited Oct. 18, 2009, five pages.

Williamson, S.K. et al. (Dec. 20, 2005). "Phase III Trial of Paclitaxel Plus Carboplatin With or Without Tirapazamine in Advanced Non-Small-Cell Lung Cancer: Southwest Oncology Group Trial S0003," *J. Clin. Oncol.* 23(36):9097-9104.

Winger, J.A. (2004). *Activation and Deactivation of Soluble Guanylate Cyclase: Domain Organization and the Requirement for Non-Heme Equivalents of Nitric Oxide*, Dissertation in partial fulfillment for Doctor of Philosophy (Medicinal Chemistry), University of Michigan, Ann Arbor, MI. , 201 pages.

Winger, J.A. et al. (Jan. 12, 2007; e-published on Nov. 10, 2006). "Dissociation of Nitric Oxide from Soluble Guanylate Cyclase and Heme-Nitric Oxide/Oxygen Binding Domain Constructs," *The Journal of Biological Chemistry* 282(2):897-907.

Winslow, R.M. (2003). "Current Status of Blood Substitute Research: Towards a New Paradigm," *J. Internal Med.* 253:508-517.

Winslow, R.M. et al. (Oct. 2004, e-published on Jun. 18, 2004). "Comparison of PEG-Modified Albumin and Hemoglobin in Extreme Hemodilution in the Rat," *J. Appl. Physiol.* 97(4):1527-1534.

Winslow, R.M. (Jan. 2007). "Red Cell Substitutes," *Seminars in Hematology* 44(1):51-59.

Yao, Z. et al. (Feb. 1992). "Site-Directed Mutagenesis of Herpesvirus Glycoprotein Phosphorylation Sites by Recombination Polymerase Chain Reaction," *PCR Methods and Applications* 1(3):205-207.

Yu, M. et al. (Dec. 2008, e-published Dec. 9, 2008). "Influences of PEG-Conjugated Hemoglobin on Tumor Oxygenation and Response to Chemotherapy," *Artif Cells Blood Substit. and Biotechno.l* 36(6):551-561.

Zhao, Y. et al. (Dec. 21, 1999). "A Molecular Basis for Nitric Oxide Sensing by Soluble Guanylate Cyclase," *Proc. Natl. Acad. Sci. USA* 96(26):14753-14758.

U.S. Appl. No. 14/490,597, filed Sep. 18, 2014, for Cary et al.

* cited by examiner

Figure 5A

```
---------+---------+---------+---------+---------+---------+
        10        20        30        40        50        60
---------+---------+---------+---------+---------+---------+
MYGFVNHALELLVIRNYGPEVWEDIKKEAQLDEEGQFLVRIIYDDSKTYDLVAAASKVLN   H.s. β1
MYGFVNHALELLVIRNYGPEVWEDIKKEAQLDQEGQFLVRIIYDHSKTYDLVAAASKVLN   R.n. β1
MYGFVNYALELLVLKHFGEEIWEKIKKKAMVSMEGQFLVRQIYDDEITYNLIGAAVEILN   D.m. β1
MYGMLYESVQHYVQEEYGVDIWRKVCHIIDCKHN-SFKTHQIYPDKLMPDIAEALSACTG   D.m. CG14885-PA
MFGWIHESFRQLVTRKYGKDIWEKIVHMSKFELGTESEIAHYYNDDETLRLVNSMANVIG   C.e. GCY-35
MYGLVNKAIQDMVCSRFGEETWKQIKHKAEVDVD-VFLSMEGYPDDITHKLVKAASVILS   N.p.
MKGVIFNLLQEVVSAAHGADAWDDILDEAGVSG--AYTSLGSYDDEEWETLVETASARLS   C.c.
MKGIIFNVLEDMVVAQCGMSVWNELLEKHAPKDR-VYVSAKSYAESELFSIVQDVAQRLN   S.o.
MKGIIFNEFLNFVEKSESYTLVDQIIMDSHLKSHGAYTSIGTYSPKELFQLVKALAMKNG   L.p. (ORF2)
MKGTVVGTWVKTCKRLYGETVVENALEKVGFERKKIFSPFEDVEDSKVNNFIEDISKKVN   C.a.
MKGTIVGTWIKTLRDLYGNDVVDESLKSVGWEPDRVITPLEDIDDDEVRRIFAKVSEKTG   T.t.
V V s   s   s   s   s                            s s s   ss

---------+---------+------------+------------+---------+-----
        70        80          90           100       110
---------+---------+------------+------------+---------+-----
LNAGEILQMFGKMFFVFCQESGYDTILRVLGSN-VREFLQNL-DALHDHLATIYPG--MR   H.s. β1
LNAGEILQMFGKMFFVFCQESGYDTILRVLGSN-VREFLQNL-DALHDHLATIYPG--MR   R.n. β1
IPADDILELFGKTFFEFCQDSGYDKILQVLGAT-PRDFLQNL-DALHDHLGTLYPG--MR   D.m. β1
ESFDFCMNFFGRCFVRFFSNFGYDKMIRSTGRY-FCDFLQSI-DNIHLIMRFTYPK--MK   D.m. CG14885-PA
IPIEEIWEAYGGFLIQFTMETGWDELLRAMAPD-LEGFLDSL-DSLHYFIDHVVYKTKLR   C.e. GCY-35
LSPKQIMQAFGEFWVQYTAQEGYGEMLDMSGDT-LPEFLENL-DNLHARVGVSFPK--LQ   N.p.
LSRGELLRWFGQEAMPHLAR---AYPVFFEGHVSSRSFLAGVNDIIHAEVHKLYAG--AA   C.c.
MPIQDVVKAFGQFLFNGLAS---RHTDVVDKFDDFTSLVMGIHDVIHLEVNKLYHEP--S   S.o.
KPTSVILQEYGEYLFEVFAK---KYPQFFREKKSVFQFLEALETHIHFEVKKLYDY--TE   L.p. (ORF2)
EEKSIIWEKIGEDNVIAFHK---DFPAFFEHEN-LYSFFKSM-FDVHVVMTKKFPG--AK   C.a.
KNVNEIWREVGRQNIKTFSE---WFPSYFAGRR-LVNFLMMM-DEVHLQLTKMIKG--AT   T.t.
          sV   s                              s  V  s   s

------+-----------+-----------+---------+-----------+------
    120        130         140       150         160
------+-----------+-----------+---------+-----------+------
APSFRCTDAEKGKGLILHYYSEREGLQDIVIGIIKTVAQQIHGTEIDMKVIQQRNE   H.s. β1
APSFRCTDAEKGKGLILHYYSEREGLQDIVIGIIKTVAQQIHGTEIDMKVIQQRSE   R.n. β1
APSFRCTEKD-GE-LLLHYYSERPGLEHIVIGIVKAVASKLHGVEVEIDIVKRKGE   D.m. β1
SPSMQLTNMDDNG-AVILYRSSRTGMSKYLIGQMTEVAREFYGLEIKAYVIESQND   D.m. CG14885-PA
GPSFRCDVQADGT-LLLHYYSKRSGLYPIVKGVVREVARRIYDTEVVMKVQERKQE   C.e. GCY-35
PPSFECTDMEENS-LSLHYRSDREGLTPMVIGLIKGLGTREED-TEVHITQTQNRDE   N.p.
GPHLKLRAIDAGG-VAMAYTSQR-RMCALAQGFTEGAARQFH-EVITFEHAACVEK   C.c.
LPHINGQLLPNNQ-IALRYSSPR-RLCFCAEGLLFGAAQHFQ-QKIQISHDTCMHT   S.o.
LPHFECQYHSQNQ-MEMIYTSSR-PLADFAEGLIKGCLKYHKENMTIVRENLPAKT   L.p. (ORF2)
PPLILIKPISKRE-AIFTYRSKR-GMFDYLKGLIKGSANHFN-EKIEIEEVEKTKE   C.a.
PPRLIAKPVAKDA-IEMEYVSKR-KMYDHFLGLIEGSSKFFK-EEISVEEVER---   T.t
V                VVV  s   H  V▲s s s    s
```

a.

b.

Sequences of Mutant H-NOX and the Parent WT H-NOX

NUCLEOTIDES followed by AMINO ACIDS

*Thermoanaerobacter tengcongensis* H-NOX

***Tt.* WT**

(SEQ ID NO:53)
ATGAAGGGGACAATCGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:54)
MKGTIVGTWIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKRKMYDYFLGLIEGSSKFFKEEISVEEVERGEKDGFSRLKVRIKFKNPVFE

***Tt.* Y140F**

(SEQ ID NO:55)
ATGAAGGGGACAATCGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTTCTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:56)
MKGTIVGTWIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKRKMYDFFLGLIEGSSKFFKEEISVEEVERGEKDGFSRLKVRIKFKNPVFE

(SEQ ID NO:57)
ATGAAGGGGACAATCGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATCTTTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:58)
MKGTIVGTWIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKRKMYDLFLGLIEGSSKFFKEEISVEEVERGEKDGFSRLKVRIKFKNPVFE

***Tt.* Y140H**

(SEQ ID NO:59)
ATGAAGGGGACAATCGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATCACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:60)
MKGTIVGTWIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKRKMYDHFLGLIEGSSKFFKEEISVEEVERGEKDGFSRLKVRIKFKNPVFE

***Tt.* Y140A**

(SEQ ID NO:61)
ATGAAGGGGACAATCGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATGCCTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:62)
MKGTIVGTWIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKRKMYDAFLGLIEGSSKFFKEEISVEEVERGEKDGFSRLKVRIKFKNPVFE

(SEQ ID NO:63)
ATGAAGGGGACAATCGTCGGGACATTTATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:64)
MKGTIVGTFIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKRKMYDYFLGLIEGSSKFFKEEISVEEVERGEKDGFSRLKVRIKFKNPVFE

***Tt.* W9F/Y140L**

(SEQ ID NO:65)
ATGAAGGGGACAATCGTCGGGACATTTATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTTTTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:66)
MKGTIVGTFIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKRKMYDFFLGLIEGSSKFFKEEISVEEVERGEKDGFSRLKVRIKFKNPVFE

***Tt.* W9F/Y140H**

(SEQ ID NO:67)
ATGAAGGGGACAATCGTCGGGACATTTATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATCACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:68)
MKGTIVGTFIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKRKMYDHFLGLIEGSSKFFKEEISVEEVERGEKDGFSRLKVRIKFKNPVFE

(SEQ ID NO:69)
ATGAAGGGGACAATCGTCGGGACATTTATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGGCAATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:70)
MKGTIVGTFIKTLRDLYGNDVVDESLKSVGWEPDRVITPLEDIDDDEVRRIFAKVSEKTGKNVNEI
WREVGRQAIKTFSEWFPSYFAGRRLVNFLMMMDEVHLQLTKMIKGATPPRLIAKPVAKDAIEME
YVSKRKMYDYFLGLIEGSSKFFKEEISVEEVERGEKDGFSRLKVRIKFKNPVFE

***Tt.* W9Y**

(SEQ ID NO:71)
ATGAAGGGGACAATCGTCGGGACATACATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:72)
MKGTIVGTYIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKRKMYDYFLGLIEGSSKFFKEEISVEEVERGEKDGFSRLKVRIKFKNPVFE

***Tt.* W9N**

(SEQ ID NO:73)
ATGAAGGGGACAATCGTCGGGACAAATATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:74)
MKGTIVGTNIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKRKMYDYFLGLIEGSSKFFKEEISVEEVERGEKDGFSRLKVRIKFKNPVFE

Figure 8D

*Tt.* W9H (SEQ ID NO:75)
ATGAAGGGGACAATCGTCGGGACACACATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:76)
MKGTIVGTHIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKRKMYDYFLGLIEGSSKFFKEEISVEEVERGEKDGFSRLKVRIKFKNPVFE

*Tt.* I5A (SEQ ID NO:77)
ATGAAGGGGACAGCAGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:78)
MKGTAVGTWIKTLRDLYGNDVVDESLKSVGWEPDRVITPLEDIDDDEVRRIFAKVSEKTGKNVNE
IWREVGRQNIKTFSEWFPSYFAGRRLVNFLMMMDEVHLQLTKMIKGATPPRLIAKPVAKDAIEME
YVSKRKMYDYFLGLIEGSSKFFKEEISVEEVERGEKDGFSRLKVRIKFKNPVFE

*Tt.* I5L (SEQ ID NO:79)
ATGAAGGGGACACTTGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:80)
MKGTLVGTWIKTLRDLYGNDVVDESLKSVGWEPDRVITPLEDIDDDEVRRIFAKVSEKTGKNVNE
IWREVGRQNIKTFSEWFPSYFAGRRLVNFLMMMDEVHLQLTKMIKGATPPRLIAKPVAKDAIEME
YVSKRKMYDYFLGLIEGSSKFFKEEISVEEVERGEKDGFSRLKVRIKFKNPVFE

(SEQ ID NO:81)
ATGAAGGGGACACTTGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTGCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:82)
MKGTLVGTWIKTLRDLYGNDVVDESLKSVGWEPDRVITPLEDIDDDEVRRIFAKVSEKTGKNVNE
IWREVGRQNIKTFSEWFPSYFAGRRLVNFLMMMDEVHLQLTKMIKGATPARLIAKPVAKDAIEME
YVSKRKMYDYFLGLIEGSSKFFKEEISVEEVERGEKDGFSRLKVRIKFKNPVFE

***Tt.* P115A**

(SEQ ID NO:83)
ATGAAGGGGACAATCGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTGCCAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTGA (SEQ ID NO:84)
MKGTIVGTWIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPARLIAKPVAKDAIEME
YVSKRKMYDYFLGLIEGSSKFFKEEISVEEVERGEKDGFSRLKVRIKFKNPVFE

***Tt.* N74E**

(SEQ ID NO:85)
ATGAAGGGGACAATCGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGGAAATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTATAAGAAA
AATTGA (SEQ ID NO:86)
MKGTIVGTWIKTLRDLYGNDVVDESLKSVGWEPDRVITPLEDIDDDEVRRIFAKVSEKTGKNVNEI
WREVGRQEIKTFSEWFPSYFAGRRLVNFLMMMDEVHLQLTKMIKGATPPRLIAKPVAKDAIEMEY
VSKRKMYDYFLGLIEGSSKFFKEEISVEEVERGEKDGFSRLKVRIKFKNPVFEYKKN

(SEQ ID NO:87)
ATGAAGGGGACAATCGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGGCCATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATCACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTATAAGAAA
AATTGA (SEQ ID NO:88)
MKGTIVGTWIKTLRDLYGNDVVDESLKSVGWEPDRVITPLEDIDDDEVRRIFAKVSEKTGKNVNEI
WREVGRQAIKTFSEWFPSYFAGRRLVNFLMMMDEVHLQLTKMIKGATPPRLIAKPVAKDAIEME
YVSKRKMYDHFLGLIEGSSKFFKEEISVEEVERGEKDGFSRLKVRIKFKNPVFEYKKN

Tt. R135Q-His6

(SEQ ID NO:89)
ATGAAGGGGACAATCGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAACAGAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTATAAGAAA
AATCTCGAGCACCACCACCACCACCACTGA (SEQ ID NO:90)
MKGTIVGTWIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKQKMYDYFLGLIEGSSKFFKEEISVEEVERGEKDGFSRLKVRIKFKNPVFEYKKNLEHHHHHH

(SEQ ID NO:91)
ATGAAGGGGACAATCGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGGCCATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTATAAGAAA
AATTGA (SEQ ID NO:92)
MKGTIVGTWIKTLRDLYGNDVVDESLKSVGWEPDRVITPLEDIDDDEVRRIFAKVSEKTGKNVNEI
WREVGRQAIKTFSEWFPSYFAGRRLVNFLMMMDEVHLQLTKMIKGATPPRLIAKPVAKDAIEME
YVSKRKMYDYFLGLIEGSSKFFKEEISVEEVERGEKDGFSRLKVRIKFKNPVFEYKKN

***Tt.* N74A-His6**

(SEQ ID NO:93)
ATGAAGGGGACAATCGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGGCCATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTATAAGAAA
AATCTCGAGCACCACCACCACCACCACTGA (SEQ ID NO:94)
MKGTIVGTWIKTLRDLYGNDVVDESLKSVGWEPDRVITPLEDIDDDEVRRIFAKVSEKTGKNVNEI
WREVGRQAIKTFSEWFPSYFAGRRLVNFLMMMDEVHLQLTKMIKGATPPRLIAKPVAKDAIEME
YVSKRKMYDYFLGLIEGSSKFFKEEISVEEVERGEKDGFSRLKVRIKFKNPVFEYKKNLEHHHHHH

Figure 8H

*Tt.* W9N (SEQ ID NO:95)
ATGAAGGGGACAATCGTCGGGACAAATATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTATAAGAAA
AATTGA (SEQ ID NO:96)
MKGTIVGTNIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKRKMYDYFLGLIEGSSKFFKEEISVEEVERGEKDGFSRLKVRIKFKNPVFEYKKN

*Tt.* W9H (SEQ ID NO:97)
ATGAAGGGGACAATCGTCGGGACACATATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTATAAGAAA
AATTGA (SEQ ID NO:98)
MKGTIVGTHIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKRKMYDYFLGLIEGSSKFFKEEISVEEVERGEKDGFSRLKVRIKFKNPVFEYKKN

(SEQ ID NO:99)
ATGAAGGGGACAATCGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGCATATAAAAACTTTCAGCGAATGGTTTCC
CTCCTATTTTGCAGGGAGAAGGCTAGTGAATTTTTTAATGATGATGGATGAGGTACACCTACA
GCTTACCA·AGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTATAAGAAA
AATTGA (SEQ ID NO:100)
MKGTIVGTWIKTLRDLYGNDVVDESLKSVGWEPDRVITPLEDIDDDEVRRIFAKVSEKTGKNVNEI
WREVGRQHIKTFSEWFPSYFAGRRLVNFLMMMDEVHLQLTKMIKGATPPRLIAKPVAKDAIEME
YVSKRKMYDYFLGLIEGSSKFFKEEISVEEVERGEKDGFSRLKVRIKFKNPVFEYKKN

***Tt.* I75F**

(SEQ ID NO:101)
ATGAAGGGGACAATCGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACTTCAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGCACCACCAC
CACCACCACTGA (SEQ ID NO:102)
MKGTIVGTWIKTLRDLYGNDVVDESLKSVGWEPDRVITPLEDIDDDEVRRIFAKVSEKTGKNVNEI
WREVGRQNFKTFSEWFPSYFAGRRLVNFLMMMDEVHLQLTKMIKGATPPRLIAKPVAKDAIEME
YVSKRKMYDYFLGLIEGSSKFFKEEISVEEVERGEKDGFSRLKVRIKFKNPVFEHHHHHH

(SEQ ID NO:103)
ATGAAGGGGACAATCGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGTTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGCACCACCAC
CACCACCACTGA (SEQ ID NO:104)
MKGTIVGTWIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKRKMYDYFLGFIEGSSKFFKEEISVEEVERGEKDGFSRLKVRIKFKNPVFEHHHHHH

***Tt.* WT-His6**

(SEQ ID NO:105)
ATGAAGGGGACAATCGTCGGGACATGGATAAAGACCCTGAGGGACCTTTACGGGAATGATGT
GGTTGATGAATCTTTAAAAAGTGTGGGTTGGGAACCAGATAGGGTAATTACACCTCTGGAGG
ATATTGATGACGATGAGGTTAGGAGAATTTTTGCTAAGGTGAGTGAAAAAACTGGTAAAAAT
GTCAACGAAATATGGAGAGAGGTAGGAAGGCAGAACATAAAAACTTTCAGCGAATGGTTTCC
CTCCTATTTTGCAGGGAGAAGGCTAGTGAATTTTTTAATGATGATGGATGAGGTACACCTACA
GCTTACCAAGATGATAAAAGGAGCCACTCCTCCAAGGCTTATTGCAAAGCCTGTTGCAAAAG
ATGCCATTGAAATGGAGTACGTTTCTAAAAGAAAGATGTACGATTACTTTTTAGGGCTTATAG
AGGGTAGTTCTAAATTTTTCAAGGAAGAAATTTCAGTGGAAGAGGTCGAAAGAGGCGAAAAA
GATGGCTTTTCAAGGCTAAAAGTCAGGATAAAATTTAAAAACCCCGTTTTTGAGTATAAGAAA
AATCTCGAGCACCACCACCACCACCACTGA (SEQ ID NO:106)
MKGTIVGTWIKTLRDLYGNDVVDESLKSVGWEPDRVITPLEDIDDDEVRRIFAKVSEKTGKNVNEI
WREVGRQNIKTFSEWFPSYFAGRRLVNFLMMMDEVHLQLTKMIKGATPPRLIAKPVAKDAIEME
YVSKRKMYDYFLGLIEGSSKFFKEEISVEEVERGEKDGFSRLKVRIKFKNPVFEYKKNLEHHHHHH

Figure 8K

*Legionella pneumophila ORF2*

*L2* WT (SEQ ID NO:107)
ATGATGTCTATGAAAGGAATCATATTCAACGAATTTCTCAATTTTGTAGAAAAAAGTGAATCC
TACACCCTGGTAGATCAAATTATTATGGATAGTCATTTGAAGTCCCATGGTGCCTACACGTCT
ATCGGTACATACTCTCCCAAAGAATTATTTCAATTGGTTAAAGCGCTTGCTATGAAAAATGGC
AAACCAACATCAGTGATTTTACAAGAATATGGTGAGTATTTGTTTGAGGTTTTTGCAAAAAAA
TATCCTCAATTTTTTCAGGGAAAAAAAGTCGGTGTTTCAATTTTTGGAAGCGCTTGAAACACAT
ATTCATTTCGAAGTGAAAAAATTGTATGACTATACTGAACTACCCCATTTTGAATGCCAATAT
CACAGTCAAAATCAAATGGAAATGATTTACACTTCTTCGCGTCCTTTGGCCGATTTTGCGGAA
GGTTTAATAAAAGGTTGTATTAAATATCATAAAGAAAACATGACTATTGTTCGTGAAAATCTG
CCTGCAAAAACAGGCTTTAAGGTAAGATTTGTATTAACAAAAGGCGATCCTGATGAGTGA (SEQ ID NO:108)
MMSMKGIIFNEFLNFVEKSESYTLVDQIIMDSHLKSHGAYTSIGTYSPKELFQLVKALAMKNGKPT
SVILQEYGEYLFEVFAKKYPQFFREKKSVFQFLEALETHIHFEVKKLYDYTELPHFECQYHSQNQM
EMIYTSSRPLADFAEGLIKGCIKYHKENMTIVRENLPAKTGFKVRFVLTKGDPDE

*L2* F142Y (SEQ ID NO:109)
ATGATGTCTATGAAAGGAATCATATTCAACGAATTTCTCAATTTTGTAGAAAAAAGTGAATCC
TACACCCTGGTAGATCAAATTATTATGGATAGTCATTTGAAGTCCCATGGTGCCTACACGTCT
ATCGGTACATACTCTCCCAAAGAATTATTTCAATTGGTTAAAGCGCTTGCTATGAAAAATGGC
AAACCAACATCAGTGATTTTACAAGAATATGGTGAGTATTTGTTTGAGGTTTTTGCAAAAAAA
TATCCTCAATTTTTTCAGGGAAAAAAAGTCGGTGTTTCAATTTTTGGAAGCGCTTGAAACACAT
ATTCATTTCGAAGTGAAAAAATTGTATGACTATACTGAACTACCCCATTTTGAATGCCAATAT
CACAGTCAAAATCAAATGGAAATGATTTACACTTCTTCGCGTCCTTTGGCCGATTATGCGGAA
GGTTTAATAAAAGGTTGTATTAAATATCATAAAGAAAACATGACTATTGTTCGTGAAAATCTG
CCTGCAAAAACAGGCTTTAAGGTAAGATTTGTATTAACAAAAGGCGATCCTGATGAGTGA (SEQ ID NO:110)
MMSMKGIIFNEFLNFVEKSESYTLVDQIIMDSHLKSHGAYTSIGTYSPKELFQLVKALAMKNGKPT
SVILQEYGEYLFEVFAKKYPQFFREKKSVFQFLEALETHIHFEVKKLYDYTELPHFECQYHSQNQM
EMIYTSSRPLADYAEGLIKGCIKYHKENMTIVRENLPAKTGFKVRFVLTKGDPDE

(SEQ ID NO:111)
ATGATGTCTATGAAAGGAATCATATGGAACGAATTTCTCAATTTTGTAGAAAAAAGTGAATCC
TACACCCTGGTAGATCAAATTATTATGGATAGTCATTTGAAGTCCCATGGTGCCTACACGTCT
ATCGGTACATACTCTCCCAAAGAATTATTTCAATTGGTTAAAGCGCTTGCTATGAAAAATGGC
AAACCAACATCAGTGATTTTACAAGAATATGGTGAGTATTTGTTTGAGGTTTTTGCAAAAAAA
TATCCTCAATTTTTCAGGGAAAAAAAGTCGGTGTTTCAATTTTTGGAAGCGCTTGAAACACAT
ATTCATTTCGAAGTGAAAAAATTGTATGACTATACTGAACTACCCCATTTTGAATGCCAATAT
CACAGTCAAAATCAAATGGAAATGATTTACACTTCTTCGCGTCCTTTGGCCGATTATGCGGAA
GGTTTAATAAAAGGTTGTATTAAATATCATAAAGAAAACATGACTATTGTTCGTGAAAATCTG
CCTGCAAAAACAGGCTTTAAGGTAAGATTTGTATTAACAAAAGGCGATCCTGATGAGTGA (SEQ ID NO:112)
MMSMKGIIWNEFLNFVEKSESYTLVDQIIMDSHLKSHGAYTSIGTYSPKELFQLVKALAMKNGKP
TSVILQEYGEYLFEVFAKKYPQFFREKKSVFQFLEALETHIHFEVKKLYDYTELPHFECQYHSQNQ
MEMIYTSSRPLADYAEGLIKGCIKYHKENMTIVRENLPAKTGFKVRFVLTKGDPDE

*Legionella pneumophila ORF1*

***L1* WT**

(SEQ ID NO:113)
ATGAAAGGTATCGTTTTTACCTCCTTAAATGACATGATTATAGAACAATTTGGCATAGAAACC
TGGGACCAACTCGTATCCTCACTAGACCTTCCAAGTGGTGGAAGTTATACAGCAGGCGGCACT
TACTCGGATACAGAATTTCAGCAATTGATTAAGGCCATTGCGAAGAGGACCAATCAGCACGCT
TCTGTTTTTTTAGAGGCCTTTGGTGAATACATGTTTCCTATCTTATCGAGTAAGTGCGCAATTTT
TTTAAAAAAGGACATGACATTAAAAGAATTTTTAAAAAGCATTGATGGAACAATTCATGTGG
AAGTAGAAAAGTTATACCCAGATGAAACATTACCTACCATTAGCTATGAAGAGCCTGCTGCA
AACCAATTGGTTATGGTGTATCGATCGCATAGAAGACTCTGTCATTTTGCAATGGGGCTCATC
CAGGGAGCAGCGCAACATTTTAAAAAGAAAATTACCATTAAGCAGACTCACTGCATGTTAAA
AAAAGATGATCATTGTCGTTTGGAGATTACCTTTGAGTGA (SEQ ID NO:114)
MKGIVFTSLNDMIIEQFGIETWDQLVSSLDLPSGGSYTAGGTYSDTEFQQLIKAIAKRTNQHASVFL
EAFGEYMFPILSSKCAIFLKKDMTLKEFLKSIDGTIHVEVEKLYPDETLPTISYEEPAANQLVMVYR
SHRRLCHFAMGLIQGAAQHFKKKITIKQTHCMLKKDDHCRLEITFE

Figure 8M

*Ll* F142Y (SEQ ID NO:115)
ATGAAAGGTATCGTTTTTACCTCCTTAAATGACATGATTATAGAACAATTTGGCATAGAAACC
TGGGACCAACTCGTATCCTCACTAGACCTTCCAAGTGGTGGAAGTTATACAGCAGGCGGCACT
TACTCGGATACAGAATTTCAGCAATTGATTAAGGCCATTGCGAAGAGGACCAATCAGCACGCT
TCTGTTTTTTAGAGGCCTTTGGTGAATACATGTTTCCTATCTTATCGAGTAAGTGCGCAATTTT
TTTAAAAAAGGACATGACATTAAAAGAATTTTTAAAAAGCATTGATGGAACAATTCATGTGG
AAGTAGAAAAGTTATACCCAGATGAAACATTACCTACCATTAGCTATGAAGAGCCTGCTGCA
AACCAATTGGTTATGGTGTATCGATCGCATAGAAGACTCTGTCATTACGCAATGGGGCTCATC
CAGGGAGCAGCGCAACATTTTAAAAAGAAAATTACCATTAAGCAGACTCACTGCATGTTAAA
AAAAGATGATCATTGTCGTTTGGAGATTACCTTTGAGTGA (SEQ ID NO:116)
MKGIVFTSLNDMIIEQFGIETWDQLVSSLDLPSGGSYTAGGTYSDTEFQQLIKAIAKRTNQHASVFL
EAFGEYMFPILSSKCAIFLKKDMTLKEFLKSIDGTIHVEVEKLYPDETLPTISYEEPAANQLVMVYR
SHRRLCHYAMGLIQGAAQHFKKKITIKQTHCMLKKDDHCRLEITFE

*Desulfovibrio desulfuricans*

*Dd* H-NOX(728-899)

(SEQ ID NO:117)
ATGAAGATGCGCGGTATTTTGCCGAAAATATTTATGAATTTTATAAAAGAGATCTATGGGGAT
GACGTGTTTGCTCATGTTTCTAAAACCATGGGCGAGCCTGTCTTCATGCCGGGAAATTCCTACC
CTGATCAGGTGTTGCGCCAGATGGCTGAAATAGTATGCCAGCGCACGGGCGAACAGCCCAAG
TTGTTTTTTGAAAAAGCAGGGCGTGCAAGCCTGCAGGCTTTTAACAGAATGTACAGGCAGTAC
TTTAAAGGGGAAACCCTTAAAGAGTTTCTGCTGGCCATGAATGATATCCACAGGCACCTGACA
AAGGACAATCCCGGCGTACGCCCGCCTAAATTTGAGTATGACGATCAGGGCGATACGCTTGTT
ATGACATATAAGTCGCAGAGGGATTACGGAGAATACTTTGTGGGCATCATCAAGGCAGCTGC
GGAGTTTAAAAAGGAAAAGTGCGTATCAGCTCGGAGCATGCCGGTAAGGGGCGAACAACG
GCAAGGGTTACATTTATTAAATGA (SEQ ID NO:118)
MKMRGILPKIFMNFIKEIYGDDVFAHVSKTMGEPVFMPGNSYPDQVLRQMAEIVCQRTGEQPKLF
FEKAGRASLQAFNRMYRQYFKGETLKEFLLAMNDIHRHLTKDNPGVRPPKFEYDDQGDTLVMTY
KSQRDYGEYFVGIIKAAAEFKKEKVRISSEHAGKGRTTARVTFIK

***Dd.* Y139L (728-899)**

(SEQ ID NO:119)
ATGAAGATGCGCGGTATTTTGCCGAAAATATTTATGAATTTTATAAAAGAGATCTATGGGGAT
GACGTGTTTGCTCATGTTTCTAAAACCATGGGCGAGCCTGTCTTCATGCCGGGAAATTCCTACC
CTGATCAGGTGTTGCGCCAGATGGCTGAAATAGTATGCCAGCGCACGGGCGAACAGCCCAAG
TTGTTTTTTGAAAAAGCAGGGCGTGCAAGCCTGCAGGCTTTTAACAGAATGTACAGGCAGTAC
TTTAAAGGGGAAACCCTTAAAGAGTTTCTGCTGGCCATGAATGATATCCACAGGCACCTGACA
AAGGACAATCCCGGCGTACGCCCGCCTAAATTTGAGTATGACGATCAGGGCGATACGCTTGTT
ATGACATATAAGTCGCAGAGGGATTACGGAGAACTTTTTGTGGGCATCATCAAGGCAGCTGC
GGAGTTTAAAAAGGAAAAAGTGCGTATCAGCTCGGAGCATGCCGGTAAGGGGCGAACAACG
GCAAGGGTTACATTTATTAAATGA (SEQ ID NO:120)
MKMRGILPKIFMNFIKEIYGDDVFAHVSKTMGEPVFMPGNSYPDQVLRQMAEIVCQRTGEQPKLF
FEKAGRASLQAFNRMYRQYFKGETLKEFLLAMNDIHRHLTKDNPGVRPPKFEYDDQGDTLVMTY
KSQRDYGELFVGIIKAAAEFKKEKVRISSEHAGKGRTTARVTFIK

*Homo sapiens* β1(1-385)

***Hs.* WT (1-385)**

(SEQ ID NO:121)
ATGTACGGATTTGTGAATCACGCCCTGGAGTTGCTGGTGATCCGCAATTACGGCCCCGAGGTG
TGGGAAGACATCAAAAAAGAGGCACAGTTAGATGAAGAAGGACAGTTTCTTGTCAGAATAAT
ATATGATGACTCCAAAACTTATGATTTGGTTGCTGCTGCAAGCAAAGTCCTCAATCTCAATGC
TGGAGAAATCCTCCAAATGTTTGGGAAGATGTTTTTCGTCTTTTGCCAAGAATCTGGTTATGAT
ACAATCTTGCGTGTCCTGGGCTCTAATGTCAGAGAATTTCTACAGAACCTTGATGCTCTGCAC
GACCACCTTGCTACCATCTACCCAGGAATGCGTGCACCTTCCTTTAGGTGCACTGATGCAGAA
AAGGGCAAAGGACTCATTTTGCACTACTACTCAGAGAGAGAAGGACTTCAGGATATTGTCATT
GGAATCATCAAAACAGTGGCACAACAAATCCATGGCACTGAAATAGACATGAAGGTTATTCA
GCAAAGAAATGAAGAATGTGATCATACTCAATTTTTAATTGAAGAAAAAGAGTCAAAAGAAG
AGGATTTTTATGAAGATCTTGACAGATTTGAAGAAAATGGTACCCAGGAATCACGCATCAGCC
CATATACATTCTGCAAAGCTTTTCCTTTTCATATAATATTTGACCGGGACCTAGTGGTCACTCA
GTGTGGCAATGCTATATACAGAGTTCTCCCCCAGCTCCAGCCTGGGAATTGCAGCCTTCTGTCT
GTCTTCTCGCTGGTTCGTCCTCATATTGATATTAGTTTCCATGGGATCCTTTCTCACATCAATAC
TGTTTTTGTATTGAGAAGCAAGGAAGGATTGTTGGATGTGGAGAAATTAGAATGTGAGGATG
AACTGACTGGGACTGAGATCAGCTGCTTACGTCTCAAGGGTCAAATGATCTACTTACCTGAAG
CAGATAGCATACTTTTTCTATGTTCACCAAGTGTCATGAACCTGGACGATTTGACAAGGAGAG
GGCTGTATCTAAGTGACATCCCTCTGCATGATGCCACGCGCGATCTTGTTCTTTTGGGAGAAC
AATTTAGAGAGGAATACAAACTCACCCAAGAACTGGAAATCCTCACTGACAGGCTACAGCTC
ACGTTAAGAGCCCTGGAAGATTGA (SEQ ID NO:122)
MYGFVNHALELLVIRNYGPEVWEDIKKEAQLDEEGQFLVRIIYDDSKTYDLVAAASKVLNLNAGE
ILQMFGKMFFVFCQESGYDTILRVLGSNVREFLQNLDALHDHLATIYPGMRAPSFRCTDAEKGKG
LILHYYSEREGLQDIVIGIIKTVAQQIHGTEIDMKVIQQRNEECDHTQFLIEEKESKEEDFYEDLDRF
EENGTQESRISPYTFCKAFPFHIIFDRDLVVTQCGNAIYRVLPQLQPGNCSLLSVFSLVRPHIDISFHG
ILSHINTVFVLRSKEGLLDVEKLECEDELTGTEISCLRLKGQMIYLPEADSILFLCSPSVMNLDDLTR
RGLYLSDIPLHDATRDLVLLGEQFREEYKLTQELEILTDRLQLTLRALED

(SEQ ID NO:123)
ATGTACGGATTTGTGAATCACGCCCTGGAGTTGCTGGTGATCCGCAATTACGGCCCCGAGGTG
TGGGAAGACATCAAAAAAGAGGCACAGTTAGATGAAGAAGGACAGTTTCTTGTCAGAATAAT
ATATGATGACTCCAAAACTTATGATTTGGTTGCTGCTGCAAGCAAAGTCCTCAATCTCAATGC
TGGAGAAATCCTCCAAATGTTTGGGAAGATGTTTTTCGTCTTTTGCCAAGAATCTGGTTATGAT
ACAATCTTGCGTGTCCTGGGCTCTAATGTCAGAGAATTTCTACAGAACCTTGATGCTCTGCAC
GACCACCTTGCTACCATCTACCCAGGAATGCGTGCACCTTCCTTTAGGTGCACTGATGCAGAA
AAGGGCAAAGGACTCATTTTGCACTACTACTCAGAGAGAGAAGGACTTCAGGATTATGTCATT
GGAATCATCAAAACAGTGGCACAACAAATCCATGGCACTGAAATAGACATGAAGGTTATTCA
GCAAAGAAATGAAGAATGTGATCATACTCAATTTTTAATTGAAGAAAAAGAGTCAAAAGAAG
AGGATTTTTATGAAGATCTTGACAGATTTGAAGAAAATGGTACCCAGGAATCACGCATCAGCC
CATATACATTCTGCAAAGCTTTTCCTTTTCATATAATATTTGACCGGGACCTAGTGGTCACTCA
GTGTGGCAATGCTATATACAGAGTTCTCCCCCAGCTCCAGCCTGGGAATTGCAGCCTTCTGTCT
GTCTTCTCGCTGGTTCGTCCTCATATTGATATTAGTTTCCATGGGATCCTTTCTCACATCAATAC
TGTTTTTGTATTGAGAAGCAAGGAAGGATTGTTGGATGTGGAGAAATTAGAATGTGAGGATG
AACTGACTGGGACTGAGATCAGCTGCTTACGTCTCAAGGGTCAAATGATCTACTTACCTGAAG
CAGATAGCATACTTTTTCTATGTTCACCAAGTGTCATGAACCTGGACGATTTGACAAGGAGAG
GGCTGTATCTAAGTGACATCCCTCTGCATGATGCCACGCGCGATCTTGTTCTTTTGGGAGAAC
AATTTAGAGAGGAATACAAACTCACCCAAGAACTGGAAATCCTCACTGACAGGCTACAGCTC
ACGTTAAGAGCCCTGGAAGATTGA (SEQ ID NO:124)
MYGFVNHALELLVIRNYGPEVWEDIKKEAQLDEEGQFLVRIIYDDSKTYDLVAAASKVLNLNAGE
ILQMFGKMFFVFCQESGYDTILRVLGSNVREFLQNLDALHDHLATIYPGMRAPSFRCTDAEKGKG
LILHYYSEREGLQDYVIGIIKTVAQQIHGTEIDMKVIQQRNEECDHTQFLIEEKESKEEDFYEDLDRF
EENGTQESRISPYTFCKAFPFHIIFDRDLVVTQCGNAIYRVLPQLQPGNCSLLSVFSLVRPHIDISFHG
ILSHINTVFVLRSKEGLLDVEKLECEDELTGTEISCLRLKGQMIYLPEADSILFLCSPSVMNLDDLTR
RGLYLSDIPLHDATRDLVLLGEQFREEYKLTQELEILTDRLQLTLRALED

(SEQ ID NO:125)
ATGTACGGATTTGTGAATCACGCCCTGGAGTTGCTGGTGATCCGCAATTACGGCCCCGAGGTG
TGGGAAGACATCAAAAAAGAGGCACAGTTAGATGAAGAAGGACAGTTTCTTGTCAGAATAAT
ATATGATGACTCCAAAACTTATGATTTGGTTGCTGCTGCAAGCAAAGTCCTCAATCTCAATGC
TGGAGAAATCCTCCAAATGTTTGGGAAGATGTTTTTCGTCTTTTGCCAAGAATCTGGTTATGAT
ACAATCTTGCGTGTCCTGGGCTCTAATGTCAGAGAATTTCTACAGAACCTTGATGCTCTGCAC
GACCACCTTGCTACCATCTACCCAGGAATGCGTGCACCTTCCTTTAGGTGCACTGATGCAGAA
AAGGGCAAAGGACTCATTTTGCACTACTACTCAGAGAGAGAAGGACTTCAGGATCATGTCATT
GGAATCATCAAAACAGTGGCACAACAAATCCATGGCACTGAAATAGACATGAAGGTTATTCA
GCAAAGAAATGAAGAATGTGATCATACTCAATTTTTAATTGAAGAAAAAGAGTCAAAAGAAG
AGGATTTTTATGAAGATCTTGACAGATTTGAAGAAAATGGTACCCAGGAATCACGCATCAGCC
CATATACATTCTGCAAAGCTTTTCCTTTTCATATAATATTTGACCGGGACCTAGTGGTCACTCA
GTGTGGCAATGCTATATACAGAGTTCTCCCCCAGCTCCAGCCTGGGAATTGCAGCCTTCTGTCT
GTCTTCTCGCTGGTTCGTCCTCATATTGATATTAGTTTCCATGGGATCCTTTCTCACATCAATAC
TGTTTTTGTATTGAGAAGCAAGGAAGGATTGTTGGATGTGGAGAAATTAGAATGTGAGGATG
AACTGACTGGGACTGAGATCAGCTGCTTACGTCTCAAGGGTCAAATGATCTACTTACCTGAAG
CAGATAGCATACTTTTTCTATGTTCACCAAGTGTCATGAACCTGGACGATTTGACAAGGAGAG
GGCTGTATCTAAGTGACATCCCTCTGCATGATGCCACGCGCGATCTTGTTCTTTTGGGAGAAC
AATTTAGAGAGGAATACAAACTCACCCAAGAACTGGAAATCCTCACTGACAGGCTACAGCTC
ACGTTAAGAGCCCTGGAAGATTGA (SEQ ID NO:126)
MYGFVNHALELLVIRNYGPEVWEDIKKEAQLDEEGQFLVRIIYDDSKTYDLVAAASKVLNLNAGE
ILQMFGKMFFVFCQESGYDTILRVLGSNVREFLQNLDALHDHLATIYPGMRAPSFRCTDAEKGKG
LILHYYSEREGLQDHVIGIIKTVAQQIHGTEIDMKVIQQRNEECDHTQFLIEEKESKEEDFYEDLDRF
EENGTQESRISPYTFCKAFPFHIIFDRDLVVTQCGNAIYRVLPQLQPGNCSLLSVFSLVRPHIDISFHG
ILSHINTVFVLRSKEGLLDVEKLECEDELTGTEISCLRLKGQMIYLPEADSILFLCSPSVMNLDDLTR
RGLYLSDIPLHDATRDLVLLGEQFREEYKLTQELEILTDRLQLTLRALED

(SEQ ID NO:127)
ATGTACGGATTTGTGAATCACGCCCTGGAGTTGCTGGTGATCCGCAATTACGGCCCCGAGGTG
TGGGAAGACATCAAAAAAGAGGCACAGTTAGATGAAGAAGGACAGTTTCTTGTCAGAATAAT
ATATGATGACTCCAAAACTTATGATTTGGTTGCTGCTGCAAGCAAAGTCCTCAATCTCAATGC
TGGAGAAATCCTCCAAATGTTTGGGAAGATGTTTTTCGTCTTTTACCAAGAATCTGGTTATGAT
ACAATCTTGCGTGTCCTGGGCTCTAATGTCAGAGAATTTCTACAGAACCTTGATGCTCTGCAC
GACCACCTTGCTACCATCTACCCAGGAATGCGTGCACCTTCCTTTAGGTGCACTGATGCAGAA
AAGGGCAAAGGACTCATTTTGCACTACTACTCAGAGAGAGAAGGACTTCAGGATATTGTCATT
GGAATCATCAAAACAGTGGCACAACAAATCCATGGCACTGAAATAGACATGAAGGTTATTCA
GCAAAGAAATGAAGAATGTGATCATACTCAATTTTTAATTGAAGAAAAAGAGTCAAAAGAAG
AGGATTTTTATGAAGATCTTGACAGATTTGAAGAAAATGGTACCCAGGAATCACGCATCAGCC
CATATACATTCTGCAAAGCTTTTCCTTTTCATATAATATTTGACCGGGACCTAGTGGTCACTCA
GTGTGGCAATGCTATATACAGAGTTCTCCCCCAGCTCCAGCCTGGGAATTGCAGCCTTCTGTCT
GTCTTCTCGCTGGTTCGTCCTCATATTGATATTAGTTTCCATGGGATCCTTTCTCACATCAATAC
TGTTTTTGTATTGAGAAGCAAGGAAGGATTGTTGGATGTGGAGAAATTAGAATGTGAGGATG
AACTGACTGGGACTGAGATCAGCTGCTTACGTCTCAAGGGTCAAATGATCTACTTACCTGAAG
CAGATAGCATACTTTTTCTATGTTCACCAAGTGTCATGAACCTGGACGATTTGACAAGGAGAG
GGCTGTATCTAAGTGACATCCCTCTGCATGATGCCACGCGCGATCTTGTTCTTTTGGGAGAAC
AATTTAGAGAGGAATACAAACTCACCCAAGAACTGGAAATCCTCACTGACAGGCTACAGCTC
ACGTTAAGAGCCCTGGAAGATTGA (SEQ ID NO:128)
MYGFVNHALELLVIRNYGPEVWEDIKKEAQLDEEGQFLVRIIYDDSKTYDLVAAASKVLNLNAGE
ILQMFGKMFFVFYQESGYDTILRVLGSNVREFLQNLDALHDHLATIYPGMRAPSFRCTDAEKGKG
LILHYYSEREGLQDIVIGIIKTVAQQIHGTEIDMKVIQQRNEECDHTQFLIEEKESKEEDFYEDLDRF
EENGTQESRISPYTFCKAFPFHIIFDRDLVVTQCGNAIYRVLPQLQPGNCSLLSVFSLVRPHIDISFHG
ILSHINTVFVLRSKEGLLDVEKLECEDELTGTEISCLRLKGQMIYLPEADSILFLCSPSVMNLDDLTR
RGLYLSDIPLHDATRDLVLLGEQFREEYKLTQELEILTDRLQLTLRALED

(SEQ ID NO:129)
ATGTACGGATTTGTGAATCACGCCCTGGAGTTGCTGGTGATCCGCAATTACGGCCCCGAGGTG
TGGGAAGACATCAAAAAAGAGGCACAGTTAGATGAAGAAGGACAGTTTCTTGTCAGAATAAT
ATATGATGACTCCAAAACTTATGATTTGGTTGCTGCTGCAAGCAAAGTCCTCAATCTCAATGC
TGGAGAAATCCTCCAAATGTTTGGGAAGATGTTTTTCGTCTTTTGCCAAGAATCTGGTTATGAT
ACAATCTTGCGTGTCCTGGGCTCTAATGTCAGAGAATTTCTACAGAACCTTGATGCTCTGTTCG
ACCACCTTGCTACCATCTACCCAGGAATGCGTGCACCTTCCTTTAGGTGCACTGATGCAGAAA
AGGGCAAAGGACTCATTTTGCACTACTACTCAGAGAGAGAAGGACTTCAGGATATTGTCATTG
GAATCATCAAAACAGTGGCACAACAAATCCATGGCACTGAAATAGACATGAAGGTTATTCAG
CAAAGAAATGAAGAATGTGATCATACTCAATTTTTAATTGAAGAAAAAGAGTCAAAAGAAGA
GGATTTTTATGAAGATCTTGACAGATTTGAAGAAAATGGTACCCAGGAATCACGCATCAGCCC
ATATACATTCTGCAAAGCTTTTCCTTTTCATATAATATTTGACCGGGACCTAGTGGTCACTCAG
TGTGGCAATGCTATATACAGAGTTCTCCCCCAGCTCCAGCCTGGGAATTGCAGCCTTCTGTCTG
TCTTCTCGCTGGTTCGTCCTCATATTGATATTAGTTTCCATGGGATCCTTTCTCACATCAATACT
GTTTTTGTATTGAGAAGCAAGGAAGGATTGTTGGATGTGGAGAAATTAGAATGTGAGGATGA
ACTGACTGGGACTGAGATCAGCTGCTTACGTCTCAAGGGTCAAATGATCTACTTACCTGAAGC
AGATAGCATACTTTTTCTATGTTCACCAAGTGTCATGAACCTGGACGATTTGACAAGGAGAGG
GCTGTATCTAAGTGACATCCCTCTGCATGATGCCACGCGCGATCTTGTTCTTTTGGGAGAACA
ATTTAGAGAGGAATACAAACTCACCCAAGAACTGGAAATCCTCACTGACAGGCTACAGCTCA
CGTTAAGAGCCCTGGAAGATTGA (SEQ ID NO:130)
MYGFVNHALELLVIRNYGPEVWEDIKKEAQLDEEGQFLVRIIYDDSKTYDLVAAASKVLNLNAGE
ILQMFGKMFFVFCQESGYDTILRVLGSNVREFLQNLDALFDHLATIYPGMRAPSFRCTDAEKGKGL
ILHYYSEREGLQDIVIGIIKTVAQQIHGTEIDMKVIQQRNEECDHTQFLIEEKESKEEDFYEDLDRFE
ENGTQESRISPYTFCKAFPFHIIFDRDLVVTQCGNAIYRVLPQLQPGNCSLLSVFSLVRPHIDISFHGI
LSHINTVFVLRSKEGLLDVEKLECEDELTGTEISCLRLKGQMIYLPEADSILFLCSPSVMNLDDLTRR
GLYLSDIPLHDATRDLVLLGEQFREEYKLTQELEILTDRLQLTLRALED

(SEQ ID NO:131)
ATGTACGGATTTGTGAATCACGCCCTGGAGTTGCTGGTGATCCGCAATTACGGCCCCGAGGTG
TGGGAAGACATCAAAAAAGAGGCACAGTTAGATGAAGAAGGACAGTTTCTTGTCAGAATAAT
ATATGATGACTCCAAAACTTATGATTTGGTTGCTGCTGCAAGCAAAGTCCTCAATCTCAATGC
TGGAGAAATCCTCCAAATGTTTGGGAAGATGTTTTTCGTCTTTTGCCAAGAATCTGGTTATGAT
ACAATCTTGCGTGTCCTGGGCTCTAATGTCAGAGAATTTCTACAGAACCTTGATGCTCTGGGT
GACCACCTTGCTACCATCTACCCAGGAATGCGTGCACCTTCCTTTAGGTGCACTGATGCAGAA
AAGGGCAAAGGACTCATTTTGCACTACTACTCAGAGAGAGAAGGACTTCAGGATATTGTCATT
GGAATCATCAAAACAGTGGCACAACAAATCCATGGCACTGAAATAGACATGAAGGTTATTCA
GCAAAGAAATGAAGAATGTGATCATACTCAATTTTTAATTGAAGAAAAAGAGTCAAAAGAAG
AGGATTTTTATGAAGATCTTGACAGATTTGAAGAAAATGGTACCCAGGAATCACGCATCAGCC
CATATACATTCTGCAAAGCTTTTCCTTTTCATATAATATTTGACCGGGACCTAGTGGTCACTCA
GTGTGGCAATGCTATATACAGAGTTCTCCCCCAGCTCCAGCCTGGGAATTGCAGCCTTCTGTCT
GTCTTCTCGCTGGTTCGTCCTCATATTGATATTAGTTTCCATGGGATCCTTTCTCACATCAATAC
TGTTTTTGTATTGAGAAGCAAGGAAGGATTGTTGGATGTGGAGAAATTAGAATGTGAGGATG
AACTGACTGGGACTGAGATCAGCTGCTTACGTCTCAAGGGTCAAATGATCTACTTACCTGAAG
CAGATAGCATACTTTTTCTATGTTCACCAAGTGTCATGAACCTGGACGATTTGACAAGGAGAG
GGCTGTATCTAAGTGACATCCCTCTGCATGATGCCACGCGCGATCTTGTTCTTTTGGGAGAAC
AATTTAGAGAGGAATACAAACTCACCCAAGAACTGGAAATCCTCACTGACAGGCTACAGCTC
ACGTTAAGAGCCCTGGAAGATTGA (SEQ ID NO:132)
MYGFVNHALELLVIRNYGPEVWEDIKKEAQLDEEGQFLVRIIYDDSKTYDLVAAASKVLNLNAGE
ILQMFGKMFFVFCQESGYDTILRVLGSNVREFLQNLDALGDHLATIYPGMRAPSFRCTDAEKGKG
LILHYYSEREGLQDIVIGIIKTVAQQIHGTEIDMKVIQQRNEECDHTQFLIEEKESKEEDFYEDLDRF
EENGTQESRISPYTFCKAFPFHIIFDRDLVVTQCGNAIYRVLPQLQPGNCSLLSVFSLVRPHIDISFHG
ILSHINTVFVLRSKEGLLDVEKLECEDELTGTEISCLRLKGQMIYLPEADSILFLCSPSVMNLDDLTR
RGLYLSDIPLHDATRDLVLLGEQFREEYKLTQELEILTDRLQLTLRALED

***Hs.* β1(1-194)**

(SEQ ID NO:133)
ATGTACGGATTTGTGAATCACGCCCTGGAGTTGCTGGTGATCCGCAATTACGGCCCCGAGGTG
TGGGAAGACATCAAAAAAGAGGCACAGTTAGATGAAGAAGGACAGTTTCTTGTCAGAATAAT
ATATGATGACTCCAAAACTTATGATTTGGTTGCTGCTGCAAGCAAAGTCCTCAATCTCAATGC
TGGAGAAATCCTCCAAATGTTTGGGAAGATGTTTTTCGTCTTTTGCCAAGAATCTGGTTATGAT
ACAATCTTGCGTGTCCTGGGCTCTAATGTCAGAGAATTTCTACAGAACCTTGATGCTCTGCAC
GACCACCTTGCTACCATCTACCCAGGAATGCGTGCACCTTCCTTTAGGTGCACTGATGCAGAA
AAGGGCAAAGGACTCATTTTGCACTACTACTCAGAGAGAGAAGGACTTCAGGATATTGTCATT
GGAATCATCAAAACAGTGGCACAACAAATCCATGGCACTGAAATAGACATGAAGGTTATTCA
GCAAAGAAATGAAGAATGTGATCATACTCAATTTTTAATTGAAGAAAAAGAGTCAAAAGAAG
AGGATTTTTATGAAGATTGA (SEQ ID NO:134)
MYGFVNHALELLVIRNYGPEVWEDIKKEAQLDEEGQFLVRIIYDDSKTYDLVAAASKVLNLNAGE
ILQMFGKMFFVFCQESGYDTILRVLGSNVREFLQNLDALHDHLATIYPGMRAPSFRCTDAEKGKG
LILHYYSEREGLQDIVIGIIKTVAQQIHGTEIDMKVIQQRNEECDHTQFLIEEKESKEEDFYED

(SEQ ID NO:135)
ATGTACGGATTTGTGAATCACGCCCTGGAGTTGCTGGTGATCCGCAATTACGGCCCCGAGGTG
TGGGAAGACATCAAAAAAGAGGCACAGTTAGATGAAGAAGGACAGTTTCTTGTCAGAATAAT
ATATGATGACTCCAAAACTTATGATTTGGTTGCTGCTGCAAGCAAAGTCCTCAATCTCAATGC
TGGAGAAATCCTCCAAATGTTTGGGAAGATGTTTTTCGTCTTTTGCCAAGAATCTGGTTATGAT
ACAATCTTGCGTGTCCTGGGCTCTAATGTCAGAGAATTTCTACAGAACCTTGATGCTCTGCAC
GACCACCTTGCTACCATCTACCCAGGAATGCGTGCACCTTCCTTTAGGTGCACTGATGCAGAA
AAGGGCAAAGGACTCATTTTGCACTACTACTCAGAGAGAGAAGGACTTCAGGATTATGTCATT
GGAATCATCAAAACAGTGGCACAACAAATCCATGGCACTGAAATAGACATGAAGGTTATTCA
GCAAAGAAATGAAGAATGTGATCATACTCAATTTTTAATTGAAGAAAAAGAGTCAAAAGAAG
AGGATTTTTATGAAGATTGA (SEQ ID NO:136)
MYGFVNHALELLVIRNYGPEVWEDIKKEAQLDEEGQFLVRIIYDDSKTYDLVAAASKVLNLNAGE
ILQMFGKMFFVFCQESGYDTILRVLGSNVREFLQNLDALHDHLATIYPGMRAPSFRCTDAEKGKG
LILHYYSEREGLQDYVIGIIKTVAQQIHGTEIDMKVIQQRNEECDHTQFLIEEKESKEEDFYED

***Hs.* β1(1-194) L9W-I145Y**

(SEQ ID NO:137)
ATGTACGGATTTGTGAATCACGCCTGGGAGTTGCTGGTGATCCGCAATTACGGCCCCGAGGTG
TGGGAAGACATCAAAAAAGAGGCACAGTTAGATGAAGAAGGACAGTTTCTTGTCAGAATAAT
ATATGATGACTCCAAAACTTATGATTTGGTTGCTGCTGCAAGCAAAGTCCTCAATCTCAATGC
TGGAGAAATCCTCCAAATGTTTGGGAAGATGTTTTTCGTCTTTTGCCAAGAATCTGGTTATGAT
ACAATCTTGCGTGTCCTGGGCTCTAATGTCAGAGAATTTCTACAGAACCTTGATGCTCTGCAC
GACCACCTTGCTACCATCTACCCAGGAATGCGTGCACCTTCCTTTAGGTGCACTGATGCAGAA
AAGGGCAAAGGACTCATTTTGCACTACTACTCAGAGAGAGAAGGACTTCAGGATTATGTCATT
GGAATCATCAAAACAGTGGCACAACAAATCCATGGCACTGAAATAGACATGAAGGTTATTCA
GCAAAGAAATGAAGAATGTGATCATACTCAATTTTTAATTGAAGAAAAAGAGTCAAAAGAAG
AGGATTTTTATGAAGATTGA (SEQ ID NO:138)
MYGFVNHAWELLVIRNYGPEVWEDIKKEAQLDEEGQFLVRIIYDDSKTYDLVAAASKVLNLNAG
EILQMFGKMFFVFCQESGYDTILRVLGSNVREFLQNLDALHDHLATIYPGMRAPSFRCTDAEKGK
GLILHYYSEREGLQDYVIGIIKTVAQQIHGTEIDMKVIQQRNEECDHTQFLIEEKESKEEDFYED

Figure 8U

*Rattus norvegicus* β1(1-385)

***Rn.* WT (1-385)**

(SEQ ID NO:139)
ATGTACGGTTTTGTGAACCATGCCCTGGAGCTGCTGGTGATCCGCAATTACGGTCCCGAGGTG
TGGGAAGACATCAAAAAAGAGGCGCAGCTGGATGAAGAAGGCCAGTTTCTTGTGAGAATAAT
CTACGATGATTCCAAAACCTATGACTTGGTGGCTGCTGCGAGCAAAGTCCTCAACCTCAATGC
TGGTGAAATCCTGCAGATGTTTGGGAAGATGTTTTTCGTCTTCTGTCAAGAGTCTGGCTATGAT
ACCATCTTGCGTGTCCTGGGATCTAATGTCAGGGAGTTTTTGCAGAACCTCGACGCCCTGCAC
GACCACCTCGCCACCATCTACCCAGGGATGCGCGCACCTTCCTTCCGGTGCACCGATGCAGAA
AAAGGCAAAGGGCTCATTCTGCACTACTACTCGGAAAGAGAGGGGCTTCAGGACATTGTGAT
CGGGATTATCAAGACTGTAGCTCAACAGATCCATGGCACTGAGATAGACATGAAGGTTATTCA
GCAAAGAAGTGAAGAATGTGATCATACCCAATTTTTAATTGAAGAAAAAGAATCAAAAGAAG
AGGATTTTTATGAAGATCTGGACAGGTTTGAAGAGAACGGTACCCAGGACTCCCGTATCAGCC
CGTACACCTTCTGCAAAGCGTTTCCTTTTCACATCATATTTGACCGGGACCTAGTAGTCACGCA
GTGTGGAAATGCTATCTACAGAGTGCTCCCCCAGCTCCAGCCTGGGAAGTGCAGCCTTCTGTC
TGTCTTCTCTCTGGTCCGCCCTCATATTGACATCAGTTTCCACGGGATTCTTTCACACATCAAT
ACCGTCTTTGTACTGAGAAGCAAGGAAGGGTTGCTGGATGTTGAGAAACTTGAATGTGAGGA
TGAACTGACTGGGGCAGAGATTAGCTGCCTCCGTCTCAAAGGCCAAATGATCTATTTACCGGA
AGCAGATAGCATCCTCTTCCTCTGTTCACCAAGTGTGATGAACTTGGATGACCTAACAAGAAG
AGGCCTGTACCTGAGTGACATCCCTCTCCATGATGCTACACGAGACCTGGTCCTTTTGGGAGA
ACAGTTCCGGGAGGAGTACAAACTGACACAAGAGCTGGAAATCCTCACAGACAGGCTGCAGC
TCACACTGAGGGCTTTGGAGGATTGA (SEQ ID NO:140)
MYGFVNHALELLVIRNYGPEVWEDIKKEAQLDEEGQFLVRIIYDDSKTYDLVAAASKVLNLNAGE
ILQMFGKMFFVFCQESGYDTILRVLGSNVREFLQNLDALHDHLATIYPGMRAPSFRCTDAEKGKG
LILHYYSEREGLQDIVIGIIKTVAQQIHGTEIDMKVIQQRSEECDHTQFLIEEKESKEEDFYEDLDRFE
ENGTQDSRISPYTFCKAFPFHIIFDRDLVVTQCGNAIYRVLPQLQPGKCSLLSVFSLVRPHIDISFHGI
LSHINTVFVLRSKEGLLDVEKLECEDELTGAEISCLRLKGQMIYLPEADSILFLCSPSVMNLDDLTR
RGLYLSDIPLHDATRDLVLLGEQFREEYKLTQELEILTDRLQLTLRALED

Figure 8V

_Rn_ β1(1-385) I145Y (SEQ ID NO:141)
ATGTACGGTTTTGTGAACCATGCCCTGGAGCTGCTGGTGATCCGCAATTACGGTCCCGAGGTG
TGGGAAGACATCAAAAAAGAGGCGCAGCTGGATGAAGAAGGCCAGTTTCTTGTGAGAATAAT
CTACGATGATTCCAAAACCTATGACTTGGTGGCTGCTGCGAGCAAAGTCCTCAACCTCAATGC
TGGTGAAATCCTGCAGATGTTTGGGAAGATGTTTTTCGTCTTCTGTCAAGAGTCTGGCTATGAT
ACCATCTTGCGTGTCCTGGGATCTAATGTCAGGGAGTTTTTGCAGAACCTCGACGCCCTGCAC
GACCACCTCGCCACCATCTACCCAGGGATGCGCGCACCTTCCTTCCGGTGCACCGATGCAGAA
AAAGGCAAAGGGCTCATTCTGCACTACTACTCGGAAAGAGAGGGGCTTCAGGACTACGTGAT
CGGGATTATCAAGACTGTAGCTCAACAGATCCATGGCACTGAGATAGACATGAAGGTTATTCA
GCAAAGAAGTGAAGAATGTGATCATACCCAATTTTTAATTGAAGAAAAAGAATCAAAAGAAG
AGGATTTTTATGAAGATCTGGACAGGTTTGAAGAGAACGGTACCCAGGACTCCCGTATCAGCC
CGTACACCTTCTGCAAAGCGTTTCCTTTTCACATCATATTTGACCGGGACCTAGTAGTCACGCA
GTGTGGAAATGCTATCTACAGAGTGCTCCCCCAGCTCCAGCCTGGGAAGTGCAGCCTTCTGTC
TGTCTTCTCTCTGGTCCGGCCTCATATTGACATCAGTTTCCACGGGATTCTTTCACACATCAAT
ACCGTCTTTGTACTGAGAAGCAAGGAAGGGTTGCTGGATGTTGAGAAACTTGAATGTGAGGA
TGAACTGACTGGGGCAGAGATTAGCTGCCTCCGTCTCAAAGGCCAAATGATCTATTTACCGGA
AGCAGATAGCATCCTCTTCCTCTGTTCACCAAGTGTGATGAACTTGGATGACCTAACAAGAAG
AGGCCTGTACCTGAGTGACATCCCTCTCCATGATGCTACACGAGACCTGGTCCTTTTGGGAGA
ACAGTTCCGGGAGGAGTACAAACTGACACAAGAGCTGGAAATCCTCACAGACAGGCTGCAGC
TCACACTGAGGGCTTTGGAGGATTGA (SEQ ID NO:142)
MYGFVNHALELLVIRNYGPEVWEDIKKEAQLDEEGQFLVRIIYDDSKTYDLVAAASKVLNLNAGE
ILQMFGKMFFVFCQESGYDTILRVLGSNVREFLQNLDALHDHLATIYPGMRAPSFRCTDAEKGKG
LILHYYSEREGLQDYVIGIIKTVAQQIHGTEIDMKVIQQRSEECDHTQFLIEEKESKEEDFYEDLDRF
EENGTQDSRISPYTFCKAFPFHIIFDRDLVVTQCGNAIYRVLPQLQPGKCSLLSVFSLVRPHIDISFHG
ILSHINTVFVLRSKEGLLDVEKLECEDELTGAEISCLRLKGQMIYLPEADSILFLCSPSVMNLDDLTR
RGLYLSDIPLHDATRDLVLLGEQFREEYKLTQELEILTDRLQLTLRALED

Figure 8W

_Rn._ β1(1-385) I145H (SEQ ID NO:143)
ATGTACGGTTTTGTGAACCATGCCCTGGAGCTGCTGGTGATCCGCAATTACGGTCCCGAGGTG
TGGGAAGACATCAAAAAAGAGGCGCAGCTGGATGAAGAAGGCCAGTTTCTTGTGAGAATAAT
CTACGATGATTCCAAAACCTATGACTTGGTGGCTGCTGCGAGCAAAGTCCTCAACCTCAATGC
TGGTGAAATCCTGCAGATGTTTGGGAAGATGTTTTTCGTCTTCTGTCAAGAGTCTGGCTATGAT
ACCATCTTGCGTGTCCTGGGATCTAATGTCAGGGAGTTTTTGCAGAACCTCGACGCCCTGCAC
GACCACCTCGCCACCATCTACCCAGGGATGCGCGCACCTTCCTTCCGGTGCACCGATGCAGAA
AAAGGCAAAGGGCTCATTCTGCACTACTACTCGGAAAGAGAGGGGCTTCAGGACCATGTGAT
CGGGATTATCAAGACTGTAGCTCAACAGATCCATGGCACTGAGATAGACATGAAGGTTATTCA
GCAAAGAAGTGAAGAATGTGATCATACCCAATTTTTAATTGAAGAAAAAGAATCAAAAGAAG
AGGATTTTTATGAAGATCTGGACAGGTTTGAAGAGAACGGTACCCAGGACTCCCGTATCAGCC
CGTACACCTTCTGCAAAGCGTTTCCTTTTCACATCATATTTGACCGGGACCTAGTAGTCACGCA
GTGTGGAAATGCTATCTACAGAGTGCTCCCCCAGCTCCAGCCTGGGAAGTGCAGCCTTCTGTC
TGTCTTCTCTCTGGTCCGCCCTCATATTGACATCAGTTTCCACGGGATTCTTTCACACATCAAT
ACCGTCTTTGTACTGAGAAGCAAGGAAGGGTTGCTGGATGTTGAGAAACTTGAATGTGAGGA
TGAACTGACTGGGGCAGAGATTAGCTGCCTCCGTCTCAAAGGCCAAATGATCTATTTACCGGA
AGCAGATAGCATCCTCTTCCTCTGTTCACCAAGTGTGATGAACTTGGATGACCTAACAAGAAG
AGGCCTGTACCTGAGTGACATCCCTCTCCATGATGCTACACGAGACCTGGTCCTTTTGGGAGA
ACAGTTCCGGGAGGAGTACAAACTGACACAAGAGCTGGAAATCCTCACAGACAGGCTGCAGC
TCACACTGAGGGCTTTGGAGGATTGA (SEQ ID NO:144)
MYGFVNHALELLVIRNYGPEVWEDIKKEAQLDEEGQFLVRIIYDDSKTYDLVAAASKVLNLNAGE
ILQMFGKMFFVFCQESGYDTILRVLGSNVREFLQNLDALHDHLATIYPGMRAPSFRCTDAEKGKG
LILHYYSEREGLQDHVIGIIKTVAQQIHGTEIDMKVIQQRSEECDHTQFLIEEKESKEEDFYEDLDRF
EENGTQDSRISPYTFCKAFPFHIIFDRDLVVTQCGNAIYRVLPQLQPGKCSLLSVFSLVRPHIDISFHG
ILSHINTVFVLRSKEGLLDVEKLECEDELTGAEISCLRLKGQMIYLPEADSILFLCSPSVMNLDDLTR
RGLYLSDIPLHDATRDLVLLGEQFREEYKLTQELEILTDRLQLTLRALED

(SEQ ID NO:145)
ATGTACGGTTTTGTGAACCATGCCCTGGAGCTGCTGGTGATCCGCAATTACGGTCCCGAGGTG
TGGGAAGACATCAAAAAAGAGGCGCAGCTGGATGAAGAAGGCCAGTTTCTTGTGAGAATAAT
CTACGATGATTCCAAAACCTATGACTTGGTGGCTGCTGCGAGCAAAGTCCTCAACCTCAATGC
TGGTGAAATCCTGCAGATGTTTGGGAAGATGTTTTTCGTCTTCTATCAAGAGTCTGGCTATGAT
ACCATCTTGCGTGTCCTGGGATCTAATGTCAGGGAGTTTTTGCAGAACCTCGACGCCCTGCAC
GACCACCTCGCCACCATCTACCCAGGGATGCGCGCACCTTCCTTCCGGTGCACCGATGCAGAA
AAAGGCAAAGGGCTCATTCTGCACTACTACTCGGAAAGAGAGGGGCTTCAGGACATTGTGAT
CGGGATTATCAAGACTGTAGCTCAACAGATCCATGGCACTGAGATAGACATGAAGGTTATTCA
GCAAAGAAGTGAAGAATGTGATCATACCCAATTTTTAATTGAAGAAAAAGAATCAAAAGAAG
AGGATTTTTATGAAGATCTGGACAGGTTTGAAGAGAACGGTACCCAGGACTCCCGTATCAGCC
CGTACACCTTCTGCAAAGCGTTTCCTTTTCACATCATATTTGACCGGGACCTAGTAGTCACGCA
GTGTGGAAATGCTATCTACAGAGTGCTCCCCCAGCTCCAGCCTGGGAAGTGCAGCCTTCTGTC
TGTCTTCTCTCTGGTCCGCCCTCATATTGACATCAGTTTCCACGGGATTCTTTCACACATCAAT
ACCGTCTTTGTACTGAGAAGCAAGGAAGGGTTGCTGGATGTTGAGAAACTTGAATGTGAGGA
TGAACTGACTGGGGCAGAGATTAGCTGCCTCCGTCTCAAAGGCCAAATGATCTATTTACCGGA
AGCAGATAGCATCCTCTTCCTCTGTTCACCAAGTGTGATGAACTTGGATGACCTAACAAGAAG
AGGCCTGTACCTGAGTGACATCCCTCTCCATGATGCTACACGAGACCTGGTCCTTTTGGGAGA
ACAGTTCCGGGAGGAGTACAAACTGACACAAGAGCTGGAAATCCTCACAGACAGGCTGCAGC
TCACACTGAGGGCTTTGGAGGATTGA (SEQ ID NO:146)
MYGFVNHALELLVIRNYGPEVWEDIKKEAQLDEEGQFLVRIIYDDSKTYDLVAAASKVLNLNAGE
ILQMFGKMFFVFYQESGYDTILRVLGSNVREFLQNLDALHDHLATIYPGMRAPSFRCTDAEKGKG
LILHYYSEREGLQDIVIGIIKTVAQQIHGTEIDMKVIQQRSEECDHTQFLIEEKESKEEDFYEDLDRFE
ENGTQDSRISPYTFCKAFPFHIIFDRDLVVTQCGNAIYRVLPQLQPGKCSLLSVFSLVRPHIDISFHGI
LSHINTVFVLRSKEGLLDVEKLECEDELTGAEISCLRLKGQMIYLPEADSILFLCSPSVMNLDDLTR
RGLYLSDIPLHDATRDLVLLGEQFREEYKLTQELEILTDRLQLTLRALED

Figure 8Y

*Rn.* β1 (1-385) H105F (SEQ ID NO:147)
ATGTACGGTTTTGTGAACCATGCCCTGGAGCTGCTGGTGATCCGCAATTACGGTCCCGAGGTG
TGGGAAGACATCAAAAAAGAGGCGCAGCTGGATGAAGAAGGCCAGTTTCTTGTGAGAATAAT
CTACGATGATTCCAAAACCTATGACTTGGTGGCTGCTGCGAGCAAAGTCCTCAACCTCAATGC
TGGTGAAATCCTGCAGATGTTTGGGAAGATGTTTTTCGTCTTCTGTCAAGAGTCTGGCTATGAT
ACCATCTTGCGTGTCCTGGGATCTAATGTCAGGGAGTTTTTGCAGAACCTCGACGCCCTGTTCG
ACCACCTCGCCACCATCTACCCAGGGATGCGCGCACCTTCCTTCCGGTGCACCGATGCAGAAA
AAGGCAAAGGGCTCATTCTGCACTACTACTCGGAAAGAGAGGGGCTTCAGGACATTGTGATC
GGGATTATCAAGACTGTAGCTCAACAGATCCATGGCACTGAGATAGACATGAAGGTTATTCA
GCAAAGAAGTGAAGAATGTGATCATACCCAATTTTTAATTGAAGAAAAAGAATCAAAAGAAG
AGGATTTTTATGAAGATCTGGACAGGTTTGAAGAGAACGGTACCCAGGACTCCCGTATCAGCC
CGTACACCTTCTGCAAAGCGTTTCCTTTTCACATCATATTTGACCGGGACCTAGTAGTCACGCA
GTGTGGAAATGCTATCTACAGAGTGCTCCCCCAGCTCCAGCCTGGGAAGTGCAGCCTTCTGTC
TGTCTTCTCTCTGGTCCGCCCTCATATTGACATCAGTTTCCACGGGATTCTTTCACACATCAAT
ACCGTCTTTGTACTGAGAAGCAAGGAAGGGTTGCTGGATGTTGAGAAACTTGAATGTGAGGA
TGAACTGACTGGGGCAGAGATTAGCTGCCTCCGTCTCAAAGGCCAAATGATCTATTTACCGGA
AGCAGATAGCATCCTCTTCCTCTGTTCACCAAGTGTGATGAACTTGGATGACCTAACAAGAAG
AGGCCTGTACCTGAGTGACATCCCTCTCCATGATGCTACACGAGACCTGGTCCTTTTGGGAGA
ACAGTTCCGGGAGGAGTACAAACTGACACAAGAGCTGGAAATCCTCACAGACAGGCTGCAGC
TCACACTGAGGGCTTTGGAGGATTGA (SEQ ID NO:148)
MYGFVNHALELLVIRNYGPEVWEDIKKEAQLDEEGQFLVRIIYDDSKTYDLVAAASKVLNLNAGE
ILQMFGKMFFVFCQESGYDTILRVLGSNVREFLQNLDALFDHLATIYPGMRAPSFRCTDAEKGKGL
ILHYYSEREGLQDIVIGIIKTVAQQIHGTEIDMKVIQQRSEECDHTQFLIEEKESKEEDFYEDLDRFEE
NGTQDSRISPYTFCKAFPFHIIFDRDLVVTQCGNAIYRVLPQLQPGKCSLLSVFSLVRPHIDISFHGIL
SHINTVFVLRSKEGLLDVEKLECEDELTGAEISCLRLKGQMIYLPEADSILFLCSPSVMNLDDLTRR
GLYLSDIPLHDATRDLVLLGEQFREEYKLTQELEILTDRLQLTLRALED

(SEQ ID NO:149)
ATGTACGGTTTTGTGAACCATGCCCTGGAGCTGCTGGTGATCCGCAATTACGGTCCCGAGGTG
TGGGAAGACATCAAAAAAGAGGCGCAGCTGGATGAAGAAGGCCAGTTTCTTGTGAGAATAAT
CTACGATGATTCCAAAACCTATGACTTGGTGGCTGCTGCGAGCAAAGTCCTCAACCTCAATGC
TGGTGAAATCCTGCAGATGTTTGGGAAGATGTTTTTCGTCTTCTGTCAAGAGTCTGGCTATGAT
ACCATCTTGCGTGTCCTGGGATCTAATGTCAGGGAGTTTTTGCAGAACCTCGACGCCCTGGGG
GACCACCTCGCCACCATCTACCCAGGGATGCGCGCACCTTCCTTCCGGTGCACCGATGCAGAA
AAAGGCAAAGGGCTCATTCTGCACTACTACTCGGAAAGAGAGGGGCTTCAGGACATTGTGAT
CGGGATTATCAAGACTGTAGCTCAACAGATCCATGGCACTGAGATAGACATGAAGGTTATTCA
GCAAAGAAGTGAAGAATGTGATCATACCCAATTTTTAATTGAAGAAAAAGAATCAAAAGAAG
AGGATTTTTATGAAGATCTGGACAGGTTTGAAGAGAACGGTACCCAGGACTCCCGTATCAGCC
CGTACACCTTCTGCAAAGCGTTTCCTTTTCACATCATATTTGACCGGGACCTAGTAGTCACGCA
GTGTGGAAATGCTATCTACAGAGTGCTCCCCCAGCTCCAGCCTGGGAAGTGCAGCCTTCTGTC
TGTCTTCTCTCTGGTCCGCCCTCATATTGACATCAGTTTCCACGGGATTCTTTCACACATCAAT
ACCGTCTTTGTACTGAGAAGCAAGGAAGGGTTGCTGGATGTTGAGAAACTTGAATGTGAGGA
TGAACTGACTGGGGCAGAGATTAGCTGCCTCCGTCTCAAAGGCCAAATGATCTATTTACCGGA
AGCAGATAGCATCCTCTTCCTCTGTTCACCAAGTGTGATGAACTTGGATGACCTAACAAGAAG
AGGCCTGTACCTGAGTGACATCCCTCTCCATGATGCTACACGAGACCTGGTCCTTTTGGGAGA
ACAGTTCCGGGAGGAGTACAAACTGACACAAGAGCTGGAAATCCTCACAGACAGGCTGCAGC
TCACACTGAGGGCTTTGGAGGATTGA (SEQ ID NO:150)
MYGFVNHALELLVIRNYGPEVWEDIKKEAQLDEEGQFLVRIIYDDSKTYDLVAAASKVLNLNAGE
ILQMFGKMFFVFCQESGYDTILRVLGSNVREFLQNLDALGDHLATIYPGMRAPSFRCTDAEKGKG
LILHYYSEREGLQDIVIGIIKTVAQQIHGTEIDMKVIQQRSEECDHTQFLIEEKESKEEDFYEDLDRFE
ENGTQDSRISPYTFCKAFPFHIIFDRDLVVTQCGNAIYRVLPQLQPGKCSLLSVFSLVRPHIDISFHGI
LSHINTVFVLRSKEGLLDVEKLECEDELTGAEISCLRLKGQMIYLPEADSILFLCSPSVMNLDDLTR
RGLYLSDIPLHDATRDLVLLGEQFREEYKLTQELEILTDRLQLTLRALED

***Rn.* β1(1-194)**

(SEQ ID NO:151)
ATGTACGGTTTTGTGAACCATGCCCTGGAGCTGCTGGTGATCCGCAATTACGGTCCCGAGGTG
TGGGAAGACATCAAAAAAGAGGCGCAGCTGGATGAAGAAGGCCAGTTTCTTGTGAGAATAAT
CTACGATGATTCCAAAACCTATGACTTGGTGGCTGCTGCGAGCAAAGTCCTCAACCTCAATGC
TGGTGAAATCCTGCAGATGTTTGGGAAGATGTTTTTCGTCTTCTGTCAAGAGTCTGGCTATGAT
ACCATCTTGCGTGTCCTGGGATCTAATGTCAGGGAGTTTTTGCAGAACCTCGACGCCCTGCAC
GACCACCTCGCCACCATCTACCCAGGGATGCGCGCACCTTCCTTCCGGTGCACCGATGCAGAA
AAAGGCAAAGGGCTCATTCTGCACTACTACTCGGAAAGAGAGGGGCTTCAGGACATTGTGAT
CGGGATTATCAAGACTGTAGCTCAACAGATCCATGGCACTGAGATAGACATGAAGGTTATTCA
GCAAAGAAGTGAAGAATGTGATCATACCCAATTTTTAATTGAAGAAAAAGAATCAAAAGAAG
AGGATTTTTATGAAGATTGA (SEQ ID NO:152)
MYGFVNHALELLVIRNYGPEVWEDIKKEAQLDEEGQFLVRIIYDDSKTYDLVAAASKVLNLNAGE
ILQMFGKMFFVFCQESGYDTILRVLGSNVREFLQNLDALHDHLATIYPGMRAPSFRCTDAEKGKG
LILHYYSEREGLQDIVIGIIKTVAQQIHGTEIDMKVIQQRSEECDHTQFLIEEKESKEEDFYED

(SEQ ID NO:153)
ATGTACGGTTTTGTGAACCATGCCCTGGAGCTGCTGGTGATCCGCAATTACGGTCCCGAGGTG
TGGGAAGACATCAAAAAAGAGGCGCAGCTGGATGAAGAAGGCCAGTTTCTTGTGAGAATAAT
CTACGATGATTCCAAAACCTATGACTTGGTGGCTGCTGCGAGCAAAGTCCTCAACCTCAATGC
TGGTGAAATCCTGCAGATGTTTGGGAAGATGTTTTTCGTCTTCTGTCAAGAGTCTGGCTATGAT
ACCATCTTGCGTGTCCTGGGATCTAATGTCAGGGAGTTTTTGCAGAACCTCGACGCCCTGCAC
GACCACCTCGCCACCATCTACCCAGGGATGCGCGCACCTTCCTTCCGGTGCACCGATGCAGAA
AAAGGCAAAGGGCTCATTCTGCACTACTACTCGGAAAGAGAGGGGCTTCAGGACTACGTGAT
CGGGATTATCAAGACTGTAGCTCAACAGATCCATGGCACTGAGATAGACATGAAGGTTATTCA
GCAAAGAAGTGAAGAATGTGATCATACCCAATTTTTAATTGAAGAAAAAGAATCAAAAGAAG
AGGATTTTTATGAAGATTGA (SEQ ID NO:154)
MYGFVNHALELLVIRNYGPEVWEDIKKEAQLDEEGQFLVRIIYDDSKTYDLVAAASKVLNLNAGE
ILQMFGKMFFVFCQESGYDTILRVLGSNVREFLQNLDALHDHLATIYPGMRAPSFRCTDAEKGKG
LILHYYSEREGLQDYVIGIIKTVAQQIHGTEIDMKVIQQRSEECDHTQFLIEEKESKEEDFYED

***Rn.* β1(1-194) L9W-I145Y**

(SEQ ID NO:155)
ATGTACGGTTTTGTGAACCATGCCTGGGAGCTGCTGGTGATCCGCAATTACGGTCCCGAGGTG
TGGGAAGACATCAAAAAAGAGGCGCAGCTGGATGAAGAAGGCCAGTTTCTTGTGAGAATAAT
CTACGATGATTCCAAAACCTATGACTTGGTGGCTGCTGCGAGCAAAGTCCTCAACCTCAATGC
TGGTGAAATCCTGCAGATGTTTGGGAAGATGTTTTTCGTCTTCTGTCAAGAGTCTGGCTATGAT
ACCATCTTGCGTGTCCTGGGATCTAATGTCAGGGAGTTTTTGCAGAACCTCGACGCCCTGCAC
GACCACCTCGCCACCATCTACCCAGGGATGCGCGCACCTTCCTTCCGGTGCACCGATGCAGAA
AAAGGCAAAGGGCTCATTCTGCACTACTACTCGGAAAGAGAGGGGCTTCAGGACTACGTGAT
CGGGATTATCAAGACTGTAGCTCAACAGATCCATGGCACTGAGATAGACATGAAGGTTATTCA
GCAAAGAAGTGAAGAATGTGATCATACCCAATTTTTAATTGAAGAAAAAGAATCAAAAGAAG
AGGATTTTTATGAAGATTGA (SEQ ID NO:156)
MYGFVNHAWELLVIRNYGPEVWEDIKKEAQLDEEGQFLVRIIYDDSKTYDLVAAASKVLNLNAG
EILQMFGKMFFVFCQESGYDTILRVLGSNVREFLQNLDALHDHLATIYPGMRAPSFRCTDAEKGK
GLILHYYSEREGLQDYVIGIIKTVAQQIHGTEIDMKVIQQRSEECDHTQFLIEEKESKEEDFYED

Figure 8BB

***Rattus norvegicus* β2**

(SEQ ID NO:157)
ATGTATGGATTCATCAACACCTGCCTGCAGTCTCTTGTGACAGAGAAATTTGGTGAGGAGACA
TGGGAGAAGCTGAAGGCTCCTGCAGAAGTGCAAGATGTCTTCATGACCTACACCGTGTATGAT
GACATCATCACCATTAAGCTCATCCAAGAAGCCTGCAAGGTTCTGGATGTGTCCATGGAAGCC
ATTCTGAAGCTCTTTGGCGAATACTTCTTTAAGTTCTGTAAGATGTCTGGCTATGACAGGATGC
TGCGGACACTTGGAGGAAATCTCACCGAGTTTATTGAAAACCTAGATGCACTCCACAGTTACC
TGGCACTGTCCTATCAGGAAATGAACGCACCATCCTTTCGAGTGGAGGAAGGAGCTGACGGG
GCGATGCTTCTCCACTACTACTCAGACAGACATGGTCTGTGTCACATTGTACCAGGTATCATTG
AAGCTGTGGCCAAGGACTTCTTTGACACTGATGTGGCCATGAGTATCCTGGATATGAACGAAG
AGGTGGAAAGGACAGGGAAGAAAGAACATGTTGTGTTTCTGGTCGTGCAGAAGGCTCACAGA
CAGATAAGAGGAGCAAAGGCAAGCCGGCCACAAGGCAGTGAGGACAGCCAGGCAGACCAGG
AGGCTCTCCAGGGAACACTCCTTCGGATGAAGGAGAGATATTTAAACATCCCTGTTTGCCCTG
GGGAGAAATCTCACTCAACTGCTGTGAGGGCATCGGTCCTTTTTGGAAAAGGGCCCCTCAGGG
ACACCTTCCAGCCCGTCTATCCTGAGAGACTATGGGTCGAAGAGGAGGTGTTCTGTGATGCTT
TTCCTTTCCACATTGTCTTTGATGAAGCACTAAGGGTCAAGCAAGCTGGAGTGAATATTCAGA
AGTATGTCCCTGGAATCTTAACCCAGAAGTTTGCACTAGATGAGTATTTTTCCATCATCCACCC
TCAAGTTACTTTCAACATCTCCAGCATCTGCAAGTTCATTAACAGTCAGTTTGTCTTGAAGACA
AGAAAAGAAATGATGCCCAAAGCAAGGAAGAGCCAGCCGATGCTCAAACTCCGGGGTCAGA
TGATCTGGATGGAGTCTCTGAGGTGCATGATCTTCATGTGTTCCCCAAACGTCCGCAGCCTGC
AAGAGCTGGAAGAGAGCAAGATGCATCTTTCTGATATCGCTCCGCACGACACGACCAGGGAT
CTCATCCTCCTCAACCAGCAGAGGCTGGCAGAGATGGAGCTGTCCTGCCAACTGGAAAAGAA
GAAGGAGGAGTTGCGTGTCCTTTCCAATCACCTGGCCATCGAGAAGAAGAAGACAGAGACCT
TGCTGTATGCCATGCTGCCTGAACATGTGGCCAACCAACTCAAGGAGGGCAGAAAGGTGGCT
GCAGGAGAATTTGAAACATGTACAATCCTTTTCAGCGATGTTGTGACATTTACCAACATCTGT
GCAGCCTGTGAACCTATCCAAATCGTGAACATGCTGAATTCAATGTACTCCAAGTTTGACAGG
TTAACCAGTGTCCATGATGTCTACAAAGTAGAAACAATAGGGGATGCTTACATGGTGGTGGGT
GGAGTACCAGTACCCGTTGAAAGCCATGCTCAAAGAGTCGCCAATTTTGCTCTGGGGATGAGA
ATTTCTGCAAAAGAAGTGATGAATCCTGTCACTGGGGAACCTATCCAGATCAGAGTGGGAATC
CACACTGGACCAGTCTTAGCAGGTGTTGTGGGAGACAAGATGCCTCGGTACTGCTTGTTTGGT
GACACTGTAAACACAGCCTCTAGGATGGAAAGTCACGGGCTTCCCAGCAAAGTGCATCTGAG
CCCCACAGCCCACAGAGCCCTGAAAAACAAAGGGTTTGAAATTGTCAGGAGAGGCGAGATCG
AAGTGAAGGGGAAAGGAAAGATGACCACATACTTTCTGATCCAGAACCTGAATGCCACCGAG
GATGAGATAATGGGGCGACCTTCAGCCCCCGCTGATGGGAAGGAAGTATGTACTCCCGGAAA
CCAAGTCAGGAAGTCCCCTGCTGTCCCGAGGAACACAGACCATCAGCAACAAGTCTACAAAG
GAGACCCAGCAGACGCTTCTAATGAAGTCACACTTGCTGGGAGCCCAGTGGCAGGGCGAAAC
TCCACAGATGCAGTCAATAACCAGCCATCACCAGATGAGACCAAGACAAGTGTCGTTGCTAG
TGGCCCTGTGCTGTCTGCTTTCTGTGTTGTGCTGTGA (SEQ ID NO:158)
MYGFINTCLQSLVTEKFGEETWEKLKAPAEVQDVFMTYTVYDDIITIKLIQEACKVLDVSMEAILK
LFGEYFFKFCKMSGYDRMLRTLGGNLTEFIENLDALHSYLALSYQEMNAPSFRVEEGADGAMLLH
YYSDRHGLCHIVPGIIEAVAKDFFDTDVAMSILDMNEEVERTGKKEHVVFLVVQKAHRQIRGAKA
SRPQGSEDSQADQEALQGTLLRMKERYLNIPVCPGEKSHSTAVRASVLFGKGPLRDTFQPVYPERL
WVEEEVFCDAFPFHIVFDEALRVKQAGVNIQKYVPGILTQKFALDEYFSIIHPQVTFNISSICKFINSQ
FVLKTRKEMMPKARKSQPMLKLRGQMIWMESLRCMIFMCSPNVRSLQELEESKMHLSDIAPHDT
TRDLILLNQQRLAEMELSCQLEKKKEELRVLSNHLAIEKKKTETLLYAMLPEHVANQLKEGRKVA
AGEFETCTILFSDVVTFTNICAACEPIQIVNMLNSMYSKFDRLTSVHDVYKVETIGDAYMVVGGVP
VPVESHAQRVANFALGMRISAKEVMNPVTGEPIQIRVGIHTGPVLAGVVGDKMPRYCLFGDTVNT
ASRMESHGLPSKVHLSPTAHRALKNKGFEIVRRGEIEVKGKGKMTTYFLIQNLNATEDEIMGRPSA
PADGKEVCTPGNQVRKSPAVPRNTDHQQQVYKGDPADASNEVTLAGSPVAGRNSTDAVNNQPSP
DETKTSVVASGPVLSAFCVVL

Figure 8CC

*Homo sapiens* β2 (1-217)

(SEQ ID NO:159)
ATGTATGGATTCATCAACACCTGCCTGCAGTCTCTTGTGACAGAGAAATTTGGTGAGGAGACA
TGGGAGAAGCTGAAGGCTCCTGCAGAAGTGCAAGATGTCTTCATGACCTACACCGTGTATGAT
GACATCATCACCATTAAGCTCATCCAAGAAGCCTGCAAGGTTCTGGATGTGTCCATGGAAGCC
ATTCTGAAGCTCTTTGGCGAATACTTCTTTAAGTTCTGTAAGATGTCTGGCTATGACAGGATGC
TGCGGACACTTGGAGGAAATCTCACCGAGTTTATTGAAAACCTAGATGCACTCCACAGTTACC
TGGCACTGTCCTATCAGGAAATGAACGCACCATCCTTTCGAGTGGAGGAAGGAGCTGACGGG
GCGATGCTTCTCCACTACTACTCAGACAGACATGGTCTGTGTCACATTGTACCAGGTATCATTG
AAGCTGTGGCCAAGGACTTCTTTGACACTGATGTGGCCATGAGTATCCTGGATATGAACGAAG
AGGTGGAAAGGACAGGGAAGAAAGAACATGTTGTGTTTCTGGTCGTGCAGAAGGCTCACAGA
CAGATAAGAGGAGCAAAGGCAAGCCGGCCACAAGGCAGTGAGGACAGCCAGGCAGACCAGG
AGGCTCTCCAGGGAACACTCCTT (SEQ ID NO:160)
MYGFINTCLQSLVTEKFGEETWEKLKAPAEVQDVFMTYTVYDDIITIKLIQEACKVLDVSMEAILK
LFGEYFFKFCKMSGYDRMLRTLGGNLTEFIENLDALHSYLALSYQEMNAPSFRVEEGADGAMLLH
YYSDRHGLCHIVPGIIEAVAKDFFDTDVAMSILDMNEEVERTGKKEHVVFLVVQKAHRQIRGAKA
SRPQGSEDSQADQEALQGTLL

*Homo sapiens* β2 (1-217) I142Y (SEQ ID NO:161)
ATGTATGGATTCATCAACACCTGCCTGCAGTCTCTTGTGACAGAGAAATTTGGTGAGGAGACA
TGGGAGAAGCTGAAGGCTCCTGCAGAAGTGCAAGATGTCTTCATGACCTACACCGTGTATGAT
GACATCATCACCATTAAGCTCATCCAAGAAGCCTGCAAGGTTCTGGATGTGTCCATGGAAGCC
ATTCTGAAGCTCTTTGGCGAATACTTCTTTAAGTTCTGTAAGATGTCTGGCTATGACAGGATGC
TGCGGACACTTGGAGGAAATCTCACCGAGTTTATTGAAAACCTAGATGCACTCCACAGTTACC
TGGCACTGTCCTATCAGGAAATGAACGCACCATCCTTTCGAGTGGAGGAAGGAGCTGACGGG
GCGATGCTTCTCCACTACTACTCAGACAGACATGGTCTGTGTCACTATGTACCAGGTATCATTG
AAGCTGTGGCCAAGGACTTCTTTGACACTGATGTGGCCATGAGTATCCTGGATATGAACGAAG
AGGTGGAAAGGACAGGGAAGAAAGAACATGTTGTGTTTCTGGTCGTGCAGAAGGCTCACAGA
CAGATAAGAGGAGCAAAGGCAAGCCGGCCACAAGGCAGTGAGGACAGCCAGGCAGACCAGG
AGGCTCTCCAGGGAACACTCCTT (SEQ ID NO:162)
MYGFINTCLQSLVTEKFGEETWEKLKAPAEVQDVFMTYTVYDDIITIKLIQEACKVLDVSMEAILK
LFGEYFFKFCKMSGYDRMLRTLGGNLTEFIENLDALHSYLALSYQEMNAPSFRVEEGADGAMLLH
YYSDRHGLCHYVPGIIEAVAKDFFDTDVAMSILDMNEEVERTGKKEHVVFLVVQKAHRQIRGAK
ASRPQGSEDSQADQEALQGTLL

Figure 8DD

SEQUENCE LISTING

```
<160> NUMBER OF SEQ ID NOS: 162

<210> SEQ ID NO 1
<211> LENGTH: 190
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 33
<223> OTHER INFORMATION: Xaa = Any Amino Acid

<400> SEQUENCE: 1

Met Tyr Gly Leu Leu Val Glu Ser Val Ala Glu Tyr Ile Lys Glu Leu
 1               5                  10                  15

Tyr Gly Glu Asp Val Trp Glu Asp Val Leu Lys Gln Ala Gly Val Glu
            20                  25                  30

Xaa Lys Ser Phe Ser Val His Gln Val Tyr Pro Asp Asp Leu Val Pro
        35                  40                  45

Arg Leu Ala Lys Ala Ala Ser Glu Val Thr Gly Ile Pro Val Asp Glu
    50                  55                  60

Ile Met Asp Gln Ile Gly Arg Phe Phe Val Gly Phe Phe Ser Glu Phe
65                  70                  75                  80

Gly Tyr Asp Lys Val Leu Arg Val Leu Gly Arg His Leu Arg Asp Phe
                85                  90                  95

Leu Asn Gly Leu Asp Asn Leu His Glu Tyr Leu Arg Phe Ser Tyr Pro
            100                 105                 110

Lys Met Lys Ala Pro Ser Phe Ile Cys Glu Asn Glu Ser Lys Asp Gly
        115                 120                 125

Leu Thr Leu His Tyr Arg Ser Lys Arg Arg Gly Phe Val Asp Tyr Val
    130                 135                 140

Ile Gly Gln Ile Arg Glu Val Ala Arg Glu Phe Tyr Glu Lys Glu Val
145                 150                 155                 160

Val Ile Glu Val Leu Pro Glu Glu Glu Asp Gly Asp Leu Val His Val
                165                 170                 175

Thr Phe Ile Leu Thr Phe Asp Asn Val Ala Phe Thr Leu Ala
            180                 185                 190


<210> SEQ ID NO 2
<211> LENGTH: 190
<212> TYPE: PRT
<213> ORGANISM: Caenorhabditis elegans

<400> SEQUENCE: 2

Met Tyr Gly Leu Ile Ile Asp His Ile Ala Thr Tyr Ile Lys Glu Lys
 1               5                  10                  15

Tyr Gly Glu Ser Thr Trp Ser Glu Val Lys Phe Val Ser Gly Val Thr
            20                  25                  30

Asp Asp Thr Phe Gln Met Asp Lys Lys Phe Ser Glu Gly Leu Ser His
```

35 40 45

Lys Leu Ile Trp Ala Cys His Asp Val Thr Gly Asp Pro Val Asp Glu
50 55 60

Leu Met Thr Asn Ile Gly Thr Ser Phe Tyr Lys Phe Leu Thr Lys Phe
65 70 75 80

Glu Phe Asn Lys Val Leu Arg Val Leu Gly Arg Thr Phe Pro Gln Phe
85 90 95

Leu Asn Gly Leu Asp Asn Leu His Glu Tyr Leu Arg Phe Thr Phe Pro
100 105 110

Lys Leu Lys Pro Pro Ser Phe Tyr Cys Glu His Glu Ser Arg Thr Gly
115 120 125

Leu Thr Leu His Tyr Arg Ser Lys Arg Arg Gly Phe Leu His Tyr Val
130 135 140

Gln Gly Gln Ile Arg Asn Ile Ser Gln Glu Leu Phe Gln Thr Glu Val
145 150 155 160

Val Ile Glu Leu Leu Asp Ile Glu His Asp Leu Asn Leu Glu His Val
165 170 175

Ile Met Arg Leu His Phe Asn Asn Leu Asp Phe Asn Arg Gln
180 185 190

<210> SEQ ID NO 3
<211> LENGTH: 190
<212> TYPE: PRT
<213> ORGANISM: Caenorhabditis elegans

<400> SEQUENCE: 3

Met Tyr Gly Leu Val Ile Glu Gly Val Arg Phe Met Ile Gln Glu Asn
1 5 10 15

Trp Gly Pro Gln Val Leu Leu Gln Val Gln Lys Leu Thr Ser Leu Ser
20 25 30

Glu Lys Ser Val Ser Thr His Asp Gln Tyr Ser Glu His Val Val Pro
35 40 45

Gln Met Phe Lys Ala Ile His Glu Ile Thr Gly Thr Pro Tyr Glu Gln
50 55 60

Ile Gly Val Leu Ala Gly Arg Phe Phe Val Gln Phe Leu Ile Arg Asn
65 70 75 80

Gly Tyr Gly Asp Leu Met Asn Val Met Gly Arg Arg Phe Ser Asp Phe
85 90 95

Ile Lys Gly Leu Asp Asn Ile His Glu Tyr Phe Arg Phe Ser Tyr Pro
100 105 110

Lys Leu Arg Ala Pro Ser Phe Tyr Cys Lys Ser Glu Ser Glu Asp Gly
115 120 125

Leu Ile Leu His Tyr Arg Ser Arg Arg Thr Gly Tyr Leu Ser Tyr Val
130 135 140

Ile Gly Gln Leu Val Glu Leu Ala Arg Val Phe Tyr Gln Leu Asp Ile
145 150 155 160

Gly Ile Gln Val Leu Lys Lys Lys Glu Lys Gly Arg Phe Thr Phe Val
165 170 175

Val Leu Lys Ile Ser Phe Asp Asn Val Gly Leu Gly Gln Asp
180 185 190

<210> SEQ ID NO 4
<211> LENGTH: 190
<212> TYPE: PRT
<213> ORGANISM: Caenorhabditis elegans -continued

<400> SEQUENCE: 4

```
Met Phe Gly Trp Ile His Glu Ser Phe Arg Gln Leu Val Thr Arg Lys
 1               5                  10                  15

Tyr Gly Lys Asp Ile Trp Glu Lys Ile Val His Met Ser Lys Phe Glu
            20                  25                  30

Leu Gly Thr Glu Ser Glu Ile Ala His Tyr Tyr Asn Asp Asp Glu Thr
        35                  40                  45

Leu Arg Leu Val Asn Ser Met Ala Asn Val Ile Gly Ile Pro Ile Glu
    50                  55                  60

Glu Ile Trp Glu Ala Tyr Gly Gly Phe Leu Ile Gln Phe Thr Met Glu
65                  70                  75                  80

Thr Gly Trp Asp Glu Leu Leu Arg Ala Met Ala Pro Asp Leu Glu Gly
                85                  90                  95

Phe Leu Asp Ser Leu Asp Ser Leu His Tyr Phe Ile Asp His Val Val
            100                 105                 110

Tyr Lys Thr Lys Leu Arg Gly Pro Ser Phe Arg Cys Asp Val Gln Ala
        115                 120                 125

Asp Gly Thr Leu Leu Leu His Tyr Tyr Ser Lys Arg Ser Gly Leu Tyr
    130                 135                 140

Pro Ile Val Lys Gly Val Val Arg Glu Val Ala Arg Arg Ile Tyr Asp
145                 150                 155                 160

Thr Glu Val Val Met Lys Val Gln Glu Arg Lys Gln Glu His Leu Asp
                165                 170                 175

Ala Phe Val Thr Glu His Val Val Phe Val Ile Thr Gln Ile
            180                 185                 190
```

<210> SEQ ID NO 5
<211> LENGTH: 190
<212> TYPE: PRT
<213> ORGANISM: Drosophila melanogaster

<400> SEQUENCE: 5

```
Met Tyr Gly Met Leu Tyr Glu Ser Val Gln His Tyr Val Gln Glu Glu
 1               5                  10                  15

Tyr Gly Val Asp Ile Trp Arg Lys Val Cys His Ile Ile Asp Cys Lys
            20                  25                  30

His Asn Ser Phe Lys Thr His Gln Ile Tyr Pro Asp Lys Leu Met Pro
        35                  40                  45

Asp Ile Ala Glu Ala Leu Ser Ala Cys Thr Gly Glu Ser Phe Asp Phe
    50                  55                  60

Cys Met Asn Phe Phe Gly Arg Cys Phe Val Arg Phe Phe Ser Asn Phe
65                  70                  75                  80

Gly Tyr Asp Lys Met Ile Arg Ser Thr Gly Arg Tyr Phe Cys Asp Phe
                85                  90                  95

Leu Gln Ser Ile Asp Asn Ile His Leu Ile Met Arg Phe Thr Tyr Pro
            100                 105                 110

Lys Met Lys Ser Pro Ser Met Gln Leu Thr Asn Met Asp Asp Asn Gly
        115                 120                 125

Ala Val Ile Leu Tyr Arg Ser Ser Arg Thr Gly Met Ser Lys Tyr Leu
    130                 135                 140

Ile Gly Gln Met Thr Glu Val Ala Arg Glu Phe Tyr Gly Leu Glu Ile
145                 150                 155                 160

Lys Ala Tyr Val Ile Glu Ser Gln Asn Asp Ile Ser Gly Gly Thr Ala
                165                 170                 175
```

-continued

```
Gly Pro Ile Lys Leu Thr Asp Gly Pro Leu Thr Val Ile Val
            180                 185                 190


<210> SEQ ID NO 6
<211> LENGTH: 190
<212> TYPE: PRT
<213> ORGANISM: Drosophila melanogaster

<400> SEQUENCE: 6

Met Tyr Gly Leu Leu Leu Glu Asn Leu Ser Glu Tyr Ile Lys Ser Val
1               5                   10                  15

Tyr Gly Glu Glu Lys Trp Glu Asp Ile Arg Arg Gln Ala Gly Ile Asp
            20                  25                  30

Ser Pro Ser Phe Ser Val His Gln Val Tyr Pro Glu Asn Leu Leu Gln
        35                  40                  45

Lys Leu Ala Lys Lys Ala Gln Gln Val Leu Gly Val Ser Glu Arg Asp
    50                  55                  60

Phe Met Asp Gln Met Gly Val Tyr Phe Val Gly Phe Val Gly Gln Tyr
65                  70                  75                  80

Gly Tyr Asp Arg Val Leu Ser Val Leu Gly Arg His Met Arg Asp Phe
                85                  90                  95

Leu Asn Gly Leu Asp Asn Leu His Glu Tyr Leu Lys Phe Ser Tyr Pro
            100                 105                 110

Arg Met Arg Ala Pro Ser Phe Ile Cys Glu Asn Glu Thr Lys Gln Gly
        115                 120                 125

Leu Thr Leu His Tyr Arg Ser Lys Arg Arg Gly Phe Val Tyr Tyr Thr
    130                 135                 140

Met Gly Gln Ile Arg Glu Val Ala Arg Tyr Phe Tyr His Lys Glu Met
145                 150                 155                 160

His Ile Glu Leu Val Arg Glu Glu Ile Leu Phe Asp Thr Val His Val
                165                 170                 175

Thr Phe Gln Leu Thr Phe Asp Asn Arg Ala Phe Thr Leu Ala
            180                 185                 190


<210> SEQ ID NO 7
<211> LENGTH: 190
<212> TYPE: PRT
<213> ORGANISM: Manduca sexta

<400> SEQUENCE: 7

Met Tyr Gly Leu Leu Leu Glu Asn Met Ala Glu Tyr Ile Arg Gln Thr
1               5                   10                  15

Tyr Gly Glu Glu Arg Trp Glu Asp Ile Arg Arg Gln Ala Gly Val Glu
            20                  25                  30

Gln Pro Ser Phe Ser Val His Gln Val Tyr Pro Glu Asn Leu Ile Thr
        35                  40                  45

Arg Leu Ala Lys Lys Ala Gln Glu Val Leu Gly Ile Thr Glu Arg Glu
    50                  55                  60

Phe Met Asp Gln Met Gly Val Tyr Phe Val Gly Phe Val Ser Gln Tyr
65                  70                  75                  80

Gly Tyr Asp Arg Val Leu Ser Val Leu Gly Arg His Met Arg Asp Phe
                85                  90                  95

Leu Asn Gly Leu Asp Asn Leu His Glu Tyr Leu Lys Phe Ser Tyr Pro
            100                 105                 110

Arg Met Arg Ala Pro Ser Phe Ile Cys Glu Asn Glu Thr Arg Gln Gly
        115                 120                 125
```

-continued

```
Leu Thr Leu His Tyr Arg Ser Lys Arg Arg Gly Phe Val Tyr Tyr Ala
    130                 135                 140

Met Gly Gln Ile Arg Glu Val Ala Arg His Phe Tyr His Lys Glu Met
145                 150                 155                 160

Arg Ile Glu Leu Leu Arg Glu Glu Leu Leu Phe Asp Thr Val His Val
                165                 170                 175

Thr Phe Gln Leu Thr Phe Asp Asn Arg Ala Phe Thr Leu Ala
            180                 185                 190


<210> SEQ ID NO 8
<211> LENGTH: 190
<212> TYPE: PRT
<213> ORGANISM: Thermoanaerobacter tengcongensis

<400> SEQUENCE: 8

Met Lys Gly Thr Ile Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu Tyr Lys Lys Asn Val Trp
            180                 185                 190


<210> SEQ ID NO 9
<211> LENGTH: 190
<212> TYPE: PRT
<213> ORGANISM: Clostridium acetobutiylicum

<400> SEQUENCE: 9

Met Lys Gly Thr Val Val Gly Thr Trp Val Lys Thr Cys Lys Arg Leu
 1               5                  10                  15

Tyr Gly Glu Thr Val Val Glu Asn Ala Leu Glu Lys Val Gly Phe Glu
            20                  25                  30

Arg Lys Lys Ile Phe Ser Pro Phe Glu Asp Val Glu Asp Ser Lys Val
        35                  40                  45

Asn Asn Phe Ile Glu Asp Ile Ser Lys Lys Val Asn Glu Glu Lys Ser
    50                  55                  60

Ile Ile Trp Glu Lys Ile Gly Glu Asp Asn Val Ile Ala Phe His Lys
65                  70                  75                  80
```

-continued

Asp Phe Pro Ala Phe Phe Glu His Glu Asn Leu Tyr Ser Phe Phe Lys
85 90 95

Ser Met Phe Asp Val His Val Val Met Thr Lys Lys Phe Pro Gly Ala
100 105 110

Lys Pro Pro Leu Ile Leu Ile Lys Pro Ile Ser Lys Arg Glu Ala Ile
115 120 125

Phe Thr Tyr Arg Ser Lys Arg Gly Met Phe Asp Tyr Leu Lys Gly Leu
130 135 140

Ile Lys Gly Ser Ala Asn His Phe Asn Glu Lys Ile Glu Ile Glu Glu
145 150 155 160

Val Glu Lys Thr Lys Glu Ser Val Val Leu Lys Phe Thr Phe Asp Lys
165 170 175

Asp Ile Tyr Tyr Lys Lys Ser Phe Lys Ile Asn Lys Leu Leu
180 185 190

<210> SEQ ID NO 10
<211> LENGTH: 189
<212> TYPE: PRT
<213> ORGANISM: Artificial Sequence
<220> FEATURE:
<223> OTHER INFORMATION: Synthetic Construct

<400> SEQUENCE: 10

Met Tyr Gly Phe Val Asn His Ala Leu Glu Leu Leu Val Leu Arg Asn
1 5 10 15

Tyr Gly Pro Glu Val Trp Glu Asp Ile Lys Lys Glu Ala Gln Val Asp
20 25 30

Ile Glu Gly Gln Phe Leu Val Arg Ile Ile Tyr Asp Asp Ser Lys Thr
35 40 45

Tyr Asp Leu Val Ala Ala Ala Ser Lys Val Leu Asn Ile Asn Ala Gly
50 55 60

Asp Ile Leu Gln Leu Phe Gly Lys Met Phe Phe Glu Phe Cys Gln Glu
65 70 75 80

Ser Gly Tyr Asp Thr Ile Leu Arg Val Leu Gly Ser Asn Val Arg Glu
85 90 95

Phe Leu Gln Asn Leu Asp Ala Leu His Asp His Leu Gly Thr Ile Tyr
100 105 110

Pro Gly Met Arg Ala Pro Ser Phe Arg Cys Thr Asp Ala Glu Lys Gly
115 120 125

Gly Ala Leu Ile Leu His Tyr Tyr Ser Glu Arg Glu Gly Leu Gln Asp
130 135 140

Ile Val Ile Gly Ile Ile Lys Thr Val Ala Gln Gln Ile His Gly Thr
145 150 155 160

Glu Ile Glu Met Lys Ile Ile Gln Gln Lys Asn Glu Glu Cys Asp His
165 170 175

Val Gln Phe Leu Ile Glu Glu Lys Glu Ser Glu Glu Glu
180 185

<210> SEQ ID NO 11
<211> LENGTH: 186
<212> TYPE: PRT
<213> ORGANISM: Drosophila melanogaster

<400> SEQUENCE: 11

Met Tyr Gly Phe Val Asn Tyr Ala Leu Glu Leu Leu Val Leu Lys His
1 5 10 15

Phe Gly Glu Glu Ile Trp Glu Lys Ile Lys Lys Lys Ala Met Val Ser

```
            20                  25                  30

Met Glu Gly Gln Phe Leu Val Arg Gln Ile Tyr Asp Asp Glu Ile Thr
        35                  40                  45

Tyr Asn Leu Ile Gly Ala Ala Val Glu Ile Leu Asn Ile Pro Ala Asp
    50                  55                  60

Asp Ile Leu Glu Leu Phe Gly Lys Thr Phe Phe Glu Phe Cys Gln Asp
65                  70                  75                  80

Ser Gly Tyr Asp Lys Ile Leu Gln Val Leu Gly Ala Thr Pro Arg Asp
                85                  90                  95

Phe Leu Gln Asn Leu Asp Ala Leu His Asp His Leu Gly Thr Leu Tyr
            100                 105                 110

Pro Gly Met Arg Ala Pro Ser Phe Arg Cys Thr Glu Lys Asp Gly Glu
        115                 120                 125

Leu Leu Leu His Tyr Tyr Ser Glu Arg Pro Gly Leu Glu His Ile Val
    130                 135                 140

Ile Gly Ile Val Lys Ala Val Ala Ser Lys Leu His Gly Val Glu Val
145                 150                 155                 160

Glu Ile Asp Ile Val Lys Arg Lys Gly Glu Pro Ile Asp Glu Ala Glu
                165                 170                 175

Lys Glu Arg Ala Ile Ala Arg Glu Asn Gln
            180                 185


<210> SEQ ID NO 12
<211> LENGTH: 189
<212> TYPE: PRT
<213> ORGANISM: Rattus norvegicus

<400> SEQUENCE: 12

Met Tyr Gly Phe Val Asn His Ala Leu Glu Leu Leu Val Leu Arg Glu
 1               5                  10                  15

His Gly Lys Asp Lys Trp Glu Glu Ile Lys Arg Glu Ala Ala Val Glu
            20                  25                  30

Ile Glu Gly Ser Phe Leu Val Arg Ile Val Tyr Asp Asp Val Leu Ser
        35                  40                  45

Tyr Asp Leu Val Gly Ala Ala Val Lys Val Leu Glu Ile Ser Ala Asn
    50                  55                  60

Asp Leu Leu Glu Ala Phe Gly Arg Met Phe Phe Glu Phe Cys Val Glu
65                  70                  75                  80

Ser Gly Tyr Asp Asn Ile Leu Asn Val Leu Gly Ser Thr Thr Arg His
                85                  90                  95

Phe Leu Gln Asn Leu Asp Ala Leu His Asp His Leu Ala Ser Ile Tyr
            100                 105                 110

Pro Gly Met Arg Ala Pro Ser Phe Arg Cys Ser Thr Arg Glu Ser Asp
        115                 120                 125

Gly Ala Leu Val Leu His Tyr Tyr Ser Glu Arg Pro Gly Leu Glu His
    130                 135                 140

Ile Val Ile Gly Leu Val Arg Ser Val Ala Lys Thr Leu His Gly Ser
145                 150                 155                 160

Glu Val His Val Glu Ile Ile Lys Asn Lys Gly Glu Asp Cys Asp His
                165                 170                 175

Val Gln Phe Ala Ile Ile Glu Lys Val Glu Thr Ala Lys
            180                 185


<210> SEQ ID NO 13
<211> LENGTH: 188
```

-continued

<212> TYPE: PRT
<213> ORGANISM: Homo sapiens

<400> SEQUENCE: 13

Met Tyr Gly Phe Val Asn His Ala Leu Glu Leu Leu Val Ile Arg Asn
1 5 10 15

Tyr Gly Pro Glu Val Trp Glu Asp Ile Lys Lys Glu Ala Gln Leu Asp
20 25 30

Glu Glu Gly Phe Leu Val Arg Ile Ile Tyr Asp Asp Ser Lys Thr Tyr
35 40 45

Asp Leu Val Ala Ala Ala Ser Lys Val Leu Asn Leu Asn Ala Gly Glu
50 55 60

Ile Leu Gln Met Phe Gly Lys Met Phe Phe Val Phe Cys Gln Glu Ser
65 70 75 80

Gly Tyr Asp Thr Ile Leu Arg Val Leu Gly Ser Asn Val Arg Glu Phe
85 90 95

Leu Gln Asn Leu Asp Ala Leu His Asp His Leu Ala Thr Ile Tyr Pro
100 105 110

Gly Met Arg Ala Pro Ser Phe Arg Cys Thr Asp Ala Glu Lys Gly Lys
115 120 125

Gly Leu Ile Leu His Tyr Tyr Ser Glu Arg Glu Gly Leu Gln Asp Ile
130 135 140

Val Ile Gly Ile Ile Lys Thr Val Ala Gln Gln Ile His Gly Thr Glu
145 150 155 160

Ile Asp Met Lys Val Ile Gln Gln Arg Asn Glu Glu Cys Asp His Thr
165 170 175

Gln Phe Leu Ile Glu Glu Lys Glu Ser Lys Glu Glu
180 185

<210> SEQ ID NO 14
<211> LENGTH: 190
<212> TYPE: PRT
<213> ORGANISM: Homo sapiens

<400> SEQUENCE: 14

Met Tyr Gly Phe Ile Asn Thr Cys Leu Gln Ser Leu Val Thr Glu Lys
1 5 10 15

Phe Gly Glu Glu Thr Trp Glu Lys Leu Lys Ala Pro Ala Glu Val Gln
20 25 30

Asp Val Phe Met Thr Tyr Thr Val Tyr Asp Asp Ile Ile Thr Ile Lys
35 40 45

Leu Ile Gln Glu Ala Cys Lys Val Leu Asp Val Ser Met Glu Ala Ile
50 55 60

Leu Lys Leu Phe Gly Glu Tyr Phe Phe Lys Phe Cys Lys Met Ser Gly
65 70 75 80

Tyr Asp Arg Met Leu Arg Thr Leu Gly Gly Asn Leu Thr Glu Phe Ile
85 90 95

Glu Asn Leu Asp Ala Leu Asn Ser Tyr Leu Ala Leu Ser Tyr Gln Glu
100 105 110

Met Asn Ala Pro Ser Phe Arg Val Glu Glu Gly Ala Asp Gly Ala Met
115 120 125

Leu Leu His Tyr Tyr Ser Asp Arg His Gly Leu Cys His Ile Val Pro
130 135 140

Gly Ile Ile Glu Ala Val Ala Lys Asp Phe Phe Asp Thr Asp Val Ala
145 150 155 160

```
Met Ser Ile Leu Asp Met Asn Glu Glu Val Glu Arg Thr Gly Lys Lys
                165                 170                 175

Glu His Val Val Phe Leu Val Val Gln Lys Ala His Arg Gln
            180                 185                 190


<210> SEQ ID NO 15
<211> LENGTH: 188
<212> TYPE: PRT
<213> ORGANISM: Manduca sexta

<400> SEQUENCE: 15

Met Tyr Gly Phe Val Asn Tyr Ala Leu Glu Leu Leu Val Met Lys Thr
 1               5                  10                  15

Phe Asp Glu Glu Thr Trp Glu Thr Ile Lys Lys Lys Ala Asp Val Ala
            20                  25                  30

Met Glu Gly Ser Phe Leu Val Arg Gln Ile Tyr Glu Asp Glu Ile Thr
        35                  40                  45

Tyr Asn Leu Ile Thr Ala Ala Val Glu Val Leu Gln Ile Pro Ala Asp
    50                  55                  60

Ala Ile Leu Glu Leu Phe Gly Lys Thr Phe Phe Glu Phe Cys Gln Asp
65                  70                  75                  80

Ser Gly Tyr Asp Lys Ile Leu Gln Val Leu Gly Ala Thr Pro Arg Asp
                85                  90                  95

Phe Leu Gln Asn Leu Pro Gly Leu His Asp His Leu Gly Thr Leu Tyr
            100                 105                 110

Pro Gly Met Arg Ser Pro Ser Phe Arg Cys Thr Glu Arg Pro Glu Asp
        115                 120                 125

Gly Ala Leu Val Leu His Tyr Tyr Ser Asp Arg Pro Gly Leu Glu His
    130                 135                 140

Ile Val Ile Gly Ile Val Lys Thr Val Ala Ser Lys Leu His Asn Thr
145                 150                 155                 160

Glu Val Lys Val Glu Ile Leu Lys Thr Lys Glu Glu Cys Asp His Val
                165                 170                 175

Gln Phe Leu Ile Thr Glu Thr Ser Thr Thr Gly Arg
            180                 185


<210> SEQ ID NO 16
<211> LENGTH: 189
<212> TYPE: PRT
<213> ORGANISM: Mus musculus

<400> SEQUENCE: 16

Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Thr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110
```

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Asn Glu Glu Cys Asp His
                165                 170                 175

Thr Gln Phe Leu Ile Glu Glu Lys Glu Ser Lys Glu Glu
            180                 185

<210> SEQ ID NO 17
<211> LENGTH: 183
<212> TYPE: PRT
<213> ORGANISM: Nostoc punctiforme

<400> SEQUENCE: 17

Met Tyr Gly Leu Val Asn Lys Ala Ile Gln Asp Met Val Cys Ser Arg
1               5                   10                  15

Phe Gly Glu Glu Thr Trp Lys Gln Ile Lys His Lys Ala Glu Val Asp
            20                  25                  30

Val Asp Val Phe Leu Ser Met Glu Gly Tyr Pro Asp Asp Ile Thr His
        35                  40                  45

Lys Leu Val Lys Ala Ala Ser Val Ile Leu Ser Leu Ser Pro Lys Gln
    50                  55                  60

Ile Met Gln Ala Phe Gly Glu Phe Trp Val Gln Tyr Thr Ala Gln Glu
65                  70                  75                  80

Gly Tyr Gly Glu Met Leu Asp Met Ser Gly Asp Thr Leu Pro Glu Phe
                85                  90                  95

Leu Glu Asn Leu Asp Asn Leu His Ala Arg Val Gly Val Ser Phe Pro
            100                 105                 110

Lys Leu Gln Pro Pro Ser Phe Glu Cys Thr Asp Met Glu Glu Asn Ser
        115                 120                 125

Leu Ser Leu His Tyr Arg Ser Asp Arg Glu Gly Leu Thr Pro Met Val
    130                 135                 140

Ile Gly Leu Ile Lys Gly Leu Gly Thr Arg Phe Asp Thr Glu Val His
145                 150                 155                 160

Ile Thr Gln Thr Gln Asn Arg Asp Glu Gly Ala Glu His Asp Glu Phe
                165                 170                 175

Leu Val Ile Tyr Lys Pro Asn
            180

<210> SEQ ID NO 18
<211> LENGTH: 189
<212> TYPE: PRT
<213> ORGANISM: Takifugu rubripes

<400> SEQUENCE: 18

Met Tyr Gly Phe Val Asn His Ala Leu Glu Leu Leu Val Leu Arg Asn
1               5                   10                  15

Tyr Gly Pro Glu Val Trp Glu Asp Ile Lys Arg Glu Ala Gln Leu Asp
            20                  25                  30

Ile Glu Gly Gln Phe Leu Val Arg Ile Ile Tyr Glu Asp Ala Lys Thr
        35                  40                  45

Tyr Asp Leu Val Ala Ala Ala Ser Lys Val Leu Lys Ile Asp Ala Gly
    50                  55                  60

```
Asp Ile Leu Gln Leu Phe Gly Lys Met Phe Phe Glu Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Gly Thr Ile Tyr
            100                 105                 110

Pro Gly Met Arg Ala Pro Ser Phe Arg Cys Thr Asp Ala Glu Lys Gly
        115                 120                 125

Asn Ser Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Glu Met Lys Met Ile Gln Pro Lys Ser Lys Glu Cys Asp His
                165                 170                 175

Ile Lys Phe Leu Ile Glu Glu Lys Asp Ser Glu Glu Glu
            180                 185


<210> SEQ ID NO 19
<211> LENGTH: 185
<212> TYPE: PRT
<213> ORGANISM: Anopheles gambiae

<400> SEQUENCE: 19

Tyr Gly Phe Val Asn Tyr Ala Leu Glu Leu Leu Val Leu Lys Asn Phe
 1               5                  10                  15

Gly Leu Asn Ile Trp Glu Gln Ile Lys Lys Lys Ala Gln Val Asn Met
            20                  25                  30

Glu Gly Gln Phe Leu Val Arg Gln Ile Tyr Glu Asp Asp Ile Thr Tyr
        35                  40                  45

Asn Leu Ile Glu Ala Ala Val Asp Ile Leu Asn Ile Pro Ala Gly Asp
    50                  55                  60

Ile Leu Glu Leu Phe Gly Lys Thr Phe Phe Glu Phe Cys Gln Asp Ser
65                  70                  75                  80

Gly Tyr Asp Lys Ile Leu Gln Val Leu Gly Ala Thr Pro Arg Asp Phe
                85                  90                  95

Leu Gln Asn Leu Asp Ala Leu His Asp His Leu Gly Thr Leu Tyr Pro
            100                 105                 110

Gly Met Arg Ala Pro Ser Phe Arg Cys Thr Glu Thr Asn Gly Gln Leu
        115                 120                 125

Val Leu His Tyr Tyr Ser Glu Arg Pro Gly Leu Glu His Ile Val Ile
    130                 135                 140

Gly Ile Val Lys Ala Val Ala Ser Lys Leu His Gly Val Asp Val Glu
145                 150                 155                 160

Ile Lys Ile Ile Arg Arg Lys Gly Asp Pro Val Glu Pro Glu Ala Lys
                165                 170                 175

Lys Arg Arg Thr Ala Val Pro Ile Thr
            180                 185


<210> SEQ ID NO 20
<211> LENGTH: 188
<212> TYPE: PRT
<213> ORGANISM: Apis mellifera

<400> SEQUENCE: 20

Met Tyr Gly Phe Val Asn Tyr Ala Leu Glu Leu Leu Val Val Lys Thr
 1               5                  10                  15
```

-continued

```
Phe Asp Ser Glu Thr Trp Glu Ala Ile Lys Lys Asp Ala Ala Val Asn
            20                  25                  30

Met Glu Gly Gln Phe Leu Val Arg Gln Ile Tyr Asp Asp Glu Ile Thr
        35                  40                  45

Tyr Asn Ile Ile Ser Ala Ala Val Asn Arg Leu Asn Ile Pro Ala Asn
    50                  55                  60

Glu Ile Leu Glu Leu Phe Gly Arg Met Phe Phe Glu Phe Cys Gln Asp
65                  70                  75                  80

Ser Gly Tyr Asp Lys Ile Leu Gln Val Leu Gly Ala Thr Pro Arg Asp
                85                  90                  95

Phe Leu Gln Asn Leu Asp Ala Leu His Asp His Leu Gly Thr Leu Tyr
            100                 105                 110

Pro Gly Met Arg Ala Pro Ser Phe Arg Cys Thr Glu Arg Pro Glu Asp
        115                 120                 125

Gly Ala Leu Ile Leu His Tyr Tyr Ser Asp Arg Pro Gly Leu Glu His
    130                 135                 140

Ile Val Ile Gly Ile Val Lys Thr Val Ala Lys Lys Leu His Gly Thr
145                 150                 155                 160

Asp Ile Glu Met Arg Ile Leu Lys Thr Lys Asn Glu Cys Asp His Val
                165                 170                 175

Gln Phe Leu Ile Thr Asn Thr Ser Gly Pro Gly Val
            180                 185


<210> SEQ ID NO 21
<211> LENGTH: 189
<212> TYPE: PRT
<213> ORGANISM: Bos taurus

<400> SEQUENCE: 21

Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Asp Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Asn Glu Glu Cys Asp His
                165                 170                 175

Thr Gln Phe Leu Ile Glu Glu Lys Glu Ser Lys Glu Glu
            180                 185


<210> SEQ ID NO 22
```

<211> LENGTH: 190
<212> TYPE: PRT
<213> ORGANISM: Chlamydomonas reinhardtii

<400> SEQUENCE: 22

Met Leu Gly Trp Tyr Asp Arg Ala Ile Glu Ser Phe Leu Lys Gln Leu
1 5 10 15

Gly Ala Asp Ala Trp Arg Gly Thr Leu His Ser Ala Val Gly Gln Asp
20 25 30

Pro Val Leu Trp Cys Thr Pro Ser Cys Pro Ala Gly Asp Thr Ala Thr
35 40 45

Leu Ala Leu Phe Cys Ser Ala Ala Gln Ser Asn Thr Leu Glu Ala Thr
50 55 60

Pro His Gln Leu Leu Glu Glu Phe Gly Glu Tyr Phe Val Ser Tyr Leu
65 70 75 80

Thr Glu Gln Gly Tyr Ser Asn Leu Leu Arg Thr Leu Gly Thr Ser Leu
85 90 95

Leu Glu Phe Leu Gln Asn Leu Asp Asp Val His Leu His Leu Gly Leu
100 105 110

Met Phe Pro Ala Met Ala Val Pro Ala Phe Glu Cys Thr Asp Val Gly
115 120 125

Pro Thr Cys Leu Lys Leu His Tyr His Ser His Arg Pro Ala Leu Gly
130 135 140

Pro Ile Val Val Gly Val Leu Lys Gly Leu Ala Glu Gln Tyr Trp Gly
145 150 155 160

Leu Gly Gly Glu Gln Leu Gln Val Glu Leu Leu Arg Gly Arg Asp Asp
165 170 175

Cys Gly Ser Glu Asp Asp Asp His Asp Val Phe Arg Val Ser
180 185 190

<210> SEQ ID NO 23
<211> LENGTH: 189
<212> TYPE: PRT
<213> ORGANISM: Oryzias curvinotus

<400> SEQUENCE: 23

Met Tyr Gly Phe Val Asn His Ala Leu Glu Leu Leu Val Leu Arg Asn
1 5 10 15

Tyr Gly Pro Glu Val Trp Glu Asp Ile Lys Arg Glu Ala Gln Leu Asp
20 25 30

Ile Glu Gly Gln Phe Leu Val Arg Ile Ile Tyr Glu Asp Ala Lys Thr
35 40 45

Tyr Asp Leu Val Ala Ala Ala Ser Lys Val Leu Lys Ile Asn Ala Gly
50 55 60

Asp Ile Leu Gln Met Phe Gly Lys Met Phe Phe Glu Phe Cys Gln Glu
65 70 75 80

Ser Gly Tyr Asp Thr Ile Leu Arg Val Leu Gly Ser Asn Val Arg Glu
85 90 95

Phe Leu Gln Asn Leu Asp Ala Leu His Asp His Leu Gly Thr Ile Tyr
100 105 110

Pro Gly Met Arg Ala Pro Ser Phe Arg Cys Thr Asp Ala Glu Lys Gly
115 120 125

Asn Asn Leu Ile Leu His Tyr Tyr Ser Glu Arg Glu Gly Leu Gln Asp
130 135 140

Ile Val Ile Gly Ile Ile Lys Thr Val Ala Gln Gln Ile His Gly Thr
145 150 155 160

```
Glu Ile Glu Met Lys Val Ile Gln Gln Lys Ser Glu Glu Cys Asp His
                165                 170                 175

Ile Lys Phe Leu Ile Glu Glu Lys Asp Ser Glu Glu Glu
            180                 185


<210> SEQ ID NO 24
<211> LENGTH: 189
<212> TYPE: PRT
<213> ORGANISM: Oryzias latipes

<400> SEQUENCE: 24

Met Tyr Gly Phe Val Asn His Ala Leu Glu Leu Leu Val Leu Arg Asn
 1               5                  10                  15

Tyr Gly Pro Glu Val Trp Glu Asp Ile Lys Arg Glu Ala Gln Leu Asp
            20                  25                  30

Ile Glu Gly Gln Phe Leu Val Arg Ile Ile Tyr Glu Asp Ala Lys Thr
        35                  40                  45

Tyr Asp Leu Val Ala Ala Ala Ser Lys Val Leu Lys Ile Asn Ala Gly
    50                  55                  60

Asp Ile Leu Gln Met Phe Gly Lys Met Phe Phe Glu Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Gly Thr Ile Tyr
            100                 105                 110

Pro Gly Met Arg Ala Pro Ser Phe Arg Cys Thr Asp Ala Glu Lys Gly
        115                 120                 125

Asn Asn Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Glu Met Lys Val Ile Gln Gln Lys Ser Glu Glu Cys Asp His
                165                 170                 175

Ile Lys Phe Leu Ile Glu Glu Lys Asp Ser Glu Glu Glu
            180                 185


<210> SEQ ID NO 25
<211> LENGTH: 189
<212> TYPE: PRT
<213> ORGANISM: Strongylocentrotus purpuratus

<400> SEQUENCE: 25

Met Tyr Gly Phe Val Asn His Ala Leu Glu Leu Leu Val Leu Arg Glu
 1               5                  10                  15

His Gly Gln Asp Lys Trp Glu Glu Ile Lys Arg Glu Ala Ala Val Glu
            20                  25                  30

Ile Glu Gly Ser Phe Leu Val Arg Ile Val Tyr Asp Asp Val Leu Ser
        35                  40                  45

Tyr Asp Leu Val Gly Ala Ala Val Lys Val Leu Glu Ile Ser Ala Asn
    50                  55                  60

Asp Leu Leu Glu Ala Phe Gly Arg Met Phe Phe Glu Phe Cys Val Glu
65                  70                  75                  80

Ser Gly Tyr Asp Asn Ile Leu Asn Val Leu Gly Ser Thr Thr Arg His
                85                  90                  95

Phe Leu Gln Asn Leu Asp Ala Leu His Asp His Leu Ala Ser Ile Tyr
            100                 105                 110
```

Pro Gly Met Arg Ala Pro Ser Phe Arg Cys Ser Thr Arg Asp Ser Asp
115 120 125

Gly Ala Leu Val Leu His Tyr Tyr Ser Glu Arg Pro Gly Leu Glu His
130 135 140

Ile Val Ile Gly Leu Val Arg Ser Val Ala Lys Thr Leu His Gly Ser
145 150 155 160

Glu Val His Val Glu Ile Ile Lys Asn Lys Gly Glu Asp Cys Asp His
165 170 175

Val Gln Phe Ala Ile Ile Glu Lys Val Glu Thr Ala Lys
180 185

<210> SEQ ID NO 26
<211> LENGTH: 189
<212> TYPE: PRT
<213> ORGANISM: Sus scrofa

<400> SEQUENCE: 26

Met Tyr Gly Phe Val Asn His Ala Leu Glu Leu Leu Val Ile Arg Asn
1 5 10 15

Tyr Gly Pro Glu Val Trp Glu Asp Ile Lys Lys Glu Ala Gln Leu Asp
20 25 30

Glu Glu Gly Gln Phe Leu Val Arg Ile Ile Tyr Asp Asp Ser Lys Thr
35 40 45

Tyr Asp Leu Val Ala Ala Ala Ser Lys Val Leu Asn Leu Asn Ala Gly
50 55 60

Glu Ile Leu Gln Met Phe Gly Lys Met Phe Phe Val Phe Cys Gln Glu
65 70 75 80

Ser Gly Tyr Asp Thr Ile Leu Arg Val Leu Gly Ser Asn Val Arg Glu
85 90 95

Phe Leu Gln Asn Leu Asp Ala Leu His Asp His Leu Ala Ala Ile Tyr
100 105 110

Pro Gly Met Arg Ala Pro Ser Phe Arg Cys Thr Asp Ala Glu Lys Gly
115 120 125

Lys Gly Leu Ile Leu His Tyr Tyr Ser Glu Arg Glu Gly Leu Gln Asp
130 135 140

Ile Val Ile Gly Ile Ile Lys Thr Val Ala Gln Gln Ile His Gly Thr
145 150 155 160

Glu Ile Asp Met Lys Val Ile Gln Gln Arg Asn Glu Glu Cys Asp His
165 170 175

Thr Gln Phe Leu Ile Glu Glu Lys Glu Ser Lys Glu Glu
180 185

<210> SEQ ID NO 27
<211> LENGTH: 184
<212> TYPE: PRT
<213> ORGANISM: Artificial Sequence
<220> FEATURE:
<223> OTHER INFORMATION: Synthetic Construct

<400> SEQUENCE: 27

Met Tyr Gly Phe Val Asn His Ala Leu Glu Leu Leu Val Leu Arg Asn
1 5 10 15

Tyr Gly Glu Glu Val Trp Glu Asp Ile Lys Lys Glu Ala Gly Val Asp
20 25 30

Glu Gly Ser Phe Leu Val Arg Ile Ile Tyr Asp Asp Ser Leu Thr Tyr
35 40 45

-continued

Asp Leu Val Ala Ala Ala Ser Lys Val Leu Gly Ile Ser Ala Gly Asp
    50                  55                  60

Ile Leu Gln Leu Phe Gly Lys Met Phe Phe Glu Phe Cys Gln Glu Ser
65                  70                  75                  80

Gly Tyr Asp Thr Ile Leu Arg Val Leu Gly Ser Asn Val Arg Glu Phe
                85                  90                  95

Leu Gln Asn Leu Asp Ala Leu His Asp His Leu Ala Thr Ile Tyr Pro
            100                 105                 110

Gly Met Arg Ala Pro Ser Phe Arg Cys Thr Asp Ala Glu Gly Gly Gly
        115                 120                 125

Leu Ile Leu His Tyr Tyr Ser Glu Arg Glu Gly Leu Gln Asp Ile Tyr
    130                 135                 140

Ile Gly Ile Ile Lys Thr Val Ala Gln Gln Phe His Gly Thr Glu Ile
145                 150                 155                 160

Glu Ile Glu Val Ile Gln Gln Lys Gly Glu Glu Cys Asp His Val Gln
                165                 170                 175

Phe Leu Ile Glu Glu Lys Asn Ser
            180

<210> SEQ ID NO 28
<211> LENGTH: 172
<212> TYPE: PRT
<213> ORGANISM: Homo sapiens

<400> SEQUENCE: 28

Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Asn Glu
                165                 170

<210> SEQ ID NO 29
<211> LENGTH: 172
<212> TYPE: PRT
<213> ORGANISM: Rattus norvegicus

<400> SEQUENCE: 29

Met Tyr Gly Phe Val Asn His Ala Leu Glu Leu Leu Val Ile Arg Asn
 1               5                  10                  15

-continued

```
Tyr Gly Pro Glu Val Trp Glu Asp Ile Lys Lys Glu Ala Gln Leu Asp
            20                  25                  30

Gln Glu Gly Gln Phe Leu Val Arg Ile Ile Tyr Asp His Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Ser Glu
                165                 170


<210> SEQ ID NO 30
<211> LENGTH: 170
<212> TYPE: PRT
<213> ORGANISM: Drosophila melangaster

<400> SEQUENCE: 30

Met Tyr Gly Phe Val Asn Tyr Ala Leu Glu Leu Leu Val Leu Lys His
 1               5                  10                  15

Phe Gly Glu Glu Ile Trp Glu Lys Ile Lys Lys Lys Ala Met Val Ser
            20                  25                  30

Met Glu Gly Gln Phe Leu Val Arg Gln Ile Tyr Asp Asp Glu Ile Thr
        35                  40                  45

Tyr Asn Leu Ile Gly Ala Ala Val Glu Ile Leu Asn Ile Pro Ala Asp
    50                  55                  60

Asp Ile Leu Glu Leu Phe Gly Lys Thr Phe Phe Glu Phe Cys Gln Asp
65                  70                  75                  80

Ser Gly Tyr Asp Lys Ile Leu Gln Val Leu Gly Ala Thr Pro Arg Asp
                85                  90                  95

Phe Leu Gln Asn Leu Asp Ala Leu His Asp His Leu Gly Thr Leu Tyr
            100                 105                 110

Pro Gly Met Arg Ala Pro Ser Phe Arg Cys Thr Glu Lys Asp Gly Glu
        115                 120                 125

Leu Leu Leu His Tyr Tyr Ser Glu Arg Pro Gly Leu Glu His Ile Val
    130                 135                 140

Ile Gly Ile Val Lys Ala Val Ala Ser Lys Leu His Gly Val Glu Val
145                 150                 155                 160

Glu Ile Asp Ile Val Lys Arg Lys Gly Glu
                165                 170


<210> SEQ ID NO 31
<211> LENGTH: 170
<212> TYPE: PRT
<213> ORGANISM: Drosophila melangaster

<400> SEQUENCE: 31
```

-continued

```
Met Tyr Gly Met Leu Tyr Glu Ser Val Gln His Tyr Val Gln Glu Glu
 1               5                  10                  15

Tyr Gly Val Asp Ile Trp Arg Lys Val Cys His Ile Ile Asp Cys Lys
            20                  25                  30

His Asn Ser Phe Lys Thr His Gln Ile Tyr Pro Asp Lys Leu Met Pro
        35                  40                  45

Asp Ile Ala Glu Ala Leu Ser Ala Cys Thr Gly Glu Ser Phe Asp Phe
    50                  55                  60

Cys Met Asn Phe Phe Gly Arg Cys Phe Val Arg Phe Phe Ser Asn Phe
65                  70                  75                  80

Gly Tyr Asp Lys Met Ile Arg Ser Thr Gly Arg Tyr Phe Cys Asp Phe
                85                  90                  95

Leu Gln Ser Ile Asp Asn Ile His Leu Ile Met Arg Phe Thr Tyr Pro
            100                 105                 110

Lys Met Lys Ser Pro Ser Met Gln Leu Thr Asn Met Asp Asp Asn Gly
        115                 120                 125

Ala Val Ile Leu Tyr Arg Ser Ser Arg Thr Gly Met Ser Lys Tyr Leu
    130                 135                 140

Ile Gly Gln Met Thr Glu Val Ala Arg Glu Phe Tyr Gly Leu Glu Ile
145                 150                 155                 160

Lys Ala Tyr Val Ile Glu Ser Gln Asn Asp
                165                 170
```

<210> SEQ ID NO 32
<211> LENGTH: 173
<212> TYPE: PRT
<213> ORGANISM: Caenorhabditis elegans

<400> SEQUENCE: 32

```
Met Phe Gly Trp Ile His Glu Ser Phe Arg Gln Leu Val Thr Arg Lys
 1               5                  10                  15

Tyr Gly Lys Asp Ile Trp Glu Lys Ile Val His Met Ser Lys Phe Glu
            20                  25                  30

Leu Gly Thr Glu Ser Glu Ile Ala His Tyr Tyr Asn Asp Asp Glu Thr
        35                  40                  45

Leu Arg Leu Val Asn Ser Met Ala Asn Val Ile Gly Ile Pro Ile Glu
    50                  55                  60

Glu Ile Trp Glu Ala Tyr Gly Gly Phe Leu Ile Gln Phe Thr Met Glu
65                  70                  75                  80

Thr Gly Trp Asp Glu Leu Leu Arg Ala Met Ala Pro Asp Leu Glu Gly
                85                  90                  95

Phe Leu Asp Ser Leu Asp Ser Leu His Tyr Phe Ile Asp His Val Val
            100                 105                 110

Tyr Lys Thr Lys Leu Arg Gly Pro Ser Phe Arg Cys Asp Val Gln Ala
        115                 120                 125

Asp Gly Thr Leu Leu Leu His Tyr Tyr Ser Lys Arg Ser Gly Leu Tyr
    130                 135                 140

Pro Ile Val Lys Gly Val Val Arg Glu Val Ala Arg Arg Ile Tyr Asp
145                 150                 155                 160

Thr Glu Val Val Met Lys Val Gln Glu Arg Lys Gln Glu
                165                 170
```

<210> SEQ ID NO 33
<211> LENGTH: 169
<212> TYPE: PRT
<213> ORGANISM: Nostoc punctiforme

<400> SEQUENCE: 33

Met Tyr Gly Leu Val Asn Lys Ala Ile Gln Asp Met Val Cys Ser Arg
1 5 10 15

Phe Gly Glu Glu Thr Trp Lys Gln Ile Lys His Lys Ala Glu Val Asp
20 25 30

Val Asp Val Phe Leu Ser Met Glu Gly Tyr Pro Asp Asp Ile Thr His
35 40 45

Lys Leu Val Lys Ala Ala Ser Val Ile Leu Ser Leu Ser Pro Lys Gln
50 55 60

Ile Met Gln Ala Phe Gly Glu Phe Trp Val Gln Tyr Thr Ala Gln Glu
65 70 75 80

Gly Tyr Gly Glu Met Leu Asp Met Ser Gly Asp Thr Leu Pro Glu Phe
85 90 95

Leu Glu Asn Leu Asp Asn Leu His Ala Arg Val Gly Val Ser Phe Pro
100 105 110

Lys Leu Gln Pro Pro Ser Phe Glu Cys Thr Asp Met Glu Glu Asn Ser
115 120 125

Leu Ser Leu His Tyr Arg Ser Asp Arg Glu Gly Leu Thr Pro Met Val
130 135 140

Ile Gly Leu Ile Lys Gly Leu Gly Thr Arg Phe Asp Thr Glu Val His
145 150 155 160

Ile Thr Gln Thr Gln Asn Arg Asp Glu
165

<210> SEQ ID NO 34
<211> LENGTH: 166
<212> TYPE: PRT
<213> ORGANISM: Caulobacter crescentus

<400> SEQUENCE: 34

Met Lys Gly Val Ile Phe Asn Leu Leu Gln Glu Val Val Ser Ala Ala
1 5 10 15

His Gly Ala Asp Ala Trp Asp Asp Ile Leu Asp Glu Ala Gly Val Ser
20 25 30

Gly Ala Tyr Thr Ser Leu Gly Ser Tyr Asp Asp Glu Glu Trp Glu Thr
35 40 45

Leu Val Glu Thr Ala Ser Ala Arg Leu Ser Leu Ser Arg Gly Glu Leu
50 55 60

Leu Arg Trp Phe Gly Gln Glu Ala Met Pro His Leu Ala Arg Ala Tyr
65 70 75 80

Pro Val Phe Phe Glu Gly His Val Ser Ser Arg Ser Phe Leu Ala Gly
85 90 95

Val Asn Asp Ile Ile His Ala Glu Val His Lys Leu Tyr Ala Gly Ala
100 105 110

Ala Cys Pro His Leu Lys Leu Arg Ala Ile Asp Ala Gly Gly Val Ala
115 120 125

Met Ala Tyr Thr Ser Gln Arg Arg Met Cys Ala Leu Ala Gln Gly Phe
130 135 140

Thr Glu Gly Ala Ala Arg Gln Phe His Glu Val Ile Thr Phe Glu His
145 150 155 160

Ala Ala Cys Val Glu Lys
165

<210> SEQ ID NO 35

<211> LENGTH: 167
<212> TYPE: PRT
<213> ORGANISM: Shewanella oneidensis

<400> SEQUENCE: 35

```
Met Lys Gly Ile Ile Phe Asn Val Leu Glu Asp Met Val Val Ala Gln
 1               5                  10                  15

Cys Gly Met Ser Val Trp Asn Glu Leu Leu Glu Lys His Ala Pro Lys
            20                  25                  30

Asp Arg Val Tyr Val Ser Ala Lys Ser Tyr Ala Glu Ser Glu Leu Phe
        35                  40                  45

Ser Ile Val Gln Asp Val Ala Gln Arg Leu Asn Met Pro Ile Gln Asp
    50                  55                  60

Val Val Lys Ala Phe Gly Gln Phe Leu Phe Asn Gly Leu Ala Ser Arg
65                  70                  75                  80

His Thr Asp Val Val Asp Lys Phe Asp Asp Phe Thr Ser Leu Val Met
                85                  90                  95

Gly Ile His Asp Val Ile His Leu Glu Val Asn Lys Leu Tyr His Glu
            100                 105                 110

Pro Ser Leu Pro His Ile Asn Gly Gln Leu Leu Pro Asn Asn Gln Ile
        115                 120                 125

Ala Leu Arg Tyr Ser Ser Pro Arg Arg Leu Cys Phe Cys Ala Glu Gly
    130                 135                 140

Leu Leu Phe Gly Ala Ala Gln His Phe Gln Gln Lys Ile Gln Ile Ser
145                 150                 155                 160

His Asp Thr Cys Met His Thr
                165
```

<210> SEQ ID NO 36
<211> LENGTH: 169
<212> TYPE: PRT
<213> ORGANISM: Legionella pneumophila

<400> SEQUENCE: 36

```
Met Lys Gly Ile Ile Phe Asn Glu Phe Leu Asn Phe Val Glu Lys Ser
 1               5                  10                  15

Glu Ser Tyr Thr Leu Val Asp Gln Ile Ile Met Asp Ser His Leu Lys
            20                  25                  30

Ser His Gly Ala Tyr Thr Ser Ile Gly Thr Tyr Ser Pro Lys Glu Leu
        35                  40                  45

Phe Gln Leu Val Lys Ala Leu Ala Met Lys Asn Gly Lys Pro Thr Ser
    50                  55                  60

Val Ile Leu Gln Glu Tyr Gly Glu Tyr Leu Phe Glu Val Phe Ala Lys
65                  70                  75                  80

Lys Tyr Pro Gln Phe Phe Arg Glu Lys Lys Ser Val Phe Gln Phe Leu
                85                  90                  95

Glu Ala Leu Glu Thr His Ile His Phe Glu Val Lys Lys Leu Tyr Asp
            100                 105                 110

Tyr Thr Glu Leu Pro His Phe Glu Cys Gln Tyr His Ser Gln Asn Gln
        115                 120                 125

Met Glu Met Ile Tyr Thr Ser Ser Arg Pro Leu Ala Asp Phe Ala Glu
    130                 135                 140

Gly Leu Ile Lys Gly Cys Ile Lys Tyr His Lys Glu Asn Met Thr Ile
145                 150                 155                 160

Val Arg Glu Asn Leu Pro Ala Lys Thr
                165
```

<210> SEQ ID NO 37
<211> LENGTH: 166
<212> TYPE: PRT
<213> ORGANISM: Clostridium acetobutylicum

<400> SEQUENCE: 37

```
Met Lys Gly Thr Val Val Gly Thr Trp Val Lys Thr Cys Lys Arg Leu
 1               5                  10                  15

Tyr Gly Glu Thr Val Val Glu Asn Ala Leu Glu Lys Val Gly Phe Glu
            20                  25                  30

Arg Lys Lys Ile Phe Ser Pro Phe Glu Asp Val Glu Asp Ser Lys Val
        35                  40                  45

Asn Asn Phe Ile Glu Asp Ile Ser Lys Lys Val Asn Glu Glu Lys Ser
    50                  55                  60

Ile Ile Trp Glu Lys Ile Gly Glu Asp Asn Val Ile Ala Phe His Lys
65                  70                  75                  80

Asp Phe Pro Ala Phe Phe Glu His Glu Asn Leu Tyr Ser Phe Phe Lys
                85                  90                  95

Ser Met Phe Asp Val His Val Val Met Thr Lys Lys Phe Pro Gly Ala
            100                 105                 110

Lys Pro Pro Leu Ile Leu Ile Lys Pro Ile Ser Lys Arg Glu Ala Ile
        115                 120                 125

Phe Thr Tyr Arg Ser Lys Arg Gly Met Phe Asp Tyr Leu Lys Gly Leu
    130                 135                 140

Ile Lys Gly Ser Ala Asn His Phe Asn Glu Lys Ile Glu Ile Glu Glu
145                 150                 155                 160

Val Glu Lys Thr Lys Glu
                165
```

<210> SEQ ID NO 38
<211> LENGTH: 163
<212> TYPE: PRT
<213> ORGANISM: Thermoanaerobacter tengcongensis

<400> SEQUENCE: 38

```
Met Lys Gly Thr Ile Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160
```

Val Glu Arg

<210> SEQ ID NO 39
<211> LENGTH: 188
<212> TYPE: PRT
<213> ORGANISM: Thermoanaerobacter tengcongensis

<400> SEQUENCE: 39

Met Lys Gly Thr Ile Val Gly Thr Trp Ile Lys Thr Leu Arg Asp Leu
1 5 10 15

Tyr Gly Asn Asp Val Val Asp Glu Ser Leu Lys Ser Val Gly Trp Glu
20 25 30

Pro Asp Arg Val Ile Thr Pro Leu Glu Asp Ile Asp Asp Asp Glu Val
35 40 45

Arg Arg Ile Pro Ala Lys Val Ser Glu Lys Thr Gly Lys Asn Val Asn
50 55 60

Glu Ile Trp Arg Glu Val Gly Arg Gln Asn Ile Lys Thr Phe Ser Glu
65 70 75 80

Trp Phe Pro Ser Tyr Phe Ala Gly Arg Arg Leu Val Asn Phe Leu Met
85 90 95

Met Met Asp Glu Val His Leu Gln Leu Thr Lys Met Ile Lys Gly Ala
100 105 110

Thr Pro Pro Arg Leu Ile Ala Lys Pro Val Ala Lys Asp Ala Ile Glu
115 120 125

Met Glu Tyr Val Ser Lys Arg Lys Met Tyr Asp Tyr Phe Leu Gly Leu
130 135 140

Ile Glu Gly Ser Ser Lys Phe Phe Lys Glu Glu Ile Ser Val Glu Glu
145 150 155 160

Val Glu Arg Gly Glu Lys Asp Gly Phe Ser Arg Leu Lys Val Arg Ile
165 170 175

Lys Phe Lys Asn Pro Val Phe Glu Tyr Lys Lys Asn
180 185

<210> SEQ ID NO 40
<211> LENGTH: 184
<212> TYPE: PRT
<213> ORGANISM: Clostridium acetobutiylicum

<400> SEQUENCE: 40

Met Lys Gly Thr Val Val Gly Thr Trp Val Lys Thr Cys Lys Arg Leu
1 5 10 15

Tyr Gly Glu Thr Val Val Glu Asn Ala Leu Glu Lys Val Gly Phe Glu
20 25 30

Arg Lys Lys Ile Phe Ser Pro Phe Glu Asp Val Glu Asp Ser Lys Val
35 40 45

Asn Asn Phe Ile Glu Asp Ile Ser Lys Lys Val Asn Glu Glu Lys Ser
50 55 60

Ile Ile Trp Glu Lys Ile Gly Glu Asp Asn Val Ile Ala Phe His Lys
65 70 75 80

Asp Phe Pro Ala Phe Phe Glu His Glu Asn Leu Tyr Ser Phe Phe Lys
85 90 95

Ser Met Phe Asp Val His Val Val Met Thr Lys Lys Phe Pro Gly Ala
100 105 110

Lys Pro Pro Leu Ile Leu Ile Lys Pro Ile Ser Lys Arg Glu Ala Ile
115 120 125

-continued

Phe Thr Tyr Arg Ser Lys Arg Gly Met Phe Asp Tyr Leu Lys Gly Leu
    130                 135                 140

Ile Lys Gly Ser Ala Asn His Phe Asn Glu Lys Ile Glu Ile Glu Glu
145                 150                 155                 160

Val Glu Lys Thr Lys Glu Ser Val Val Leu Lys Phe Thr Phe Asp Lys
                165                 170                 175

Asp Ile Tyr Tyr Lys Lys Ser Phe
            180

<210> SEQ ID NO 41
<211> LENGTH: 184
<212> TYPE: PRT
<213> ORGANISM: Clostridium tetani

<400> SEQUENCE: 41

Met Lys Gly Thr Ile Val Ala Thr Trp Met Arg Thr Cys Arg Lys Leu
 1               5                  10                  15

Tyr Asn Asp Asp Val Val Asn Lys Ala Met Ser Ser Val Gly Trp Asp
            20                  25                  30

Ser Asn Lys Ile Phe Lys Pro Thr Glu Asn Val Glu Asp Ser Asp Leu
        35                  40                  45

Lys Lys Val Ile Glu Tyr Ile Ala Lys Ser Glu Lys Leu Glu Leu Gly
    50                  55                  60

His Leu Trp Arg Gln Ile Gly Lys Asp Asn Leu Val Ser Phe Tyr Asn
65                  70                  75                  80

Asp Phe Pro Ala Phe Phe Gln His Glu Asn Leu Tyr Ser Phe Phe Asn
                85                  90                  95

Ser Leu Phe Asp Ile His Val Val Met Thr Lys Lys Phe Pro Gly Ala
            100                 105                 110

Lys Pro Pro Leu Val Thr Ile Glu Pro Ile Ser Ser Lys Glu Ala Ile
        115                 120                 125

Phe Tyr Tyr Glu Ser Lys Arg Gly Met Phe Asp Tyr Leu Leu Gly Leu
    130                 135                 140

Ile Glu Gly Ser Ile Lys Tyr Phe Lys Glu Asp Ile Glu Ile Glu Glu
145                 150                 155                 160

Leu Glu Arg Thr Asn Glu Ser Leu Lys Leu Lys Leu Lys Phe Gln Lys
                165                 170                 175

Asn Ile Tyr Leu Lys Lys Glu Phe
            180

<210> SEQ ID NO 42
<211> LENGTH: 172
<212> TYPE: PRT
<213> ORGANISM: Desulfovibrio desulfuricans

<400> SEQUENCE: 42

Met Arg Gly Ile Leu Pro Lys Ile Phe Met Asn Phe Ile Lys Glu Ile
 1               5                  10                  15

Tyr Gly Asp Asp Val Phe Ala His Val Ser Lys Thr Met Gly Glu Pro
            20                  25                  30

Val Phe Met Pro Gly Asn Ser Tyr Pro Asp Gln Val Leu Arg Gln Met
        35                  40                  45

Ala Glu Ile Val Cys Gln Arg Thr Gly Glu Gln Pro Lys Leu Phe Phe
    50                  55                  60

Glu Lys Ala Gly Arg Ala Ser Leu Gln Ala Phe Asn Arg Met Tyr Arg
65                  70                  75                  80

-continued

```
Gln Tyr Phe Lys Gly Glu Thr Leu Lys Glu Phe Leu Leu Ala Met Asn
                85                  90                  95

Asp Ile His Arg His Leu Thr Lys Asp Asn Pro Gly Val Arg Pro Pro
            100                 105                 110

Lys Phe Glu Tyr Asp Asp Gln Gly Asp Thr Leu Val Met Thr Tyr Lys
        115                 120                 125

Ser Gln Arg Asp Tyr Gly Glu Tyr Phe Val Gly Ile Ile Lys Ala Ala
    130                 135                 140

Ala Glu Phe Lys Lys Glu Lys Val Arg Ile Ser Ser Glu His Ala Gly
145                 150                 155                 160

Lys Gly Arg Thr Thr Ala Arg Val Thr Phe Ile Lys
                165                 170


<210> SEQ ID NO 43
<211> LENGTH: 185
<212> TYPE: PRT
<213> ORGANISM: Vibrio vulnificus

<400> SEQUENCE: 43

Met Lys Gly Ile Ile Phe Thr Glu Phe Leu Glu Leu Val Glu Glu Lys
 1               5                  10                  15

Phe Gly Leu Thr Val Leu Asp Asp Ile Leu Asp Arg Ala Gly Asp Glu
            20                  25                  30

Gly Val Tyr Thr Ala Val Gly Ser Tyr Asp His Arg Lys Leu Val Ser
        35                  40                  45

Leu Ile Val His Leu Ser Gln Val Thr Gly Leu Ser Val Glu Gln Leu
    50                  55                  60

Gln Glu Val Phe Gly Glu Ala Val Phe Asp Asn Leu Leu Ala Ser Ile
65                  70                  75                  80

Ser Asn Arg Ser Ser Leu His Gln Cys His Ser Thr Phe Gln Phe Ile
                85                  90                  95

Arg His Val Glu Glu Tyr Ile His Val Glu Val Lys Lys Leu Tyr Pro
            100                 105                 110

Asp Ala Lys Pro Pro Glu Phe Ile Phe Ile Glu Gln Asp Arg Met Lys
        115                 120                 125

Met Val Phe Asp Tyr Lys Ser Ala Arg Cys Met Gly His Val Cys Leu
    130                 135                 140

Gly Leu Met Arg Gly Cys Ala Lys His Phe Gly Glu Glu Leu Ala Ile
145                 150                 155                 160

Gln Met Glu Thr Leu Asn Pro Thr Gly Ser His Val Arg Phe Asn Val
                165                 170                 175

Ala Leu Val Lys Gly Lys Gln Asp Gly
            180                 185


<210> SEQ ID NO 44
<211> LENGTH: 186
<212> TYPE: PRT
<213> ORGANISM: Caulobacter crescentus

<400> SEQUENCE: 44

Met Lys Gly Val Ile Phe Asn Leu Leu Gln Glu Val Val Ser Ala Ala
 1               5                  10                  15

His Gly Ala Asp Ala Trp Asp Asp Ile Leu Asp Glu Ala Gly Val Ser
            20                  25                  30

Gly Ala Tyr Thr Ser Leu Gly Ser Tyr Asp Asp Glu Glu Trp Glu Thr
        35                  40                  45
```

-continued

```
Leu Val Glu Thr Ala Ser Ala Arg Leu Ser Leu Ser Arg Gly Glu Leu
    50                  55                  60

Leu Arg Trp Phe Gly Gln Glu Ala Met Pro His Leu Ala Arg Ala Tyr
65                  70                  75                  80

Pro Val Phe Phe Glu Gly His Val Ser Ser Arg Ser Phe Leu Ala Gly
                85                  90                  95

Val Asn Asp Ile Ile His Ala Glu Val His Lys Leu Tyr Ala Gly Ala
            100                 105                 110

Ala Cys Pro His Leu Lys Leu Arg Ala Ile Asp Ala Gly Gly Val Ala
        115                 120                 125

Met Ala Tyr Thr Ser Gln Arg Arg Met Cys Ala Leu Ala Gln Gly Phe
    130                 135                 140

Thr Glu Gly Ala Ala Arg Gln Phe His Glu Val Ile Thr Phe Glu His
145                 150                 155                 160

Ala Ala Cys Val Glu Lys Gly Asp Ser Ala Cys Val Phe His Ile Gly
                165                 170                 175

Trp Pro Ser Leu Glu Ala Ala Ala Asn Asp
            180                 185


<210> SEQ ID NO 45
<211> LENGTH: 180
<212> TYPE: PRT
<213> ORGANISM: Microbulbifer degradans

<400> SEQUENCE: 45

Met Lys Gly Ala Val Leu Ile Ala Leu Asn Asp Met Val Glu Glu Val
 1               5                  10                  15

Phe Ser Met Ala Val Trp Asp Gln Val Leu Ala Lys Val Lys Pro Asp
            20                  25                  30

Ser Glu Gly Ile Tyr Ile Ser Ala Glu Ser Tyr Asp Asp Ala Glu Val
        35                  40                  45

Val Gly Leu Val Val Ala Leu Ser Glu Leu Thr Gly Val Pro Val Asn
    50                  55                  60

Glu Leu Val Arg Ser Phe Gly Thr Tyr Leu Phe His Gln Leu Asn Ser
65                  70                  75                  80

Lys Phe Pro Ile Phe Cys Asp Leu His Thr Asn Ile Phe Asp Leu Leu
                85                  90                  95

Ser Ser Ile His Gly Val Ile His Lys Glu Val Asp Lys Leu Tyr Ser
            100                 105                 110

Asn Ala Ser Leu Pro Thr Ile Asn Cys Thr Lys Leu Ser Asp Ser His
        115                 120                 125

Leu Gln Met Arg Tyr Tyr Ser Pro Arg Lys Leu Cys Val Leu Ala Glu
    130                 135                 140

Gly Leu Ile Ile Gly Ala Ala Glu His Tyr Lys Ala Asp Val Ser Val
145                 150                 155                 160

Ser Gln Cys Gln Cys Val His Gln Gly Ala Asp Glu Cys Leu Ile Asp
                165                 170                 175

Val Lys Ile Ile
            180


<210> SEQ ID NO 46
<211> LENGTH: 181
<212> TYPE: PRT
<213> ORGANISM: Vibrio cholerae

<400> SEQUENCE: 46
```

```
Met Gln Gly Ile Ile Tyr Thr Val Leu Ser Asp Met Val Ile Glu Lys
 1               5                  10                  15

Phe Gly Val Leu Phe Trp Asp Gln Met Leu Glu Asp Leu Lys Pro Ser
            20                  25                  30

Ser Glu Gly Val Tyr Thr Ser Gly Gln Gln Tyr Asn Asp Asp Glu Leu
        35                  40                  45

Leu Ala Met Val Gly Tyr Leu Ser Glu Lys Ala Gln Ile Pro Ala Pro
    50                  55                  60

Asp Leu Val Arg Ala Tyr Gly Glu Tyr Leu Phe Thr His Leu Phe Asn
65                  70                  75                  80

Ser Leu Pro Glu Asn Tyr Pro His Lys Ser Asp Leu Lys Thr Phe Leu
                85                  90                  95

Leu Ser Val Asp Lys Val Ile His Lys Glu Val Gln Arg Leu Tyr Pro
            100                 105                 110

Asp Ala Tyr Leu Pro Gln Phe Glu Asn Arg Val Glu Glu Lys Thr Leu
        115                 120                 125

Thr Met Ser Tyr Tyr Ser Lys Arg Gln Leu Cys Ala Ala Ala Glu Gly
    130                 135                 140

Leu Ile Leu Gly Ala Ala Lys Gln Phe Asn Gln Pro Val Lys Ile Thr
145                 150                 155                 160

Gln Pro Val Cys Met His Cys Gly Ala Asp His Cys Glu Ile Val Val
                165                 170                 175

Glu Phe Leu Pro Ser
            180
```

<210> SEQ ID NO 47
<211> LENGTH: 181
<212> TYPE: PRT
<213> ORGANISM: Shewanella oneidensis

<400> SEQUENCE: 47

```
Met Lys Gly Ile Ile Phe Asn Val Leu Glu Asp Met Val Val Ala Gln
 1               5                  10                  15

Cys Gly Met Ser Val Trp Asn Glu Leu Leu Glu Lys His Ala Pro Lys
            20                  25                  30

Asp Arg Val Tyr Val Ser Ala Lys Ser Tyr Ala Glu Ser Glu Leu Phe
        35                  40                  45

Ser Ile Val Gln Asp Val Ala Gln Arg Leu Asn Met Pro Ile Gln Asp
    50                  55                  60

Val Val Lys Ala Phe Gly Gln Phe Leu Phe Asn Gly Leu Ala Ser Arg
65                  70                  75                  80

His Thr Asp Val Val Asp Lys Phe Asp Asp Phe Thr Ser Leu Val Met
                85                  90                  95

Gly Ile His Asp Val Ile His Leu Glu Val Asn Lys Leu Tyr His Glu
            100                 105                 110

Pro Ser Leu Pro His Ile Asn Gly Gln Leu Leu Pro Asn Asn Gln Ile
        115                 120                 125

Ala Leu Arg Tyr Ser Ser Pro Arg Arg Leu Cys Phe Cys Ala Glu Gly
    130                 135                 140

Leu Leu Phe Gly Ala Ala Gln His Phe Gln Gln Lys Ile Gln Ile Ser
145                 150                 155                 160

His Asp Thr Cys Met His Thr Gly Ala Asp His Cys Met Leu Ile Ile
                165                 170                 175

Glu Leu Gln Asn Asp
            180
```

<210> SEQ ID NO 48
<211> LENGTH: 189
<212> TYPE: PRT
<213> ORGANISM: Rattus norvegicus

<400> SEQUENCE: 48

```
Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Ser Glu Glu Cys Asp His
                165                 170                 175

Thr Gln Phe Leu Ile Glu Glu Lys Glu Ser Lys Glu Glu
            180                 185
```

<210> SEQ ID NO 49
<211> LENGTH: 191
<212> TYPE: PRT
<213> ORGANISM: Rattus norvegicus

<400> SEQUENCE: 49

```
Met Tyr Gly Phe Ile Asn Thr Cys Leu Gln Ser Leu Val Thr Glu Lys
 1               5                  10                  15

Phe Gly Glu Glu Thr Trp Glu Lys Leu Lys Ala Pro Ala Glu Val Gln
            20                  25                  30

Asp Val Phe Met Thr Tyr Thr Val Tyr Asp Asp Ile Ile Thr Ile Lys
        35                  40                  45

Leu Ile Gln Glu Ala Cys Lys Val Leu Asp Val Ser Met Glu Ala Ile
    50                  55                  60

Leu Lys Leu Phe Gly Glu Tyr Phe Phe Lys Phe Cys Lys Met Ser Gly
65                  70                  75                  80

Tyr Asp Arg Met Leu Arg Thr Leu Gly Gly Asn Leu Thr Glu Phe Ile
                85                  90                  95

Glu Asn Leu Asp Ala Leu His Ser Tyr Leu Ala Leu Ser Tyr Gln Glu
            100                 105                 110

Met Asn Ala Pro Ser Phe Arg Val Glu Glu Gly Ala Asp Gly Ala Met
        115                 120                 125

Leu Leu His Tyr Tyr Ser Asp Arg His Gly Leu Cys His Ile Val Pro
    130                 135                 140
```

Gly Ile Ile Glu Ala Val Ala Lys Asp Phe Phe Asp Thr Asp Val Ala
145 150 155 160

Met Ser Ile Leu Asp Met Asn Glu Glu Val Glu Arg Thr Gly Lys Lys
165 170 175

Glu His Val Val Phe Leu Val Val Gln Lys Ala His Arg Gln Ile
180 185 190

<210> SEQ ID NO 50
<211> LENGTH: 183
<212> TYPE: PRT
<213> ORGANISM: Nostoc punctiforme

<400> SEQUENCE: 50

Met Tyr Gly Leu Val Asn Lys Ala Ile Gln Asp Met Val Cys Ser Arg
1 5 10 15

Phe Gly Glu Glu Thr Trp Lys Gln Ile Lys His Lys Ala Glu Val Asp
20 25 30

Val Asp Val Phe Leu Ser Met Glu Gly Tyr Pro Asp Asp Ile Thr His
35 40 45

Lys Leu Val Lys Ala Ala Ser Val Ile Leu Ser Leu Ser Pro Lys Gln
50 55 60

Ile Met Gln Ala Phe Gly Glu Phe Trp Val Gln Tyr Thr Ala Gln Glu
65 70 75 80

Gly Tyr Gly Glu Met Leu Asp Met Ser Gly Asp Thr Leu Pro Glu Phe
85 90 95

Leu Glu Asn Leu Asp Asn Leu His Ala Arg Val Gly Val Ser Phe Pro
100 105 110

Lys Leu Gln Pro Pro Ser Phe Glu Cys Thr Asp Met Glu Glu Asn Ser
115 120 125

Leu Ser Leu His Tyr Arg Ser Asp Arg Glu Gly Leu Thr Pro Met Val
130 135 140

Ile Gly Leu Ile Lys Gly Leu Gly Thr Arg Phe Asp Thr Glu Val His
145 150 155 160

Ile Thr Gln Thr Gln Asn Arg Asp Glu Gly Ala Glu His Asp Glu Phe
165 170 175

Leu Val Ile Tyr Lys Pro Asn
180

<210> SEQ ID NO 51
<211> LENGTH: 187
<212> TYPE: PRT
<213> ORGANISM: Nostoc sp.

<400> SEQUENCE: 51

Met Tyr Gly Leu Val Asn Lys Ala Ile Gln Asp Met Ile Ser Lys His
1 5 10 15

His Gly Glu Asp Thr Trp Glu Ala Ile Lys Gln Lys Ala Gly Leu Glu
20 25 30

Asp Ile Asp Phe Phe Val Gly Met Glu Ala Tyr Ser Asp Asp Val Thr
35 40 45

Tyr His Leu Val Gly Ala Ala Ser Glu Val Leu Gly Lys Pro Ala Glu
50 55 60

Glu Leu Leu Ile Ala Phe Gly Glu Tyr Trp Val Thr Tyr Thr Ser Glu
65 70 75 80

Glu Gly Tyr Gly Glu Leu Leu Ala Ser Ala Gly Asp Ser Leu Pro Glu
85 90 95

```
Phe Met Glu Asn Leu Asp Asn Leu His Ala Arg Val Gly Leu Ser Phe
            100                 105                 110

Pro Gln Leu Arg Pro Pro Ala Phe Glu Cys Gln His Thr Ser Ser Lys
        115                 120                 125

Ser Met Glu Leu His Tyr Gln Ser Thr Arg Cys Gly Leu Ala Pro Met
    130                 135                 140

Val Leu Gly Leu Leu His Gly Leu Gly Lys Arg Phe Gln Thr Lys Val
145                 150                 155                 160

Glu Val Thr Gln Thr Ala Phe Arg Glu Thr Gly Glu Asp His Asp Ile
                165                 170                 175

Phe Ser Ile Lys Tyr Glu Asp Ser Asn Leu Tyr
            180                 185


<210> SEQ ID NO 52
<211> LENGTH: 73
<212> TYPE: PRT
<213> ORGANISM: Artificial Sequence
<220> FEATURE:
<223> OTHER INFORMATION: Synthetic Construct

<400> SEQUENCE: 52

Met Lys Gly Ile Gln Asp Met Val Tyr Gly Glu Asp Val Trp Asp Asp
 1               5                  10                  15

Ile Leu Gly Glu Glu Val Phe Glu Tyr Asp Asp Leu Val Ser Glu Glu
            20                  25                  30

Phe Gly Glu Asn Leu Glu Phe Leu Leu Asp Asp Ile His Val Lys Tyr
        35                  40                  45

Pro Ala Pro Pro Phe Leu Met Tyr Ser Arg Leu Gly Leu Ile Gly Ala
    50                  55                  60

Phe Glu Glu Ile Ile Gln Glu Val Phe
65                  70


<210> SEQ ID NO 53
<211> LENGTH: 555
<212> TYPE: DNA
<213> ORGANISM: Thermoanaerobacter tengcongensis

<400> SEQUENCE: 53

atgaagggga caatcgtcgg gacatggata aagaccctga gggaccttta cgggaatgat      60

gtggttgatg aatctttaaa aagtgtgggt tgggaaccag atagggtaat tacacctctg     120

gaggatattg atgacgatga ggttaggaga atttttgcta aggtgagtga aaaaactggt     180

aaaaatgtca acgaaatatg gagagaggta ggaaggcaga acataaaaac tttcagcgaa     240

tggtttccct cctattttgc agggagaagg ctagtgaatt ttttaatgat gatggatgag     300

gtacacctac agcttaccaa gatgataaaa ggagccactc ctccaaggct tattgcaaag     360

cctgttgcaa aagatgccat tgaaatggag tacgtttcta aaagaaagat gtacgattac     420

tttttagggc ttatagaggg tagttctaaa tttttcaagg aagaaatttc agtggaagag     480

gtcgaaagag gcgaaaaaga tggcttttca aggctaaaag tcaggataaa atttaaaaac     540

cccgtttttg agtga                                                      555


<210> SEQ ID NO 54
<211> LENGTH: 184
<212> TYPE: PRT
<213> ORGANISM: Thermoanaerobacter tengcongensis

<400> SEQUENCE: 54
```

```
Met Lys Gly Thr Ile Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu
            180
```

<210> SEQ ID NO 55
<211> LENGTH: 555
<212> TYPE: DNA
<213> ORGANISM: Thermoanaerobacter tengcongensis

<400> SEQUENCE: 55

```
atgaagggga caatcgtcgg gacatggata aagaccctga gggaccttta cgggaatgat      60

gtggttgatg aatctttaaa aagtgtgggt tgggaaccag atagggtaat tacacctctg     120

gaggatattg atgacgatga ggttaggaga atttttgcta aggtgagtga aaaaactggt     180

aaaaatgtca acgaaatatg gagagaggta ggaaggcaga acataaaaac tttcagcgaa     240

tggtttccct cctattttgc agggagaagg ctagtgaatt ttttaatgat gatggatgag     300

gtacacctac agcttaccaa gatgataaaa ggagccactc ctccaaggct tattgcaaag     360

cctgttgcaa aagatgccat tgaaatggag tacgtttcta aaagaaagat gtacgatttc     420

tttttagggc ttatagaggg tagttctaaa tttttcaagg aagaaatttc agtggaagag     480

gtcgaaagag gcgaaaaaga tggcttttca aggctaaaag tcaggataaa atttaaaaac     540

cccgtttttg agtga                                                      555
```

<210> SEQ ID NO 56
<211> LENGTH: 184
<212> TYPE: PRT
<213> ORGANISM: Thermoanaerobacter tengcongensis

<400> SEQUENCE: 56

```
Met Lys Gly Thr Ile Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30
```

Pro Asp Arg Val Ile Thr Pro Leu Glu Asp Ile Asp Asp Asp Glu Val
35 40 45

Arg Arg Ile Phe Ala Lys Val Ser Glu Lys Thr Gly Lys Asn Val Asn
50 55 60

Glu Ile Trp Arg Glu Val Gly Arg Gln Asn Ile Lys Thr Phe Ser Glu
65 70 75 80

Trp Phe Pro Ser Tyr Phe Ala Gly Arg Arg Leu Val Asn Phe Leu Met
85 90 95

Met Met Asp Glu Val His Leu Gln Leu Thr Lys Met Ile Lys Gly Ala
100 105 110

Thr Pro Pro Arg Leu Ile Ala Lys Pro Val Ala Lys Asp Ala Ile Glu
115 120 125

Met Glu Tyr Val Ser Lys Arg Lys Met Tyr Asp Phe Phe Leu Gly Leu
130 135 140

Ile Glu Gly Ser Ser Lys Phe Phe Lys Glu Glu Ile Ser Val Glu Glu
145 150 155 160

Val Glu Arg Gly Glu Lys Asp Gly Phe Ser Arg Leu Lys Val Arg Ile
165 170 175

Lys Phe Lys Asn Pro Val Phe Glu
180

<210> SEQ ID NO 57
<211> LENGTH: 555
<212> TYPE: DNA
<213> ORGANISM: Thermoanaerobacter tengcongensis

<400> SEQUENCE: 57
atgaagggga caatcgtcgg gacatggata aagaccctga gggaccttta cgggaatgat 60
gtggttgatg aatctttaaa aagtgtgggt tgggaaccag atagggtaat tacacctctg 120
gaggatattg atgacgatga ggttaggaga atttttgcta aggtgagtga aaaaactggt 180
aaaaatgtca acgaaatatg gagagaggta ggaaggcaga acataaaaac tttcagcgaa 240
tggtttccct cctattttgc agggagaagg ctagtgaatt ttttaatgat gatggatgag 300
gtacacctac agcttaccaa gatgataaaa ggagccactc ctccaaggct tattgcaaag 360
cctgttgcaa aagatgccat tgaaatggag tacgtttcta aaagaaagat gtacgatctt 420
tttttagggc ttatagaggg tagttctaaa tttttcaagg aagaaatttc agtggaagag 480
gtcgaaagag gcgaaaaaga tggcttttca aggctaaaag tcaggataaa atttaaaaac 540
cccgtttttg agtga 555

<210> SEQ ID NO 58
<211> LENGTH: 184
<212> TYPE: PRT
<213> ORGANISM: Thermoanaerobacter tengcongensis

<400> SEQUENCE: 58

Met Lys Gly Thr Ile Val Gly Thr Trp Ile Lys Thr Leu Arg Asp Leu
1 5 10 15

Tyr Gly Asn Asp Val Val Asp Glu Ser Leu Lys Ser Val Gly Trp Glu
20 25 30

Pro Asp Arg Val Ile Thr Pro Leu Glu Asp Ile Asp Asp Asp Glu Val
35 40 45

Arg Arg Ile Phe Ala Lys Val Ser Glu Lys Thr Gly Lys Asn Val Asn
50 55 60

Glu Ile Trp Arg Glu Val Gly Arg Gln Asn Ile Lys Thr Phe Ser Glu

-continued

```
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Leu Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu
            180


<210> SEQ ID NO 59
<211> LENGTH: 555
<212> TYPE: DNA
<213> ORGANISM: Thermoanaerobacter tengcongensis

<400> SEQUENCE: 59

atgaagggga caatcgtcgg gacatggata aagaccctga gggaccttta cgggaatgat      60

gtggttgatg aatctttaaa aagtgtgggt tgggaaccag atagggtaat tacacctctg     120

gaggatattg atgacgatga ggttaggaga atttttgcta aggtgagtga aaaaactggt     180

aaaaatgtca acgaaatatg gagagaggta ggaaggcaga acataaaaac tttcagcgaa     240

tggtttccct cctattttgc agggagaagg ctagtgaatt ttttaatgat gatggatgag     300

gtacacctac agcttaccaa gatgataaaa ggagccactc ctccaaggct tattgcaaag     360

cctgttgcaa aagatgccat tgaaatggag tacgtttcta aaagaaagat gtacgatcac     420

tttttagggc ttatagaggg tagttctaaa tttttcaagg aagaaatttc agtggaagag     480

gtcgaaagag gcgaaaaaga tggcttttca aggctaaaag tcaggataaa atttaaaaac     540

cccgtttttg agtga                                                      555


<210> SEQ ID NO 60
<211> LENGTH: 184
<212> TYPE: PRT
<213> ORGANISM: Thermoanaerobacter tengcongensis

<400> SEQUENCE: 60

Met Lys Gly Thr Ile Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110
```

-continued

```
Thr Pro Pro Arg Leu Ile Ala Lys Pro Val Ala Lys Asp Ala Ile Glu
        115                 120                 125

Met Glu Tyr Val Ser Lys Arg Lys Met Tyr Asp His Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu
            180


<210> SEQ ID NO 61
<211> LENGTH: 555
<212> TYPE: DNA
<213> ORGANISM: Thermoanaerobacter tengcongensis

<400> SEQUENCE: 61

atgaagggga caatcgtcgg gacatggata aagaccctga gggaccttta cgggaatgat      60

gtggttgatg aatctttaaa aagtgtgggt tgggaaccag atagggtaat tacacctctg     120

gaggatattg atgacgatga ggttaggaga atttttgcta aggtgagtga aaaaactggt     180

aaaaatgtca acgaaatatg gagagaggta ggaaggcaga acataaaaac tttcagcgaa     240

tggtttccct cctattttgc agggagaagg ctagtgaatt ttttaatgat gatggatgag     300

gtacacctac agcttaccaa gatgataaaa ggagccactc ctccaaggct tattgcaaag     360

cctgttgcaa aagatgccat tgaaatggag tacgtttcta aaagaaagat gtacgatgcc     420

tttttagggc ttatagaggg tagttctaaa tttttcaagg aagaaatttc agtggaagag     480

gtcgaaagag gcgaaaaaga tggcttttca aggctaaaag tcaggataaa atttaaaaac     540

cccgtttttg agtga                                                      555


<210> SEQ ID NO 62
<211> LENGTH: 184
<212> TYPE: PRT
<213> ORGANISM: Thermoanaerobacter tengcongensis

<400> SEQUENCE: 62

Met Lys Gly Thr Ile Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Ala Phe Leu Gly Leu
    130                 135                 140
```

```
Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu
            180


<210> SEQ ID NO 63
<211> LENGTH: 555
<212> TYPE: DNA
<213> ORGANISM: Thermoanaerobacter tengcongensis

<400> SEQUENCE: 63

atgaagggga caatcgtcgg gacatttata aagaccctga gggaccttta cgggaatgat      60

gtggttgatg aatctttaaa aagtgtgggt tgggaaccag atagggtaat tacacctctg     120

gaggatattg atgacgatga ggttaggaga atttttgcta aggtgagtga aaaaactggt     180

aaaaatgtca acgaaatatg gagagaggta ggaaggcaga acataaaaac tttcagcgaa     240

tggtttccct cctattttgc agggagaagg ctagtgaatt ttttaatgat gatggatgag     300

gtacacctac agcttaccaa gatgataaaa ggagccactc ctccaaggct tattgcaaag     360

cctgttgcaa aagatgccat tgaaatggag tacgtttcta aaagaaagat gtacgattac     420

tttttagggc ttatagaggg tagttctaaa tttttcaagg aagaaatttc agtggaagag     480

gtcgaaagag gcgaaaaaga tggcttttca aggctaaaag tcaggataaa atttaaaaac     540

cccgtttttg agtga                                                      555


<210> SEQ ID NO 64
<211> LENGTH: 184
<212> TYPE: PRT
<213> ORGANISM: Thermoanaerobacter tengcongensis

<400> SEQUENCE: 64

Met Lys Gly Thr Ile Val Gly Thr Phe Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu
```

180

<210> SEQ ID NO 65
<211> LENGTH: 555
<212> TYPE: DNA
<213> ORGANISM: Thermoanaerobacter tengcongensis

<400> SEQUENCE: 65
atgaagggga caatcgtcgg gacatttata aagaccctga gggaccttta cgggaatgat 60
gtggttgatg aatctttaaa aagtgtgggt tgggaaccag atagggtaat tacacctctg 120
gaggatattg atgacgatga ggttaggaga atttttgcta aggtgagtga aaaaactggt 180
aaaaatgtca acgaaatatg gagagaggta ggaaggcaga acataaaaac tttcagcgaa 240
tggtttccct cctattttgc agggagaagg ctagtgaatt ttttaatgat gatggatgag 300
gtacacctac agcttaccaa gatgataaaa ggagccactc ctccaaggct tattgcaaag 360
cctgttgcaa aagatgccat tgaaatggag tacgtttcta aaagaaagat gtacgatttt 420
tttttagggc ttatagaggg tagttctaaa tttttcaagg aagaaatttc agtggaagag 480
gtcgaaagag gcgaaaaaga tggcttttca aggctaaaag tcaggataaa atttaaaaac 540
cccgtttttg agtga 555

<210> SEQ ID NO 66
<211> LENGTH: 184
<212> TYPE: PRT
<213> ORGANISM: Thermoanaerobacter tengcongensis

<400> SEQUENCE: 66

Met Lys Gly Thr Ile Val Gly Thr Phe Ile Lys Thr Leu Arg Asp Leu
1 5 10 15

Tyr Gly Asn Asp Val Val Asp Glu Ser Leu Lys Ser Val Gly Trp Glu
20 25 30

Pro Asp Arg Val Ile Thr Pro Leu Glu Asp Ile Asp Asp Asp Glu Val
35 40 45

Arg Arg Ile Phe Ala Lys Val Ser Glu Lys Thr Gly Lys Asn Val Asn
50 55 60

Glu Ile Trp Arg Glu Val Gly Arg Gln Asn Ile Lys Thr Phe Ser Glu
65 70 75 80

Trp Phe Pro Ser Tyr Phe Ala Gly Arg Arg Leu Val Asn Phe Leu Met
85 90 95

Met Met Asp Glu Val His Leu Gln Leu Thr Lys Met Ile Lys Gly Ala
100 105 110

Thr Pro Pro Arg Leu Ile Ala Lys Pro Val Ala Lys Asp Ala Ile Glu
115 120 125

Met Glu Tyr Val Ser Lys Arg Lys Met Tyr Asp Phe Phe Leu Gly Leu
130 135 140

Ile Glu Gly Ser Ser Lys Phe Phe Lys Glu Glu Ile Ser Val Glu Glu
145 150 155 160

Val Glu Arg Gly Glu Lys Asp Gly Phe Ser Arg Leu Lys Val Arg Ile
165 170 175

Lys Phe Lys Asn Pro Val Phe Glu
180

<210> SEQ ID NO 67
<211> LENGTH: 555
<212> TYPE: DNA
<213> ORGANISM: Thermoanaerobacter tengcongensis

<400> SEQUENCE: 67

```
atgaagggga caatcgtcgg gacatttata aagaccctga gggaccttta cgggaatgat     60

gtggttgatg aatctttaaa aagtgtgggt tgggaaccag atagggtaat tacacctctg    120

gaggatattg atgacgatga ggttaggaga atttttgcta aggtgagtga aaaaactggt    180

aaaaatgtca acgaaatatg gagagaggta ggaaggcaga acataaaaac tttcagcgaa    240

tggtttccct cctattttgc agggagaagg ctagtgaatt ttttaatgat gatggatgag    300

gtacacctac agcttaccaa gatgataaaa ggagccactc ctccaaggct tattgcaaag    360

cctgttgcaa aagatgccat tgaaatggag tacgtttcta aaagaaagat gtacgatcac    420

tttttagggc ttatagaggg tagttctaaa tttttcaagg aagaaatttc agtggaagag    480

gtcgaaagag gcgaaaaaga tggcttttca aggctaaaag tcaggataaa atttaaaaac    540

cccgtttttg agtga                                                     555
```

<210> SEQ ID NO 68
<211> LENGTH: 184
<212> TYPE: PRT
<213> ORGANISM: Thermoanaerobacter tengcongensis

<400> SEQUENCE: 68

```
Met Lys Gly Thr Ile Val Gly Thr Phe Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp His Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu
            180
```

<210> SEQ ID NO 69
<211> LENGTH: 555
<212> TYPE: DNA
<213> ORGANISM: Thermoanaerobacter tengcongensis

<400> SEQUENCE: 69

```
atgaagggga caatcgtcgg gacatttata aagaccctga gggaccttta cgggaatgat     60

gtggttgatg aatctttaaa aagtgtgggt tgggaaccag atagggtaat tacacctctg    120
```

-continued

```
gaggatattg atgacgatga ggttaggaga atttttgcta aggtgagtga aaaaactggt    180

aaaaatgtca acgaaatatg gagagaggta ggaaggcagg caataaaaac tttcagcgaa    240

tggtttccct cctattttgc agggagaagg ctagtgaatt ttttaatgat gatggatgag    300

gtacacctac agcttaccaa gatgataaaa ggagccactc ctccaaggct tattgcaaag    360

cctgttgcaa aagatgccat tgaaatggag tacgtttcta aaagaaagat gtacgattac    420

tttttagggc ttatagaggg tagttctaaa tttttcaagg aagaaatttc agtggaagag    480

gtcgaaagag gcgaaaaaga tggcttttca aggctaaaag tcaggataaa atttaaaaac    540

cccgtttttg agtga                                                     555
```

<210> SEQ ID NO 70
<211> LENGTH: 184
<212> TYPE: PRT
<213> ORGANISM: Thermoanaerobacter tengcongensis

<400> SEQUENCE: 70

```
Met Lys Gly Thr Ile Val Gly Thr Phe Ile Lys Thr Leu Arg Asp Leu
1               5                   10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Ala Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu
            180
```

<210> SEQ ID NO 71
<211> LENGTH: 555
<212> TYPE: DNA
<213> ORGANISM: Thermoanaerobacter tengcongensis

<400> SEQUENCE: 71

```
atgaagggga caatcgtcgg gacatacata aagaccctga gggaccttta cgggaatgat     60

gtggttgatg aatctttaaa aagtgtgggt tgggaaccag atagggtaat tacacctctg    120

gaggatattg atgacgatga ggttaggaga atttttgcta aggtgagtga aaaaactggt    180

aaaaatgtca acgaaatatg gagagaggta ggaaggcaga acataaaaac tttcagcgaa    240

tggtttccct cctattttgc agggagaagg ctagtgaatt ttttaatgat gatggatgag    300

gtacacctac agcttaccaa gatgataaaa ggagccactc ctccaaggct tattgcaaag    360
```

```
cctgttgcaa aagatgccat tgaaatggag tacgtttcta aaagaaagat gtacgattac    420

tttttagggc ttatagaggg tagttctaaa tttttcaagg aagaaatttc agtggaagag    480

gtcgaaagag gcgaaaaaga tggcttttca aggctaaaag tcaggataaa atttaaaaac    540

cccgtttttg agtga                                                     555


<210> SEQ ID NO 72
<211> LENGTH: 184
<212> TYPE: PRT
<213> ORGANISM: Thermoanaerobacter tengcongensis

<400> SEQUENCE: 72

Met Lys Gly Thr Ile Val Gly Thr Tyr Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu
            180


<210> SEQ ID NO 73
<211> LENGTH: 555
<212> TYPE: DNA
<213> ORGANISM: Thermoanaerobacter tengcongensis

<400> SEQUENCE: 73

atgaagggga caatcgtcgg gacaaatata aagaccctga gggaccttta cgggaatgat     60

gtggttgatg aatctttaaa aagtgtgggt tgggaaccag atagggtaat tacacctctg    120

gaggatattg atgacgatga ggttaggaga atttttgcta aggtgagtga aaaaactggt    180

aaaaatgtca acgaaatatg gagagaggta ggaaggcaga acataaaaac tttcagcgaa    240

tggtttccct cctattttgc agggagaagg ctagtgaatt ttttaatgat gatggatgag    300

gtacacctac agcttaccaa gatgataaaa ggagccactc ctccaaggct tattgcaaag    360

cctgttgcaa aagatgccat tgaaatggag tacgtttcta aaagaaagat gtacgattac    420

tttttagggc ttatagaggg tagttctaaa tttttcaagg aagaaatttc agtggaagag    480

gtcgaaagag gcgaaaaaga tggcttttca aggctaaaag tcaggataaa atttaaaaac    540
```

-continued

```
cccgttttg agtga                                                  555


<210> SEQ ID NO 74
<211> LENGTH: 184
<212> TYPE: PRT
<213> ORGANISM: Thermoanaerobacter tengcongensis

<400> SEQUENCE: 74

Met Lys Gly Thr Ile Val Gly Thr Asn Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu
            180


<210> SEQ ID NO 75
<211> LENGTH: 555
<212> TYPE: DNA
<213> ORGANISM: Thermoanaerobacter tengcongensis

<400> SEQUENCE: 75

atgaagggga caatcgtcgg gacacacata aagaccctga gggaccttta cgggaatgat     60

gtggttgatg aatctttaaa aagtgtgggt tgggaaccag atagggtaat tacacctctg    120

gaggatattg atgacgatga ggttaggaga atttttgcta aggtgagtga aaaaactggt    180

aaaaatgtca acgaaatatg gagagaggta ggaaggcaga acataaaaac tttcagcgaa    240

tggtttccct cctattttgc agggagaagg ctagtgaatt ttttaatgat gatggatgag    300

gtacacctac agcttaccaa gatgataaaa ggagccactc ctccaaggct tattgcaaag    360

cctgttgcaa aagatgccat tgaaatggag tacgtttcta aaagaaagat gtacgattac    420

tttttagggc ttatagaggg tagttctaaa tttttcaagg aagaaatttc agtggaagag    480

gtcgaaagag gcgaaaaaga tggcttttca aggctaaaag tcaggataaa atttaaaaac    540

cccgttttg agtga                                                  555


<210> SEQ ID NO 76
<211> LENGTH: 184
<212> TYPE: PRT
<213> ORGANISM: Thermoanaerobacter tengcongensis
```

<400> SEQUENCE: 76

Met Lys Gly Thr Ile Val Gly Thr His Ile Lys Thr Leu Arg Asp Leu
1 5 10 15

Tyr Gly Asn Asp Val Val Asp Glu Ser Leu Lys Ser Val Gly Trp Glu
20 25 30

Pro Asp Arg Val Ile Thr Pro Leu Glu Asp Ile Asp Asp Asp Glu Val
35 40 45

Arg Arg Ile Phe Ala Lys Val Ser Glu Lys Thr Gly Lys Asn Val Asn
50 55 60

Glu Ile Trp Arg Glu Val Gly Arg Gln Asn Ile Lys Thr Phe Ser Glu
65 70 75 80

Trp Phe Pro Ser Tyr Phe Ala Gly Arg Arg Leu Val Asn Phe Leu Met
85 90 95

Met Met Asp Glu Val His Leu Gln Leu Thr Lys Met Ile Lys Gly Ala
100 105 110

Thr Pro Pro Arg Leu Ile Ala Lys Pro Val Ala Lys Asp Ala Ile Glu
115 120 125

Met Glu Tyr Val Ser Lys Arg Lys Met Tyr Asp Tyr Phe Leu Gly Leu
130 135 140

Ile Glu Gly Ser Ser Lys Phe Phe Lys Glu Glu Ile Ser Val Glu Glu
145 150 155 160

Val Glu Arg Gly Glu Lys Asp Gly Phe Ser Arg Leu Lys Val Arg Ile
165 170 175

Lys Phe Lys Asn Pro Val Phe Glu
180

<210> SEQ ID NO 77
<211> LENGTH: 555
<212> TYPE: DNA
<213> ORGANISM: Thermoanaerobacter tengcongensis

<400> SEQUENCE: 77
atgaagggga cagcagtcgg gacatggata aagaccctga gggaccttta cgggaatgat 60
gtggttgatg aatctttaaa aagtgtgggt tgggaaccag atagggtaat tacacctctg 120
gaggatattg atgacgatga ggttaggaga atttttgcta aggtgagtga aaaaactggt 180
aaaaatgtca acgaaatatg gagagaggta ggaaggcaga acataaaaac tttcagcgaa 240
tggtttccct cctattttgc agggagaagg ctagtgaatt ttttaatgat gatggatgag 300
gtacacctac agcttaccaa gatgataaaa ggagccactc ctccaaggct tattgcaaag 360
cctgttgcaa aagatgccat tgaaatggag tacgtttcta aaagaaagat gtacgattac 420
tttttagggc ttatagaggg tagttctaaa tttttcaagg aagaaatttc agtggaagag 480
gtcgaaagag gcgaaaaaga tggcttttca aggctaaaag tcaggataaa atttaaaaac 540
cccgtttttg agtga 555

<210> SEQ ID NO 78
<211> LENGTH: 184
<212> TYPE: PRT
<213> ORGANISM: Thermoanaerobacter tengcongensis

<400> SEQUENCE: 78

Met Lys Gly Thr Ala Val Gly Thr Trp Ile Lys Thr Leu Arg Asp Leu
1 5 10 15

Tyr Gly Asn Asp Val Val Asp Glu Ser Leu Lys Ser Val Gly Trp Glu

```
            20                  25                  30

Pro Asp Arg Val Ile Thr Pro Leu Glu Asp Ile Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu
            180


<210> SEQ ID NO 79
<211> LENGTH: 555
<212> TYPE: DNA
<213> ORGANISM: Thermoanaerobacter tengcongensis

<400> SEQUENCE: 79

atgaagggga cacttgtcgg gacatggata aagaccctga gggaccttta cgggaatgat      60

gtggttgatg aatctttaaa aagtgtgggt tgggaaccag atagggtaat tacacctctg     120

gaggatattg atgacgatga ggttaggaga atttttgcta aggtgagtga aaaaactggt     180

aaaaatgtca acgaaatatg gagagaggta ggaaggcaga acataaaaac tttcagcgaa     240

tggtttccct cctattttgc agggagaagg ctagtgaatt ttttaatgat gatggatgag     300

gtacacctac agcttaccaa gatgataaaa ggagccactc ctccaaggct tattgcaaag     360

cctgttgcaa aagatgccat tgaaatggag tacgtttcta aaagaaagat gtacgattac     420

tttttagggc ttatagaggg tagttctaaa tttttcaagg aagaaatttc agtggaagag     480

gtcgaaagag gcgaaaaaga tggcttttca aggctaaaag tcaggataaa atttaaaaac     540

cccgtttttg agtga                                                      555


<210> SEQ ID NO 80
<211> LENGTH: 184
<212> TYPE: PRT
<213> ORGANISM: Thermoanaerobacter tengcongensis

<400> SEQUENCE: 80

Met Lys Gly Thr Leu Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Glu Val
        35                  40                  45

Arg Arg Ile Phe Ala Lys Val Ser Glu Lys Thr Gly Lys Asn Val Asn
    50                  55                  60
```

```
Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu
            180
```

<210> SEQ ID NO 81
<211> LENGTH: 555
<212> TYPE: DNA
<213> ORGANISM: Thermoanaerobacter tengcongensis

<400> SEQUENCE: 81

```
atgaagggga cacttgtcgg gacatggata aagaccctga gggaccttta cgggaatgat      60

gtggttgatg aatctttaaa aagtgtgggt tgggaaccag atagggtaat tacacctctg     120

gaggatattg atgacgatga ggttaggaga atttttgcta aggtgagtga aaaaactggt     180

aaaaatgtca acgaaatatg gagagaggta ggaaggcaga acataaaaac tttcagcgaa     240

tggtttccct cctattttgc agggagaagg ctagtgaatt ttttaatgat gatggatgag     300

gtacacctac agcttaccaa gatgataaaa ggagccactc ctgcaaggct tattgcaaag     360

cctgttgcaa aagatgccat tgaaatggag tacgtttcta aaagaaagat gtacgattac     420

tttttagggc ttatagaggg tagttctaaa tttttcaagg aagaaatttc agtggaagag     480

gtcgaaagag gcgaaaaaga tggcttttca aggctaaaag tcaggataaa atttaaaaac     540

cccgtttttg agtga                                                      555
```

<210> SEQ ID NO 82
<211> LENGTH: 184
<212> TYPE: PRT
<213> ORGANISM: Thermoanaerobacter tengcongensis

<400> SEQUENCE: 82

```
Met Lys Gly Thr Leu Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95
```

```
Met Met Asp Glu Val His Leu Gln Leu Thr Lys Met Ile Lys Gly Ala
            100                 105                 110

Thr Pro Ala Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu
            180
```

```
<210> SEQ ID NO 83
<211> LENGTH: 555
<212> TYPE: DNA
<213> ORGANISM: Thermoanaerobacter tengcongensis

<400> SEQUENCE: 83

atgaagggga caatcgtcgg gacatggata aagaccctga gggaccttta cgggaatgat      60

gtggttgatg aatctttaaa aagtgtgggt tgggaaccag atagggtaat tacacctctg     120

gaggatattg atgacgatga ggttaggaga atttttgcta aggtgagtga aaaaactggt     180

aaaaatgtca acgaaatatg gagagaggta ggaaggcaga acataaaaac tttcagcgaa     240

tggtttccct cctattttgc agggagaagg ctagtgaatt ttttaatgat gatggatgag     300

gtacacctac agcttaccaa gatgataaaa ggagccactc ctgccaggct tattgcaaag     360

cctgttgcaa aagatgccat tgaaatggag tacgtttcta aaagaaagat gtacgattac     420

tttttagggc ttatagaggg tagttctaaa tttttcaagg aagaaatttc agtggaagag     480

gtcgaaagag gcgaaaaaga tggcttttca aggctaaaag tcaggataaa atttaaaaac     540

cccgtttttg agtga                                                      555
```

```
<210> SEQ ID NO 84
<211> LENGTH: 184
<212> TYPE: PRT
<213> ORGANISM: Thermoanaerobacter tengcongensis

<400> SEQUENCE: 84

Met Lys Gly Thr Ile Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Ala Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
```

-continued

```
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu
            180


<210> SEQ ID NO 85
<211> LENGTH: 567
<212> TYPE: DNA
<213> ORGANISM: Thermoanaerobacter tengcongensis

<400> SEQUENCE: 85

atgaagggga caatcgtcgg gacatggata aagaccctga gggaccttta cgggaatgat      60

gtggttgatg aatctttaaa aagtgtgggt tgggaaccag atagggtaat tacacctctg     120

gaggatattg atgacgatga ggttaggaga atttttgcta aggtgagtga aaaaactggt     180

aaaaatgtca acgaaatatg gagagaggta ggaaggcagg aaataaaaac tttcagcgaa     240

tggtttccct cctattttgc agggagaagg ctagtgaatt ttttaatgat gatggatgag     300

gtacacctac agcttaccaa gatgataaaa ggagccactc ctccaaggct tattgcaaag     360

cctgttgcaa aagatgccat tgaaatggag tacgtttcta aaagaaagat gtacgattac     420

tttttagggc ttatagaggg tagttctaaa tttttcaagg aagaaatttc agtggaagag     480

gtcgaaagag gcgaaaaaga tggcttttca aggctaaaag tcaggataaa atttaaaaac     540

cccgtttttg agtataagaa aaattga                                         567


<210> SEQ ID NO 86
<211> LENGTH: 188
<212> TYPE: PRT
<213> ORGANISM: Thermoanaerobacter tengcongensis

<400> SEQUENCE: 86

Met Lys Gly Thr Ile Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Glu Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175
```

```
Lys Phe Lys Asn Pro Val Phe Glu Tyr Lys Lys Asn
            180                 185


<210> SEQ ID NO 87
<211> LENGTH: 567
<212> TYPE: DNA
<213> ORGANISM: Thermoanaerobacter tengcongensis

<400> SEQUENCE: 87

atgaagggga caatcgtcgg gacatggata aagaccctga gggaccttta cgggaatgat     60

gtggttgatg aatctttaaa aagtgtgggt tgggaaccag atagggtaat tacacctctg    120

gaggatattg atgacgatga ggttaggaga atttttgcta aggtgagtga aaaaactggt    180

aaaaatgtca acgaaatatg gagagaggta ggaaggcagg ccataaaaac tttcagcgaa    240

tggtttccct cctattttgc agggagaagg ctagtgaatt ttttaatgat gatggatgag    300

gtacacctac agcttaccaa gatgataaaa ggagccactc ctccaaggct tattgcaaag    360

cctgttgcaa aagatgccat tgaaatggag tacgtttcta aaagaaagat gtacgatcac    420

tttttagggc ttatagaggg tagttctaaa tttttcaagg aagaaatttc agtggaagag    480

gtcgaaagag gcgaaaaaga tggcttttca aggctaaaag tcaggataaa atttaaaaac    540

cccgtttttg agtataagaa aaattga                                        567


<210> SEQ ID NO 88
<211> LENGTH: 188
<212> TYPE: PRT
<213> ORGANISM: Thermoanaerobacter tengcongensis

<400> SEQUENCE: 88

Met Lys Gly Thr Ile Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Ala Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp His Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu Tyr Lys Lys Asn
            180                 185


<210> SEQ ID NO 89
<211> LENGTH: 591
```

```
<212> TYPE: DNA
<213> ORGANISM: Thermoanaerobacter tengcongensis

<400> SEQUENCE: 89

atgaagggga caatcgtcgg gacatggata aagaccctga gggaccttta cgggaatgat      60

gtggttgatg aatctttaaa aagtgtgggt tgggaaccag atagggtaat tacacctctg     120

gaggatattg atgacgatga ggttaggaga atttttgcta aggtgagtga aaaaactggt     180

aaaaatgtca acgaaatatg gagagaggta ggaaggcaga acataaaaac tttcagcgaa     240

tggtttccct cctattttgc agggagaagg ctagtgaatt ttttaatgat gatggatgag     300

gtacacctac agcttaccaa gatgataaaa ggagccactc ctccaaggct tattgcaaag     360

cctgttgcaa aagatgccat tgaaatggag tacgtttcta aacagaagat gtacgattac     420

tttttagggc ttatagaggg tagttctaaa tttttcaagg aagaaatttc agtggaagag     480

gtcgaaagag gcgaaaaaga tggcttttca aggctaaaag tcaggataaa atttaaaaac     540

cccgtttttg agtataagaa aaatctcgag caccaccacc accaccactg a              591


<210> SEQ ID NO 90
<211> LENGTH: 196
<212> TYPE: PRT
<213> ORGANISM: Thermoanaerobacter tengcongensis

<400> SEQUENCE: 90

Met Lys Gly Thr Ile Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Gln Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu Tyr Lys Lys Asn Leu Glu His His
            180                 185                 190

His His His His
        195


<210> SEQ ID NO 91
<211> LENGTH: 567
<212> TYPE: DNA
<213> ORGANISM: Thermoanaerobacter tengcongensis

<400> SEQUENCE: 91
```

```
atgaagggga caatcgtcgg gacatggata aagaccctga gggaccttta cgggaatgat      60

gtggttgatg aatctttaaa aagtgtgggt tgggaaccag atagggtaat tacacctctg    120

gaggatattg atgacgatga ggttaggaga atttttgcta aggtgagtga aaaaactggt    180

aaaaatgtca acgaaatatg gagagaggta ggaaggcagg ccataaaaac tttcagcgaa    240

tggtttccct cctattttgc agggagaagg ctagtgaatt ttttaatgat gatggatgag    300

gtacacctac agcttaccaa gatgataaaa ggagccactc ctccaaggct tattgcaaag    360

cctgttgcaa aagatgccat tgaaatggag tacgtttcta aaagaaagat gtacgattac    420

tttttagggc ttatagaggg tagttctaaa tttttcaagg aagaaatttc agtggaagag    480

gtcgaaagag gcgaaaaaga tggcttttca aggctaaaag tcaggataaa atttaaaaac    540

cccgtttttg agtataagaa aaattga                                        567
```

<210> SEQ ID NO 92
<211> LENGTH: 188
<212> TYPE: PRT
<213> ORGANISM: Thermoanaerobacter tengcongensis

<400> SEQUENCE: 92

```
Met Lys Gly Thr Ile Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Ala Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu Tyr Lys Lys Asn
            180                 185
```

<210> SEQ ID NO 93
<211> LENGTH: 591
<212> TYPE: DNA
<213> ORGANISM: Thermoanaerobacter tengcongensis

<400> SEQUENCE: 93

```
atgaagggga caatcgtcgg gacatggata aagaccctga gggaccttta cgggaatgat      60

gtggttgatg aatctttaaa aagtgtgggt tgggaaccag atagggtaat tacacctctg    120

gaggatattg atgacgatga ggttaggaga atttttgcta aggtgagtga aaaaactggt    180
```

```
aaaaatgtca acgaaatatg gagagaggta ggaaggcagg ccataaaaac tttcagcgaa    240

tggtttccct cctattttgc agggagaagg ctagtgaatt ttttaatgat gatggatgag    300

gtacacctac agcttaccaa gatgataaaa ggagccactc ctccaaggct tattgcaaag    360

cctgttgcaa aagatgccat tgaaatggag tacgtttcta aaagaaagat gtacgattac    420

tttttagggc ttatagaggg tagttctaaa tttttcaagg aagaaatttc agtggaagag    480

gtcgaaagag gcgaaaaaga tggcttttca aggctaaaag tcaggataaa atttaaaaac    540

cccgtttttg agtataagaa aaatctcgag caccaccacc accaccactg a             591
```

<210> SEQ ID NO 94
<211> LENGTH: 196
<212> TYPE: PRT
<213> ORGANISM: Thermoanaerobacter tengcongensis

<400> SEQUENCE: 94

```
Met Lys Gly Thr Ile Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Ala Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu Tyr Lys Lys Asn Leu Glu His His
            180                 185                 190

His His His His
        195
```

<210> SEQ ID NO 95
<211> LENGTH: 567
<212> TYPE: DNA
<213> ORGANISM: Thermoanaerobacter tengcongensis

<400> SEQUENCE: 95

```
atgaagggga caatcgtcgg gacaaatata aagaccctga gggaccttta cgggaatgat     60

gtggttgatg aatctttaaa aagtgtgggt tgggaaccag atagggtaat tacacctctg    120

gaggatattg atgacgatga ggttaggaga atttttgcta aggtgagtga aaaaactggt    180

aaaaatgtca acgaaatatg gagagaggta ggaaggcaga acataaaaac tttcagcgaa    240

tggtttccct cctattttgc agggagaagg ctagtgaatt ttttaatgat gatggatgag    300
```

-continued

```
gtacacctac agcttaccaa gatgataaaa ggagccactc ctccaaggct tattgcaaag    360

cctgttgcaa aagatgccat tgaaatggag tacgtttcta aaagaaagat gtacgattac    420

tttttagggc ttatagaggg tagttctaaa tttttcaagg aagaaatttc agtggaagag    480

gtcgaaagag gcgaaaaaga tggcttttca aggctaaaag tcaggataaa atttaaaaac    540

cccgtttttg agtataagaa aaattga                                        567
```

<210> SEQ ID NO 96
<211> LENGTH: 188
<212> TYPE: PRT
<213> ORGANISM: Thermoanaerobacter tengcongensis

<400> SEQUENCE: 96

```
Met Lys Gly Thr Ile Val Gly Thr Asn Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu Tyr Lys Lys Asn
            180                 185
```

<210> SEQ ID NO 97
<211> LENGTH: 567
<212> TYPE: DNA
<213> ORGANISM: Thermoanaerobacter tengcongensis

<400> SEQUENCE: 97

```
atgaagggga caatcgtcgg gacacatata aagaccctga gggaccttta cgggaatgat     60

gtggttgatg aatctttaaa aagtgtgggt tgggaaccag atagggtaat tacacctctg    120

gaggatattg atgacgatga ggttaggaga atttttgcta aggtgagtga aaaaactggt    180

aaaaatgtca acgaaatatg gagagaggta ggaaggcaga acataaaaac tttcagcgaa    240

tggtttccct cctattttgc agggagaagg ctagtgaatt ttttaatgat gatggatgag    300

gtacacctac agcttaccaa gatgataaaa ggagccactc ctccaaggct tattgcaaag    360

cctgttgcaa aagatgccat tgaaatggag tacgtttcta aaagaaagat gtacgattac    420

tttttagggc ttatagaggg tagttctaaa tttttcaagg aagaaatttc agtggaagag    480

gtcgaaagag gcgaaaaaga tggcttttca aggctaaaag tcaggataaa atttaaaaac    540
```

cccgtttttg agtataagaa aaattga 567

<210> SEQ ID NO 98
<211> LENGTH: 188
<212> TYPE: PRT
<213> ORGANISM: Thermoanaerobacter tengcongensis

<400> SEQUENCE: 98

Met Lys Gly Thr Ile Val Gly Thr His Ile Lys Thr Leu Arg Asp Leu
1 5 10 15

Tyr Gly Asn Asp Val Val Asp Glu Ser Leu Lys Ser Val Gly Trp Glu
20 25 30

Pro Asp Arg Val Ile Thr Pro Leu Glu Asp Ile Asp Asp Asp Glu Val
35 40 45

Arg Arg Ile Phe Ala Lys Val Ser Glu Lys Thr Gly Lys Asn Val Asn
50 55 60

Glu Ile Trp Arg Glu Val Gly Arg Gln Asn Ile Lys Thr Phe Ser Glu
65 70 75 80

Trp Phe Pro Ser Tyr Phe Ala Gly Arg Arg Leu Val Asn Phe Leu Met
85 90 95

Met Met Asp Glu Val His Leu Gln Leu Thr Lys Met Ile Lys Gly Ala
100 105 110

Thr Pro Pro Arg Leu Ile Ala Lys Pro Val Ala Lys Asp Ala Ile Glu
115 120 125

Met Glu Tyr Val Ser Lys Arg Lys Met Tyr Asp Tyr Phe Leu Gly Leu
130 135 140

Ile Glu Gly Ser Ser Lys Phe Phe Lys Glu Glu Ile Ser Val Glu Glu
145 150 155 160

Val Glu Arg Gly Glu Lys Asp Gly Phe Ser Arg Leu Lys Val Arg Ile
165 170 175

Lys Phe Lys Asn Pro Val Phe Glu Tyr Lys Lys Asn
180 185

<210> SEQ ID NO 99
<211> LENGTH: 567
<212> TYPE: DNA
<213> ORGANISM: Thermoanaerobacter tengcongensis

<400> SEQUENCE: 99
atgaagggga caatcgtcgg gacatggata aagaccctga gggaccttta cgggaatgat 60
gtggttgatg aatctttaaa aagtgtgggt tgggaaccag atagggtaat tacacctctg 120
gaggatattg atgacgatga ggttaggaga atttttgcta aggtgagtga aaaaactggt 180
aaaaatgtca acgaaatatg gagagaggta ggaaggcagc atataaaaac tttcagcgaa 240
tggtttccct cctattttgc agggagaagg ctagtgaatt ttttaatgat gatggatgag 300
gtacacctac agcttaccaa gatgataaaa ggagccactc ctccaaggct tattgcaaag 360
cctgttgcaa aagatgccat tgaaatggag tacgtttcta aaagaaagat gtacgattac 420
tttttagggc ttatagaggg tagttctaaa tttttcaagg aagaaatttc agtggaagag 480
gtcgaaagag gcgaaaaaga tggcttttca aggctaaaag tcaggataaa atttaaaaac 540
cccgtttttg agtataagaa aaattga 567

<210> SEQ ID NO 100
<211> LENGTH: 188
<212> TYPE: PRT

-continued

<213> ORGANISM: Thermoanaerobacter tengcongensis

<400> SEQUENCE: 100

```
Met Lys Gly Thr Ile Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln His Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu Tyr Lys Lys Asn
            180                 185
```

<210> SEQ ID NO 101
<211> LENGTH: 573
<212> TYPE: DNA
<213> ORGANISM: Thermoanaerobacter tengcongensis

<400> SEQUENCE: 101

```
atgaagggga caatcgtcgg gacatggata aagaccctga gggaccttta cgggaatgat      60

gtggttgatg aatctttaaa aagtgtgggt tgggaaccag atagggtaat tacacctctg     120

gaggatattg atgacgatga ggttaggaga atttttgcta aggtgagtga aaaaactggt     180

aaaaatgtca acgaaatatg gagagaggta ggaaggcaga acttcaaaac tttcagcgaa     240

tggtttccct cctattttgc agggagaagg ctagtgaatt ttttaatgat gatggatgag     300

gtacacctac agcttaccaa gatgataaaa ggagccactc ctccaaggct tattgcaaag     360

cctgttgcaa aagatgccat tgaaatggag tacgtttcta aaagaaagat gtacgattac     420

tttttagggc ttatagaggg tagttctaaa tttttcaagg aagaaatttc agtggaagag     480

gtcgaaagag gcgaaaaaga tggcttttca aggctaaaag tcaggataaa atttaaaaac     540

cccgtttttg agcaccacca ccaccaccac tga                                  573
```

<210> SEQ ID NO 102
<211> LENGTH: 190
<212> TYPE: PRT
<213> ORGANISM: Thermoanaerobacter tengcongensis

<400> SEQUENCE: 102

```
Met Lys Gly Thr Ile Val Gly Thr Trp Ile Lys Thr Leu Arg Asp Leu
 1               5                  10                  15
```

-continued

```
Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Phe Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu His His His His His His
            180                 185                 190


<210> SEQ ID NO 103
<211> LENGTH: 573
<212> TYPE: DNA
<213> ORGANISM: Thermoanaerobacter tengcongensis

<400> SEQUENCE: 103

atgaagggga caatcgtcgg gacatggata aagaccctga gggaccttta cgggaatgat      60

gtggttgatg aatctttaaa aagtgtgggt tgggaaccag atagggtaat tacacctctg     120

gaggatattg atgacgatga ggttaggaga atttttgcta aggtgagtga aaaaactggt     180

aaaaatgtca acgaaatatg gagagaggta ggaaggcaga acataaaaac tttcagcgaa     240

tggtttccct cctattttgc agggagaagg ctagtgaatt ttttaatgat gatggatgag     300

gtacacctac agcttaccaa gatgataaaa ggagccactc ctccaaggct tattgcaaag     360

cctgttgcaa aagatgccat tgaaatggag tacgtttcta aaagaaagat gtacgattac     420

tttttagggt ttatagaggg tagttctaaa tttttcaagg aagaaatttc agtggaagag     480

gtcgaaagag gcgaaaaaga tggcttttca aggctaaaag tcaggataaa atttaaaaac     540

cccgtttttg agcaccacca ccaccaccac tga                                  573


<210> SEQ ID NO 104
<211> LENGTH: 190
<212> TYPE: PRT
<213> ORGANISM: Thermoanaerobacter tengcongensis

<400> SEQUENCE: 104

Met Lys Gly Thr Ile Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
```

-continued

```
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Phe
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu His His His His His His
            180                 185                 190


<210> SEQ ID NO 105
<211> LENGTH: 591
<212> TYPE: DNA
<213> ORGANISM: Thermoanaerobacter tengcongensis

<400> SEQUENCE: 105

atgaagggga caatcgtcgg gacatggata aagaccctga gggaccttta cgggaatgat      60

gtggttgatg aatctttaaa aagtgtgggt tgggaaccag atagggtaat tacacctctg     120

gaggatattg atgacgatga ggttaggaga atttttgcta aggtgagtga aaaaactggt     180

aaaaatgtca acgaaatatg gagagaggta ggaaggcaga acataaaaac tttcagcgaa     240

tggtttccct cctattttgc agggagaagg ctagtgaatt ttttaatgat gatggatgag     300

gtacacctac agcttaccaa gatgataaaa ggagccactc ctccaaggct tattgcaaag     360

cctgttgcaa aagatgccat tgaaatggag tacgtttcta aaagaaagat gtacgattac     420

tttttagggc ttatagaggg tagttctaaa tttttcaagg aagaaatttc agtggaagag     480

gtcgaaagag gcgaaaaaga tggcttttca aggctaaaag tcaggataaa atttaaaaac     540

cccgtttttg agtataagaa aaatctcgag caccaccacc accaccactg a              591


<210> SEQ ID NO 106
<211> LENGTH: 196
<212> TYPE: PRT
<213> ORGANISM: Thermoanaerobacter tengcongensis

<400> SEQUENCE: 106

Met Lys Gly Thr Ile Val Gly Thr Trp Ile Lys Thr Leu Arg Asp Leu
 1               5                  10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95
```

```
Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu Tyr Lys Lys Asn Leu Glu His His
            180                 185                 190

His His His His
        195


<210> SEQ ID NO 107
<211> LENGTH: 564
<212> TYPE: DNA
<213> ORGANISM: Legionella pneumophila

<400> SEQUENCE: 107

atgatgtcta tgaaaggaat catattcaac gaatttctca attttgtaga aaaaagtgaa      60

tcctacaccc tggtagatca aattattatg gatagtcatt tgaagtccca tggtgcctac     120

acgtctatcg gtacatactc tcccaaagaa ttatttcaat tggttaaagc gcttgctatg     180

aaaaatggca aaccaacatc agtgatttta caagaatatg gtgagtattt gtttgaggtt     240

tttgcaaaaa aatatcctca atttttcagg gaaaaaaagt cggtgtttca atttttggaa     300

gcgcttgaaa cacatattca tttcgaagtg aaaaaattgt atgactatac tgaactaccc     360

cattttgaat gccaatatca cagtcaaaat caaatggaaa tgatttacac ttcttcgcgt     420

cctttggccg attttgcgga aggtttaata aaaggttgta ttaaatatca taaagaaaac     480

atgactattg ttcgtgaaaa tctgcctgca aaaacaggct ttaaggtaag atttgtatta     540

acaaaaggcg atcctgatga gtga                                            564


<210> SEQ ID NO 108
<211> LENGTH: 187
<212> TYPE: PRT
<213> ORGANISM: Legionella pneumophila

<400> SEQUENCE: 108

Met Met Ser Met Lys Gly Ile Ile Phe Asn Glu Phe Leu Asn Phe Val
 1               5                  10                  15

Glu Lys Ser Glu Ser Tyr Thr Leu Val Asp Gln Ile Ile Met Asp Ser
            20                  25                  30

His Leu Lys Ser His Gly Ala Tyr Thr Ser Ile Gly Thr Tyr Ser Pro
        35                  40                  45

Lys Glu Leu Phe Gln Leu Val Lys Ala Leu Ala Met Lys Asn Gly Lys
    50                  55                  60

Pro Thr Ser Val Ile Leu Gln Glu Tyr Gly Glu Tyr Leu Phe Glu Val
65                  70                  75                  80

Phe Ala Lys Lys Tyr Pro Gln Phe Phe Arg Glu Lys Lys Ser Val Phe
                85                  90                  95

Gln Phe Leu Glu Ala Leu Glu Thr His Ile His Phe Glu Val Lys Lys
            100                 105                 110
```

```
Leu Tyr Asp Tyr Thr Glu Leu Pro His Phe Glu Cys Gln Tyr His Ser
        115                 120                 125

Gln Asn Gln Met Glu Met Ile Tyr Thr Ser Ser Arg Pro Leu Ala Asp
    130                 135                 140

Phe Ala Glu Gly Leu Ile Lys Gly Cys Ile Lys Tyr His Lys Glu Asn
145                 150                 155                 160

Met Thr Ile Val Arg Glu Asn Leu Pro Ala Lys Thr Gly Phe Lys Val
                165                 170                 175

Arg Phe Val Leu Thr Lys Gly Asp Pro Asp Glu
            180                 185
```

<210> SEQ ID NO 109
<211> LENGTH: 564
<212> TYPE: DNA
<213> ORGANISM: Legionella pneumophila

<400> SEQUENCE: 109

```
atgatgtcta tgaaaggaat catattcaac gaatttctca attttgtaga aaaaagtgaa      60

tcctacaccc tggtagatca aattattatg gatagtcatt tgaagtccca tggtgcctac     120

acgtctatcg gtacatactc tcccaaagaa ttatttcaat tggttaaagc gcttgctatg     180

aaaaatggca aaccaacatc agtgatttta caagaatatg gtgagtattt gtttgaggtt     240

tttgcaaaaa aatatcctca atttttcagg gaaaaaaagt cggtgtttca atttttggaa     300

gcgcttgaaa cacatattca tttcgaagtg aaaaaattgt atgactatac tgaactaccc     360

cattttgaat gccaatatca cagtcaaaat caaatggaaa tgatttacac ttcttcgcgt     420

cctttggccg attatgcgga aggtttaata aaaggttgta ttaaatatca taaagaaaac     480

atgactattg ttcgtgaaaa tctgcctgca aaaacaggct ttaaggtaag atttgtatta     540

acaaaaggcg atcctgatga gtga                                            564
```

<210> SEQ ID NO 110
<211> LENGTH: 187
<212> TYPE: PRT
<213> ORGANISM: Legionella pneumophila

<400> SEQUENCE: 110

```
Met Met Ser Met Lys Gly Ile Ile Phe Asn Glu Phe Leu Asn Phe Val
 1               5                  10                  15

Glu Lys Ser Glu Ser Tyr Thr Leu Val Asp Gln Ile Ile Met Asp Ser
            20                  25                  30

His Leu Lys Ser His Gly Ala Tyr Thr Ser Ile Gly Thr Tyr Ser Pro
        35                  40                  45

Lys Glu Leu Phe Gln Leu Val Lys Ala Leu Ala Met Lys Asn Gly Lys
    50                  55                  60

Pro Thr Ser Val Ile Leu Gln Glu Tyr Gly Glu Tyr Leu Phe Glu Val
65                  70                  75                  80

Phe Ala Lys Lys Tyr Pro Gln Phe Phe Arg Glu Lys Lys Ser Val Phe
                85                  90                  95

Gln Phe Leu Glu Ala Leu Glu Thr His Ile His Phe Glu Val Lys Lys
            100                 105                 110

Leu Tyr Asp Tyr Thr Glu Leu Pro His Phe Glu Cys Gln Tyr His Ser
        115                 120                 125

Gln Asn Gln Met Glu Met Ile Tyr Thr Ser Ser Arg Pro Leu Ala Asp
    130                 135                 140

Tyr Ala Glu Gly Leu Ile Lys Gly Cys Ile Lys Tyr His Lys Glu Asn
```

-continued

```
145                 150                 155                 160

Met Thr Ile Val Arg Glu Asn Leu Pro Ala Lys Thr Gly Phe Lys Val
                165                 170                 175

Arg Phe Val Leu Thr Lys Gly Asp Pro Asp Glu
            180                 185


<210> SEQ ID NO 111
<211> LENGTH: 564
<212> TYPE: DNA
<213> ORGANISM: Legionella pneumophila

<400> SEQUENCE: 111

atgatgtcta tgaaaggaat catatggaac gaatttctca attttgtaga aaaaagtgaa     60

tcctacaccc tggtagatca aattattatg gatagtcatt tgaagtccca tggtgcctac    120

acgtctatcg gtacatactc tcccaaagaa ttatttcaat tggttaaagc gcttgctatg    180

aaaaatggca aaccaacatc agtgatttta caagaatatg gtgagtattt gtttgaggtt    240

tttgcaaaaa aatatcctca atttttcagg gaaaaaaagt cggtgtttca atttttggaa    300

gcgcttgaaa cacatattca tttcgaagtg aaaaaattgt atgactatac tgaactaccc    360

cattttgaat gccaatatca cagtcaaaat caaatggaaa tgatttacac ttcttcgcgt    420

cctttggccg attatgcgga aggtttaata aaaggttgta ttaaatatca taaagaaaac    480

atgactattg ttcgtgaaaa tctgcctgca aaaacaggct ttaaggtaag atttgtatta    540

acaaaaggcg atcctgatga gtga                                           564


<210> SEQ ID NO 112
<211> LENGTH: 187
<212> TYPE: PRT
<213> ORGANISM: Legionella pneumophila

<400> SEQUENCE: 112

Met Met Ser Met Lys Gly Ile Ile Trp Asn Glu Phe Leu Asn Phe Val
 1               5                  10                  15

Glu Lys Ser Glu Ser Tyr Thr Leu Val Asp Gln Ile Ile Met Asp Ser
            20                  25                  30

His Leu Lys Ser His Gly Ala Tyr Thr Ser Ile Gly Thr Tyr Ser Pro
        35                  40                  45

Lys Glu Leu Phe Gln Leu Val Lys Ala Leu Ala Met Lys Asn Gly Lys
    50                  55                  60

Pro Thr Ser Val Ile Leu Gln Glu Tyr Gly Glu Tyr Leu Phe Glu Val
65                  70                  75                  80

Phe Ala Lys Lys Tyr Pro Gln Phe Phe Arg Glu Lys Lys Ser Val Phe
                85                  90                  95

Gln Phe Leu Glu Ala Leu Glu Thr His Ile His Phe Glu Val Lys Lys
            100                 105                 110

Leu Tyr Asp Tyr Thr Glu Leu Pro His Phe Glu Cys Gln Tyr His Ser
        115                 120                 125

Gln Asn Gln Met Glu Met Ile Tyr Thr Ser Ser Arg Pro Leu Ala Asp
    130                 135                 140

Tyr Ala Glu Gly Leu Ile Lys Gly Cys Ile Lys Tyr His Lys Glu Asn
145                 150                 155                 160

Met Thr Ile Val Arg Glu Asn Leu Pro Ala Lys Thr Gly Phe Lys Val
                165                 170                 175

Arg Phe Val Leu Thr Lys Gly Asp Pro Asp Glu
            180                 185
```

<210> SEQ ID NO 113
<211> LENGTH: 543
<212> TYPE: DNA
<213> ORGANISM: Legionella pneumophila

<400> SEQUENCE: 113
atgaaaggta tcgtttttac ctccttaaat gacatgatta tagaacaatt tggcatagaa 60
acctgggacc aactcgtatc ctcactagac cttccaagtg gtggaagtta tacagcaggc 120
ggcacttact cggatacaga atttcagcaa ttgattaagg ccattgcgaa gaggaccaat 180
cagcacgctt ctgttttttt agaggccttt ggtgaataca tgtttcctat cttatcgagt 240
aagtgcgcaa ttttttaaa aaaggacatg acattaaaag aatttttaaa aagcattgat 300
ggaacaattc atgtggaagt agaaaagtta tacccagatg aaacattacc taccattagc 360
tatgaagagc ctgctgcaaa ccaattggtt atggtgtatc gatcgcatag aagactctgt 420
cattttgcaa tggggctcat ccagggagca gcgcaacatt ttaaaaagaa aattaccatt 480
aagcagactc actgcatgtt aaaaaaagat gatcattgtc gtttggagat tacctttgag 540
tga 543

<210> SEQ ID NO 114
<211> LENGTH: 180
<212> TYPE: PRT
<213> ORGANISM: Legionella pneumophila

<400> SEQUENCE: 114

Met Lys Gly Ile Val Phe Thr Ser Leu Asn Asp Met Ile Ile Glu Gln
1 5 10 15

Phe Gly Ile Glu Thr Trp Asp Gln Leu Val Ser Ser Leu Asp Leu Pro
20 25 30

Ser Gly Gly Ser Tyr Thr Ala Gly Gly Thr Tyr Ser Asp Thr Glu Phe
35 40 45

Gln Gln Leu Ile Lys Ala Ile Ala Lys Arg Thr Asn Gln His Ala Ser
50 55 60

Val Phe Leu Glu Ala Phe Gly Glu Tyr Met Phe Pro Ile Leu Ser Ser
65 70 75 80

Lys Cys Ala Ile Phe Leu Lys Lys Asp Met Thr Leu Lys Glu Phe Leu
85 90 95

Lys Ser Ile Asp Gly Thr Ile His Val Glu Val Glu Lys Leu Tyr Pro
100 105 110

Asp Glu Thr Leu Pro Thr Ile Ser Tyr Glu Glu Pro Ala Ala Asn Gln
115 120 125

Leu Val Met Val Tyr Arg Ser His Arg Arg Leu Cys His Phe Ala Met
130 135 140

Gly Leu Ile Gln Gly Ala Ala Gln His Phe Lys Lys Lys Ile Thr Ile
145 150 155 160

Lys Gln Thr His Cys Met Leu Lys Lys Asp Asp His Cys Arg Leu Glu
165 170 175

Ile Thr Phe Glu
180

<210> SEQ ID NO 115
<211> LENGTH: 543
<212> TYPE: DNA
<213> ORGANISM: Legionella pneumophila -continued

<400> SEQUENCE: 115

```
atgaaaggta tcgtttttac ctccttaaat gacatgatta tagaacaatt tggcatagaa     60
acctgggacc aactcgtatc ctcactagac cttccaagtg gtggaagtta tacagcaggc    120
ggcacttact cggatacaga atttcagcaa ttgattaagg ccattgcgaa gaggaccaat    180
cagcacgctt ctgttttttt agaggccttt ggtgaataca tgtttcctat cttatcgagt    240
aagtgcgcaa ttttttttaaa aaaggacatg acattaaaag aatttttaaa aagcattgat    300
ggaacaattc atgtggaagt agaaaagtta tacccagatg aaacattacc taccattagc    360
tatgaagagc ctgctgcaaa ccaattggtt atggtgtatc gatcgcatag aagactctgt    420
cattacgcaa tggggctcat ccagggagca gcgcaacatt ttaaaaagaa aattaccatt    480
aagcagactc actgcatgtt aaaaaaagat gatcattgtc gtttggagat tacctttgag    540
tga                                                                   543
```

<210> SEQ ID NO 116
<211> LENGTH: 180
<212> TYPE: PRT
<213> ORGANISM: Legionella pneumophila

<400> SEQUENCE: 116

```
Met Lys Gly Ile Val Phe Thr Ser Leu Asn Asp Met Ile Ile Glu Gln
1               5                   10                  15

Phe Gly Ile Glu Thr Trp Asp Gln Leu Val Ser Ser Leu Asp Leu Pro
            20                  25                  30

Ser Gly Gly Ser Tyr Thr Ala Gly Gly Thr Tyr Ser Asp Thr Glu Phe
        35                  40                  45

Gln Gln Leu Ile Lys Ala Ile Ala Lys Arg Thr Asn Gln His Ala Ser
    50                  55                  60

Val Phe Leu Glu Ala Phe Gly Glu Tyr Met Phe Pro Ile Leu Ser Ser
65                  70                  75                  80

Lys Cys Ala Ile Phe Leu Lys Lys Asp Met Thr Leu Lys Glu Phe Leu
                85                  90                  95

Lys Ser Ile Asp Gly Thr Ile His Val Glu Val Glu Lys Leu Tyr Pro
            100                 105                 110

Asp Glu Thr Leu Pro Thr Ile Ser Tyr Glu Glu Pro Ala Ala Asn Gln
        115                 120                 125

Leu Val Met Val Tyr Arg Ser His Arg Arg Leu Cys His Tyr Ala Met
    130                 135                 140

Gly Leu Ile Gln Gly Ala Ala Gln His Phe Lys Lys Lys Ile Thr Ile
145                 150                 155                 160

Lys Gln Thr His Cys Met Leu Lys Lys Asp Asp His Cys Arg Leu Glu
                165                 170                 175

Ile Thr Phe Glu
            180
```

<210> SEQ ID NO 117
<211> LENGTH: 525
<212> TYPE: DNA
<213> ORGANISM: Desulfovibrio desulfuricans

<400> SEQUENCE: 117

```
atgaagatgc gcggtatttt gccgaaaata tttatgaatt ttataaaaga gatctatggg     60
gatgacgtgt ttgctcatgt ttctaaaacc atgggcgagc ctgtcttcat gccgggaaat    120
tcctaccctg atcaggtgtt gcgccagatg gctgaaatag tatgccagcg cacgggcgaa    180
```

```
cagcccaagt tgtttttga aaaagcaggg cgtgcaagcc tgcaggcttt taacagaatg    240

tacaggcagt actttaaagg ggaaaccctt aaagagtttc tgctggccat gaatgatatc    300

cacaggcacc tgacaaagga caatcccggc gtacgcccgc ctaaatttga gtatgacgat    360

cagggcgata cgcttgttat gacatataag tcgcagaggg attacggaga atactttgtg    420

ggcatcatca aggcagctgc ggagtttaaa aaggaaaaag tgcgtatcag ctcggagcat    480

gccggtaagg ggcgaacaac ggcaagggtt acatttatta aatga                   525
```

<210> SEQ ID NO 118
<211> LENGTH: 174
<212> TYPE: PRT
<213> ORGANISM: Desulfovibrio desulfuricans

<400> SEQUENCE: 118

```
Met Lys Met Arg Gly Ile Leu Pro Lys Ile Phe Met Asn Phe Ile Lys
 1               5                  10                  15

Glu Ile Tyr Gly Asp Asp Val Phe Ala His Val Ser Lys Thr Met Gly
            20                  25                  30

Glu Pro Val Phe Met Pro Gly Asn Ser Tyr Pro Asp Gln Val Leu Arg
        35                  40                  45

Gln Met Ala Glu Ile Val Cys Gln Arg Thr Gly Glu Gln Pro Lys Leu
    50                  55                  60

Phe Phe Glu Lys Ala Gly Arg Ala Ser Leu Gln Ala Phe Asn Arg Met
65                  70                  75                  80

Tyr Arg Gln Tyr Phe Lys Gly Glu Thr Leu Lys Glu Phe Leu Leu Ala
                85                  90                  95

Met Asn Asp Ile His Arg His Leu Thr Lys Asp Asn Pro Gly Val Arg
            100                 105                 110

Pro Pro Lys Phe Glu Tyr Asp Asp Gln Gly Asp Thr Leu Val Met Thr
        115                 120                 125

Tyr Lys Ser Gln Arg Asp Tyr Gly Glu Tyr Phe Val Gly Ile Ile Lys
    130                 135                 140

Ala Ala Ala Glu Phe Lys Lys Glu Lys Val Arg Ile Ser Ser Glu His
145                 150                 155                 160

Ala Gly Lys Gly Arg Thr Thr Ala Arg Val Thr Phe Ile Lys
                165                 170
```

<210> SEQ ID NO 119
<211> LENGTH: 525
<212> TYPE: DNA
<213> ORGANISM: Desulfovibrio desulfuricans

<400> SEQUENCE: 119

```
atgaagatgc gcggtatttt gccgaaaata tttatgaatt ttataaaaga gatctatggg     60

gatgacgtgt ttgctcatgt ttctaaaacc atgggcgagc ctgtcttcat gccgggaaat    120

tcctaccctg atcaggtgtt gcgccagatg gctgaaatag tatgccagcg cacgggcgaa    180

cagcccaagt tgtttttga aaaagcaggg cgtgcaagcc tgcaggcttt taacagaatg    240

tacaggcagt actttaaagg ggaaaccctt aaagagtttc tgctggccat gaatgatatc    300

cacaggcacc tgacaaagga caatcccggc gtacgcccgc ctaaatttga gtatgacgat    360

cagggcgata cgcttgttat gacatataag tcgcagaggg attacggaga actttttgtg    420

ggcatcatca aggcagctgc ggagtttaaa aaggaaaaag tgcgtatcag ctcggagcat    480

gccggtaagg ggcgaacaac ggcaagggtt acatttatta aatga                   525
```

<210> SEQ ID NO 120
<211> LENGTH: 174
<212> TYPE: PRT
<213> ORGANISM: Desulfovibrio desulfuricans

<400> SEQUENCE: 120

```
Met Lys Met Arg Gly Ile Leu Pro Lys Ile Phe Met Asn Phe Ile Lys
 1               5                  10                  15

Glu Ile Tyr Gly Asp Asp Val Phe Ala His Val Ser Lys Thr Met Gly
            20                  25                  30

Glu Pro Val Phe Met Pro Gly Asn Ser Tyr Pro Asp Gln Val Leu Arg
        35                  40                  45

Gln Met Ala Glu Ile Val Cys Gln Arg Thr Gly Glu Gln Pro Lys Leu
    50                  55                  60

Phe Phe Glu Lys Ala Gly Arg Ala Ser Leu Gln Ala Phe Asn Arg Met
65                  70                  75                  80

Tyr Arg Gln Tyr Phe Lys Gly Glu Thr Leu Lys Glu Phe Leu Leu Ala
                85                  90                  95

Met Asn Asp Ile His Arg His Leu Thr Lys Asp Asn Pro Gly Val Arg
            100                 105                 110

Pro Pro Lys Phe Glu Tyr Asp Asp Gln Gly Asp Thr Leu Val Met Thr
        115                 120                 125

Tyr Lys Ser Gln Arg Asp Tyr Gly Glu Leu Phe Val Gly Ile Ile Lys
    130                 135                 140

Ala Ala Ala Glu Phe Lys Lys Glu Lys Val Arg Ile Ser Ser Glu His
145                 150                 155                 160

Ala Gly Lys Gly Arg Thr Thr Ala Arg Val Thr Phe Ile Lys
                165                 170
```

<210> SEQ ID NO 121
<211> LENGTH: 1158
<212> TYPE: DNA
<213> ORGANISM: Homo sapiens

<400> SEQUENCE: 121

```
atgtacggat ttgtgaatca cgccctggag ttgctggtga tccgcaatta cggccccgag     60

gtgtgggaag acatcaaaaa agaggcacag ttagatgaag aaggacagtt tcttgtcaga    120

ataatatatg atgactccaa aacttatgat ttggttgctg ctgcaagcaa agtcctcaat    180

ctcaatgctg gagaaatcct ccaaatgttt gggaagatgt ttttcgtctt ttgccaagaa    240

tctggttatg atacaatctt gcgtgtcctg ggctctaatg tcagagaatt tctacagaac    300

cttgatgctc tgcacgacca ccttgctacc atctacccag gaatgcgtgc accttccttt    360

aggtgcactg atgcagaaaa gggcaaagga ctcattttgc actactactc agagagagaa    420

ggacttcagg atattgtcat tggaatcatc aaaacagtgg cacaacaaat ccatggcact    480

gaaatagaca tgaaggttat tcagcaaaga aatgaagaat gtgatcatac tcaattttta    540

attgaagaaa aagagtcaaa agaagaggat ttttatgaag atcttgacag atttgaagaa    600

aatggtaccc aggaatcacg catcagccca tatacattct gcaaagcttt tccttttcat    660

ataatatttg accgggacct agtggtcact cagtgtggca atgctatata cagagttctc    720

ccccagctcc agcctgggaa ttgcagcctt ctgtctgtct tctcgctggt tcgtcctcat    780

attgatatta gtttccatgg gatcctttct cacatcaata ctgtttttgt attgagaagc    840

aaggaaggat tgttggatgt ggagaaatta gaatgtgagg atgaactgac tgggactgag    900
```

```
atcagctgct tacgtctcaa gggtcaaatg atctacttac ctgaagcaga tagcatactt    960

tttctatgtt caccaagtgt catgaacctg gacgatttga caaggagagg gctgtatcta   1020

agtgacatcc ctctgcatga tgccacgcgc gatcttgttc ttttgggaga acaatttaga   1080

gaggaataca aactcaccca agaactggaa atcctcactg acaggctaca gctcacgtta   1140

agagccctgg aagattga                                                 1158


<210> SEQ ID NO 122
<211> LENGTH: 385
<212> TYPE: PRT
<213> ORGANISM: Homo sapiens

<400> SEQUENCE: 122

Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Asn Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Asp Arg Phe Glu Glu Asn Gly Thr Gln Glu Ser Arg Ile
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Asn Cys Ser Leu Leu Ser Val Phe Ser Leu
                245                 250                 255

Val Arg Pro His Ile Asp Ile Ser Phe His Gly Ile Leu Ser His Ile
            260                 265                 270

Asn Thr Val Phe Val Leu Arg Ser Lys Glu Gly Leu Leu Asp Val Glu
        275                 280                 285

Lys Leu Glu Cys Glu Asp Glu Leu Thr Gly Thr Glu Ile Ser Cys Leu
    290                 295                 300

Arg Leu Lys Gly Gln Met Ile Tyr Leu Pro Glu Ala Asp Ser Ile Leu
305                 310                 315                 320
```

-continued

```
Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
            340                 345                 350

Val Leu Leu Gly Glu Gln Phe Arg Glu Glu Tyr Lys Leu Thr Gln Glu
        355                 360                 365

Leu Glu Ile Leu Thr Asp Arg Leu Gln Leu Thr Leu Arg Ala Leu Glu
    370                 375                 380

Asp
385
```

<210> SEQ ID NO 123
<211> LENGTH: 1158
<212> TYPE: DNA
<213> ORGANISM: Homo sapiens

<400> SEQUENCE: 123

```
atgtacggat ttgtgaatca cgccctggag ttgctggtga tccgcaatta cggccccgag      60

gtgtgggaag acatcaaaaa agaggcacag ttagatgaag aaggacagtt tcttgtcaga     120

ataatatatg atgactccaa aacttatgat ttggttgctg ctgcaagcaa agtcctcaat     180

ctcaatgctg gagaaatcct ccaaatgttt gggaagatgt tttcgtcttt ttgccaagaa     240

tctggttatg atacaatctt gcgtgtcctg ggctctaatg tcagagaatt tctacagaac     300

cttgatgctc tgcacgacca ccttgctacc atctacccag gaatgcgtgc accttccttt     360

aggtgcactg atgcagaaaa gggcaaagga ctcattttgc actactactc agagagagaa     420

ggacttcagg attatgtcat tggaatcatc aaaacagtgg cacaacaaat ccatggcact     480

gaaatagaca tgaaggttat tcagcaaaga aatgaagaat gtgatcatac tcaattttta     540

attgaagaaa aagagtcaaa agaagaggat ttttatgaag atcttgacag atttgaagaa     600

aatggtaccc aggaatcacg catcagccca tatacattct gcaaagcttt tccttttcat     660

ataatatttg accgggacct agtggtcact cagtgtggca atgctatata cagagttctc     720

ccccagctcc agcctgggaa ttgcagcctt ctgtctgtct tctcgctggt tcgtcctcat     780

attgatatta gtttccatgg gatcctttct cacatcaata ctgtttttgt attgagaagc     840

aaggaaggat tgttggatgt ggagaaatta gaatgtgagg atgaactgac tgggactgag     900

atcagctgct tacgtctcaa gggtcaaatg atctacttac ctgaagcaga tagcatactt     960

tttctatgtt caccaagtgt catgaacctg gacgatttga caaggagagg gctgtatcta    1020

agtgacatcc ctctgcatga tgccacgcgc gatcttgttc ttttgggaga acaatttaga    1080

gaggaataca aactcaccca agaactggaa atcctcactg acaggctaca gctcacgtta    1140

agagccctgg aagattga                                                 1158
```

<210> SEQ ID NO 124
<211> LENGTH: 385
<212> TYPE: PRT
<213> ORGANISM: Homo sapiens

<400> SEQUENCE: 124

```
Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45
```

```
Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Tyr Val Ile Gly Ile Ile Lys Thr Val Ala Gln Gln Ile His Gly Thr
145                 150                 155                 160

Glu Ile Asp Met Lys Val Ile Gln Gln Arg Asn Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Asp Arg Phe Glu Glu Asn Gly Thr Gln Glu Ser Arg Ile
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Asn Cys Ser Leu Leu Ser Val Phe Ser Leu
                245                 250                 255

Val Arg Pro His Ile Asp Ile Ser Phe His Gly Ile Leu Ser His Ile
            260                 265                 270

Asn Thr Val Phe Val Leu Arg Ser Lys Glu Gly Leu Leu Asp Val Glu
        275                 280                 285

Lys Leu Glu Cys Glu Asp Glu Leu Thr Gly Thr Glu Ile Ser Cys Leu
    290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
            340                 345                 350

Val Leu Leu Gly Glu Gln Phe Arg Glu Glu Tyr Lys Leu Thr Gln Glu
        355                 360                 365

Leu Glu Ile Leu Thr Asp Arg Leu Gln Leu Thr Leu Arg Ala Leu Glu
    370                 375                 380

Asp
385


<210> SEQ ID NO 125
<211> LENGTH: 1158
<212> TYPE: DNA
<213> ORGANISM: Homo sapiens

<400> SEQUENCE: 125

atgtacggat ttgtgaatca cgccctggag ttgctggtga tccgcaatta cggccccgag      60

gtgtgggaag acatcaaaaa agaggcacag ttagatgaag aaggacagtt tcttgtcaga     120
```

-continued

```
ataatatatg atgactccaa aacttatgat ttggttgctg ctgcaagcaa agtcctcaat    180

ctcaatgctg gagaaatcct ccaaatgttt gggaagatgt ttttcgtctt ttgccaagaa    240

tctggttatg atacaatctt gcgtgtcctg ggctctaatg tcagagaatt tctacagaac    300

cttgatgctc tgcacgacca ccttgctacc atctacccag gaatgcgtgc accttccttt    360

aggtgcactg atgcagaaaa gggcaaagga ctcattttgc actactactc agagagagaa    420

ggacttcagg atcatgtcat tggaatcatc aaaacagtgg cacaacaaat ccatggcact    480

gaaatagaca tgaaggttat tcagcaaaga aatgaagaat gtgatcatac tcaattttta    540

attgaagaaa aagagtcaaa agaagaggat ttttatgaag atcttgacag atttgaagaa    600

aatggtaccc aggaatcacg catcagccca tatacattct gcaaagcttt tccttttcat    660

ataatatttg accgggacct agtggtcact cagtgtggca atgctatata cagagttctc    720

ccccagctcc agcctgggaa ttgcagcctt ctgtctgtct tctcgctggt tcgtcctcat    780

attgatatta gtttccatgg gatcctttct cacatcaata ctgtttttgt attgagaagc    840

aaggaaggat tgttggatgt ggagaaatta gaatgtgagg atgaactgac tgggactgag    900

atcagctgct tacgtctcaa gggtcaaatg atctacttac ctgaagcaga tagcatactt    960

tttctatgtt caccaagtgt catgaacctg gacgatttga caaggagagg gctgtatcta   1020

agtgacatcc ctctgcatga tgccacgcgc gatcttgttc ttttgggaga acaatttaga   1080

gaggaataca aactcaccca agaactggaa atcctcactg acaggctaca gctcacgtta   1140

agagccctgg aagattga                                                 1158
```

<210> SEQ ID NO 126
<211> LENGTH: 385
<212> TYPE: PRT
<213> ORGANISM: Homo sapiens

<400> SEQUENCE: 126

```
Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

His Val Ile Gly Ile Ile Lys Thr Val Ala Gln Gln Ile His Gly Thr
145                 150                 155                 160

Glu Ile Asp Met Lys Val Ile Gln Gln Arg Asn Glu Glu Cys Asp His
                165                 170                 175

Thr Gln Phe Leu Ile Glu Glu Lys Glu Ser Lys Glu Glu Asp Phe Tyr
            180                 185                 190
```

```
Glu Asp Leu Asp Arg Phe Glu Glu Asn Gly Thr Gln Glu Ser Arg Ile
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Asn Cys Ser Leu Leu Ser Val Phe Ser Leu
                245                 250                 255

Val Arg Pro His Ile Asp Ile Ser Phe His Gly Ile Leu Ser His Ile
            260                 265                 270

Asn Thr Val Phe Val Leu Arg Ser Lys Glu Gly Leu Leu Asp Val Glu
        275                 280                 285

Lys Leu Glu Cys Glu Asp Glu Leu Thr Gly Thr Glu Ile Ser Cys Leu
    290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
            340                 345                 350

Val Leu Leu Gly Glu Gln Phe Arg Glu Glu Tyr Lys Leu Thr Gln Glu
        355                 360                 365

Leu Glu Ile Leu Thr Asp Arg Leu Gln Leu Thr Leu Arg Ala Leu Glu
    370                 375                 380

Asp
385


<210> SEQ ID NO 127
<211> LENGTH: 1158
<212> TYPE: DNA
<213> ORGANISM: Homo sapiens

<400> SEQUENCE: 127

atgtacggat ttgtgaatca cgccctggag ttgctggtga tccgcaatta cggccccgag      60

gtgtgggaag acatcaaaaa agaggcacag ttagatgaag aaggacagtt tcttgtcaga     120

ataaatatatg atgactccaa aacttatgat ttggttgctg ctgcaagcaa agtcctcaat     180

ctcaatgctg gagaaatcct ccaaatgttt gggaagatgt tttcgtcttt ttaccaagaa     240

tctggttatg atacaatctt gcgtgtcctg ggctctaatg tcagagaatt tctacagaac     300

cttgatgctc tgcacgacca ccttgctacc atctacccag gaatgcgtgc accttccttt     360

aggtgcactg atgcagaaaa gggcaaagga ctcattttgc actactactc agagagagaa     420

ggacttcagg atattgtcat tggaatcatc aaaacagtgg cacaacaaat ccatggcact     480

gaaatagaca tgaaggttat tcagcaaaga aatgaagaat gtgatcatac tcaattttta     540

attgaagaaa aagagtcaaa agaagaggat ttttatgaag atcttgacag atttgaagaa     600

aatggtaccc aggaatcacg catcagccca tatacattct gcaaagcttt tccttttcat     660

ataatatttg accgggacct agtggtcact cagtgtggca atgctatata cagagttctc     720

ccccagctcc agcctgggaa ttgcagcctt ctgtctgtct tctcgctggt tcgtcctcat     780

attgatatta gtttccatgg gatcctttct cacatcaata ctgtttttgt attgagaagc     840

aaggaaggat tgttggatgt ggagaaatta gaatgtgagg atgaactgac tgggactgag     900

atcagctgct tacgtctcaa gggtcaaatg atctacttac ctgaagcaga tagcatactt     960
```

-continued

```
tttctatgtt caccaagtgt catgaacctg gacgatttga caaggagagg gctgtatcta   1020

agtgacatcc ctctgcatga tgccacgcgc gatcttgttc ttttgggaga acaatttaga   1080

gaggaataca aactcaccca agaactggaa atcctcactg acaggctaca gctcacgtta   1140

agagccctgg aagattga                                                 1158


<210> SEQ ID NO 128
<211> LENGTH: 385
<212> TYPE: PRT
<213> ORGANISM: Homo sapiens

<400> SEQUENCE: 128

Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Tyr Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Asn Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Asp Arg Phe Glu Glu Asn Gly Thr Gln Glu Ser Arg Ile
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Asn Cys Ser Leu Leu Ser Val Phe Ser Leu
                245                 250                 255

Val Arg Pro His Ile Asp Ile Ser Phe His Gly Ile Leu Ser His Ile
            260                 265                 270

Asn Thr Val Phe Val Leu Arg Ser Lys Glu Gly Leu Leu Asp Val Glu
        275                 280                 285

Lys Leu Glu Cys Glu Asp Glu Leu Thr Gly Thr Glu Ile Ser Cys Leu
    290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335
```

-continued

Gly Leu Tyr Leu Ser Asp Ile Pro Leu His Asp Ala Thr Arg Asp Leu
340 345 350

Val Leu Leu Gly Glu Gln Phe Arg Glu Glu Tyr Lys Leu Thr Gln Glu
355 360 365

Leu Glu Ile Leu Thr Asp Arg Leu Gln Leu Thr Leu Arg Ala Leu Glu
370 375 380

Asp
385

<210> SEQ ID NO 129
<211> LENGTH: 1158
<212> TYPE: DNA
<213> ORGANISM: Homo sapiens

<400> SEQUENCE: 129
atgtacggat ttgtgaatca cgccctggag ttgctggtga tccgcaatta cggccccgag 60
gtgtgggaag acatcaaaaa agaggcacag ttagatgaag aaggacagtt tcttgtcaga 120
ataatatatg atgactccaa aacttatgat ttggttgctg ctgcaagcaa agtcctcaat 180
ctcaatgctg gagaaatcct ccaaatgttt gggaagatgt tttcgtcttt ttgccaagaa 240
tctggttatg atacaatctt gcgtgtcctg ggctctaatg tcagagaatt tctacagaac 300
cttgatgctc tgttcgacca ccttgctacc atctacccag gaatgcgtgc accttccttt 360
aggtgcactg atgcagaaaa gggcaaagga ctcattttgc actactactc agagagagaa 420
ggacttcagg atattgtcat tggaatcatc aaaacagtgg cacaacaaat ccatggcact 480
gaaatagaca tgaaggttat tcagcaaaga aatgaagaat gtgatcatac tcaattttta 540
attgaagaaa aagagtcaaa agaagaggat ttttatgaag atcttgacag atttgaagaa 600
aatggtaccc aggaatcacg catcagccca tatacattct gcaaagcttt tccttttcat 660
ataatatttg accgggacct agtggtcact cagtgtggca atgctatata cagagttctc 720
ccccagctcc agcctgggaa ttgcagcctt ctgtctgtct tctcgctggt tcgtcctcat 780
attgatatta gtttccatgg gatcctttct cacatcaata ctgtttttgt attgagaagc 840
aaggaaggat tgttggatgt ggagaaatta gaatgtgagg atgaactgac tgggactgag 900
atcagctgct tacgtctcaa gggtcaaatg atctacttac ctgaagcaga tagcatactt 960
tttctatgtt caccaagtgt catgaacctg gacgatttga caaggagagg gctgtatcta 1020
agtgacatcc ctctgcatga tgccacgcgc gatcttgttc ttttgggaga acaatttaga 1080
gaggaataca aactcaccca agaactggaa atcctcactg acaggctaca gctcacgtta 1140
agagccctgg aagattga 1158

<210> SEQ ID NO 130
<211> LENGTH: 385
<212> TYPE: PRT
<213> ORGANISM: Homo sapiens

<400> SEQUENCE: 130

Met Tyr Gly Phe Val Asn His Ala Leu Glu Leu Leu Val Ile Arg Asn
1 5 10 15

Tyr Gly Pro Glu Val Trp Glu Asp Ile Lys Lys Glu Ala Gln Leu Asp
20 25 30

Glu Glu Gly Gln Phe Leu Val Arg Ile Ile Tyr Asp Asp Ser Lys Thr
35 40 45

Tyr Asp Leu Val Ala Ala Ala Ser Lys Val Leu Asn Leu Asn Ala Gly

```
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu Phe Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Asn Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Asp Arg Phe Glu Glu Asn Gly Thr Gln Glu Ser Arg Ile
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Asn Cys Ser Leu Leu Ser Val Phe Ser Leu
                245                 250                 255

Val Arg Pro His Ile Asp Ile Ser Phe His Gly Ile Leu Ser His Ile
            260                 265                 270

Asn Thr Val Phe Val Leu Arg Ser Lys Glu Gly Leu Leu Asp Val Glu
        275                 280                 285

Lys Leu Glu Cys Glu Asp Glu Leu Thr Gly Thr Glu Ile Ser Cys Leu
    290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
            340                 345                 350

Val Leu Leu Gly Glu Gln Phe Arg Glu Glu Tyr Lys Leu Thr Gln Glu
        355                 360                 365

Leu Glu Ile Leu Thr Asp Arg Leu Gln Leu Thr Leu Arg Ala Leu Glu
    370                 375                 380

Asp
385


<210> SEQ ID NO 131
<211> LENGTH: 1158
<212> TYPE: DNA
<213> ORGANISM: Homo sapiens

<400> SEQUENCE: 131

atgtacggat ttgtgaatca cgccctggag ttgctggtga tccgcaatta cggcccccgag     60

gtgtgggaag acatcaaaaa agaggcacag ttagatgaag aaggacagtt tcttgtcaga    120

ataatatatg atgactccaa aacttatgat ttggttgctg ctgcaagcaa agtcctcaat    180
```

```
ctcaatgctg gagaaatcct ccaaatgttt gggaagatgt ttttcgtctt ttgccaagaa    240

tctggttatg atacaatctt gcgtgtcctg ggctctaatg tcagagaatt tctacagaac    300

cttgatgctc tgggtgacca ccttgctacc atctacccag gaatgcgtgc accttccttt    360

aggtgcactg atgcagaaaa gggcaaagga ctcattttgc actactactc agagagagaa    420

ggacttcagg atattgtcat tggaatcatc aaaacagtgg cacaacaaat ccatggcact    480

gaaatagaca tgaaggttat tcagcaaaga aatgaagaat gtgatcatac tcaattttta    540

attgaagaaa aagagtcaaa agaagaggat ttttatgaag atcttgacag atttgaagaa    600

aatggtaccc aggaatcacg catcagccca tatacattct gcaaagcttt tccttttcat    660

ataatatttg accgggacct agtggtcact cagtgtggca atgctatata cagagttctc    720

ccccagctcc agcctgggaa ttgcagcctt ctgtctgtct tctcgctggt tcgtcctcat    780

attgatatta gtttccatgg gatcctttct cacatcaata ctgtttttgt attgagaagc    840

aaggaaggat tgttggatgt ggagaaatta gaatgtgagg atgaactgac tgggactgag    900

atcagctgct tacgtctcaa gggtcaaatg atctacttac ctgaagcaga tagcatactt    960

tttctatgtt caccaagtgt catgaacctg gacgatttga caaggagagg gctgtatcta   1020

agtgacatcc ctctgcatga tgccacgcgc gatcttgttc ttttgggaga acaatttaga   1080

gaggaataca aactcaccca agaactggaa atcctcactg acaggctaca gctcacgtta   1140

agagccctgg aagattga                                                  1158
```

<210> SEQ ID NO 132
<211> LENGTH: 385
<212> TYPE: PRT
<213> ORGANISM: Homo sapiens

<400> SEQUENCE: 132

```
Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu Gly Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Asn Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Asp Arg Phe Glu Glu Asn Gly Thr Gln Glu Ser Arg Ile
```

```
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Asn Cys Ser Leu Leu Ser Val Phe Ser Leu
                245                 250                 255

Val Arg Pro His Ile Asp Ile Ser Phe His Gly Ile Leu Ser His Ile
            260                 265                 270

Asn Thr Val Phe Val Leu Arg Ser Lys Glu Gly Leu Leu Asp Val Glu
        275                 280                 285

Lys Leu Glu Cys Glu Asp Glu Leu Thr Gly Thr Glu Ile Ser Cys Leu
    290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
            340                 345                 350

Val Leu Leu Gly Glu Gln Phe Arg Glu Glu Tyr Lys Leu Thr Gln Glu
        355                 360                 365

Leu Glu Ile Leu Thr Asp Arg Leu Gln Leu Thr Leu Arg Ala Leu Glu
    370                 375                 380

Asp
385


<210> SEQ ID NO 133
<211> LENGTH: 585
<212> TYPE: DNA
<213> ORGANISM: Homo sapiens

<400> SEQUENCE: 133

atgtacggat ttgtgaatca cgccctggag ttgctggtga tccgcaatta cggccccgag      60

gtgtgggaag acatcaaaaa agaggcacag ttagatgaag aaggacagtt tcttgtcaga     120

ataatatatg atgactccaa aacttatgat ttggttgctg ctgcaagcaa agtcctcaat     180

ctcaatgctg gagaaatcct ccaaatgttt gggaagatgt ttttcgtctt ttgccaagaa     240

tctggttatg atacaatctt gcgtgtcctg ggctctaatg tcagagaatt tctacagaac     300

cttgatgctc tgcacgacca ccttgctacc atctacccag gaatgcgtgc accttccttt     360

aggtgcactg atgcagaaaa gggcaaagga ctcattttgc actactactc agagagagaa     420

ggacttcagg atattgtcat tggaatcatc aaaacagtgg cacaacaaat ccatggcact     480

gaaatagaca tgaaggttat tcagcaaaga aatgaagaat gtgatcatac tcaattttta     540

attgaagaaa aagagtcaaa agaagaggat ttttatgaag attga                    585


<210> SEQ ID NO 134
<211> LENGTH: 194
<212> TYPE: PRT
<213> ORGANISM: Homo sapiens

<400> SEQUENCE: 134

Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30
```

Glu Glu Gly Gln Phe Leu Val Arg Ile Ile Tyr Asp Asp Ser Lys Thr
35 40 45

Tyr Asp Leu Val Ala Ala Ala Ser Lys Val Leu Asn Leu Asn Ala Gly
50 55 60

Glu Ile Leu Gln Met Phe Gly Lys Met Phe Phe Val Phe Cys Gln Glu
65 70 75 80

Ser Gly Tyr Asp Thr Ile Leu Arg Val Leu Gly Ser Asn Val Arg Glu
85 90 95

Phe Leu Gln Asn Leu Asp Ala Leu His Asp His Leu Ala Thr Ile Tyr
100 105 110

Pro Gly Met Arg Ala Pro Ser Phe Arg Cys Thr Asp Ala Glu Lys Gly
115 120 125

Lys Gly Leu Ile Leu His Tyr Tyr Ser Glu Arg Glu Gly Leu Gln Asp
130 135 140

Ile Val Ile Gly Ile Ile Lys Thr Val Ala Gln Gln Ile His Gly Thr
145 150 155 160

Glu Ile Asp Met Lys Val Ile Gln Gln Arg Asn Glu Glu Cys Asp His
165 170 175

Thr Gln Phe Leu Ile Glu Glu Lys Glu Ser Lys Glu Glu Asp Phe Tyr
180 185 190

Glu Asp

<210> SEQ ID NO 135
<211> LENGTH: 585
<212> TYPE: DNA
<213> ORGANISM: Homo sapiens

<400> SEQUENCE: 135
atgtacggat ttgtgaatca cgccctggag ttgctggtga tccgcaatta cggccccgag 60
gtgtgggaag acatcaaaaa agaggcacag ttagatgaag aaggacagtt tcttgtcaga 120
ataatatatg atgactccaa aacttatgat ttggttgctg ctgcaagcaa agtcctcaat 180
ctcaatgctg gagaaatcct ccaaatgttt gggaagatgt tttcgtctt ttgccaagaa 240 tctggttatg atacaatctt gcgtgtcctg ggctctaatg tcagagaatt tctacagaac 300
cttgatgctc tgcacgacca ccttgctacc atctacccag gaatgcgtgc accttccttt 360
aggtgcactg atgcagaaaa gggcaaagga ctcattttgc actactactc agagagagaa 420
ggacttcagg attatgtcat tggaatcatc aaaacagtgg cacaacaaat ccatggcact 480
gaaatagaca tgaaggttat tcagcaaaga aatgaagaat gtgatcatac tcaattttta 540
attgaagaaa aagagtcaaa agaagaggat ttttatgaag attga 585

<210> SEQ ID NO 136
<211> LENGTH: 194
<212> TYPE: PRT
<213> ORGANISM: Homo sapiens

<400> SEQUENCE: 136

Met Tyr Gly Phe Val Asn His Ala Leu Glu Leu Leu Val Ile Arg Asn
1 5 10 15

Tyr Gly Pro Glu Val Trp Glu Asp Ile Lys Lys Glu Ala Gln Leu Asp
20 25 30

Glu Glu Gly Gln Phe Leu Val Arg Ile Ile Tyr Asp Asp Ser Lys Thr
35 40 45

Tyr Asp Leu Val Ala Ala Ala Ser Lys Val Leu Asn Leu Asn Ala Gly

```
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Tyr Val Ile Gly Ile Ile Lys Thr Val Ala Gln Gln Ile His Gly Thr
145                 150                 155                 160

Glu Ile Asp Met Lys Val Ile Gln Gln Arg Asn Glu Glu Cys Asp His
                165                 170                 175

Thr Gln Phe Leu Ile Glu Glu Lys Glu Ser Lys Glu Glu Asp Phe Tyr
            180                 185                 190

Glu Asp


<210> SEQ ID NO 137
<211> LENGTH: 585
<212> TYPE: DNA
<213> ORGANISM: Homo sapiens

<400> SEQUENCE: 137

atgtacggat ttgtgaatca cgcctgggag ttgctggtga tccgcaatta cggccccgag      60

gtgtgggaag acatcaaaaa agaggcacag ttagatgaag aaggacagtt tcttgtcaga     120

ataatatatg atgactccaa aacttatgat ttggttgctg ctgcaagcaa agtcctcaat     180

ctcaatgctg gagaaatcct ccaaatgttt gggaagatgt tttcgtcttt ttgccaagaa     240

tctggttatg atacaatctt gcgtgtcctg ggctctaatg tcagagaatt tctacagaac     300

cttgatgctc tgcacgacca ccttgctacc atctacccag gaatgcgtgc accttccttt     360

aggtgcactg atgcagaaaa gggcaaagga ctcattttgc actactactc agagagagaa     420

ggacttcagg attatgtcat tggaatcatc aaaacagtgg cacaacaaat ccatggcact     480

gaaatagaca tgaaggttat tcagcaaaga aatgaagaat gtgatcatac tcaattttta     540

attgaagaaa aagagtcaaa agaagaggat tttatgaag attga                     585


<210> SEQ ID NO 138
<211> LENGTH: 194
<212> TYPE: PRT
<213> ORGANISM: Homo sapiens

<400> SEQUENCE: 138

Met Tyr Gly Phe Val Asn His Ala Trp Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80
```

```
Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Tyr Val Ile Gly Ile Ile Lys Thr Val Ala Gln Gln Ile His Gly Thr
145                 150                 155                 160

Glu Ile Asp Met Lys Val Ile Gln Gln Arg Asn Glu Glu Cys Asp His
                165                 170                 175

Thr Gln Phe Leu Ile Glu Glu Lys Glu Ser Lys Glu Glu Asp Phe Tyr
            180                 185                 190

Glu Asp
```

<210> SEQ ID NO 139
<211> LENGTH: 1158
<212> TYPE: DNA
<213> ORGANISM: Rattus norvegicus

<400> SEQUENCE: 139

```
atgtacggtt ttgtgaacca tgccctggag ctgctggtga tccgcaatta cggtcccgag     60

gtgtgggaag acatcaaaaa agaggcgcag ctggatgaag aaggccagtt tcttgtgaga    120

ataatctacg atgattccaa aacctatgac ttggtggctg ctgcgagcaa agtcctcaac    180

ctcaatgctg gtgaaatcct gcagatgttt gggaagatgt tttcgtctt ctgtcaagag     240

tctggctatg ataccatctt gcgtgtcctg ggatctaatg tcagggagtt tttgcagaac    300

ctcgacgccc tgcacgacca cctcgccacc atctacccag ggatgcgcgc accttccttc    360

cggtgcaccg atgcagaaaa aggcaaaggg ctcattctgc actactactc ggaaagagag    420

gggcttcagg acattgtgat cgggattatc aagactgtag ctcaacagat ccatggcact    480

gagatagaca tgaaggttat tcagcaaaga agtgaagaat gtgatcatac ccaattttta    540

attgaagaaa aagaatcaaa agaagaggat tttatgaag atctggacag gtttgaagag     600

aacggtaccc aggactcccg tatcagcccg tacaccttct gcaaagcgtt tccttttcac    660

atcatatttg accgggacct agtagtcacg cagtgtggaa atgctatcta cagagtgctc    720

ccccagctcc agcctgggaa gtgcagcctt ctgtctgtct tctctctggt ccgccctcat    780

attgacatca gtttccacgg gattctttca cacatcaata ccgtctttgt actgagaagc    840

aaggaagggt tgctggatgt tgagaaactt gaatgtgagg atgaactgac tggggcagag    900

attagctgcc tccgtctcaa aggccaaatg atctatttac cggaagcaga tagcatcctc    960

ttcctctgtt caccaagtgt gatgaacttg gatgacctaa caagaagagg cctgtacctg   1020

agtgacatcc ctctccatga tgctacacga gacctggtcc ttttgggaga acagttccgg   1080

gaggagtaca aactgacaca agagctggaa atcctcacag acaggctgca gctcacactg   1140

agggctttgg aggattga                                                 1158
```

<210> SEQ ID NO 140
<211> LENGTH: 385
<212> TYPE: PRT
<213> ORGANISM: Rattus norvegicus

<400> SEQUENCE: 140

-continued

Met Tyr Gly Phe Val Asn His Ala Leu Glu Leu Leu Val Ile Arg Asn
1               5                   10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Ser Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Asp Arg Phe Glu Glu Asn Gly Thr Gln Asp Ser Arg Ile
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Lys Cys Ser Leu Leu Ser Val Phe Ser Leu
                245                 250                 255

Val Arg Pro His Ile Asp Ile Ser Phe His Gly Ile Leu Ser His Ile
            260                 265                 270

Asn Thr Val Phe Val Leu Arg Ser Lys Glu Gly Leu Leu Asp Val Glu
        275                 280                 285

Lys Leu Glu Cys Glu Asp Glu Leu Thr Gly Ala Glu Ile Ser Cys Leu
    290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
            340                 345                 350

Val Leu Leu Gly Glu Gln Phe Arg Glu Glu Tyr Lys Leu Thr Gln Glu
        355                 360                 365

Leu Glu Ile Leu Thr Asp Arg Leu Gln Leu Thr Leu Arg Ala Leu Glu
    370                 375                 380

Asp
385

<210> SEQ ID NO 141
<211> LENGTH: 1158
<212> TYPE: DNA

<213> ORGANISM: Rattus norvegicus

<400> SEQUENCE: 141

```
atgtacggtt ttgtgaacca tgccctggag ctgctggtga tccgcaatta cggtcccgag       60
gtgtgggaag acatcaaaaa agaggcgcag ctggatgaag aaggccagtt tcttgtgaga      120
ataatctacg atgattccaa aacctatgac ttggtggctg ctgcgagcaa agtcctcaac      180
ctcaatgctg gtgaaatcct gcagatgttt gggaagatgt ttttcgtctt ctgtcaagag      240
tctggctatg ataccatctt gcgtgtcctg ggatctaatg tcagggagtt tttgcagaac      300
ctcgacgccc tgcacgacca cctcgccacc atctacccag ggatgcgcgc accttccttc      360
cggtgcaccg atgcagaaaa aggcaaaggg ctcattctgc actactactc ggaaagagag      420
gggcttcagg actacgtgat cgggattatc aagactgtag ctcaacagat ccatggcact      480
gagatagaca tgaaggttat tcagcaaaga agtgaagaat gtgatcatac ccaattttta      540
attgaagaaa aagaatcaaa agaagaggat ttttatgaag atctggacag gtttgaagag      600
aacggtaccc aggactcccg tatcagcccg tacaccttct gcaaagcgtt tccttttcac      660
atcatatttg accgggacct agtagtcacg cagtgtggaa atgctatcta cagagtgctc      720
ccccagctcc agcctgggaa gtgcagcctt ctgtctgtct tctctctggt ccgcccctcat      780
attgacatca gtttccacgg gattctttca cacatcaata ccgtctttgt actgagaagc      840
aaggaagggt tgctggatgt tgagaaactt gaatgtgagg atgaactgac tggggcagag      900
attagctgcc tccgtctcaa aggccaaatg atctatttac cggaagcaga tagcatcctc      960
ttcctctgtt caccaagtgt gatgaacttg gatgacctaa caagaagagg cctgtacctg     1020
agtgacatcc ctctccatga tgctacacga gacctggtcc ttttgggaga acagttccgg     1080
gaggagtaca aactgacaca agagctggaa atcctcacag acaggctgca gctcacactg     1140
agggctttgg aggattga                                                   1158
```

<210> SEQ ID NO 142
<211> LENGTH: 385
<212> TYPE: PRT
<213> ORGANISM: Rattus norvegicus

<400> SEQUENCE: 142

```
Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
           100                 105                 110

Pro Gly Met Arg Ala Pro Ser Phe Arg Cys Thr Asp Ala Glu Lys Gly
       115                 120                 125

Lys Gly Leu Ile Leu His Tyr Tyr Ser Glu Arg Glu Gly Leu Gln Asp
   130                 135                 140
```

-continued

```
Tyr Val Ile Gly Ile Ile Lys Thr Val Ala Gln Gln Ile His Gly Thr
145                 150                 155                 160

Glu Ile Asp Met Lys Val Ile Gln Gln Arg Ser Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Asp Arg Phe Glu Glu Asn Gly Thr Gln Asp Ser Arg Ile
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Lys Cys Ser Leu Leu Ser Val Phe Ser Leu
                245                 250                 255

Val Arg Pro His Ile Asp Ile Ser Phe His Gly Ile Leu Ser His Ile
            260                 265                 270

Asn Thr Val Phe Val Leu Arg Ser Lys Glu Gly Leu Leu Asp Val Glu
        275                 280                 285

Lys Leu Glu Cys Glu Asp Glu Leu Thr Gly Ala Glu Ile Ser Cys Leu
    290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
            340                 345                 350

Val Leu Leu Gly Glu Gln Phe Arg Glu Glu Tyr Lys Leu Thr Gln Glu
        355                 360                 365

Leu Glu Ile Leu Thr Asp Arg Leu Gln Leu Thr Leu Arg Ala Leu Glu
    370                 375                 380

Asp
385
```

<210> SEQ ID NO 143
<211> LENGTH: 1158
<212> TYPE: DNA
<213> ORGANISM: Rattus norvegicus

<400> SEQUENCE: 143

```
atgtacggtt ttgtgaacca tgccctggag ctgctggtga tccgcaatta cggtcccgag     60

gtgtgggaag acatcaaaaa agaggcgcag ctggatgaag aaggccagtt tcttgtgaga    120

ataatctacg atgattccaa aacctatgac ttggtggctg ctgcgagcaa agtcctcaac    180

ctcaatgctg gtgaaatcct gcagatgttt gggaagatgt tttcgtctt ctgtcaagag     240

tctggctatg ataccatctt gcgtgtcctg ggatctaatg tcagggagtt tttgcagaac    300

ctcgacgccc tgcacgacca cctcgccacc atctacccag ggatgcgcgc accttccttc    360

cggtgcaccg atgcagaaaa aggcaaaggg ctcattctgc actactactc ggaaagagag    420

gggcttcagg accatgtgat cgggattatc aagactgtag ctcaacagat ccatggcact    480

gagatagaca tgaaggttat tcagcaaaga agtgaagaat gtgatcatac ccaatttta     540

attgaagaaa aagaatcaaa agaagaggat ttttatgaag atctggacag gtttgaagag    600

aacggtaccc aggactcccg tatcagcccg tacaccttct gcaaagcgtt tccttttcac    660

atcatatttg accgggacct agtagtcacg cagtgtggaa atgctatcta cagagtgctc    720
```

```
ccccagctcc agcctgggaa gtgcagcctt ctgtctgtct tctctctggt ccgccctcat    780

attgacatca gtttccacgg gattctttca cacatcaata ccgtctttgt actgagaagc    840

aaggaagggt tgctggatgt tgagaaactt gaatgtgagg atgaactgac tggggcagag    900

attagctgcc tccgtctcaa aggccaaatg atctatttac cggaagcaga tagcatcctc    960

ttcctctgtt caccaagtgt gatgaacttg gatgacctaa caagaagagg cctgtacctg   1020

agtgacatcc ctctccatga tgctacacga gacctggtcc ttttgggaga acagttccgg   1080

gaggagtaca aactgacaca agagctggaa atcctcacag acaggctgca gctcacactg   1140

agggctttgg aggattga                                                 1158
```

<210> SEQ ID NO 144
<211> LENGTH: 385
<212> TYPE: PRT
<213> ORGANISM: Rattus norvegicus

<400> SEQUENCE: 144

```
Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

His Val Ile Gly Ile Ile Lys Thr Val Ala Gln Gln Ile His Gly Thr
145                 150                 155                 160

Glu Ile Asp Met Lys Val Ile Gln Gln Arg Ser Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Asp Arg Phe Glu Glu Asn Gly Thr Gln Asp Ser Arg Ile
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Lys Cys Ser Leu Leu Ser Val Phe Ser Leu
                245                 250                 255

Val Arg Pro His Ile Asp Ile Ser Phe His Gly Ile Leu Ser His Ile
            260                 265                 270

Asn Thr Val Phe Val Leu Arg Ser Lys Glu Gly Leu Leu Asp Val Glu
        275                 280                 285
```

```
Lys Leu Glu Cys Glu Asp Glu Leu Thr Gly Ala Glu Ile Ser Cys Leu
    290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
            340                 345                 350

Val Leu Leu Gly Glu Gln Phe Arg Glu Glu Tyr Lys Leu Thr Gln Glu
        355                 360                 365

Leu Glu Ile Leu Thr Asp Arg Leu Gln Leu Thr Leu Arg Ala Leu Glu
    370                 375                 380

Asp
385


<210> SEQ ID NO 145
<211> LENGTH: 1158
<212> TYPE: DNA
<213> ORGANISM: Rattus norvegicus

<400> SEQUENCE: 145

atgtacggtt ttgtgaacca tgccctggag ctgctggtga tccgcaatta cggtcccgag      60

gtgtgggaag acatcaaaaa agaggcgcag ctggatgaag aaggccagtt tcttgtgaga     120

ataatctacg atgattccaa aacctatgac ttggtggctg ctgcgagcaa agtcctcaac     180

ctcaatgctg gtgaaatcct gcagatgttt gggaagatgt tttcgtctt ctatcaagag      240

tctggctatg ataccatctt gcgtgtcctg ggatctaatg tcagggagtt tttgcagaac     300

ctcgacgccc tgcacgacca cctcgccacc atctacccag ggatgcgcgc accttccttc     360

cggtgcaccg atgcagaaaa aggcaaaggg ctcattctgc actactactc ggaaagagag     420

gggcttcagg acattgtgat cgggattatc aagactgtag ctcaacagat ccatggcact     480

gagatagaca tgaaggttat tcagcaaaga agtgaagaat gtgatcatac ccaattttta     540

attgaagaaa aagaatcaaa agaagaggat ttttatgaag atctggacag gtttgaagag     600

aacggtaccc aggactcccg tatcagcccg tacaccttct gcaaagcgtt tccttttcac     660

atcatatttg accgggacct agtagtcacg cagtgtggaa atgctatcta cagagtgctc     720

ccccagctcc agcctgggaa gtgcagcctt ctgtctgtct tctctctggt ccgccctcat     780

attgacatca gtttccacgg gattctttca cacatcaata ccgtctttgt actgagaagc     840

aaggaagggt tgctggatgt tgagaaactt gaatgtgagg atgaactgac tggggcagag     900

attagctgcc tccgtctcaa aggccaaatg atctatttac cggaagcaga tagcatcctc     960

ttcctctgtt caccaagtgt gatgaacttg gatgacctaa caagaagagg cctgtacctg    1020

agtgacatcc ctctccatga tgctacacga gacctggtcc ttttgggaga acagttccgg    1080

gaggagtaca aactgacaca agagctggaa atcctcacag acaggctgca gctcacactg    1140

agggctttgg aggattga                                                  1158


<210> SEQ ID NO 146
<211> LENGTH: 385
<212> TYPE: PRT
<213> ORGANISM: Rattus norvegicus

<400> SEQUENCE: 146

Met Tyr Gly Phe Val Asn His Ala Leu Glu Leu Leu Val Ile Arg Asn
 1               5                  10                  15
```

```
Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Tyr Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Ser Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Asp Arg Phe Glu Glu Asn Gly Thr Gln Asp Ser Arg Ile
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Lys Cys Ser Leu Leu Ser Val Phe Ser Leu
                245                 250                 255

Val Arg Pro His Ile Asp Ile Ser Phe His Gly Ile Leu Ser His Ile
            260                 265                 270

Asn Thr Val Phe Val Leu Arg Ser Lys Glu Gly Leu Leu Asp Val Glu
        275                 280                 285

Lys Leu Glu Cys Glu Asp Glu Leu Thr Gly Ala Glu Ile Ser Cys Leu
    290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
            340                 345                 350

Val Leu Leu Gly Glu Gln Phe Arg Glu Glu Tyr Lys Leu Thr Gln Glu
        355                 360                 365

Leu Glu Ile Leu Thr Asp Arg Leu Gln Leu Thr Leu Arg Ala Leu Glu
    370                 375                 380

Asp
385
```

```
<210> SEQ ID NO 147
<211> LENGTH: 1158
<212> TYPE: DNA
<213> ORGANISM: Rattus norvegicus
```

<400> SEQUENCE: 147

```
atgtacggtt ttgtgaacca tgccctggag ctgctggtga tccgcaatta cggtcccgag     60
gtgtgggaag acatcaaaaa agaggcgcag ctggatgaag aaggccagtt tcttgtgaga    120
ataatctacg atgattccaa aacctatgac ttggtggctg ctgcgagcaa agtcctcaac    180
ctcaatgctg gtgaaatcct gcagatgttt gggaagatgt tttcgtctt ctgtcaagag    240
tctggctatg ataccatctt gcgtgtcctg ggatctaatg tcagggagtt tttgcagaac    300
ctcgacgccc tgttcgacca cctcgccacc atctacccag ggatgcgcgc accttccttc    360
cggtgcaccg atgcagaaaa aggcaaaggg ctcattctgc actactactc ggaaagagag    420
gggcttcagg acattgtgat cgggattatc aagactgtag ctcaacagat ccatggcact    480
gagatagaca tgaaggttat tcagcaaaga agtgaagaat gtgatcatac ccaatttta    540
attgaagaaa aagaatcaaa agaagaggat ttttatgaag atctggacag gtttgaagag    600
aacggtaccc aggactcccg tatcagcccg tacaccttct gcaaagcgtt tccttttcac    660
atcatatttg accgggacct agtagtcacg cagtgtggaa atgctatcta cagagtgctc    720
ccccagctcc agcctgggaa gtgcagcctt ctgtctgtct tctctctggt ccgccctcat    780
attgacatca gtttccacgg gattctttca cacatcaata ccgtctttgt actgagaagc    840
aaggaagggt tgctggatgt tgagaaactt gaatgtgagg atgaactgac tggggcagag    900
attagctgcc tccgtctcaa aggccaaatg atctatttac cggaagcaga tagcatcctc    960
ttcctctgtt caccaagtgt gatgaacttg gatgacctaa caagaagagg cctgtacctg   1020
agtgacatcc ctctccatga tgctacacga gacctggtcc ttttgggaga acagttccgg   1080
gaggagtaca aactgacaca agagctggaa atcctcacag acaggctgca gctcacactg   1140
agggctttgg aggattga                                                 1158
```

<210> SEQ ID NO 148
<211> LENGTH: 385
<212> TYPE: PRT
<213> ORGANISM: Rattus norvegicus

<400> SEQUENCE: 148

```
Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu Phe Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160
```

```
Glu Ile Asp Met Lys Val Ile Gln Gln Arg Ser Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Asp Arg Phe Glu Glu Asn Gly Thr Gln Asp Ser Arg Ile
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Lys Cys Ser Leu Leu Ser Val Phe Ser Leu
                245                 250                 255

Val Arg Pro His Ile Asp Ile Ser Phe His Gly Ile Leu Ser His Ile
            260                 265                 270

Asn Thr Val Phe Val Leu Arg Ser Lys Glu Gly Leu Leu Asp Val Glu
        275                 280                 285

Lys Leu Glu Cys Glu Asp Glu Leu Thr Gly Ala Glu Ile Ser Cys Leu
    290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
            340                 345                 350

Val Leu Leu Gly Glu Gln Phe Arg Glu Glu Tyr Lys Leu Thr Gln Glu
        355                 360                 365

Leu Glu Ile Leu Thr Asp Arg Leu Gln Leu Thr Leu Arg Ala Leu Glu
    370                 375                 380

Asp
385
```

<210> SEQ ID NO 149
<211> LENGTH: 1158
<212> TYPE: DNA
<213> ORGANISM: Rattus norvegicus

<400> SEQUENCE: 149

```
atgtacggtt ttgtgaacca tgccctggag ctgctggtga tccgcaatta cggtcccgag     60

gtgtgggaag acatcaaaaa agaggcgcag ctggatgaag aaggccagtt tcttgtgaga    120

ataatctacg atgattccaa aacctatgac ttggtggctg ctgcgagcaa agtcctcaac    180

ctcaatgctg gtgaaatcct gcagatgttt gggaagatgt tttcgtctt ctgtcaagag    240

tctggctatg ataccatctt gcgtgtcctg ggatctaatg tcagggagtt tttgcagaac    300

ctcgacgccc tgggggacca cctcgccacc atctacccag ggatgcgcgc accttccttc    360

cggtgcaccg atgcagaaaa aggcaaaggg ctcattctgc actactactc ggaaagagag    420

gggcttcagg acattgtgat cgggattatc aagactgtag ctcaacagat ccatggcact    480

gagatagaca tgaaggttat tcagcaaaga agtgaagaat gtgatcatac ccaattttta    540

attgaagaaa aagaatcaaa agaagaggat ttttatgaag atctggacag gtttgaagag    600

aacggtaccc aggactcccg tatcagcccg tacaccttct gcaaagcgtt tccttttcac    660

atcatatttg accgggacct agtagtcacg cagtgtggaa atgctatcta cagagtgctc    720

ccccagctcc agcctgggaa gtgcagcctt ctgtctgtct tctctctggt ccgccctcat    780
```

attgacatca gtttccacgg gattctttca cacatcaata ccgtctttgt actgagaagc 840
aaggaagggt tgctggatgt tgagaaactt gaatgtgagg atgaactgac tggggcagag 900
attagctgcc tccgtctcaa aggccaaatg atctatttac cggaagcaga tagcatcctc 960
ttcctctgtt caccaagtgt gatgaacttg gatgacctaa caagaagagg cctgtacctg 1020
agtgacatcc ctctccatga tgctacacga gacctggtcc ttttgggaga acagttccgg 1080
gaggagtaca aactgacaca agagctggaa atcctcacag acaggctgca gctcacactg 1140
agggctttgg aggattga 1158

<210> SEQ ID NO 150
<211> LENGTH: 385
<212> TYPE: PRT
<213> ORGANISM: Rattus norvegicus

<400> SEQUENCE: 150

Met Tyr Gly Phe Val Asn His Ala Leu Glu Leu Leu Val Ile Arg Asn
1 5 10 15

Tyr Gly Pro Glu Val Trp Glu Asp Ile Lys Lys Glu Ala Gln Leu Asp
20 25 30

Glu Glu Gly Gln Phe Leu Val Arg Ile Ile Tyr Asp Asp Ser Lys Thr
35 40 45

Tyr Asp Leu Val Ala Ala Ala Ser Lys Val Leu Asn Leu Asn Ala Gly
50 55 60

Glu Ile Leu Gln Met Phe Gly Lys Met Phe Phe Val Phe Cys Gln Glu
65 70 75 80

Ser Gly Tyr Asp Thr Ile Leu Arg Val Leu Gly Ser Asn Val Arg Glu
85 90 95

Phe Leu Gln Asn Leu Asp Ala Leu Gly Asp His Leu Ala Thr Ile Tyr
100 105 110

Pro Gly Met Arg Ala Pro Ser Phe Arg Cys Thr Asp Ala Glu Lys Gly
115 120 125

Lys Gly Leu Ile Leu His Tyr Tyr Ser Glu Arg Glu Gly Leu Gln Asp
130 135 140

Ile Val Ile Gly Ile Ile Lys Thr Val Ala Gln Gln Ile His Gly Thr
145 150 155 160

Glu Ile Asp Met Lys Val Ile Gln Gln Arg Ser Glu Glu Cys Asp His
165 170 175

Thr Gln Phe Leu Ile Glu Glu Lys Glu Ser Lys Glu Glu Asp Phe Tyr
180 185 190

Glu Asp Leu Asp Arg Phe Glu Glu Asn Gly Thr Gln Asp Ser Arg Ile
195 200 205

Ser Pro Tyr Thr Phe Cys Lys Ala Phe Pro Phe His Ile Ile Phe Asp
210 215 220

Arg Asp Leu Val Val Thr Gln Cys Gly Asn Ala Ile Tyr Arg Val Leu
225 230 235 240

Pro Gln Leu Gln Pro Gly Lys Cys Ser Leu Leu Ser Val Phe Ser Leu
245 250 255

Val Arg Pro His Ile Asp Ile Ser Phe His Gly Ile Leu Ser His Ile
260 265 270

Asn Thr Val Phe Val Leu Arg Ser Lys Glu Gly Leu Leu Asp Val Glu
275 280 285

Lys Leu Glu Cys Glu Asp Glu Leu Thr Gly Ala Glu Ile Ser Cys Leu
290 295 300

Arg Leu Lys Gly Gln Met Ile Tyr Leu Pro Glu Ala Asp Ser Ile Leu
305 310 315 320

Phe Leu Cys Ser Pro Ser Val Met Asn Leu Asp Asp Leu Thr Arg Arg
325 330 335

Gly Leu Tyr Leu Ser Asp Ile Pro Leu His Asp Ala Thr Arg Asp Leu
340 345 350

Val Leu Leu Gly Glu Gln Phe Arg Glu Glu Tyr Lys Leu Thr Gln Glu
355 360 365

Leu Glu Ile Leu Thr Asp Arg Leu Gln Leu Thr Leu Arg Ala Leu Glu
370 375 380

Asp
385

<210> SEQ ID NO 151
<211> LENGTH: 585
<212> TYPE: DNA
<213> ORGANISM: Rattus norvegicus

<400> SEQUENCE: 151
atgtacggtt ttgtgaacca tgccctggag ctgctggtga tccgcaatta cggtcccgag 60
gtgtgggaag acatcaaaaa agaggcgcag ctggatgaag aaggccagtt tcttgtgaga 120
ataatctacg atgattccaa aacctatgac ttggtggctg ctgcgagcaa agtcctcaac 180
ctcaatgctg gtgaaatcct gcagatgttt gggaagatgt ttttcgtctt ctgtcaagag 240
tctggctatg ataccatctt gcgtgtcctg ggatctaatg tcagggagtt tttgcagaac 300
ctcgacgccc tgcacgacca cctcgccacc atctacccag ggatgcgcgc accttccttc 360
cggtgcaccg atgcagaaaa aggcaaaggg ctcattctgc actactactc ggaaagagag 420
gggcttcagg acattgtgat cggggattatc aagactgtag ctcaacagat ccatggcact 480
gagatagaca tgaaggttat tcagcaaaga agtgaagaat gtgatcatac ccaattttta 540
attgaagaaa aagaatcaaa agaagaggat ttttatgaag attga 585

<210> SEQ ID NO 152
<211> LENGTH: 194
<212> TYPE: PRT
<213> ORGANISM: Rattus norvegicus

<400> SEQUENCE: 152

Met Tyr Gly Phe Val Asn His Ala Leu Glu Leu Leu Val Ile Arg Asn
1 5 10 15

Tyr Gly Pro Glu Val Trp Glu Asp Ile Lys Lys Glu Ala Gln Leu Asp
20 25 30

Glu Glu Gly Gln Phe Leu Val Arg Ile Ile Tyr Asp Asp Ser Lys Thr
35 40 45

Tyr Asp Leu Val Ala Ala Ala Ser Lys Val Leu Asn Leu Asn Ala Gly
50 55 60

Glu Ile Leu Gln Met Phe Gly Lys Met Phe Phe Val Phe Cys Gln Glu
65 70 75 80

Ser Gly Tyr Asp Thr Ile Leu Arg Val Leu Gly Ser Asn Val Arg Glu
85 90 95

Phe Leu Gln Asn Leu Asp Ala Leu His Asp His Leu Ala Thr Ile Tyr
100 105 110

Pro Gly Met Arg Ala Pro Ser Phe Arg Cys Thr Asp Ala Glu Lys Gly
115 120 125

```
Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Ser Glu Glu Cys Asp His
                165                 170                 175

Thr Gln Phe Leu Ile Glu Glu Lys Glu Ser Lys Glu Glu Asp Phe Tyr
            180                 185                 190

Glu Asp


<210> SEQ ID NO 153
<211> LENGTH: 585
<212> TYPE: DNA
<213> ORGANISM: Rattus norvegicus

<400> SEQUENCE: 153

atgtacggtt ttgtgaacca tgccctggag ctgctggtga tccgcaatta cggtcccgag      60

gtgtgggaag acatcaaaaa agaggcgcag ctggatgaag aaggccagtt tcttgtgaga     120

ataatctacg atgattccaa aacctatgac ttggtggctg ctgcgagcaa agtcctcaac     180

ctcaatgctg gtgaaatcct gcagatgttt gggaagatgt ttttcgtctt ctgtcaagag     240

tctggctatg ataccatctt gcgtgtcctg ggatctaatg tcagggagtt tttgcagaac     300

ctcgacgccc tgcacgacca cctcgccacc atctacccag ggatgcgcgc accttccttc     360

cggtgcaccg atgcagaaaa aggcaaaggg ctcattctgc actactactc ggaaagagag     420

gggcttcagg actacgtgat cgggattatc aagactgtag ctcaacagat ccatggcact     480

gagatagaca tgaaggttat tcagcaaaga agtgaagaat gtgatcatac ccaattttta     540

attgaagaaa aagaatcaaa agaagaggat tttatgaag attga                     585


<210> SEQ ID NO 154
<211> LENGTH: 194
<212> TYPE: PRT
<213> ORGANISM: Rattus norvegicus

<400> SEQUENCE: 154

Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Tyr Val Ile Gly Ile Ile Lys Thr Val Ala Gln Gln Ile His Gly Thr
145                 150                 155                 160
```

```
Glu Ile Asp Met Lys Val Ile Gln Gln Arg Ser Glu Glu Cys Asp His
                165                 170                 175

Thr Gln Phe Leu Ile Glu Glu Lys Glu Ser Lys Glu Glu Asp Phe Tyr
            180                 185                 190

Glu Asp


<210> SEQ ID NO 155
<211> LENGTH: 585
<212> TYPE: DNA
<213> ORGANISM: Rattus norvegicus

<400> SEQUENCE: 155

atgtacggtt ttgtgaacca tgcctgggag ctgctggtga tccgcaatta cggtcccgag      60

gtgtgggaag acatcaaaaa agaggcgcag ctggatgaag aaggccagtt tcttgtgaga     120

ataatctacg atgattccaa aacctatgac ttggtggctg ctgcgagcaa agtcctcaac     180

ctcaatgctg gtgaaatcct gcagatgttt gggaagatgt tttcgtctt ctgtcaagag      240

tctggctatg ataccatctt gcgtgtcctg ggatctaatg tcagggagtt tttgcagaac     300

ctcgacgccc tgcacgacca cctcgccacc atctacccag ggatgcgcgc accttccttc     360

cggtgcaccg atgcagaaaa aggcaaaggg ctcattctgc actactactc ggaaagagag     420

gggcttcagg actacgtgat cgggattatc aagactgtag ctcaacagat ccatggcact     480

gagatagaca tgaaggttat tcagcaaaga agtgaagaat gtgatcatac ccaattttta     540

attgaagaaa aagaatcaaa agaagaggat ttttatgaag attga                     585


<210> SEQ ID NO 156
<211> LENGTH: 194
<212> TYPE: PRT
<213> ORGANISM: Rattus norvegicus

<400> SEQUENCE: 156

Met Tyr Gly Phe Val Asn His Ala Trp Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Tyr Val Ile Gly Ile Ile Lys Thr Val Ala Gln Gln Ile His Gly Thr
145                 150                 155                 160

Glu Ile Asp Met Lys Val Ile Gln Gln Arg Ser Glu Glu Cys Asp His
                165                 170                 175

Thr Gln Phe Leu Ile Glu Glu Lys Glu Ser Lys Glu Glu Asp Phe Tyr
```

180 185 190

Glu Asp

<210> SEQ ID NO 157
<211> LENGTH: 2229
<212> TYPE: DNA
<213> ORGANISM: Rattus norvegicus

<400> SEQUENCE: 157
atgtatggat tcatcaacac ctgcctgcag tctcttgtga cagagaaatt tggtgaggag 60
acatgggaga agctgaaggc tcctgcagaa gtgcaagatg tcttcatgac ctacaccgtg 120
tatgatgaca tcatcaccat taagctcatc caagaagcct gcaaggttct ggatgtgtcc 180
atggaagcca ttctgaagct ctttggcgaa tacttcttta agttctgtaa gatgtctggc 240
tatgacagga tgctgcggac acttggagga aatctcaccg agtttattga aaacctagat 300
gcactccaca gttacctggc actgtcctat caggaaatga acgcaccatc ctttcgagtg 360
gaggaaggag ctgacggggc gatgcttctc cactactact cagacagaca tggtctgtgt 420
cacattgtac caggtatcat tgaagctgtg gccaaggact tctttgacac tgatgtggcc 480
atgagtatcc tggatatgaa cgaagaggtg gaaaggacag ggaagaaaga acatgttgtg 540
tttctggtcg tgcagaaggc tcacagacag ataagaggag caaaggcaag ccggccacaa 600
ggcagtgagg acagccaggc agaccaggag gctctccagg gaacactcct tcggatgaag 660
gagagatatt taaacatccc tgtttgccct ggggagaaat ctcactcaac tgctgtgagg 720
gcatcggtcc tttttggaaa agggcccctc agggacacct tccagcccgt ctatcctgag 780
agactatggg tcgaagagga ggtgttctgt gatgcttttc ctttccacat tgtctttgat 840
gaagcactaa gggtcaagca agctggagtg aatattcaga agtatgtccc tggaatctta 900
acccagaagt ttgcactaga tgagtatttt tccatcatcc accctcaagt tactttcaac 960
atctccagca tctgcaagtt cattaacagt cagtttgtct tgaagacaag aaaagaaatg 1020
atgcccaaag caaggaagag ccagccgatg ctcaaactcc ggggtcagat gatctggatg 1080
gagtctctga ggtgcatgat cttcatgtgt tccccaaacg tccgcagcct gcaagagctg 1140
gaagagagca agatgcatct ttctgatatc gctccgcacg acacgaccag ggatctcatc 1200
ctcctcaacc agcagaggct ggcagagatg gagctgtcct gccaactgga aaagaagaag 1260
gaggagttgc gtgtcctttc caatcacctg gccatcgaga agaagaagac agagaccttg 1320
ctgtatgcca tgctgcctga acatgtggcc aaccaactca aggagggcag aaaggtggct 1380
gcaggagaat ttgaaacatg tacaatcctt ttcagcgatg ttgtgacatt taccaacatc 1440
tgtgcagcct gtgaacctat ccaaatcgtg aacatgctga attcaatgta ctccaagttt 1500
gacaggttaa ccagtgtcca tgatgtctac aaagtagaaa caatagggga tgcttacatg 1560
gtggtgggtg gagtaccagt acccgttgaa agccatgctc aaagagtcgc caattttgct 1620
ctggggatga gaatttctgc aaaagaagtg atgaatcctg tcactgggga acctatccag 1680
atcagagtgg gaatccacac tggaccagtc ttagcaggtg ttgtgggaga caagatgcct 1740
cggtactgct tgtttggtga cactgtaaac acagcctcta ggatggaaag tcacgggctt 1800
cccagcaaag tgcatctgag ccccacagcc cacagagccc tgaaaaacaa agggtttgaa 1860
attgtcagga gaggcgagat cgaagtgaag gggaaaggaa agatgaccac atactttctg 1920
atccagaacc tgaatgccac cgaggatgag ataatggggc gaccttcagc cccccgctgat 1980 gggaaggaag tatgtactcc cggaaaccaa gtcaggaagt cccctgctgt cccgaggaac 2040

```
acagaccatc agcaacaagt ctacaaagga gacccagcag acgcttctaa tgaagtcaca   2100

cttgctggga gcccagtggc agggcgaaac tccacagatg cagtcaataa ccagccatca   2160

ccagatgaga ccaagacaag tgtcgttgct agtggccctg tgctgtctgc tttctgtgtt   2220

gtgctgtga                                                           2229
```

<210> SEQ ID NO 158
<211> LENGTH: 742
<212> TYPE: PRT
<213> ORGANISM: Rattus norvegicus

<400> SEQUENCE: 158

```
Met Tyr Gly Phe Ile Asn Thr Cys Leu Gln Ser Leu Val Thr Glu Lys
 1               5                  10                  15

Phe Gly Glu Glu Thr Trp Glu Lys Leu Lys Ala Pro Ala Glu Val Gln
            20                  25                  30

Asp Val Phe Met Thr Tyr Thr Val Tyr Asp Asp Ile Ile Thr Ile Lys
        35                  40                  45

Leu Ile Gln Glu Ala Cys Lys Val Leu Asp Val Ser Met Glu Ala Ile
    50                  55                  60

Leu Lys Leu Phe Gly Glu Tyr Phe Phe Lys Phe Cys Lys Met Ser Gly
65                  70                  75                  80

Tyr Asp Arg Met Leu Arg Thr Leu Gly Gly Asn Leu Thr Glu Phe Ile
                85                  90                  95

Glu Asn Leu Asp Ala Leu His Ser Tyr Leu Ala Leu Ser Tyr Gln Glu
            100                 105                 110

Met Asn Ala Pro Ser Phe Arg Val Glu Glu Gly Ala Asp Gly Ala Met
        115                 120                 125

Leu Leu His Tyr Tyr Ser Asp Arg His Gly Leu Cys His Ile Val Pro
    130                 135                 140

Gly Ile Ile Glu Ala Val Ala Lys Asp Phe Phe Asp Thr Asp Val Ala
145                 150                 155                 160

Met Ser Ile Leu Asp Met Asn Glu Glu Val Glu Arg Thr Gly Lys Lys
                165                 170                 175

Glu His Val Val Phe Leu Val Val Gln Lys Ala His Arg Gln Ile Arg
            180                 185                 190

Gly Ala Lys Ala Ser Arg Pro Gln Gly Ser Glu Asp Ser Gln Ala Asp
        195                 200                 205

Gln Glu Ala Leu Gln Gly Thr Leu Leu Arg Met Lys Glu Arg Tyr Leu
    210                 215                 220

Asn Ile Pro Val Cys Pro Gly Glu Lys Ser His Ser Thr Ala Val Arg
225                 230                 235                 240

Ala Ser Val Leu Phe Gly Lys Gly Pro Leu Arg Asp Thr Phe Gln Pro
                245                 250                 255

Val Tyr Pro Glu Arg Leu Trp Val Glu Glu Glu Val Phe Cys Asp Ala
            260                 265                 270

Phe Pro Phe His Ile Val Phe Asp Glu Ala Leu Arg Val Lys Gln Ala
        275                 280                 285

Gly Val Asn Ile Gln Lys Tyr Val Pro Gly Ile Leu Thr Gln Lys Phe
    290                 295                 300

Ala Leu Asp Glu Tyr Phe Ser Ile Ile His Pro Gln Val Thr Phe Asn
305                 310                 315                 320

Ile Ser Ser Ile Cys Lys Phe Ile Asn Ser Gln Phe Val Leu Lys Thr
                325                 330                 335
```

```
Arg Lys Glu Met Met Pro Lys Ala Arg Lys Ser Gln Pro Met Leu Lys
            340                 345                 350

Leu Arg Gly Gln Met Ile Trp Met Glu Ser Leu Arg Cys Met Ile Phe
        355                 360                 365

Met Cys Ser Pro Asn Val Arg Ser Leu Gln Glu Leu Glu Glu Ser Lys
    370                 375                 380

Met His Leu Ser Asp Ile Ala Pro His Asp Thr Thr Arg Asp Leu Ile
385                 390                 395                 400

Leu Leu Asn Gln Gln Arg Leu Ala Glu Met Glu Leu Ser Cys Gln Leu
                405                 410                 415

Glu Lys Lys Lys Glu Glu Leu Arg Val Leu Ser Asn His Leu Ala Ile
            420                 425                 430

Glu Lys Lys Lys Thr Glu Thr Leu Leu Tyr Ala Met Leu Pro Glu His
        435                 440                 445

Val Ala Asn Gln Leu Lys Glu Gly Arg Lys Val Ala Ala Gly Glu Phe
    450                 455                 460

Glu Thr Cys Thr Ile Leu Phe Ser Asp Val Val Thr Phe Thr Asn Ile
465                 470                 475                 480

Cys Ala Ala Cys Glu Pro Ile Gln Ile Val Asn Met Leu Asn Ser Met
                485                 490                 495

Tyr Ser Lys Phe Asp Arg Leu Thr Ser Val His Asp Val Tyr Lys Val
            500                 505                 510

Glu Thr Ile Gly Asp Ala Tyr Met Val Val Gly Gly Val Pro Val Pro
        515                 520                 525

Val Glu Ser His Ala Gln Arg Val Ala Asn Phe Ala Leu Gly Met Arg
    530                 535                 540

Ile Ser Ala Lys Glu Val Met Asn Pro Val Thr Gly Glu Pro Ile Gln
545                 550                 555                 560

Ile Arg Val Gly Ile His Thr Gly Pro Val Leu Ala Gly Val Val Gly
                565                 570                 575

Asp Lys Met Pro Arg Tyr Cys Leu Phe Gly Asp Thr Val Asn Thr Ala
            580                 585                 590

Ser Arg Met Glu Ser His Gly Leu Pro Ser Lys Val His Leu Ser Pro
        595                 600                 605

Thr Ala His Arg Ala Leu Lys Asn Lys Gly Phe Glu Ile Val Arg Arg
    610                 615                 620

Gly Glu Ile Glu Val Lys Gly Lys Gly Lys Met Thr Thr Tyr Phe Leu
625                 630                 635                 640

Ile Gln Asn Leu Asn Ala Thr Glu Asp Glu Ile Met Gly Arg Pro Ser
                645                 650                 655

Ala Pro Ala Asp Gly Lys Glu Val Cys Thr Pro Gly Asn Gln Val Arg
            660                 665                 670

Lys Ser Pro Ala Val Pro Arg Asn Thr Asp His Gln Gln Gln Val Tyr
        675                 680                 685

Lys Gly Asp Pro Ala Asp Ala Ser Asn Glu Val Thr Leu Ala Gly Ser
    690                 695                 700

Pro Val Ala Gly Arg Asn Ser Thr Asp Ala Val Asn Asn Gln Pro Ser
705                 710                 715                 720

Pro Asp Glu Thr Lys Thr Ser Val Val Ala Ser Gly Pro Val Leu Ser
                725                 730                 735

Ala Phe Cys Val Val Leu
            740
```

<210> SEQ ID NO 159
<211> LENGTH: 651
<212> TYPE: DNA
<213> ORGANISM: Homo sapiens

<400> SEQUENCE: 159

```
atgtatggat tcatcaacac ctgcctgcag tctcttgtga cagagaaatt tggtgaggag     60

acatgggaga agctgaaggc tcctgcagaa gtgcaagatg tcttcatgac ctacaccgtg    120

tatgatgaca tcatcaccat taagctcatc caagaagcct gcaaggttct ggatgtgtcc    180

atggaagcca ttctgaagct ctttggcgaa tacttcttta agttctgtaa gatgtctggc    240

tatgacagga tgctgcggac acttggagga aatctcaccg agtttattga aaacctagat    300

gcactccaca gttacctggc actgtcctat caggaaatga acgcaccatc ctttcgagtg    360

gaggaaggag ctgacggggc gatgcttctc cactactact cagacagaca tggtctgtgt    420

cacattgtac caggtatcat tgaagctgtg gccaaggact tctttgacac tgatgtggcc    480

atgagtatcc tggatatgaa cgaagaggtg gaaaggacag ggaagaaaga acatgttgtg    540

tttctggtcg tgcagaaggc tcacagacag ataagaggag caaaggcaag ccggccacaa    600

ggcagtgagg acagccaggc agaccaggag gctctccagg gaacactcct t             651
```

<210> SEQ ID NO 160
<211> LENGTH: 217
<212> TYPE: PRT
<213> ORGANISM: Homo sapiens

<400> SEQUENCE: 160

```
Met Tyr Gly Phe Ile Asn Thr Cys Leu Gln Ser Leu Val Thr Glu Lys
1               5                   10                  15

Phe Gly Glu Glu Thr Trp Glu Lys Leu Lys Ala Pro Ala Glu Val Gln
            20                  25                  30

Asp Val Phe Met Thr Tyr Thr Val Tyr Asp Asp Ile Ile Thr Ile Lys
        35                  40                  45

Leu Ile Gln Glu Ala Cys Lys Val Leu Asp Val Ser Met Glu Ala Ile
    50                  55                  60

Leu Lys Leu Phe Gly Glu Tyr Phe Phe Lys Phe Cys Lys Met Ser Gly
65                  70                  75                  80

Tyr Asp Arg Met Leu Arg Thr Leu Gly Gly Asn Leu Thr Glu Phe Ile
                85                  90                  95

Glu Asn Leu Asp Ala Leu His Ser Tyr Leu Ala Leu Ser Tyr Gln Glu
            100                 105                 110

Met Asn Ala Pro Ser Phe Arg Val Glu Glu Gly Ala Asp Gly Ala Met
        115                 120                 125

Leu Leu His Tyr Tyr Ser Asp Arg His Gly Leu Cys His Ile Val Pro
    130                 135                 140

Gly Ile Ile Glu Ala Val Ala Lys Asp Phe Phe Asp Thr Asp Val Ala
145                 150                 155                 160

Met Ser Ile Leu Asp Met Asn Glu Glu Val Glu Arg Thr Gly Lys Lys
                165                 170                 175
```

```
Glu His Val Val Phe Leu Val Val Gln Lys Ala His Arg Gln Ile Arg
            180                 185                 190

Gly Ala Lys Ala Ser Arg Pro Gln Gly Ser Glu Asp Ser Gln Ala Asp
        195                 200                 205

Gln Glu Ala Leu Gln Gly Thr Leu Leu
    210                 215
```

<210> SEQ ID NO 161
<211> LENGTH: 651
<212> TYPE: DNA
<213> ORGANISM: Homo sapiens

<400> SEQUENCE: 161

```
atgtatggat tcatcaacac ctgcctgcag tctcttgtga cagagaaatt tggtgaggag      60

acatgggaga agctgaaggc tcctgcagaa gtgcaagatg tcttcatgac ctacaccgtg     120

tatgatgaca tcatcaccat taagctcatc caagaagcct gcaaggttct ggatgtgtcc     180

atggaagcca ttctgaagct ctttggcgaa tacttcttta agttctgtaa gatgtctggc     240

tatgacagga tgctgcggac acttggagga aatctcaccg agtttattga aaacctagat     300

gcactccaca gttacctggc actgtcctat caggaaatga acgcaccatc ctttcgagtg     360

gaggaaggag ctgacggggc gatgcttctc cactactact cagacagaca tggtctgtgt     420

cactatgtac caggtatcat tgaagctgtg gccaaggact tctttgacac tgatgtggcc     480

atgagtatcc tggatatgaa cgaagaggtg gaaaggacag ggaagaaaga acatgttgtg     540

tttctggtcg tgcagaaggc tcacagacag ataagaggag caaaggcaag ccggccacaa     600

ggcagtgagg acagccaggc agaccaggag gctctccagg gaacactcct t              651
```

<210> SEQ ID NO 162
<211> LENGTH: 217
<212> TYPE: PRT
<213> ORGANISM: Homo sapiens

<400> SEQUENCE: 162

```
Met Tyr Gly Phe Ile Asn Thr Cys Leu Gln Ser Leu Val Thr Glu Lys
 1               5                  10                  15

Phe Gly Glu Glu Thr Trp Glu Lys Leu Lys Ala Pro Ala Glu Val Gln
            20                  25                  30

Asp Val Phe Met Thr Tyr Thr Val Tyr Asp Asp Ile Ile Thr Ile Lys
        35                  40                  45

Leu Ile Gln Glu Ala Cys Lys Val Leu Asp Val Ser Met Glu Ala Ile
    50                  55                  60

Leu Lys Leu Phe Gly Glu Tyr Phe Phe Lys Phe Cys Lys Met Ser Gly
65                  70                  75                  80

Tyr Asp Arg Met Leu Arg Thr Leu Gly Gly Asn Leu Thr Glu Phe Ile
                85                  90                  95

Glu Asn Leu Asp Ala Leu His Ser Tyr Leu Ala Leu Ser Tyr Gln Glu
            100                 105                 110

Met Asn Ala Pro Ser Phe Arg Val Glu Glu Gly Ala Asp Gly Ala Met
        115                 120                 125

Leu Leu His Tyr Tyr Ser Asp Arg His Gly Leu Cys His Tyr Val Pro
    130                 135                 140

Gly Ile Ile Glu Ala Val Ala Lys Asp Phe Phe Asp Thr Asp Val Ala
145                 150                 155                 160

Met Ser Ile Leu Asp Met Asn Glu Glu Val Glu Arg Thr Gly Lys Lys
                165                 170                 175
```

-continued

```
Glu His Val Val Phe Leu Val Val Gln Lys Ala His Arg Gln Ile Arg
        180                 185                 190

Gly Ala Lys Ala Ser Arg Pro Gln Gly Ser Glu Asp Ser Gln Ala Asp
    195                 200                 205

Gln Glu Ala Leu Gln Gly Thr Leu Leu
    210                 215
```

COMPOSITIONS AND METHODS FOR THE DELIVERY OF OXYGEN

CROSS-REFERENCE TO RELATED APPLICATIONS

This application is a continuation of nonprovisional patent application Ser. No. of 13/772,281, filed Feb. 20, 2013, which is a continuation of nonprovisional application Ser. No. 12/302,002, filed Jul. 26, 2010, which issued as U.S Pat. No. 8,404,631 on Mar. 26, 2013, and which is a National Phase application under 35 USC §371 of International Application No. PCT/US2007/012184, filed May 21, 2007, which claims the benefit of U.S. provisional application Ser. No. 60/921,505, filed May 22, 2006 by Michael A. Marletta, Stephen P. L. Cary, Elizabeth M. Boon, and Jonathan A. Winger, entitled "Engineering H-NOX Proteins for Therapeutic Nitric Oxide and Oxygen Delivery" (UC Case No. B06-084). This U.S. provisional application was converted from U.S. utility application Ser. No. 11/440,588, filed May 22, 2006, to a provisional application on May 1, 2007. The entire contents of each are hereby incorporated by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 627042000102SubSeqListing.txt, date recorded: May 12, 2015, size: 244 KB).

STATEMENT REGARDING FEDERALLY SPONSORED RESEARCH OR DEVELOPMENT

This work was supported by Grant No. DE-AC03-76SF. The U.S. government may have rights in any patent issuing on this application.

TECHNICAL FIELD

This application pertains to H-NOX proteins and methods of using them to deliver oxygen. H-NOX proteins provide a new therapeutic tool for delivering $O_2$ to humans and, for veterinary purposes, to animals.

BACKGROUND OF THE INVENTION

The current blood bank system has inherent risks and serious limitations. Blood typing errors, immunogenicity, transmission of bacterial agents, and viral infections such as HIV-1 and hepatitis, pose life threatening dangers to transfusion patients. In addition, the limited availability of donors, the requirement for specific blood types, the short shelf-life of red blood cells, and the need for refrigeration all limit the accessibility of transfusions to patients. Development of a stable blood substitute could eliminate the risks of the current blood bank system and increase the availability of transfusions to patients in most environments. Thus, the delivery of.

oxygen ($O_2$) to organs and tissues to alleviate symptoms due to blood loss or hypoxia is a major therapeutic goal.

No hemoglobin-based therapies have been approved for use in humans in the U.S. Potential therapies include a variety of artificial $O_2$ carriers (reviewed by Spahn, D. R. et al. (20.05). "Artificial O2 carriers: status in 2005," *Curr.*

*Pharm. Des.* 11(31):4099-4114), such as engineered hemoglobins (e.g., U.S. Pat. No. 6,022,849). However, some potential blood substitutes, such as hemoglobin-based blood substitutes, are limited due to their reactivity with nitric oxide (NO). In particular, NO acts as a chemical messenger in the control of many important processes in vivo, including neurotransmission, inflammation, platelet aggregation, and regulation of gastrointestinal and vascular smooth muscle tone. NO reacts directly with $O_2$ that is bound to hemoglobin to form methemoglobin and nitrate. Both the heme iron and NO become oxidized by the bound oxygen atoms, and the reaction occurs so rapidly that no replacement of $O_2$ by NO is observed (see, e.g., U.S. Pat. No. 6,455,676).

Since NO is produced and consumed on a continuous basis, there is a natural turnover of NO in vivo. When cell-free hemoglobin is administered, the balance between NO production and consumption is altered by reactions with cell-free hemoglobin. The oxidative reaction between NO and $O_2$ bound to hemoglobin is irreversible, resulting in the destruction of NO, $O_2$, and hemoglobin. NO binding to hemoglobin without $O_2$ bound is effectively irreversible on physiologic timescales since the half-life for dissociation of nitrosylhemoglobin is 5-6 hours, thereby effectively inactivating hemoglobin as a cell-free $O_2$ carrier.

Once an NO molecule reacts with hemoglobin, it is eliminated from the pool of signal molecules, thereby causing certain adverse conditions. For example, the binding of NO to hemoglobin (with or without $O_2$ bound) can prevent vascular relaxation and potentially lead to hypertension, which is sometimes observed after the administration of certain extracellular hemoglobin solutions.

NO is also needed to mediate certain inflammatory responses. For example, NO produced by the endothelium inhibits platelet aggregation. Consequently, as NO is bound by cell-free hemoglobin (with or without $O_2$ bound), platelet aggregation may increase. As platelets aggregate, they release potent vasoconstrictor compounds such as thromboxane $A_2$ and serotonin. These compounds may act synergistically with the reduced NO levels caused by hemoglobin scavenging to produce significant vasoconstriction. In addition to inhibiting platelet aggregation, NO also inhibits neutrophil attachment to cell walls, which in turn can lead to cell wall damage. Endothelial cell wall damage has been observed with the infusion of certain hemoglobin solutions.

Another major drawback of hemoglobin-based blood substitutes is their high affinity for $O_2$. This high affinity limits the ability of hemoglobin to release oxygen at a clinically useful rate in desired locations (such as peripheral tissues). Alternatively, the release of $O_2$ by lower affinity hemoglobin-based blood substitutes in arteries before reaching microvascular beds may cause vasoconstriction due to a hyperoxic vasoconstrictor response (Winslow hypothesis). Additionally, hemoglobin-based blood substitutes are hindered by the rapid clearance of cell-free hemoglobin from plasma due the presence of receptors for hemoglobin that remove cell-free hemoglobin from plasma. Cell-free hemoglobin may also cause kidney toxicity, possibly due to NO depletion in glomeruli, causing constriction and subsequent dysfunction.

Due to the limitations of current blood substitutes and the chronic shortage of donated blood, there remains a significant interest in and need for additional or alternative therapies for delivering oxygen. In particular, blood substitutes with a lower NO reactivity and/or a longer plasma retention time are desired. Oxygen carriers with dissociation constants or off rates for $O_2$ binding that are appropriate for particular clinical or industrial applications are also needed. An exemplary industry application for which $O_2$ carriers are desirable includes the growth of cells in culture, which is often limited by the amount of $O_2$ that reaches the cells.

BRIEF SUMMARY OF THE INVENTION

The present invention is based in part on the surprising discovery that wild-type and mutant H-NOX proteins have a much lower NO reactivity than hemoglobin and thus are desirable $O_2$ carriers. If desired, mutations can be introduced into H-NOX proteins to alter their binding of $O_2$ and NO ligands to further optimize the use of H-NOX proteins as $O_2$ carriers.

In one aspect, the invention features mutant H-NOX proteins. Accordingly, in some-embodiments, the invention provides an isolated H-NOX protein having at least one mutation that alters the $O_2$ dissociation constant or NO reactivity compared to that of a corresponding wild-type H-NOX protein. In some embodiments, the $O_2$ dissociation constant of the mutant H-NOX protein is within 2 orders of magnitude of that of hemoglobin, and the NO reactivity of the mutant H-NOX protein is at least 10-fold lower than that of hemoglobin. In some embodiments, the $O_2$ dissociation constant of the mutant H-NOX protein is between about 2 nM to about 50 μM at 20° C., about 50 nM to about 10 μM at 20° C., about 20 nM to about 2 μM at 20° C., about 100 nM to about 1.9 μM at 20° C., about 150 nM to about 1 μM at 20° C., or about 100 nM to about 255 nM at 20° C. In some embodiments, the $O_2$ dissociation constant of the mutant H-NOX protein is less than about 80 nM at 20° C., such as between about 20 nM to about 75 nM at 20° C. In some embodiments, the NO reactivity of the mutant H-NOX protein is at least 100-fold lower than that of hemoglobin, such as at least 1,000-fold lower than that of hemoglobin. In some embodiments, the NO reactivity of the mutant H-NOX protein is less than about 700 $s^{-1}$ at 20° C., such as less than about 600 $s^{-1}$, 500 $s^{-1}$, 400 $s^{-1}$, 300 $s^{-1}$, 200 $s^{-1}$, 100 $s^{-1}$, 75 $s^{-1}$, 50 $s^{-1}$, 25 $s^{-1}$, 20 $s^{-1}$, 10 $s^{-1}$, 50 $s^{-1}$, 3 $s^{-1}$, 2 $s^{-1}$, 1.8 $s^{-1}$, 1.5 $s^{-1}$, 1.2 $s^{-1}$, 1.0 $s^{-1}$, 0.8 $s^{-1}$, 0.7 $s^{-1}$, or 0.6 $s^{-1}$ at 20° C. In some embodiments, the $k_{off}$ for oxygen of the mutant H-NOX protein is between about 0.01 to about 200 $s^{-1}$ at 20° C., such as about 1.0 $s^{-1}$ to about 16.0 $s^{-1}$. In some embodiments, the $O_2$ dissociation constant of the mutant H-NOX protein is between about 100 nM to about 1.9 μM at 20° C., and the $k_{off}$ for oxygen of the mutant H-NOX protein is between about 1.35 $s^{-1}$ to about 14.5 $s^{-1}$ at 20° C. In some embodiments, the rate of heme autoxidation of the mutant H-NOX protein is less than about 1 $h^{-1}$ at 37° C. In some embodiments, the $k_{off}$ for oxygen of the mutant H-NOX protein is between about 1.35 $s^{-1}$ to about 14.5 $s^{-1}$ at 20° C., and the rate of heme autoxidation of the mutant H-NOX protein is less than about 1 $h^{-1}$ at 37° C. In some embodiments, the $k_{off}$ for oxygen of the mutant H-NOX protein is between about 1.35 $s^{-1}$ to about 14.5 $s^{-1}$ at 20° C., and the NO reactivity of the mutant H-NOX protein is less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.). In some embodiments, the rate of heme autoxidation of the mutant H-NOX protein is less than about 1 $h^{-1}$ at 37° C., and the NO reactivity of the mutant H-NOX protein is less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.).

In some embodiments, the invention features an isolated H-NOX protein having at least one mutation that alters the $k_{off}$ for oxygen or NO reactivity compared to that of a corresponding wild-type H-NOX protein. In some embodiments, the $k_{off}$ for oxygen of the mutant H-NOX protein is between about 0.01 to about 200 $s^{-1}$ at 20° C., and the NO reactivity of the mutant H-NOX protein is at least 10-fold lower than that of hemoglobin. In some embodiments, the mutant H-NOX protein has a $k_{off}$ for oxygen that is less than or equal to about 0.65 $s^{-1}$ at 20° C. (such as between about 0.21 $s^{-1}$ to about 0.65 $s^{-1}$ at 20° C.). In some embodiments, the mutant H-NOX protein derived from a *T. tengcongensis* protein and has $k_{off}$ for oxygen between about 1.35 $s^{-1}$ to about 18 $s^{-1}$ at 20° C. In some embodiments, the NO reactivity of the mutant H-NOX protein is at least 100-fold lower than that of hemoglobin, such as at least 1,000-fold lower than that of hemoglobin. In some embodiments, the NO reactivity of the mutant H-NOX protein is less than about 700 $s^{-1}$ at 20° C., such as less than about 600 $s^{-1}$, 500 $s^{-1}$, 400 $s^{-1}$, 300 $s^{-1}$, 200 $s^{-1}$, 100 $s^{-1}$, 75 $s^{-1}$, 50 $s^{-1}$, 25 $s^{-1}$, 20 $s^{-1}$, 10 $s^{-1}$, 50 $s^{-1}$, 3 $s^{-1}$, 2 $s^{-1}$, 1.8 $s^{-1}$, 1.5 $s^{-1}$, 1.2 $s^{-1}$, 1.0 $s^{-1}$, 0.8 $s^{-1}$, 0.7 $s^{-1}$ or 0.6, $s^{-1}$ at 20° C. In some embodiments, the $O_2$ dissociation constant of the mutant H-NOX protein is between about 1 nM to about 1 mM at 20° C., between about 2 nM to about 50 μM at 20° C., between about 50 nM to about 10 μM at 20° C., or between about 100 nM to about 1.9 μM at 20° C. In some embodiments, the rate of heme autoxidation of the mutant H-NOX protein is less than about 1 $h^{-1}$ at 37° C. In some embodiments, the $O_2$ dissociation constant of the mutant H-NOX protein is between about 100 nM to about 1.9 μM at 20° C., and the rate of heme autoxidation of the mutant H-NOX protein is less than about 1 $h^{-1}$ at 37° C. In some embodiments, the $O_2$ dissociation constant of the mutant H-NOX protein is between about 100 nM to about 1.9 μM at 20° C., and the NO reactivity of the mutant H-NOX protein is less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.). In some embodiments, the rate of heme autoxidation of the mutant H-NOX protein is less than about 1 $h^{-1}$ at 37° C., and the NO reactivity of the mutant H-NOX protein is less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.).

In various embodiments, the invention features an isolated H-NOX protein having at least one mutation that alters the $O_2$ dissociation constant or NO reactivity compared to that of a corresponding wild-type H-NOX protein. In some embodiments, the $O_2$ dissociation constant of the mutant H-NOX protein is within 2 orders of magnitude of that of hemoglobin, and the NO reactivity of the mutant H-NOX protein is at least 10-fold lower than that of hemoglobin. In some embodiments, the $O_2$ dissociation constant of the mutant H-NOX protein is between about 100 nM. to about 255 nM at 20° C. In some embodiments, the $O_2$ dissociation constant of the mutant H-NOX protein is less than 80 nM at 20° C., such as between about 20 nM to about 75 nM at 20° C. In some embodiments, the NO reactivity of the mutant H-NOX protein is at least 100-fold lower than that of hemoglobin, such as at least 1,000-fold lower than that of hemoglobin. In some embodiments, the mutant H-NOX protein has a $k_{off}$ for oxygen that is less than or equal to about 0.65 $s^{-1}$ at 20° C. (such as between about 0.21 $s^{-1}$ to about 0.65 $s^{-1}$ at 20° C.). In some embodiments, the $k_{off}$ for oxygen of the mutant H-NOX protein is between about 1.35 $s^{-1}$ to about 2.9 $s^{-1}$ at 20° C. In some embodiments, the $k_{off}$ for oxygen of the mutant H-NOX protein is between about 5.8 $s^{-1}$ to about 19 $s^{-1}$ at 20° C. In some embodiments, the mutant H-NOX protein is stable at 4° C. in air.

In some embodiments, the invention features an isolated H-NOX protein having at least one mutation that alters the $k_{off}$ for oxygen or NO reactivity compared to that of a corresponding wild-type H-NOX protein. In some embodiments, the $k_{off}$ for oxygen of the mutant H-NOX protein is less than or equal to about 0.65 s$^{-1}$ at 20° C., and the NO reactivity of the mutant H-NOX protein is at least 10-fold lower than that of hemoglobin. In some embodiments, the $k_{off}$ for oxygen of the mutant H-NOX protein is between about 0.21 s$^{-1}$ to about 0.65 s$^{-1}$ at 20° C. In some embodiments, the NO reactivity of the mutant H-NOX protein is at least 100-fold lower than that of hemoglobin, such as at least 1,000-fold lower than that of hemoglobin. In some embodiments, the NO reactivity of the mutant H-NOX protein is less than about 700 s$^{-1}$ at 20.° C., such as less than about 600 s$^{-1}$, 500 s$^{-1}$, 400 s$^{-1}$, 300 s$^{-1}$, 200 s$^{-1}$, 100 s$^{-1}$, 75 s$^{-1}$, 50 s$^{-1}$, 25 s$^{-1}$, 20 s$^{-1}$, 10 s$^{-1}$, 50 s$^{-1}$, 3 s$^{-1}$, 2 s$^{-1}$, 1.8 s$^{-1}$, 1.5 s$^{-1}$, 1.2 s$^{-1}$, 1.0 s$^{-1}$, 0.8 s$^{-1}$, 0.7 s$^{-1}$, or 0.6 s$^{-1}$ at 20° C. In some embodiments, the $O_2$ dissociation constant of the mutant H-NOX protein is between about 100 nM to about 1.9 μM at 20° C. In some embodiments, the rate of heme autoxidation of the mutant H-NOX protein is less than about 1 h$^{-1}$ at 37° C. In some embodiments, the $O_2$ dissociation constant of the mutant H-NOX protein is between about 100 nM to about 1.9 μM at 20° C., and the rate of heme autoxidation of the mutant H-NOX protein is less than about 1 h$^{-1}$ at 37° C. In some embodiments, the $O_2$ dissociation constant of the mutant H-NOX protein is between about 100 nM to about 1.9 μM at 20° C., and the NO reactivity of the mutant H-NOX protein is less than about 700 s$^{-1}$ at 20° C. (e.g., less than about 600 s$^{-1}$, 500 s$^{-1}$, 100 s$^{-1}$, 20 s$^{-1}$, 1.8 s$^{-1}$, or 0.7 at 20° C.). In some embodiments, the rate of heme autoxidation of the mutant H-NOX protein is less than about 1 h$^{-1}$ at 37° C., and the NO reactivity of the mutant H-NOX protein is less than about 700 s$^{-1}$ at 20° C. (e.g., less than about 600 s$^{-1}$, 500 s$^{-1}$, 100 s$^{-1}$, 20 s$^{-1}$, 1.8 s$^{-1}$, or 0.7 at 20° C.).

In various embodiments, the invention features an isolated H-NOX protein selected from the group consisting of *T. tengcongensis* H-NOX I5A, *T. tengcongensis* H-NOX I5L, *T. tengcongensis* H-NOX I5L-P115A, *T. tengcongensis* H-NOX W9F, *T. tengcongensis* H-NOX W9F-Y140L, *T. tengcongensis* H-NOX W9F-Y140H *T. tengcongensis* H-NOX W9F-N74A, *T. tengcongensis* H-NOX W9Y, *T. tengcongensis* H-NOX W9N, *T. tengcongensis* H-NOX W9H, *T. tengcongensis* H-NOX N74E, *T. tengcongensis* H-NOX N74A, *T. tengcongensis* H-NOX N74H, *T. tengcongensis* H-NOX N74A-Y140H, *T. tengcongensis* H-NOX F78Y-Y140F, *T. tengcongensis* H-NOX P115A, *T. tengcongensis* H-NOX R135Q, *T. tengcongensis* H-NOX Y140F, *T. tengcongensis* H-NOX Y140H, *T. tengcongensis* H-NOX Y140A, *T. tengcongensis* I75F-His6, *T. tengcongensis* I75F, *T. tengcongensis* L144F-His6, *T. tengcongensis* L144F, L2 F9W-F142Y, *D. desulfuricans* H-NOX(728-899), *D. desulfuricans* H-NOX Y139L, β1 (1-385), β1(1-385) I145Y, β1 (1-385) I145H, β1 (1-194), β1(1-194) I145Y, β1(1-194) L9W-I145Y, β2(1-217), β2(1-217) I142Y, *C. botulinum* H-NOX(1-175), *C. botulinum* H-NOX(1-186), *C. acetobutylicum* H-NOX(1-197), *C. acetobutylicum* H-NOX(1-183), and *C. elegans* H-NOX GCY-35(1-252). In some embodiments, the β1 or β2 protein is derived from a *R. norvegicus* or *H. sapiens* β1 or β2 protein.

In various embodiments, the invention features an isolated H-NOX protein selected from the group consisting of *T. tengcongensis* H-NOX I5A, *T. tengcongensis* H-NOX I5L, *T. tengcongensis* H-NOX I5L-P115A, *T. tengcongensis* H-NOX W9F-Y140L, *T. tengcongensis* H-NOX W9F-Y140H, *T. tengcongensis* H-NOX W9F-N74A, *T. tengcongensis* H-NOX W9Y, *T. tengcongensis* H-NOX W9N, *T. tengcongensis* H-NOX W9H, *T. tengcongensis* H-NOX N74E, *T. tengcongensis* H-NOX N74A, *T. tengcongensis* H-NOX N74H, *T. tengcongensis* H-NOX N74A-Y140H, *T. tengcongensis* H-NOX F78Y-Y140F, *T. tengcongensis* H-NOX P115A, *T. tengcongensis* H-NOX R135Q, *T. tengcongensis* H-NOX Y140H, *T. tengcongensis* H-NOX Y140A, *T. tengcongensis* 175F-His6, *T. tengcongensis* 175F, *T. tengcongensis* L144F-His6, *T. tengcongensis* L144F, *L. pneumophilia* 2 F9W-F142Y, *D. desulfuricans* H-NOX(728-899), *D. desulfuricans* H-NOX Y139L, β1 (1-385) I145H, β1(1-194), β1 (1-194) I145Y, β1 (1-194) L9W-I145Y, $β_2$(1-217), β2(1-217) I142Y, *C. botulinum* H-NOX(1-175), *C. botulinum* H-NOX(1-186), *C. acetobutylicum* H-NOX(1-197), *C. acetobutylicum* H-NOX(1-183), and *C. elegans* H-NOX GCY-35(1-252). In some embodiments, the β1 or β2 protein is derived from a *R. norvegicus* or *H. sapiens* β1 or β2. protein.

In some embodiments of the isolated H-NOX proteins, the $O_2$ dissociation constant of the H-NOX protein is within 2 orders of magnitude of that of *Homo sapiens* hemoglobin alpha, such as an $O_2$ dissociation constant between 0.1 to 10-fold or between 0.5 to 2-fold of that of *Homo sapiens* hemoglobin alpha. In some embodiments of the isolated H-NOX proteins, the NO reactivity of the H-NOX protein is at least 10-fold lower than that of *Homo sapiens* hemoglobin alpha, such as at least 100-fold or 1,000-fold lower than that of *Homo sapiens* hemoglobin alpha. In some embodiments of the isolated H-NOX proteins, the H-NOX protein contains one or more mutations (e.g., 1, 2, 3, 4, 5, 6, 7, 8, 9, or 10 mutations) compared to the H-NOX protein from which it was derived. In various embodiments of the isolated H-NOX proteins, the H-NOX protein contains less than 20, 15, 12, 10, 9, 8, 7, 6, 5, 4, 3, or 2 mutations compared to the H-NOX protein from which it was derived. In some embodiments of the isolated H-NOX proteins, the H-NOX protein has at least one distal pocket mutation. In some embodiments of the isolated H-NOX proteins, the H-NOX protein has at least one mutation that is not in the distal pocket. In some embodiments of the isolated H-NOX proteins, the H-NOX protein has at least one mutation in which a residue that corresponds to Ile5, Trp9, Asn74, Prol 15, or Arg135 of *T. tengcongensis* H-NOX or I145 of β1(1-385) is replaced by any other amino acid. In some embodiments of the isolated H-NOX proteins, the H-NOX protein has at least two mutations, wherein at least one mutation is the replacement of a residue that corresponds to Ile5, Trp9, Asn74, Prol 15, or Arg135 of *T. tengcongensis* H-NOX or 1145 of β31(1-385) by any other amino acid. In some embodiments of the isolated H-NOX proteins, the mutation in the H-NOX protein corresponds to a I5A mutation, a I5L mutation, a W9F mutation, a Y140F mutation, a Y140H mutation, a W9F Y140H double mutation, or a F78Y Y140F double mutation of *T. tengcongensis* or a I145 Y mutation of β1. In some embodiments of the isolated H-NOX proteins, the mutation in the H-NOX protein corresponds to a W9Y mutation, a W9H mutation, a W9N mutation, a N74H mutation, a N74E mutation, a N74A mutation, a P115A mutation, a R135Q mutation, a I5L P115A double mutant, a N74A Y140H double mutant, or a W9F N74A double of *T. tengcongensis*. In some embodiments of the isolated H-NOX proteins, at least one C-terminal amino acid (such as at least about 50 contiguous C-terminal amino acids or between about 25 to about 200 contiguous C-terminal amino acids) in the H-NOX protein has been removed compared to the corresponding wild-type protein.

In some embodiments of the isolated H-NOX proteins, the H-NOX protein is derived from a mammalian protein (e.g., a human protein such as β1). In various embodiments of the isolated H-NOX proteins, the H-NOX protein derived from a bacterial protein (e.g., a *T. tengcongensis* protein). In some embodiments of the isolated H-NOX proteins, the H-NOX protein is covalently bound to another molecule or moiety, such as polyethylene glycol. Herne may or may not be bound to the H-NOX protein. In some embodiments of the isolated H-NOX proteins, oxygen is bound to the H-NOX protein. In some embodiments of the isolated H-NOX proteins, the H-NOX protein is a fusion protein that includes an H-NOX domain and part or all of another protein, such as albumin (e.g., human serum albumin).

In some embodiments of the isolated H-NOX proteins, the H-NOX protein is not *T. tengcongensis* H-NOX Y40L, *T. tengcongensis* H-NOX F78Y/Y140L, wild-type *T. tengcongensis* H-NOX, or *L. pneumophilia* 2 H-NOX F142Y. In some embodiments of the isolated H-NOX proteins, the H-NOX protein is not *R. norvegicus* β2(1-217), *R. norvegicus* β1(1-194), *R. norvegicus* β1(1-385), or *R. norvegicus* β1 (1-385) I145Y. In some embodiments of the isolated H-NOX proteins, the H-NOX protein is not *T. tengcongensis* H-NOX W9F, *T. tengcongensis* H-NOX Y140F, or *H. sapiens* β1 H-NOX(1-385) I145Y. In some embodiments of the isolated H-NOX proteins, the H-NOX protein is not *T. tengcongensis* H-NOX Y140H, *H. sapiens* β1 I140Y, or *H. sapiens* β1 I145Y. In some embodiments of the isolated H-NOX proteins, the H-NOX protein is not *T. tengcongensis* H-NOX Y140F, wild-type *L. pneumophilia* 2 H-NOX, *H. sapiens* β1 H-NOX I140Y, wild-type *H. sapiens* β1 H-NOX, *R. norvegicus* sGC β1 H-NOX(1-385), *R. norvegicus* sGC β1 H-NOX(1-385) I145Y, *R. norvegicus* sGC β1 H-NOX H105G, *R. norvegicus* sGC β1 H-NOX H105F, *R. norvegicus* sGC β1 H-NOX I145Y, wild-type *R. norvegicus* β1 H-NOX, wild-type *D. melangaster* β1 H-NOX, wild-type *D. melangaster* CG14885-PA H-NOX, wild-type *C. elegans* GCY-35 H-NOX, wild-type *N. punctiforme* H-NOX, wild-type *C. crescentus* H-NOX, wild-type *S. oneidensis* H-NOX, or wild-type *C. acetobutylicum* H-NOX. In some embodiments of the isolated H-NOX proteins, the H-NOX protein is not *T. tengcongensis* H-NOX Y40L, *T. tengcongensis* H-NOX F78Y/Y140L, *T. tengcongensis* H-NOX W9F, *T. tengcongensis* H-NOX Y140F, wild-type. *T. tengcongensis* H-NOX, *L. pneumophilia* 2 H-NOX F142Y, wild-type *L. pneumophilia* 2 H-NOX, *H. sapiens* β1 H-NOX I140Y, *H. sapiens* B1 I145Y, wild-type *H. sapiens* β1 H-NOX, *R. norvegicus* sGC β1 H-NOX(1-385), *R. norvegicus* sGC β1 H-NOX(1-385) I145Y, *R. norvegicus* sGC β1 H-NOX H105G, *R. norvegicus* sGC β1 H-NOX H105F, *R. norvegicus* sGC β1 H-NOX I145Y, wild-type *R. norvegicus* β1 H-NOX, wild-type *D. melangaster* (31 H-NOX, wild-type *D. melangaster* CG14885-PA H-NOX, wild-type *C. elegans* GCY-35 H-NOX, wild-type *N. punctiforme* H-NOX, wild-type *C. crescentus* H-NOX, wild-type *S. oneidensis* H-NOX, or wild-type *C. acetobutylicum* H-NOX. In some embodiments of the isolated H-NOX proteins, the H-NOX protein is not any of the following H-NOX proteins that are listed by their gene name, followed by their species abbreviation and Genbank Identifiers (such as the following protein sequences available as of May 21, 2006; May 22, 2006; May 21, 2007; or May 22, 2007): Npun5905_Npu_23129606, alr2278_Ana_17229770, SO2144_Sone_24373702, Mdeg1343_Mde_23027521, VCA0720_Vch_15601476, CC2992_Ccr_16127222, Rsph2043_Rhsp_22958463 (gi: 46192757), Mmc10739_Mcsp_22999020, Tar4_Tte_20807169, Ddes2822_Dde_23475919, CAC3243_Cac_15896488, gcy-31_Ce_17568389, CG14885_Dm_24647455, GUCY1B3_Hs_4504215, HpGCS-beta1_Hpull 4245738, Gycbeta100B_Dm_24651577, CG4154_Dm_24646993 (gi: NP_650424.2, gi:62484298), gcy-32_Ce_13539160, gcy-36_Ce_17568391 (gi:32566352, gi:86564713), gcy-35_Ce-17507861 (gi:71990146), gcy-37_Ce_17540904 (gi: 71985505), GCY1α3_Hs_20535603, GCY1α2-Hs899477, or GYCα-99B_Dm_729270 (gi:68067738) (Lakshminarayan et al. (2003). "Ancient conserved domains shared by animal soluble guanylyl cyclases and bacterial signaling proteins," *BMG Genomics* 4:5-13). The species abbreviations used in these names include Ana—*Anabaena* Sp; Ccr—*Caulobacter crescentus*; Cac—*Clostridium acetobutylicum*; Dde—*Desulfovibrio desulfuricans*; Mcsp—*Magnetococcus* sp.; Mde—*Microbulbifer degradans*; Npu—*Nostoc punctifortne*; Rhsp—*Rhodobacter sphaeroides*; Sone—*Shewanella oneidensis*; Tte—*Thermoanaerobacter tengcongensis*; Vch—*Vibrio cholerae*; Ce—*Caenorhabditis elegans*; Dm—*Drosophila melanogaster*; Hpul—*Hemicentrotus pulcherrimus*; Hs—*Homo sapiens*. In some embodiments of the isolated H-NOX proteins, the H-NOX protein is not any of the following H-NOX proteins that are listed by their organism name and Pfam database accession number (such as the following. protein sequences available as of May 21, 2006; May 22, 2006; May 17, 2007; May 21, 2007; or May 22, 2007): *Caenorhabditis briggsae* Q622M5_CAEBR, *Caenorhabditis briggsae* Q61P44_CAEBR, *Caenorhabditis briggsae* Q61R54_CAEBR, *Caenorhabditis briggsae* Q61V90_CAEBR, *Caenorhabditis briggsae* Q61A94_CAEBR, *Caenorhabditis briggsae* Q60TP4_CAEBR, *Caenorhabditis briggsae* Q60M10_CAEBR, *Caenorhabditis elegans* GCY37_CAEEL, *Caenorhabditis elegans* GCY31_CAEEL, *Caenorhabditis elegans* GCY36_CAEEL, *Caenorhabditis elegans* GCY32 CAEEL, *Caenorhabditis elegans* GCY35_CAEEL, *Caenorhabditis elegans* GCY34_CAEEL, *Caenorhabditis elegans* GCY33_CAEEL, *Oryzias curvinotus* Q7T040_ORYCU, *Oryzias curvinotus* Q75WF0_ORYCU, *Oryzias latipes* P79998_ORYLA, *Oryzias latipes* Q7ZSZ5_ORYLA, *Tetraodon nigroviridis* Q4SW38_TETNG, *Tetraodon nigroviridis* Q4RZ94_TETNG, *Tetraodon nigroviridis* Q4S6K5_TETNG, *Fugu rubripes* Q9OVY5_FUGRU, *Xenopus laevis* Q6INK9_XENLA, *Homo sapiens* Q5T8J7_HUMAN, *Homo sapiens* GCYA2_HUMAN, *Homo sapiens* GCYB2_HUMAN, *Homo sapiens* GCYB1HUMAN, *Gorilla gorilla* Q9N193_9 PRIM, *Pongo pygmaeus* Q5RAN8_PONPY, *Pan troglodytes* Q9N192_PANTR, *Macaca mulatto* Q9N194_MACMU, *Hylobates lar* Q9N191_HYLLA, *Mus musculus* Q8BXH3_MOUSE, *Mus musculus* GCYB1_MOUSE, *Mus musculus* Q3UTI4_MOUSE, *Mus musculus* Q3UH83_MOUSE, *Mus musculus* Q6XE41_MOUSE, *Mus musculus* Q80YP4_MOUSE, *Rattus norvegicus* Q8OWX7_RAT, *Rattus norvegicus* Q8OWX8_RAT, *Rattus norvegicus* Q920Q1_RAT, *Rattus norvegicus* Q54A43_RAT, *Rattus norvegicus* Q80WY0_RAT, *Rattus norvegicus* Q80WY4_RAT, *Rattus norvegicus* Q8CH85_RAT, *Rattus norvegicus* Q80WY5_RAT, *Rattus norvegicus* GCYB1_RAT, *Rattus norvegicus* Q8CH90_RAT, *Rattus norvegicus* Q91XJ7_RAT, *Rattus norvegicus* Q8OWX9_RAT, *Rattus norvegicus* GCYB2_RAT, *Rattus norvegicus* GCYA2_RAT, *Canis familiaris* Q4ZHR9_CANFA, *Bos taurus* GCYB1_BOVIN, *Sus scrofa* Q4ZHR7_PIG, *Gryllus bimaculatus* Q59HN5_GRYBI, *Manduca sexta* O77106_MANSE, *Manduca sexta* O76340_MANSE, *Apis mellifera* Q5UAFO_APIME, *Apis mellifera* Q5FANO_APIME, *Apis mellifera* Q6L5L6_APIME, *Anopheles gambiae* str PEST Q7PYK9_ANOGA, *Anopheles gambiae* str PEST Q7Q9W6_ANOGA, *Anopheles gambiae* str PEST Q7QF31_ANOGA, *Anopheles gambiae* str PEST Q7PS01_ANOGA, *Anopheles gambiae* str PEST Q7PFY2_ANOGA, *Anopheles gambiae* Q7KQ93_ANOGA, *Drosophila melanogaster* Q24086_DROME, *Drosophila melanogaster* GCYH_DROME, *Drosophila melanogaster* GCY8E_DROME, *Drosophila melanogaster* GCYDA_DROME, *Drosophila melanogaster* GCYDB_DROME, *Drosophila melanogaster* Q9VA09_DROME, *Drosophila pseudoobscura* Q29CE1_DROPS, *Drosophila pseudoobscura* Q296C7_DROPS, *Drosophila pseudoobscura* Q296C8_DROPS, *Drosophila pseudoobscura* Q29BU7_DROPS, *Aplysia californica* Q7YWK7_APLCA, *Hemicentrotus pulcherrimus* Q95NK5_HEMPU, *Chlamydomonas reinhardtii*, Q5YLC2_CHLRE, *Anabaena* sp Q8YUQ7_ANASP, *Flavobacteria bacterium* BBFL7 Q26GR8_9 BACT, *Psychroflexus torquis* ATCC 700755 Q1VQE5_9 FLAO, marine gamma proteobacterium HTCC2207 Q1YPJ5_9 GAMM, marine gamma proteobaoterium 1-1TCC2207 QlYTK4_9 GAMM, *Caulobacter crescentus* Q9A451_CAUCR, *Acidiphilium cryptum* JF-5 Q2DG60_ACICY, *Rhodobacter sphaeroides* Q3J0U9_RHOS4, *Silicibacter pomeroyi* Q5LPV1_SILPO, *Paracoccus denitrificans* PD1222, Q3PC67_PARDE, *Silicibacter* sp TM1040 Q3QNY2_9 RHOB, *Jannaschia* sp Q28ML8_JANSC, *Magnetococcus* sp MC-1 Q3XT27_9PROT, *Legionella pneumophila* Q5WXPO_LEGPL, *Legionella pneumophila* Q5WTZ5_LEGPL, *Legionella pneumophila* Q5X268_LEGPA, *Legionella pneumophila* Q5X2R2_LEGPA, *Legionella pneumophila* subsp *pneumophila* Q5ZWM9_LEGPH, *Legionella pneumophila* subsp *pneumophila* Q5ZSQ8_LEGPH, *Colwellia psychrerythraea* Q47Y43_COLP3, *Pseudoalteromonas atlantica* T6c Q3CSZ5_ALTAT, *Shewanella oneidensis* Q8EF49_SHEON, *Saccharophagus degradans* Q21E20_SACD2, *Saccharophagus degradans* Q21ER7_SACD2, *Vibrio angustum* S14 Q1ZWE5_9 VIBR, *Vibrio vulnificus* Q8DAE2_VIBVU, *Vibrio alginolyticus* 12G01 Q1 VCP6_VIBAL, *Vibrio* sp DAT722 Q2FA22_9 VIBR, *Vibrio parahaemolyticus* Q87NJ1_VIBPA, *Vibrio fischeri* Q5E1F5_VIBF1, *Vibrio vulnificus* Q7MJS8_VIBVY, *Photobacterium* sp SKA34 Q2C6Z5_9 GAMM, *Hahella chejuensis* Q2SFY7_HAHCH, *Oceanospirillum* sp MED92 Q2BKV0_9 GAMM, *Oceanobacter* sp RED65 Q1N035_9GAMM, *Desulfovibrio desulfuricans* Q310U7_DESDG, *Halothermothrix orenii* H 168 Q2AIW5_9 FIRM, *Thermoanaerobacter tengcongensis* Q8RBX6_THETN, *Caldicellulosiruptor saccharolyticus* DSM 8903 Q2ZH17_CALSA, *Clostridium acetobutylicum* Q97E73_CLOAB, *Alkaliphilus metalliredigenes* QYMF Q3C763_9 CLOT, *Clostridium tetani* Q899J9_CLOTE, and *Clostridium beijerincki* NCIMB 8052 Q2WVN0_CLOBE. In some embodiments of the isolated H-NOX proteins, the H-NOX protein is not *R. norvegicus* sGC β1 H-NOX C78S or *R. norvegicus* sGC β1 H-NOX C78E. In some embodiments of the isolated H-NOX proteins, the H-NOX protein does not have a mutation in the Y-S-R motif, which includes Tyr135, Ser137, and Arg139 of human H-NOX.

In one aspect, the invention features a recombinant nucleic acid encoding any one or more of the mutant H-NOX proteins described herein. In particular embodiments, the nucleic acid includes a segment of or the entire nucleic acid sequence of any of the nucleic acids shown in FIGS. 2-4D or 8A-8DD. In some embodiments, the nucleic acid encodes a fusion protein that includes an H-NOX domain and part or all of another protein, such as albumin (e.g., human serum albumin). In some embodiments, the nucleic acid includes at least about 50, 100, 150, 200, 300, 400, 500, 600, 700, 800, or more contiguous nucleotides from an H-NOX nucleic acid and contains one or more mutations (e.g., 1, 2, 3, 4, 5, 6, 7, 8, 9, or 10 mutations) compared to the H-NOX nucleic acid from which it was derived. In various embodiments, a mutant H-NOX nucleic acid contains less than about any of 20, 15, 12, 10, 9, 8, 7, 6, 5, 4, 3, or 2 mutations compared to the H-NOX nucleic acid from which it was derived. The invention also features degenerate variants of any nucleic acid encoding a mutant H-NOX protein.

In yet another aspect, the invention provides a vector that includes any one or more of the mutant H-NOX nucleic acids described herein. In another aspect, the invention features a cell that includes any one or more of the mutant H-NOX nucleic acids described herein. In one aspect, the invention features a cell that includes any vector described herein.

In one aspect, the invention features a method of producing an H-NOX protein. This method involves culturing a cell having a nucleic acid encoding any one or more of the mutant H-NOX proteins described herein under conditions suitable for production of the mutant H-NOX protein. In some embodiments, the invention further includes the step of purifying the mutant H-NOX protein.

In one aspect, the invention features pharmaceutical compositions that include one or more H-NOX proteins, such as any of the wild-type or mutant H-NOX proteins described herein. In some embodiments, the pharmaceutical composition includes a pharmaceutically acceptable amount of an H-NOX protein described herein and a pharmaceutically acceptable carrier. In some embodiments, the $O_2$ dissociation constant of the H-NOX protein is between about 1 nM and about 1 mM at 20° C., and the NO reactivity of the H-NOX protein is less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.). In some embodiments, the $O_2$ dissociation constant of the H-NOX protein is between about 20 nM to about 2 μM at 20° C., and the $k_{off}$ for oxygen of the H-NOX protein is between about 1.0 $s^{-1}$ to about 16.0 $s^{-1}$ at 20° C. In some embodiments, the $O_2$ dissociation constant of the H-NOX protein is between about 20 nM to about 2 μM at 20° C., and the rate of heme autoxidation of the H-NOX protein is less than about 1 $h^{-1}$ at 37° C. In some embodiments, the $O_2$ dissociation constant of the H-NOX protein is between about 20 nM to about 2 μM at 20° C., and the NO reactivity of the H-NOX protein is less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.). In some embodiments, the $k_{off}$ for oxygen of the H-NOX protein is between about 1.0 $s^{-1}$ to about 16.0 $s^{-1}$ at 20° C., and the rate of heme autoxidation of the X protein is less than about 1 $h^{-1}$ at 37° C. In some embodiments, the $k_{off}$ for oxygen of the H-NOX protein is between about 1.0 $s^{-1}$ to about 16.0 $s^{-1}$ at 20° C., and the NO reactivity of the H-NOX protein is less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.).

In some embodiments, the invention provides a pharmaceutical composition that includes a pharmaceutically acceptable amount of an H-NOX protein and a pharmaceutically acceptable carrier. In some embodiments, the $O_2$ dissociation constant of the H-NOX protein is within 2 orders of magnitude of that of hemoglobin, and the NO reactivity of the H-NOX protein is at least 10-fold lower than that of hemoglobin. In some embodiments, the $k_{off}$ for oxygen of the H-NOX protein is between about 0.01 and about 200 $s^{-1}$ at 20° C., wherein the NO reactivity of the H-NOX protein is at least 10-fold lower than that of hemoglobin.

In some embodiments of the pharmaceutical compositions, the $O_2$ dissociation constant of the H-NOX protein is within 2 orders of magnitude of that of *Homo sapiens* hemoglobin alpha, such as an $O_2$ dissociation constant between 0.1 to 10-fold or between 0.5 to 2-fold of that of *Homo sapiens* hemoglobin alpha. In some embodiments of the pharmaceutical compositions, the NO reactivity of the H-NOX protein is at least 10-fold lower than that of *Homo sapiens* hemoglobin alpha, such as at least 100-fold or 1,000-fold lower than that of *Homo sapiens* hemoglobin alpha. In some embodiments of the pharmaceutical compositions, the H-NOX protein is a wild-type protein. In some embodiments of the pharmaceutical compositions, the H-NOX protein is a mutant protein as described herein. In various embodiments of the pharmaceutical compositions, the H-NOX protein has at least one mutation that alters the $O_2$ dissociation constant, the $k_{off}$ for oxygen, the rate of heme autoxidation, the NO reactivity, the NO stability, or any two or more of the foregoing compared to that of a corresponding wild-type protein. In some embodiments of the pharmaceutical compositions, the H-NOX protein is a selected from the group consisting of wild-type *T. tengcongensis* H-NOX, *T. tengcongensis* H-NOX I5A, *T. tengcongensis* H-NOX I5L, *T. tengcongensis* H-NOX I5L-P115A, *T. tengcongensis* H-NOX W9F, *T. tengcongensis* H-NOX W9F-Y140L, *T. tengcongensis* H-NOX W9F-Y140H, *T. tengcongensis* 11-NOX W9F-N74A, *T. tengcongensis* H-NOX W9Y, *T. tengcongensis* H-NOX W9N, *T. tengcongensis* H-NOX W9H, *T. tengcongensis* H-NOX N74E, *T. tengcongensis* H-NOX N74A, *T. tengcongensis* H-NOX N7411, *T. tengcongensis* H-NOX N74A-Y140H, *T. tengcongensis* H-NOX F78Y-Y140F, *T. tengcongensis* H-NOX F78Y/Y140L, *T. tengcongensis* H-NOX P115A, *T. tengcongensis* H-NOX R135Q, *T. tengcongensis* H-NOX Y140F, *T. tengcongensis* H-NOX Y40L, *T. tengcongensis* H-NOX Y140H, *T. tengcongensis* H-NOX Y140A, *T. tengcongensis* I75F-His6, *T. tengcongensis* I75F, *T. tengcongensis* L144F-His6, *T. tengcongensis* L144F, *L. pneumophilia* 2 H-NOX F142Y, wild-type *L. pneumophilia* 1 H-NOX, wild-type *L. pneumophilia* 2 H-NOX, *L. pneumophilia* 2 F9W-F142Y, wild-type *D. desulfuricans* H-NOX, *D. desulfuricans* H-NOX(728-899), *D. desulfuricans* H-NOX Y139L, wild-type *H. sapiens* β1 H-NOX, *H. sapiens* β1 I145Y, *H. sapiens* β1(1-385), *H. sapiens* β1(1-385) I145Y, *H. sapiens* β1(1-385) I145H, *H. sapiens* β1(1-194), *H. sapiens* β1(1-194) I145Y, *H. sapiens* β1(1-194) L9W-I145Y, *H. sapiens* β2(1-217), *H. sapiens* β2(1-217) I142Y, *H. sapiens* β1 H-NOX H105G, *H. sapiens* β1 H-NOX H105F, wild-type *R. norvegicus* β1 H-NOX, *R. norvegicus* β1(1-385), *R. norvegicus* β1(1-385) I145Y, *R. norvegicus* β1(1-385) I145H, *R. norvegicus* (1-194), *R. norvegicus* β1 (1-194) I145Y, *R. norvegicus* β1(1-194) L9W-I145Y, *R. norvegicus* β2(1-217), *R. norvegicus* β2(1-217), I142Y, *R. norvegicus* β1 H-NOX H105G, *R. norvegicus* β1 H-NOX H105F, *C. botulinum* H-NOX(1-175), *C. botulinum* H-NOX(1-186), wild-type *C. acetobutylicum* H-NOX, *C. acetobutylicum* H-NOX(1-197), *C. acetobutylicum* H-NOX(1-183), wild-type *C. elegans* GCY-35 H-NOX, *C. elegans* H-NOX GCY-35(1-252), wild-type *D. melangaster* β1 H-NOX, wild-type *D. melangaster* CG14885-PA, wild-type *D. melangaster* CG14886, wild-type *D. melangaster* CG4154; wild-type *N. punctiforme* H-NOX, wild-type *C. crescentus* H-NOX, wild-type *S. oneidensis* H-NOX, wild-type *M. musculus* H-NOX, wild-type *C. familiaris* H-NOX, wild-type B. *T. aurus* H-NOX, wild-type *R. norvegicus*; wild-type *X. laevis* H-NOX, wild-type *C. latipes* H-NOX, wild-type *O. curivatus* H-NOX, wild-type *F. rubripes* H-NOX, wild-type *A. gambiae* H-NOX, wild-type *M. sexta* H-NOX; wild-type *C. elegans* gcy-31, *C. elegans* gcy-32, wild-type *C. elegans* gcy-33, wild-type *C. elegans* gcy-34, wild-type *C. elegans* gcy-35, wild-type *C. elegans* gcy-36, wild-type *C. elegans* gcy-37; wild-type *V. cholera* H-NOX, wild-type *V. fischerii* H-NOX, and wild-type *N. punctiforme* H-NOX. In some embodiments of the pharmaceutical compositions, the pharmaceutical composition includes one or more liposomes or nanoparticles that include or encapsulate the H-NOX protein.

In some embodiments of the pharmaceutical compositions, the H-NOX protein is not *T. tengcongensis* H-NOX Y140H. In some embodiments of the pharmaceutical compositions, the H-NOX protein is not *T. tengcongensis* H-NOX Y40L, *T. tengcongensis* H-NOX F78Y/Y140L, wild-type *T. tengcongensis* H-NOX, or *L. pneumophilia* 2 H-NOX F142Y. In some embodiments of the pharmaceutical compositions, the H-NOX protein is not *R. norvegicus* β2(1-217), *R. norvegicus* β1(1-194), *R. norvegicus* β1(1-385), or *R. norvegicus* β1(1-385) I145Y. In some embodiments of the pharmaceutical compositions, the H-NOX protein is not *T. tengcongensis* H-NOX W9F, *T. tengcongensis* H-NOX Y140F, or *H. sapiens* β1 H-NOX(1-385) I145Y. In some embodiments, H-NOX protein is not *T. tengcongensis* H-NOX Y140H, *H. sapiens* β1 I140Y, or *H. sapiens* β1 I145Y. In some embodiments of the pharmaceutical compositions, the H-NOX protein is not *T. tengcongensis* H-NOX Y140F, wild-type *L. pneumophilia* 2 H-NOX, *H. sapiens* β1 H-NOX I140Y, wild-type *H. sapiens* β1 H-NOX, *R. norvegicus* sGC β1 H-NOX(1-385), *R. norvegicus* sGC β1 H-NOX(1-385) I145Y, *R. norvegicus* sGC β1 H-NOX H105G, *R. norvegicus* sGC β1 H-NOX H105F, *R. norvegicus* sGC β1 H-NOX I145Y, wild-type *R. norvegicus* β1 H-NOX, wild-type *D. melangaster* β1 H-NOX, wild-type *D. melangaster* CG14885-PA H-NOX, wild-type *C. elegans* GCY-35 H-NOX, wild-type *N. punctiforme* H-NOX, wild-type *C. crescentus* H-NOX, wild-type *S. oneidensis* H-NOX, or wild-type *C. acetobutylicum* H-NOX. In some embodiments of the pharmaceutical compositions, the H-NOX protein is not *T. tengcongensis* H-NOX Y40L, *T. tengcongensis* H-NOX F78Y/Y140L, *T. tengcongensis* H-NOXW9F, *T. tengcongensis* H-NOX Y140F, wild-type *T. tengcongensis* H-NOX, *L. pneumophilia* 2 H-NOX F142Y, wild-type *L. pneumophilia* 2 H-NOX, *H. sapiens* β1 H-NOX I140Y, *H. sapiens* β1 I145Y, wild-type *H. sapiens* β1 H-NOX, *R. norvegicus* sGC (31 H-NOX(1-385), *R. norvegicus* sGC β1 H-NOX(1-385) I145Y, *R. norvegicus* sGC H-NOX H105G, *R. norvegicus* sGC β1 H-NOX H105F, *R. norvegicus* sGC β1 H-NOX I145Y, wild-type *R. norvegicus* β1 H-NOX, wild-type *D. melangaster* β1 H-NOX, wild-type *D. melangaster* CG14885-PA H-NOX, wild-type *C. elegans* GCY-35 H-NOX, wild-type *N. punctiforme* H-NOX, wild-type *C. crescentus* H-NOX, wild-type *S. oneidensis* H-NOX, or wild-type *C. acetobutylicum* H-NOX. In some embodiments of the pharmaceutical compositions, the H-NOX protein is not any of the following H-NOX proteins that are listed by their gene name, followed by their species abbreviation and Genbank Identifiers (such as the following protein sequences available as of May 21, 2006; May 22, 2006; May 21, 2007; or May 22, 2007): Npun5905_Npu_23129606, alr2278_Ana_17229770, SO2144_Sone_24373702, Mdeg1343_Mde_23027521, VCA0720_Vch_15601476, CC2992_Ccr_16127222, Rsph2043_Rhsp_22958463 (gi: 46192757), Mmc10739 Mcsp_22999020, Tar4_Tte_20807169, Ddes2822_Dde_23475919, CAC3243_Cac_15896488, gcy-31_Ce_17568389, CG14885_Dm_24647455, GUCY1B3_Hs_4504215, HpGCS-beta1_Hpull 4245738, Gycbeta100B_Dm_24651577, CG4154_Dm_24646993 (gi: NP_650424.2, gi:62484298), gcy-32_Ce_13539160, gcy-36_Ce_17568391 (gi:32566352, gi:86564713), gcy-35_Ce-17507861 (gi:71990146), gcy-37_Ce_17540904 (gi: 71985505), GCY1α3_Hs_20535603, GCY1α2-Hs_899477, or GYCα-99B_Dm_729270 (gi:68067738) (Lakshminarayan et al. (2003). "Ancient conserved domains shared by animal soluble guanylyl cyclases and bacterial signaling proteins," BMG Genomics 4:5-13). The species abbreviations used in these names include Ana—*Anabaena* Sp; Ccr—*Caulobacter crescentus*; Cac—*Clostridium acetobutylicum*; Dde—*Desulfovibrio desulfuricans*; Mcsp—*Magnetococcus* sp.; Mde—*Microbulbifer degradans*; Npu—*Nostoc punctiforme*; Rhsp—*Rhodobacter sphaeroides*; Sone—*Shewanella oneidensis*; Tte—*Thermoanaerobacter tengcongensis*; Vch—*Vibrio cholerae*; Ce—*Caenorhabditis elegans*; Dm—*Drosophila melanogaster*; Hpul—*Hemicentrotus pulcherrimus*; Hs—*Homo sapiens*. In some embodiments of the pharmaceutical compositions, the H-NOX protein is not *R. norvegicus* sGC β1 fl-NOX C78S or *R. norvegicus* sGC β1 H-NOX C78E. In some embodiments of the pharmaceutical compositions, the H-NOX protein is not any of the following H-NOX proteins that are listed by their organism name and Pfam database accession number (such as the following protein sequences available as of May 21, 2006; May 22, 2006; May 17, 2007; May 21, 2007; or May 22, 2007): *Caenorhabditis briggsae* Q622M5_CAEBR, *Caenorhabditis briggsae* Q61P44_CAEBR, *Caenorhabditis briggsae* Q61R54_CAEBR, *Caenorhabditis briggsae* Q61V90_CAEBR, *Caenorhabditis briggsae* Q61A94_CAEBR, *Caenorhabditis briggsae* Q60TP4_CAEBR, *Caenorhabditis briggsae* Q60M10_CAEBR, *Caenorhabditis elegans* GCY37_CAEEL, *Caenorhabditis elegans* GCY31_CAEEL, *Caenorhabditis elegans* GCY36_CAEEL, *Caenorhabditis elegans* GCY32_CAEEL, *Caenorhabditis elegans* GCY35_CAEEL, *Caenorhabditis elegans* GCY34_CAEEL, *Caenorhabditis elegans* GCY33_CAEEL, *Oryzias curvinotus* Q7T040_ORYCU, *Oryzias curvinotus* Q75WF0_ORYCU, *Oryzias latipes* P79998_ORYLA, *Oryzias latipes* Q7ZSZ5_ORYLA, *Tetraodon nigroviridis* Q4SW38_TETNG, *Tetraodon nigroviridis* Q4RZ94_TETNG, *Tetraodon nigroviridis* Q4S6K5_TETNG, *Fugu rubripes* Q9OVY5_FUGRU, *Xenopus laevis* Q61NK9_XENLA, *Homo sapiens* Q5T8J7_HUMAN, *Homo sapiens* GCYA2_HUMAN, *Homo sapiens* GCYB2_HUMAN, *Homo sapiens* GCYB1_HUMAN, *Gorilla gorilla* Q9N193_9 PRIM, *Pongo pygmaeus* Q5RAN8_PONPY, *Pan troglodytes* Q9N192_PANTR, *Macaca mulatta* Q9N194 MACMU, *Hylobates lar* Q9N191_HYLLA, *Mus musculus* Q8BXH3_MOUSE, *Mus musculus* GCYB1_MOUSE, *Mus musculus* Q3UTI4_MOUSE, *Mus musculus* Q3 U H83 MOUSE, *Mus musculus* Q6XE41_MOUSE, *Mus musculus* Q80YP4_MOUSE, *Rattus norvegicus* Q8OWX7RAT, *Rattus norvegicus* Q8OWX8RAT, *Rattus norvegicus* Q920Q1_RAT, *Rattus norvegicus* Q54A43_RAT, *Rattus norvegicus* Q80WY0_RAT, *Rattus norvegicus* Q80WY4_RAT, *Rattus norvegicus* Q8CH85_RAT, *Rattus norvegicus* Q80WY5_RAT, *Rattus norvegicus* GCYB1_RAT, *Rattus norvegicus* Q8CH90_RAT, *Rattus norvegicus* Q91XJ7_RAT, *Rattus norvegicus* Q8OWX9_RAT, *Rattus norvegicus* GCYB2_RAT, *Rattus norvegicus* GCYA2_RAT, *Canis familiaris* Q4ZHR9_CANFA, *Bos taurus* GCYB1_BOVIN, *Sus scrofa* Q4ZHR7_PIG, *Gryllus bimaculatus* Q59HN5_GRYBI, *Manduca sexta* O77106_MANSE, *Manduca sexta* O76340_MANSE, *Apis mellifera* Q5UAF0_APIME, *Apis mellifera* Q5FANO_APIME, *Apis mellifera* Q6L5L6_APIME, *Anopheles gambiae* str PEST Q7PYK9_ANOGA, *Anopheles gambiae* str PEST Q7Q9W6_ANOGA, *Anopheles gambiae* str PEST Q7QF31 ANOGA, *Anopheles gambiae* str PEST Q7PS01 ANOGA, *Anopheles gambiae* str PEST Q7PFY2_ANOGA, *Anopheles gambiae* Q7KQ93_ANOGA, *Drosophila melanogaster* Q24086_DROME, *Drosophila melanogaster* GCYH_DROME, *Drosophila melanogaster* GCY8E_DROME, *Drosophila melanogaster* GCYDA_DROME, *Drosophila melanogaster* GCYDB_DROME, *Drosophila melanogaster* Q9VA09_DROME, *Drosophila pseudoobscura* Q29CE1_DROPS, *Drosophila pseudoobscura* Q296C7_DROPS, *Drosophila pseudoobscura* Q296C8_DROPS, *Drosophila pseudoobscura* Q29BU7_DROPS, *Aplysia californica* Q7YWK7_APLCA, *Hemicentrotus pulcherrimus* Q95NK5_HEMPU, *Chlamydomonas reinhardtii*, Q5YLC2_CHLRE, *Anabaena* sp Q8YUQ7_ANASP, *Flavobacteria bacterium* BBFL7 Q26GR8_9 BACT, *Psychroflexus torquis* ATCC 700755 Q1VQE5_9 FLAO, marine gamma proteobacterium HTCC2207 Q1YPJ5_9 GAMM, marine gamma proteobacterium HTCC2207 QlYTK4_9 GAMM, *Caulobacter crescentus* Q9A451_CAUCR, *Acidiphilium cryptum* JF-5 Q2DG60_ACICY, *Rhodobacter sphaeroides* Q3J0U9_RHOS4, *Silicibacter pomeroyi* Q5LPV1_SILPO, *Paracoccus denitrificans* PD1222, Q3PC67_PARDE, *Silicibacter* sp TM1040 Q3QNY2_9 RHOB, *Jannaschia* sp Q28ML8_JANSC, *Magnetococcus* sp MC-1 Q3XT27_9 PROT, *Legionella pneumophila* Q5WXPO_LEGPL, *Legionella pneumophila* Q5WTZ5_LEGPL, *Legionella pneumophila* Q5X268_LEGPA, *Legionella pneumophila* Q5X2_R2 LEGPA, *Legionella pneumophila* subsp *pneumophila* Q5ZWM9_LEGPH, *Legionella pneumophila* subsp *pneumophila* Q5ZSQ8_LEGPH, *Colwellia psychrerythraea* Q47Y43_COLP3, *Pseudoalteromonas atlantica* T6c Q3CSZ5_ALTAT, *Shewanella oneidensis* Q8EF49_SHEON, *Saccharophagus degradans* Q21E20_SACD2, *Saccharophagus degradans* Q21ER7_SACD2, *Vibrio angustum* S14 Q1ZWE5_9 VIBR, *Vibrio vulnificus* Q8DAE2_VIBVU, *Vibrio alginolyticus* 12G01 Q1VCP6_VIBAL, *Vibrio* sp DAT722 Q2FA22_9 VIBR, *Vibrio parahaemolyticus* Q87NJ1_VIBPA, *Vibrio fischeri* Q5E1F5_VIBF1, *Vibrio vulnificus* Q7MJS8_VIBVY, *Photobacterium* sp SKA34 Q2C6Z5_9 GAMM, *Hahella chejuensis* Q2SFY7_HAHCH, *Oceanospirillum* sp MED92 Q2BKV0_9 GAMM, *Oceanobacter* sp RED65 Q1N035_9 GAMM, *Desulfovibrio desulfuricans* Q310U7_DESDG, *Halothermothrix orenii* H 168 Q2AIW5_9 FIRM, *Thermoanaerobacter tengcongensis* Q8RBX6_THETN, *Caldicellulosiruptor saccharolyticus* DSM 8903 Q2ZH17_CALSA, *Clostridium acetobutylicum* Q97E73_CLOAB, *Alkaliphilus metalliredigenes* QYMF Q3C763_9 CLOT, *Clostridium tetani* Q899J9_CLOTE, and *Clostridium beijerincki* NCIMB 8052 Q2WVN0_CLOBE. In some embodiments of the pharmaceutical compositions, the H-NOX protein does not have a mutation in the Y-S-R motif, which includes Tyr135, Ser137, and Arg139 of human H-NOX.

Unless otherwise explicitly noted or dictated by context, all wild-type and mutant H-NOX proteins described herein may be used in any of the pharmaceutical compositions described. herein. The H-NOX protein may or may not have heme and/or oxygen bound and may or may not be covalently bound to another molecule or moiety, such as polyethylene glycol. In some embodiments, the H-NOX protein is a fusion protein that includes an H-NOX domain and part or all of another protein, such as albumin (e.g., human serum albumin):

In one aspect, the invention provides methods of delivering oxygen to an individual (e.g., a mammal, such as a primate (e.g., a human, a monkey, a gorilla, an ape, a lemur, etc), a bovine, an equine, a porcine, a canine, or a feline) using an H-NOX protein. In some embodiments, the individual is suffering from or at risk for a cardiovascular disease, a neurological disease, tumor hypoxia, a loss of blood, or a wound. Exemplary cardiovascular indications include myocardial infarction (e.g., ST-segment elevation myocardial infarction), cardioplegia, sickle cell anemia, perioperative ischemia, peripheral vascular occlusion, and angioplasty. Exemplary neurological indications include ischemic stroke, traumatic brain injury, and spinal cord injury. For the treatment of tumor hypoxia, H-NOX proteins can be used, e.g., as a radiation therapy adjuvant in solid tumors (e.g., individuals with poor pre-metastatic prognoses) or as a PDT therapy adjuvant in surface tumors (e.g., colon, lung, or skin cancer, or cancer in another accessible surface or location). Applications of H-NOX proteins as a blood transfusion alternative include trauma (e.g., battlefield, disaster relief, or accidents), surgery (e.g., abdominal aneurysm-surgery, orthopedic surgery such as hip replacement surgery, or any other surgery that produces high blood loss), hemorrhages, hemorrhagic shock, hemodilution, and blood extension uses (e.g., supplementing auto-donation). Examples of wound repair applications include post-radiation wound repair (e.g., hyperbaric oxygen effect), post-surgical repair, diabetic ulcer repair, and burn wounds.

Accordingly, in some embodiments, the invention provides a method of delivering oxygen to an individual (e.g., a human) by administering to an individual in need thereof an H-NOX protein in an amount sufficient to deliver an effective amount of oxygen to the individual. In sortie embodiments, the $O_2$ dissociation constant of the H-NOX protein is between about 1 nM to about 1 mM at 20° C., and the NO reactivity of the H-NOX protein is less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.). In some embodiments, the $O_2$ dissociation constant of the H-NOX protein is within 2 orders of magnitude of that of hemoglobin, and the NO reactivity of the H-NOX protein is at least 10-fold lower than that of hemoglobin.

In some embodiments of the methods, oxygen is bound to the H-NOX protein prior to the administration of the H-NOX protein to the individual. In some embodiments of the methods, oxygen is not bound to the H-NOX protein prior to the administration of the H-NOX protein to the individual, and the H-NOX protein transports oxygen from one location in the individual to another location in the individual. In some embodiments of the methods, the H-NOX protein is administered to the blood of the individual. In some embodiments of the methods, the H-NOX protein is administered to the blood, a wound, a tumor, a hypoxic tissue, or a hypoxic organ of the individual. In some embodiments of the methods, the individual is suffering from or at risk for a loss of blood. In some embodiments of the methods, the H-NOX protein is administered to the individual at least twice.

In some embodiments of the methods, the $O_2$ dissociation constant of the H-NOX protein is within 2 orders of magnitude of that of *Homo sapiens* hemoglobin alpha, such as an $O_2$ dissociation constant between 0.1 to 10-fold or between 0.5 to 2-fold of that of *Homo sapiens* hemoglobin alpha. In some embodiments of the methods, the NO reactivity of the H-NOX protein is at least 10-fold lower than that of *Homo sapiens* hemoglobin alpha, such as at least 100-fold or 1,000-fold lower than that of *Homo sapiens* hemoglobin alpha. In some embodiments of the methods, the H-NOX protein is a wild-type protein. In some embodiments of the methods, the H-NOX protein is a mutant protein as described herein. In various embodiments of the methods, the H-NOX protein has at least one mutation that alters the $O_2$ dissociation constant, the $k_{off}$ for oxygen, the rate of heme autoxidation, the NO reactivity, or any two or more of the foregoing compared to that of a corresponding wild-type protein. In some embodiments of the methods, the H-NOX protein is a selected from the group consisting of wild-type *T. tengcongensis* H-NOX, *T. tengcongensis* H-NOX I5A, *T. tengcongensis* H-NOX I5L, *T. tengcongensis* H-NOX I5L-P115A, *T. tengcongensis* H-NOX W9F, *T. tengcongensis* H-NOX W9F-Y140L, *T. tengcongensis* H-NOX-W9F-Y140H, *T. tengcongensis* H-NOX W9F-N74A, *T. tengcongensis* H-NOX W9Y, *T. tengcongensis* H-NOX W9N, *T. tengcongensis* H-NOX W9H, *T. tengcongensis* H-NOX N74E, *T. tengcongensis* H-NOX N74A, *T. tengcongensis* H-NOX N74H, *T. tengcongensis* H-NOX N74A-Y140H, *T. tengcongensis* H-NOX F78Y-Y140F, *T. tengcongensis* H-NOX F78Y/Y140L, *T. tengcongensis* H-NOX P115A, *T. tengcongensis* H-NOX R135Q, *T. tengcongensis* H-NOX Y140F, *T. tengcongensis* H-NOX Y40L, *T. tengcongensis* H-NOX Y140H, *T. tengcongensis* H-NOX Y140A, *T. tengcongensis* I75F-His6, *T. tengcongensis* I75F, *T. tengcongensis* L144F-His6, *T. tengcongensis* L144F, *L. pneumophilia* 2 H-NOX F142Y, wild-type *L. pneumophilia* 1 H-NOX, wild-type *L. pneumophilia* 2 H-NOX, *L. pneumophilia* 2 F9W-F142Y, wild-type *D. desulfuricans* H-NOX, *D. desulfuricans* H-NOX(728-899), *D. desulfuricans* H-NOX Y139L, wild-type *H. sapiens* β1 H-NOX, *H. sapiens* β1 I145Y, *H. sapiens* β1 (1-385), *H. sapiens* β1(1-385) I145Y, *H. sapiens* β1(1-385) I145H, *H. sapiens* β1(1-194), *H. sapiens* β1 (1-194) I145Y, *H. sapiens* β1 (1-194) L9W-I145Y, *H. sapiens* β2(1-217), *H. sapiens* β2(1-217) I142Y, *H. sapiens* β1 H-NOX H105G, *H. sapiens* β1 H-NOX H105F, wild-type *R. norvegicus* β1 H-NOX, *R. norvegicus* β1 (1-385), *R. norvegicus* β1 (1-385) I145Y, *R. norvegicus* β1 (1-385) I145H, *R. norvegicus* β1 (1-194), *R. norvegicus* β1 (1-194) I145Y, *R. norvegicus* β1(1-194) L9W-I145Y, *R. norvegicus* β2(1-217), *R. norvegicus* β2(1-217) I142Y, *R. norvegicus* β1 H-NOX H105G, *R. norvegicus* β1 H-NOX H105F, *C. botulinum* H-NOX(1-175), *C. botulinum* H-NOX(1-186), wild-type *C. acetobutylicum* H-NOX, *C. acetobutylicum* H-NOX (1-197), *C. acetobutylicum* H-NOX(1-183), wild-type *C. elegans* GCY-35 H-NOX, *C. elegans* H-NOX GCY-35(1-252), wild-type *D. melangaster* β1 H-NOX, wild-type *D. melangaster* CG14885-PA, wild-type *D. melangaster* CG14886, wild-type *D. melangaster* CG4154; wild-type *N. punctiforme* H-NOX, wild-type *C. crescentus* H-NOX, wild-type *S. oneidensis* H-NOX, wild-type *M. musculus* H-NOX, wild-type *C. familiaris* H-NOX, wild-type *B. Taurus* H-NOX, wild-type *R. norvegicus*; wild-type *X. laevis* H-NOX, wild-type *O. latipes* H-NOX, wild-type *O. curiva-*

*tus* H-NOX, wild-type *F. rubripes* H-NOX, wild-type *A. gambiae* H-NOX, wild-type *M. sexta* H-NOX; wild-type *C. elegans* gcy-31, *C. elegans* gcy-32, wild-type *C. elegans* gcy-33, wild-type *C. elegans* gcy-34, wild-type *C. elegans* gcy-35, wild-type *C. elegans* gcy-36, wild-type *C. elegans* gcy-37; wild-type *V. cholera* H-NOX, wild-type *V. fischerii* H-NOX, and wild-type *N. punctiforme* H-NOX. In some embodiments of the methods, one or more liposomes or nanoparticles include or encapsulate the H-NOX protein.

In some embodiments of the methods, the H-NOX protein is not *T. tengcongensis* H-NOX Y140H. In some embodiments of the methods, the H-NOX protein is not *T. tengcongensis* H-NOX Y40L, *T. tengcongensis* H-NOX F78Y/Y140L, wild-type *T. tengcongensis* H-NOX, or *L. pneumophilia* 2 H-NOX F142Y. In some embodiments of the methods, the H-NOX protein is not *R. norvegicus* β2(1-217), *R. norvegicus* β1(1-194), *R. norvegicus* β1(1-385), or *R. norvegicus* β1(1-385) I145Y. In some embodiments of the methods, the H-NOX protein is not *T. tengcongensis* H-NOX W9F, *T. tengcongensis* H-NOX Y140F, or *H. sapiens* β1 H-NOX(1-385) I145Y. In some embodiments, H-NOX protein is not *T. tengcongensis* H-NOX Y140H, *H. sapiens* β1 I140Y, or *H. sapiens* β1 I145Y. In some embodiments of the methods, the H-NOX protein is not *T. tengcongensis* H-NOX Y140F, wild-type *L. pneumophilia* 2 H-NOX, *H. sapiens* β1 H-NOX I140Y, wild-type *H. sapiens* β1 H-NOX, *R. norvegicus* sGC β1 H-NOX(1-385), *R. norvegicus* sGC β1 H-NOX(1-385) I145Y, *R. norvegicus* sGC β1 H-NOX H105G, *R. norvegicus* sGC β1 H-NOX H105F, *R. norvegicus* sGC β1 H-NOX I145Y, wild-type *R. norvegicus* β1 H-NOX, wild-type *D. melangaster* β1 H-NOX, wild-type *D. melangaster* CG14885-PA H-NOX, wild-type *C. elegans* GCY-35 H-NOX, wild-type *N. punctiforme* H-NOX, wild-type *C. crescentus* H-NOX, wild-type *S. oneidensis* H-NOX, or wild-type *C. acetobutylicum* H-NOX. In some embodiments of the methods, the H-NOX protein is not *T. tengcongensis* H-NOX Y40L, *T. tengcongensis* H-NOX F78Y/Y140L, *T. tengcongensis* H-NOX W9F, *T. tengcongensis* H-NOX Y140F, wild-type *T. tengcongensis* H-NOX, *L. pneumophilia* 2 H-NOX F142Y, wild-type *L. pneumophilia* 2 H-NOX, *H. sapiens* β1 H-NOX I140Y, *H. sapiens* B1 I145Y, wild-type *H. sapiens* β1 H-NOX, *R. norvegicus* sGC β1 H-NOX(1-385), *R. norvegicus* sGC β1 H-NOX(1-385) I145Y, *R. norvegicus* sGC β1 H-NOX H105G, *R. norvegicus* sGC β1 H-NOX H105F, *R. norvegicus* sGC β1 H-NOX I145Y, wild-type *R. norvegicus* β1 H-NOX, wild-type *D. melangaster* β1 H-NOX, wild-type *D. melangaster* CG14885-PA H-NOX, wild-type *C. elegans* GCY-35 H-NOX, wild-type *N. punctiforme* H-NOX, wild-type *C. crescentus* H-NOX, wild-type *S. oneidensis* H-NOX, or wild-type *C. acetobutylicum* H-NOX. In some embodiments of the methods, the H-NOX protein is not any of the following H-NOX proteins that are listed by their gene name, followed by their species abbreviation and Genbank Identifiers (such as the following protein sequences available as of May 21, 2006; May 22, 2006; May 21, 2007; or May 22, 2007): Npun5905 Npu_23129606, alr2278_Ana 17229770, SO2144_Sone_24373702, Mdeg1343_Mde_23027521, VCA0720_Vch_15601476, CC2992_Ccr_16127222, Rsph2043_Rhsp_22958463 (gi:46192757), Mmc10739_Mcsp_22999020, Tar4_Tte_20807169, Ddes2822_Dde_23475919, CAC3243_Cac_15896488, gcy-31_Ce_17568389, CG14885_Dm_24647455, GUCY1B3_Hs_4504215, HpGCS-beta1_Hpul_14245738, Gycbeta100B_Dm_24651577, CG4154_Dm_24646993 (gi: NP_650424.2, gi:62484298), gcy-32_Ce_13539160, gcy-36_Ce_17568391 (gi:32566352, gi:86564713), gcy-35_Ce-17507861 (gi:71990146), gcy-37_Ce_17540904 (gi: 71985505), GCY1α3_Hs_20535603, GCY1α2-Hs_899477, or GYCα-99B_Dm_729270 (gi:68067738) (Lakshminarayan et al. (2003). "Ancient conserved domains shared by animal soluble guanylyl cyclases and bacterial signaling proteins," *BMG Genomics* 4:5-13). The species abbreviations used in these names include Ana—*Anabaena* Sp; Ccr—*Caulobacter crescentus*; Cac—*Clostridium acetobutylicum*; Dde—*Desulfovibrio desulfuricans*; Mcsp—*Magnetococcus* sp.; Mde—*Microbulbifer degradans*; Npu—*Nostoc punctiforme*; Rhsp—*Rhodobacter sphaeroides*; Sone—*Shewanella oneidensis*; Tte—*Thermoanaerobacter tengcongensis*; Vch—*Vibrio cholerae*; Ce—*Caenorhabditis elegans*; Dm—*Drosophila melanogaster*; Hpul—*Hemicentrotus pulcherrimus*; Hs—*Homo sapiens*. In some embodiments of the methods, the H-NOX protein is not any of the following H-NOX proteins that are listed by their organism name and Pfam database accession number (such as the following protein sequences available as of May 21, 2006; May 22, 2006; May 17, 2007; May 21, 2007; or May 22, 2007): *Caenorhabditis briggsae* Q622M5_CAEBR, *Caenorhabditis briggsae* Q61P44_CAEBR, *Caenorhabditis briggsae* Q61R54_CAEBR, *Caenorhabditis briggsae* Q61V90_CAEBR, *Caenorhabditis briggsae* Q61A94_CAEBR, *Caenorhabditis briggsae* Q60TP4_CAEBR, *Caenorhabditis briggsae* Q60M10_CAEBR, *Caenorhabditis elegans* GCY37_CAEEL, *Caenorhabditis elegans* GCY31_CAEEL, *Caenorhabditis elegans* GCY36_CAEEL, *Caenorhabditis elegans* GCY32_CAEEL, *Caenorhabditis elegans* GCY35_CAEEL, *Caenorhabditis elegans* GCY34. CAEEL, *Caenorhabditis elegans* GCY33_CAEEL, *Oryzias curvinotus* Q7T040_ORYCU, *Oryzias curvinotus* Q75WF0_ORYCU, *Oryzias latipes* P79998_ORYLA, *Oryzias latipes* Q7ZSZ5_ORYLA, *Tetraodon nigroviridis* Q4SW38_TETNG, *Tetraodon nigroviridis* Q4RZ94_TETNG, *Tetraodon nigroviridis* Q4S6K5_TETNG, *Fugu rubripes* Q9OVY5 FUGRU, *Xenopus laevis* Q6INK9_XENLA, *Homo sapiens* Q5T8J7 HUMAN, *Homo sapiens* GCYA2_HUMAN, *Homo sapiens* GCYB2_HUMAN, *Homo sapiens* GCYB1_HUMAN, *Gorilla gorilla* Q9N193_9 PRIM, *Pongo pygmaeus* Q5RAN8_PONPY, *Pan troglodytes* Q9N192_PANTR, *Macaca mulatta* Q9N194_MACMU, *Hylobates lar* Q9N191_HYLLA, *Mus musculus* Q8BXH3_MOUSE, *Mus musculus* GCYB1_MOUSE, *Mus musculus* Q3UTI4_MOUSE, *Mus musculus* Q3UH83_MOUSE, *Mus musculus* Q6XE41_MOUSE, *Mus musculus* Q80YP4_MOUSE, *Rattus norvegicus* Q8OWX7_RAT, *Rattus norvegicus* Q8OWX8_RAT, *Rattus norvegicus* Q920Q1_RAT, *Rattus norvegicus* Q54A43_RAT, *Rattus norvegicus* Q80WY0_RAT, *Rattus norvegicus* Q80WY4_RAT, *Rattus norvegicus* Q8CH85 RAT, *Rattus norvegicus* Q80WY5_RAT, *Rattus norvegicus* GCYB1_RAT, *Rattus norvegicus* Q8CH90_RAT, *Rattus norvegicus* Q91XJ7_RAT, *Rattus norvegicus* Q8OWX9_RAT, *Rattus norvegicus* GCYB2 RAT, *Rattus norvegicus* GCYA2_RAT, *Canis familiaris* Q4ZHR9_CANFA, *Bos taurus* GCYB1_BOVIN, *Sus scrofa* Q4ZHR7_PIG, *Gryllus bimaculatus* Q59HN5_GRYBI, *Manduca sexta* O77106_MANSE, *Manduca sexta* O76340_MANSE, *Apis mellifera* Q5UAFO_APIME, *Apis mellifera* Q5FANO_APIME, *Apis mellifera* Q6L5L6_APIME, *Anopheles gambiae* str PEST Q7PYK9_ANOGA, *Anopheles gambiae* str PEST Q7Q9W6_ANOGA, *Anopheles gambiae* str PEST Q7 QF31_ANOGA, *Anopheles gambiae* str PEST Q7PS01_ANOGA, *Anopheles gambiae* str PEST Q7PFY2_ANOGA, *Anopheles gambiae* Q7KQ93_ANOGA, *Drosophila melanogaster* Q24086_DROME, *Drosophila melanogaster* GCYH_DROME, *Drosophila melanogaster* GCY8E_DROME, *Drosophila melanogaster* GCYDA_DROME, *Drosophila melanogaster* GCYDB_DROME, *Drosophila melanogaster* Q9VA09_DROME, *Drosophila pseudoobscura* Q29CE1_DROPS, *Drosophila pseudoobscura* Q296C7_DROPS, *Drosophila pseudoobscura* Q296C8_DROPS, *Drosophila pseudoobscura* Q29BU7 DROPS, *Aplysia californica* Q7YWK7_APLCA, *Hemicentrotus pulcherrimus* Q95NK5_HEMPU, *Chlamydomonas reinhardtii*, Q5YLC2_CHLRE, *Anabaena* sp Q8YUQ7_ANASP, *Flavobacteria bacterium* BBFL7 Q26GR8_9 BACT, *Psychroflexus torquis* ATCC 700755 Q1VQE5_9 FLAO, marine gamma proteobacterium HTCC2207 Q1YPJ5_9 GAMM, marine gamma proteobacterium HTCC2207 Q1YTK4_9 GAMM, *Caulobacter crescentus* Q9A451_CAUCR, *Acidiphilium cryptum* JF-5 Q2DG60_ACICY, *Rhodobacter sphaeroides* Q3J0U9_RHOS4, *Silicibacter pomeroyi* Q5LPV1_SILPO, *Paracoccus denitrificans* PD1222, Q3PC67_PARDE, *Silicibacter* sp TM1040 Q3QNY2_9 RHOB, *Jannaschia* sp Q28ML8_JANSC, *Magnetococcus* sp MC-1 Q3XT27_9 PROT, *Legionella pneumophila* Q5WXPO_LEGPL, *Legionella pneumophila* Q5WTZ5_LEGPL, *Legionella pneumophila* Q5X268_LEGPA, *Legionella pneumophila* Q5X2R2_LEGPA, *Legionella pneumophila* subsp *pneumophila* Q5ZWM9_LEGPH, *Legionella pneumophila* subsp *pneumophila* Q5ZSQ8_LEGPH, *Colwellia psychrerythraea* Q47Y43_COLP3, *Pseudoalteromonas atlantica* T6c Q3CSZ5_ALTAT, *Shewanella oneidensis* Q8EF49_SHEON, *Saccharophagus degradans* Q21E20_SACD2, *Saccharophagus degradans* Q21ER7_SACD2, *Vibrio angustum* S14 Q1ZWE5_9VIBR, *Vibrio vulnificus* Q8DAE2_VIBVU, *Vibrio alginolyticus* 12G01 Q1VCP6_VIBAL, *Vibrio* sp DAT722 Q2FA22_9 VIBR, *Vibrio parahaemolyticus* Q87NJ1_VIBPA, *Vibrio fischeri* Q5E1F5_VIBF1, *Vibrio vulnificus* Q7MJS8_VIBVY, *Photobacterium* sp SKA34 Q2C6Z5_9 GAMM, *Hahella chejuensis* Q2SFY7_HAHCH, *Oceanospirillum* sp MED92 Q2BKV0_9 GAMM, *Oceanobacter* sp RED65 Q1N035_9 GAMM, *Desulfovibrio desulfuricans* Q310U7_DESDG, *Halothermothrix orenii* H 168 Q2AIW5_9 FIRM, *Thermoanaerobacter tengcongensis* Q8RBX6_THETN, *Caldicellulosiruptor saccharolyticus* DSM 8903 Q2ZH17_CALSA, *Clostridium acetobutylicum* Q97E73_CLOAB, *Alkaliphilus metalliredigenes* QYMF Q3C763_9 CLOT, *Clostridium tetani* Q899J9_CLOTE, and *Clostridium beijerincki* NCIMB 8052 Q2WVN0_CLOBE. In some embodiments of the methods, the H-NOX protein is not *R. norvegicus* sGC β1 H-NOX C78S or *R. norvegicus* sGC β1 H-NOX C78E. In some embodiments of the methods, the H-NOX protein does not have a mutation in the Y-S-R motif, which includes Tyr135, Ser137, and Arg139 of human H-NOX.

Unless otherwise explicitly noted or dictated by context, all wild-type and mutant proteins and all pharmaceutical compositions described herein may be used in any of the methods of delivering oxygen described herein. The H-NOX protein may or may not have heme and/or oxygen bound and may or may not be covalently bound to another molecule or moiety, such as polyethylene glycol. In some embodiments, the H-NOX protein is a fusion protein that includes an H-NOX domain and part or all of another protein, such as albumin (e.g., human serum albumin).

In one aspect, the invention features kits that include one or more H-NOX proteins. In some embodiments, the invention provides a kit that includes an H-NOX protein and instructions for using the kit to deliver oxygen to an individual. In some embodiments, the $O_2$ dissociation constant of the H-NOX protein is between about 1 nM to about 1 mM at 20° C., and the NO reactivity of the H-NOX protein is less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.). In some embodiments, the $O_2$ dissociation constant of the H-NOX protein is within 2 orders of magnitude of that of hemoglobin, and the NO reactivity of the H-NOX protein is at least 10-fold lower than that of hemoglobin. In some embodiments, the $O_2$ dissociation constant of the H-NOX protein is between about 1 nM to about 1 mM at 20° C., and the NO reactivity of the H-NOX protein is less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.). In some embodiments, the H-NOX protein is not *T. tengcongensis* H-NOX Y140H. Unless otherwise explicitly noted or dictated by context, all wild-type and mutant proteins and all pharmaceutical compositions described herein may be used in any of the kits described herein. The H-NOX protein may or may not have heme and/or oxygen bound and may or may not be covalently bound to another molecule or moiety, such as polyethylene glycol. In some embodiments, the H-NOX protein is a fusion protein that includes an H-NOX domain and part or all of another protein, such as albumin (e.g., human serum albumin).

In one aspect, the invention features an H-NOX protein (such as any of the wild-type or mutant proteins described herein) for use as a medicament. In some embodiments, the invention features an H-NOX protein for use in a method of delivering oxygen to an individual. In some embodiments, the H-NOX protein is used to treat any condition for which delivery of $O_2$ is beneficial, such as a cardiovascular disease, a neurological disease, tumor hypoxia, a loss of blood, or a wound.

In some embodiments, the invention features the use of an H-NOX protein (such as any of the wild-type or mutant proteins described herein) for the manufacture of a medicament, such as a medicament for delivering oxygen to an individual. In some embodiments, the invention features the use of an H-NOX protein for delivering oxygen to an individual. In some embodiments, the H-NOX protein is used to treat any condition for which delivery of $O_2$ is beneficial, such as a cardiovascular disease, a neurological disease, tumor hypoxia, a loss of blood, or a wound.

BRIEF DESCRIPTION OF THE DRAWINGS

FIG. 1A is based on the three-dimensional structure of *T. tengcongensis* H-NOX reported by Pellicena, P. et al. (Aug. 31, 2004). "Crystal Structure of An Oxygen-Binding Heme Domain Related to Soluble Guanylate Cyclases," *Proc Natl. Acad Sci USA* 101(35): 12854-12859.

FIG. 1B is from Pellicena, P. et al. (Aug. 31, 2004). "Crystal Structure of An Oxygen-Binding Heme Domain Related to Soluble Guanylate Cyclases," *Proc Natl. Acad Sci USA* 101(35):12854-12859.

FIGS. 1C-1H were created using PYMOL (DeLano Scientific, LLP).

FIG. 5A is a sequence alignment of members of the H-NOX family. The sequence numbering is that of *T. tengcongensis* H-NOX. Invariant residues are indicated by a "V", very highly conserved residues are indicated by "s". Y140 of *T. tengcongensis* H-NOX is indicated by a "H." Predicted distal pocket tyrosine residues that may stabilize an $Fe^{II}$—$O_2$ complex in other H-NOX proteins are: position 70 for *Caenorhabditis elegans* GCY-35; position 140 in *Drosophila melanogaster* CG14885-PA; position 138 of *Caenorhabditis elegans* GCY-35; position 140 of *Clostridium acetobutylicum*; numbered according to *Thermoanaerobacter tengcongensis*. Accession numbers are: *Homo sapiens* β1 [gi:2746083] (SEQ ID NO:28), *Rattus norvegicus* β1 [gi:27127318] (SEQ ID NO:29), *Drosophila melangaster* β1 [gi:861203] (SEQ ID NO:30), *Drosophila melangaster* CG14885-PA [gi:23171476] (SEQ ID NO:31), *Caenorhabditis elegans* GCY-35 [gi:52782806] (SEQ ID NO:32), *Nostoc punctiforme* [gi:23129606] (SEQ ID NO:33), *Caulobacter crescentus* [gi:16127222] (SEQ ID NO:34), *Shewanella oneidensis* [gi:24373702] (SEQ ID NO:35), *Legionella pneumophila* (ORF 2) [CUCGC_272624] (SEQ ID NO:36), *Clostridium acetobutylicum* [gi:15896488] (SEQ ID NO:37), and *Thermoanaerobacter tengcongensis* [gi:20807169] (SEQ ID NO:38). Alignments were generated using the program MegAlign, Lasergene, DNA Star, (see, the world-wide web at "dnastar.com/productsimegalign.php"). Clustal-W default parameters were used.

FIGS. 6A and 6B are from Pellicena, P. et al. (Aug. 31, 2004). "Crystal Structure of An Oxygen-Binding Heme Domain Related to Soluble Guanylate Cyclases," *Proc Natl. Acad Sci USA* 101(35):12854-12859.

FIGS. 7A-7F are from Boon, E. M. et al. (2005). "Molecular Basis For NO Selectivity in Soluble Guanylate Cyclase," *Nature Chem. Biol.* 1:53-59.

FIGS. 8A-8DD contain polynucleotide sequences of exemplary nucleic acids that encode H-NOX proteins and the amino acid sequences of the corresponding H-NOX proteins (SEQ ID NOS:53-162).

DETAILED DESCRIPTION OF THE INVENTION

Figure 1A:
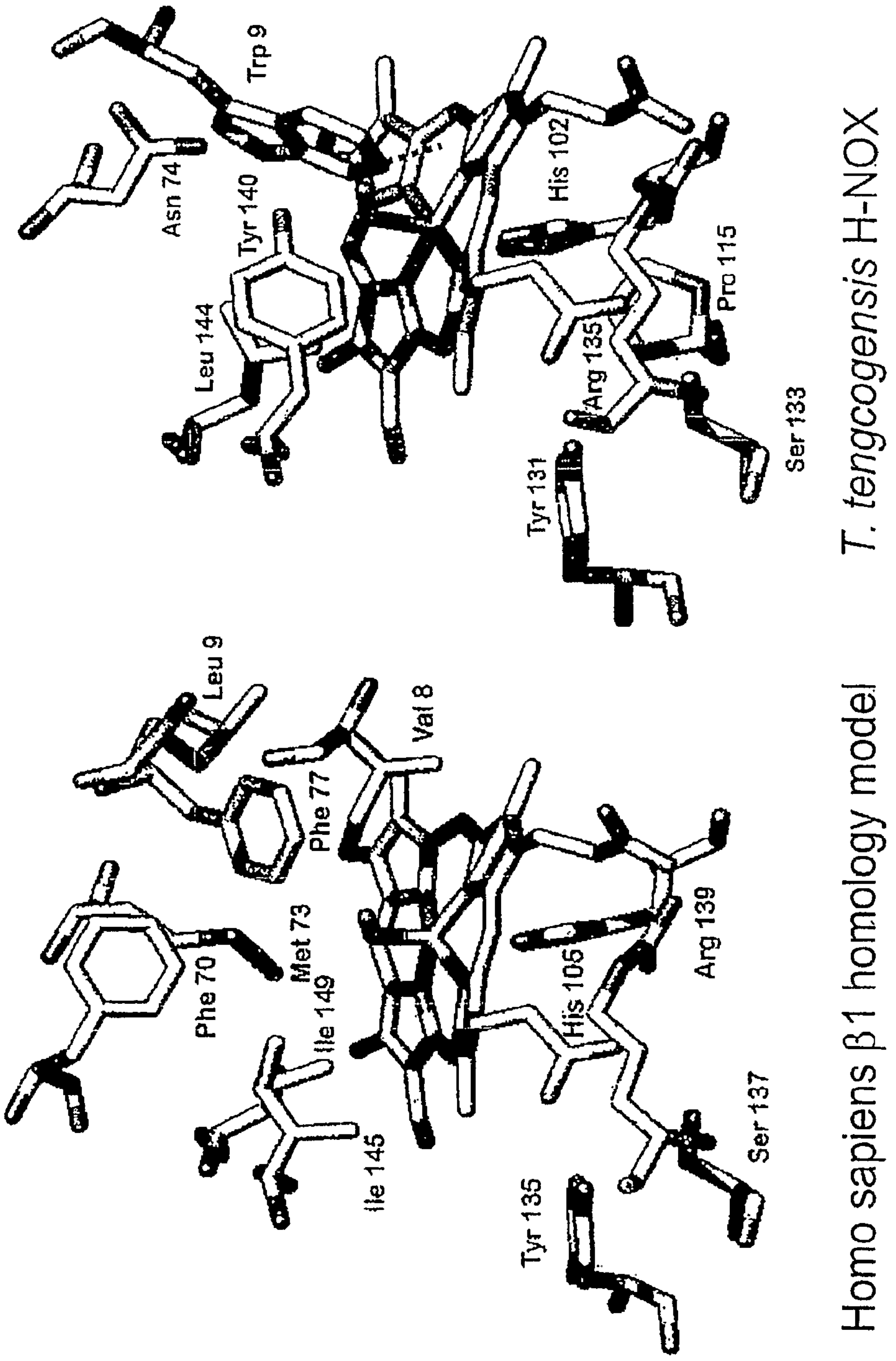
FIG. 1A is a picture of the three dimensional structure of distal pocket residues of NO-binding and $O_2$-binding H-NOX proteins (above heme). Herne coordination residues of NO-binding and $O_2$-binding H-NOX proteins are also shown (below heme).
Figure 1B:
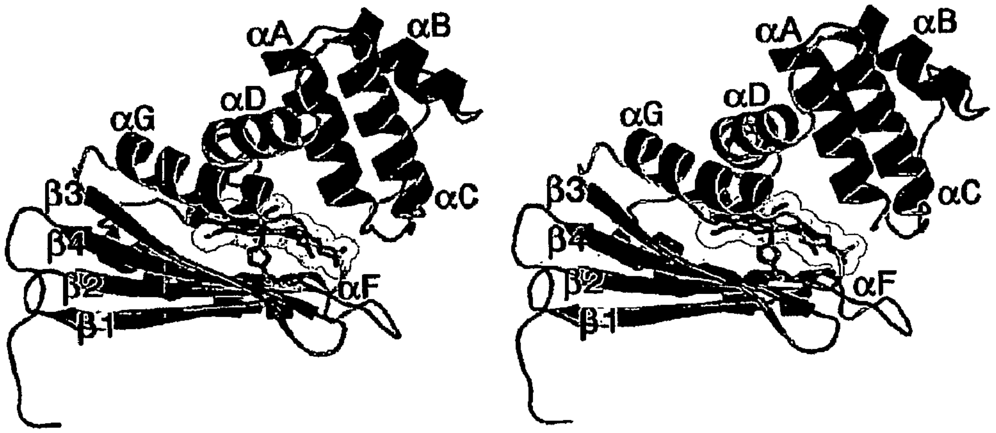
FIG. 1B is a stereo side view of the three dimensional structure of *T. tengcongensis* HNOX illustrating structural features of the H-NOX domain. The protein fold is represented by ribbon diagrams. The heme, dioxygen ligand, and proximal histidine are shown as ball-and-stick models. α-helices are labeled A-G according to the nomenclature shown in FIG. 5B. β-strands are labeled 1-4.
Figures 1C, 1D, 1E, 1F, 1G, 1H:
FIGS. 1C-1H are pictures of the three dimensional structure of *T. tengcongensis* HNOX illustrating exemplary distal pocket residues in *T. tengcongensis* HNOX. The following residues depicted in FIGS. 1C-1H are the main residues comprising the H-NOX distal pocket: Thr4, Ile5, Thr8, Trp9, Trp67, Asn74, Ile75, Phe78, Phe82, Tyr140, and Leu144, which are contained within helices A, D, E, and G.
Figure 2:
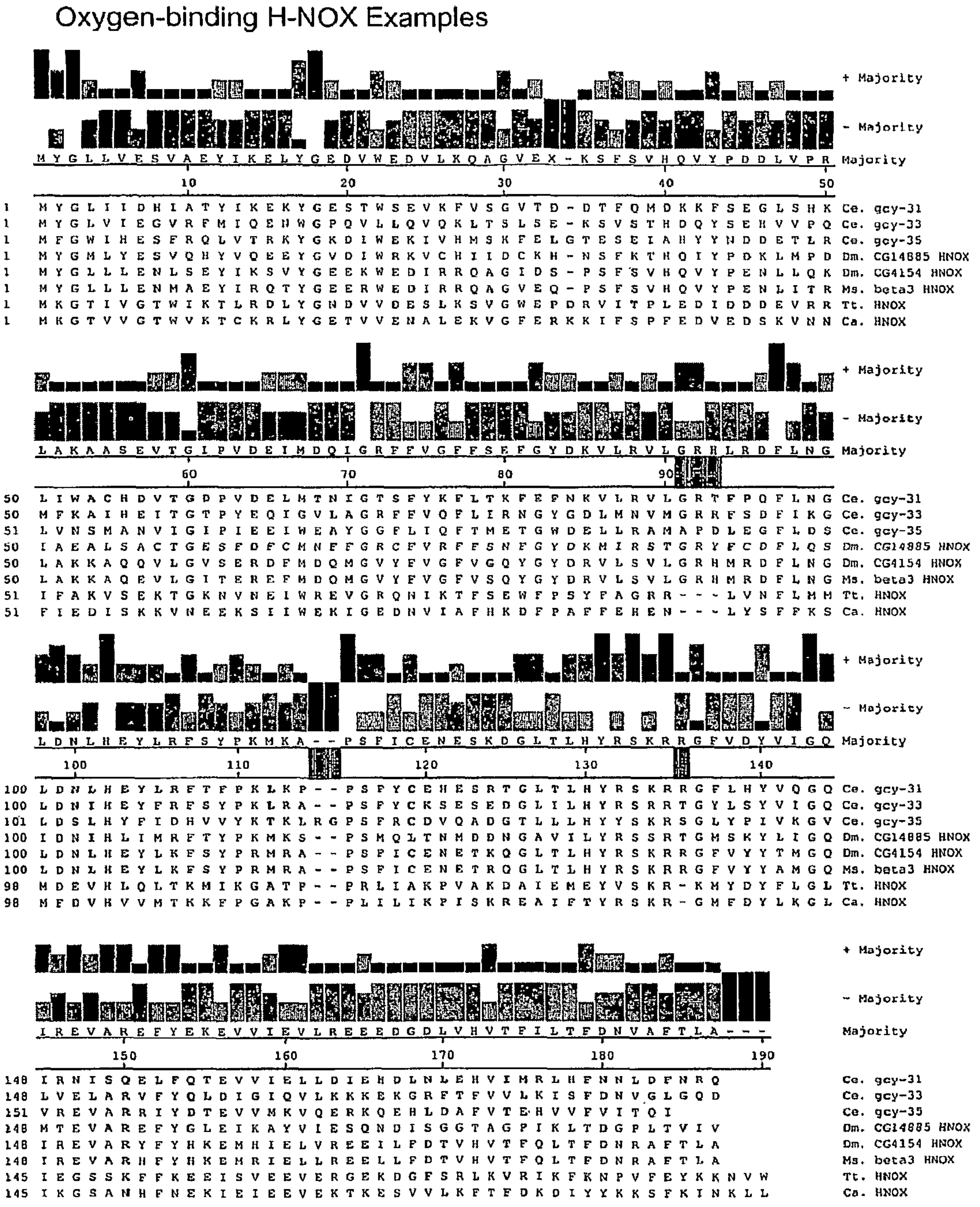
FIG. 2 is a sequence alignment of the following H-NOX proteins that bind or are predicted to bind $O_2$ and NO: Majority (SEQ ID NO:1); Ce. gcy-31 (SEQ ID NO:2); Ce. gcy-33 (SEQ ID NO:3); Ce. gcy-35 (SEQ ID NO:4); Dm. CG14885 HNOX (SEQ ID NO:5); Dm. CG4154 HNOX (SEQ ID NO:6); Ms. Beta3 H-NOX (SEQ ID NO:7); Tt HNOX (SEQ ID NO:8); and Ca HNOX (SEQ ID NO:9). These H-NOX proteins are predicted to bind $O_2$ as well as NO because they have a tyrosine at the position corresponding to Y140 of *T. tengcongensis* H-NOX. The amino acid numbering used in FIG. 2 starts with the first amino acid in the H-NOX domain or full-length protein as residue number 1. The alignment was generated using the default parameters in the program MegAlign. The abbreviations used in FIG. 2 are described below with respect to FIGS. 4A-4D.
Figure 3A:
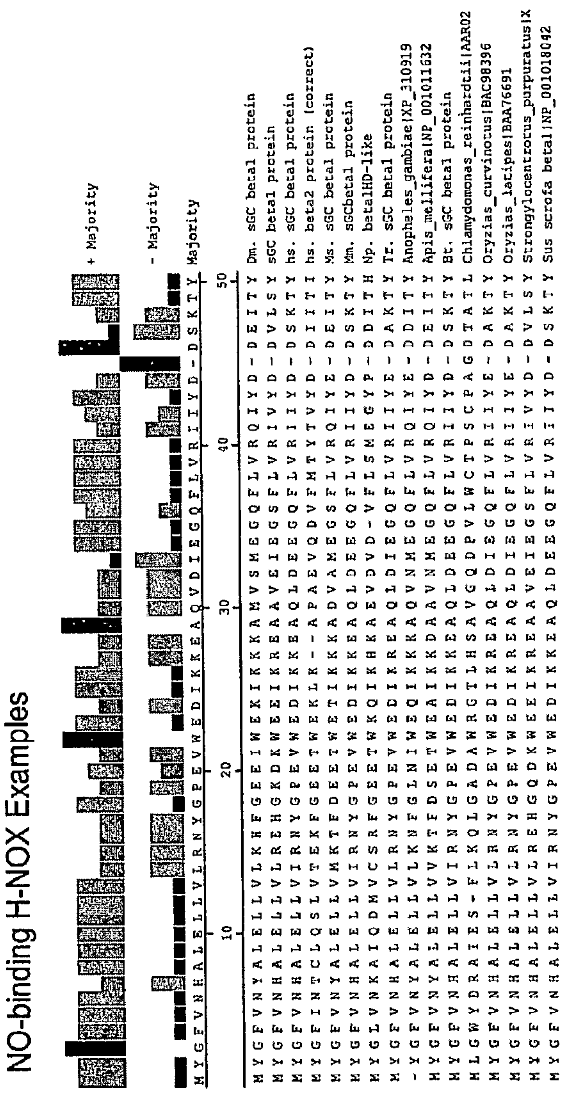
FIG. 3A-3D are a sequence alignment of the following H-NOX proteins that bind or are predicted to bind NO but not $O_2$: Majority (SEQ ID NO:10); Dm. sGC beta1 protein (SEQ ID NO:11); sGC beta1 protein (SEQ ID NO:12); hs. sGC beta1 protein (SEQ ID NO:13); hs. beta2 protein (SEQ ID NO:14); Ms. sGC beta1 protein (SEQ ID NO:15); Mm. sGC beta1 protein (SEQ ID NO:16); Np. beta1 HD-like (SEQ ID NO:17); Tr. sGC beta1 protein (SEQ ID NO:18); *Anopheles_gambiae*|XP_310919 (SEQ ID NO:19); *Apis_mellifera*|NP_001011632 (SEQ ID NO:20); Bt. sGC beta1 protein (SEQ ID NO:21); *Chlamydomonas_reinhardtii*|AAR02 (SEQ ID NO:22); *Oryzias_curvinotus*|BAC98396 (SEQ ID NO:23); *Oryzias_latipes*|BAA76691 (SEQ ID NO:24); *Strongylocentrotus_purpuratus*|X (SEQ ID NO:25); and *Sus scrofa* beta1|NP_001018042+(SEQ ID NO:26). The alignment was generated using the default parameters in the program MegAlign. The abbreviations used in FIGS. 3A-3D are described below with respect to FIG. 4.
Figure 3B:
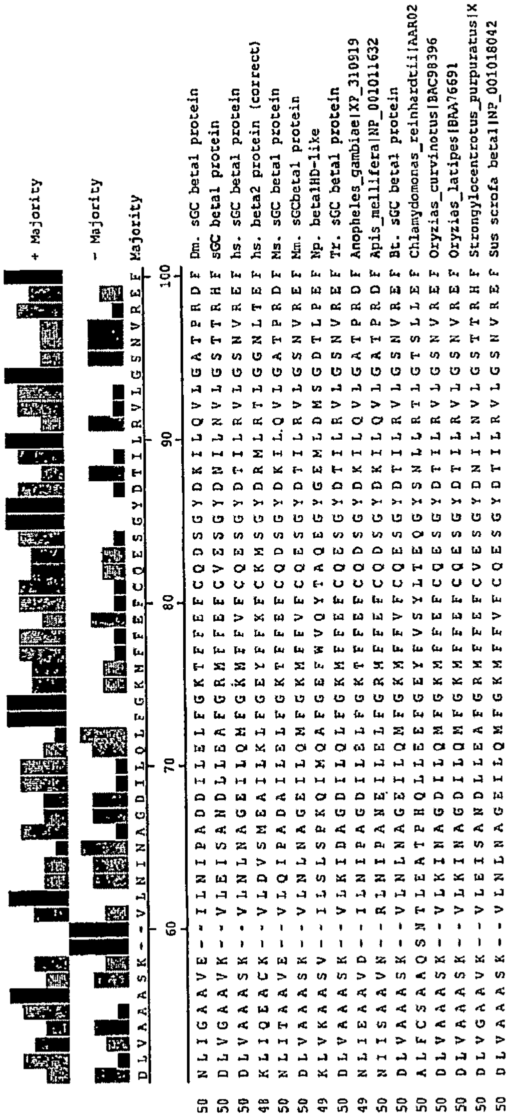
Figure 3C:
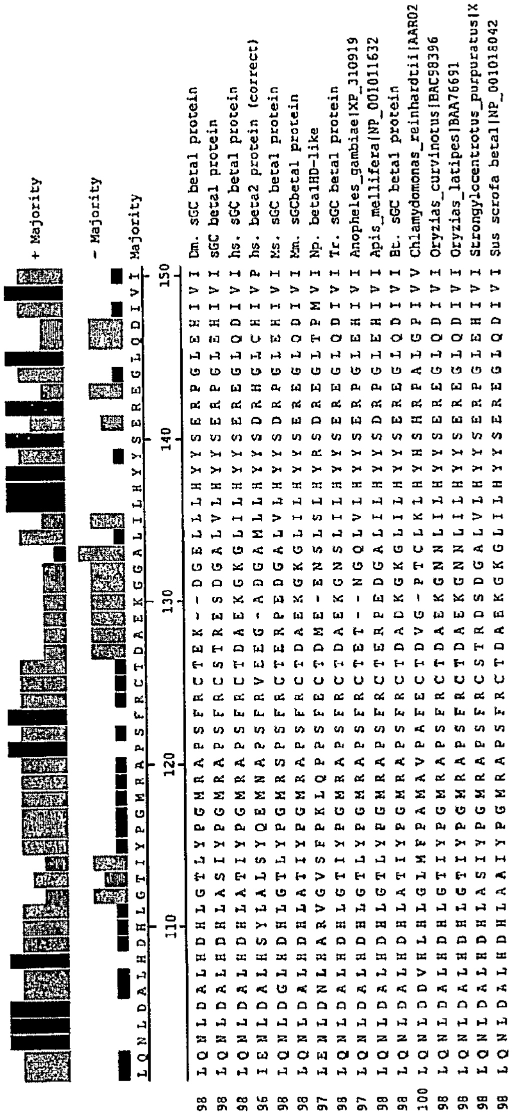
Figure 3D:
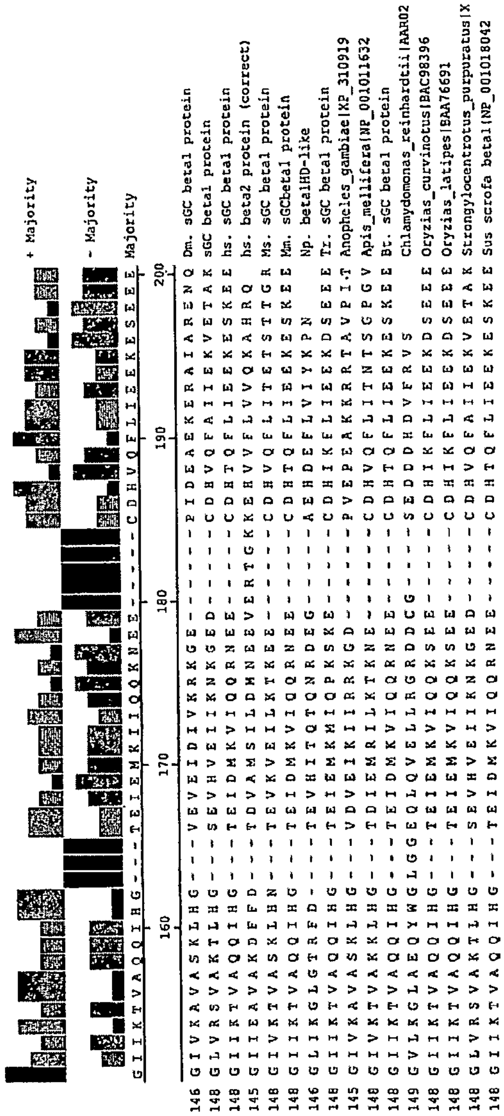
Figure 4A:
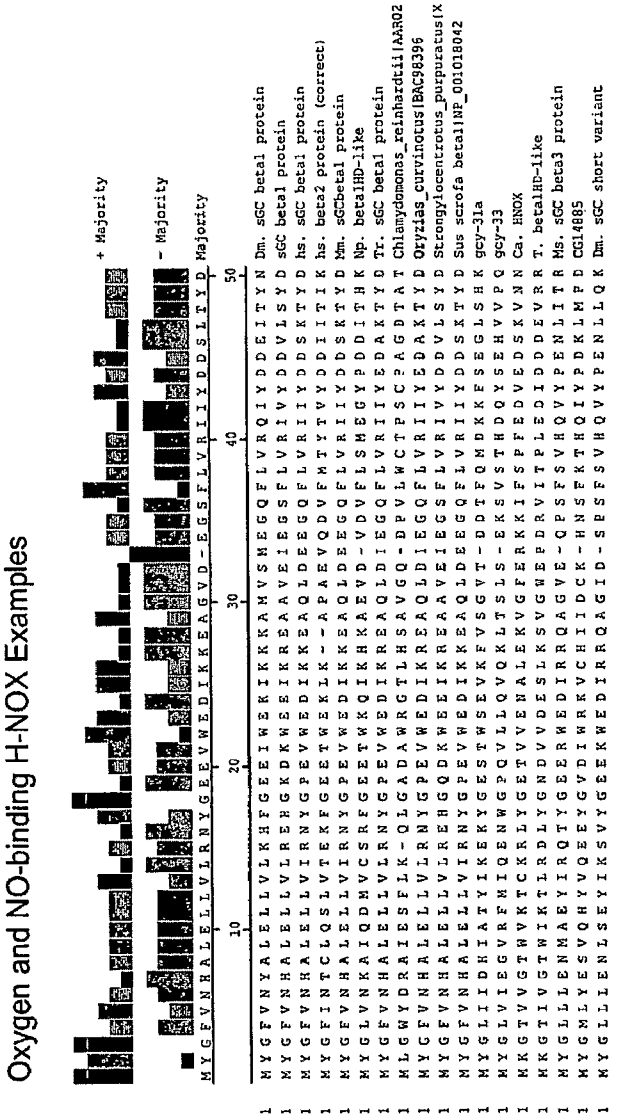
FIGS. 4A-4D are a sequence alignment of H-NOX proteins from FIGS. 2 and 3A-3D: Majority (SEQ ID NO:27); Dm. sGC beta1 protein (SEQ ID NO:11); sGC beta1 protein (SEQ ID NO:12); hs. sGC beta1 protein (SEQ ID NO:13); hs. beta2 protein (SEQ ID NO:14); Mm. sGC beta1 protein (SEQ ID NO:16); Np. beta1 HD-like (SEQ ID NO:17); Tr. sGC beta1 protein (SEQ ID NO:18); *Chlamydomonas_reinhardtii*|AAR02 (SEQ ID NO:22); *Oryzias_curvinotus*|BAC98396 (SEQ ID NO:23); *Strongylocentrotus_purpuratus*|X (SEQ ID NO:25); *Sus scrofa* beta1|NP_001018042 (SEQ ID NO:26); gcy-31a (SEQ ID NO:2); gcy-33 (SEQ ID NO:3); Ca. HNOX (SEQ ID NO:9); T. beta1HD-like (SEQ ID NO:8); Ms. sGc beta 3 protein (SEQ ID NO:7); CG14885 (SEQ ID NO:5); and Dm. sGC short variant (SEQ ID NO:6). The alignment was generated using the default parameters in the program MegAlign. For FIGS. 2-4D, "Dm. sGC beta1 protein" denotes *Drosophila melanogaster* β1 H-NOX; "sGC beta1 protein" denotes *Rattus norvegicus* β1 H-NOX; "hs. sGC beta1 protein" denotes *Homo sapiens* β1 H-NOX; "hs. beta2 protein" denotes *Homo sapiens* β2 H-NOX; "Mm. sGC beta1 protein" denotes *Mus musculus* β1 H-NOX; "Np. beta1 HD-like" denotes *Nostoc punctiforme* H-NOX; "Tr. sGC beta1 protein" denotes *Takifugu rubripes* β1 H-NOX; "*Anopheles_gambiae*|XP_310919" denotes *Anopheles gambiae* β1 H-NOX; "*Apis_mellifera*|NP_001011632" denotes *Apis mellifera* β1 H-NOX; "Bt. sGC beta1 protein" denotes *Bos taurus* β1 H-NOX; "*Chlamydomonas_reinhardtii*|AAR02" denotes *Chlamydornonas reinhardtii* β1 H-NOX; "*Oryzias_curvinotus*|BAC98396 denotes *Oryzias curvinotus* β1 H-NOX; "*Oryzias_latipes*|BAA76691" denotes *Oryzias latipes* β1 H-NOX; "*Strongylocentrotus_purpuratus*|X" denotes *Strongylocentrotus purpuratus* β1 H-NOX; "*Sus scrofa* beta1|NP_001018042+" denotes *Sus scrofa* β1 H-NOX; "gcy-31a" denotes *Caenorhabditis elegans* Gcy-31a H-NOX; "gcy-33" denotes *Caenorhabditis elegans* Gcy-33 H-NOX; "gcy-35" denotes *Caenorhabditis elegans* Gcy-35 H-NOX; "Ca. H-NOX" denotes *Clostridium acetobutiylicum* H-NOX; "T. beta1 HD-like" denotes *Thermoanaerobacter tengcongensis* H-NOX; "Ms. sGc beta 3 protein" denotes *Manduca sexta* β3 H-NOX; "CG14885" denotes *Drosophila melanogaster* CG14885 H-NOX; "Dm. sGC short variant" denotes *Drosophila melanogaster* Gcy-88-E-S H-NOX, and "Dm. CG4154 HNOX" denotes *Drosophila melanogaster* CG4154 H-NOX.
Figure 4B:
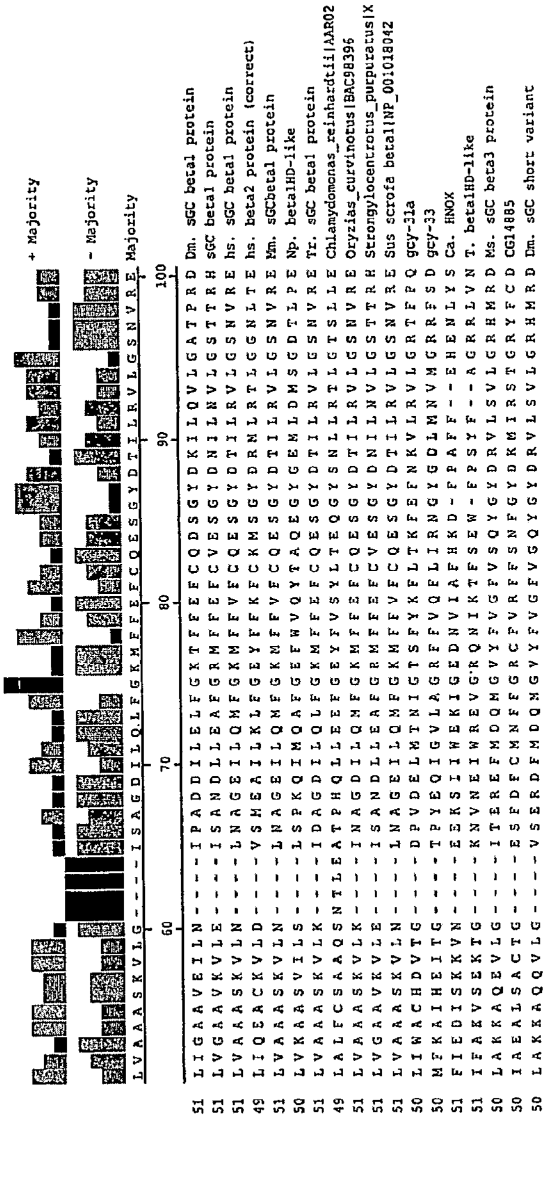
Figure 4C:
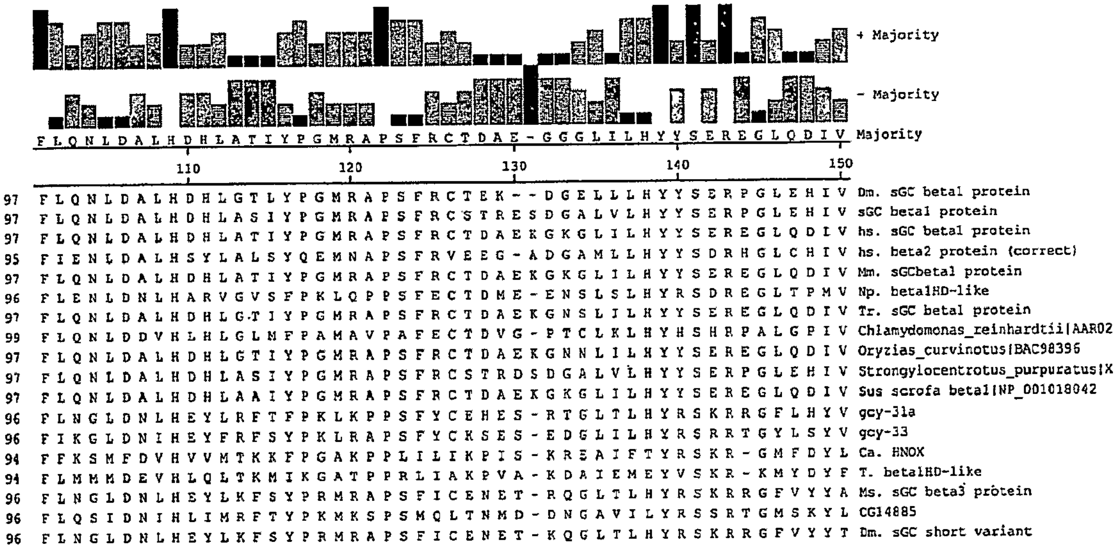
Figure 4D:
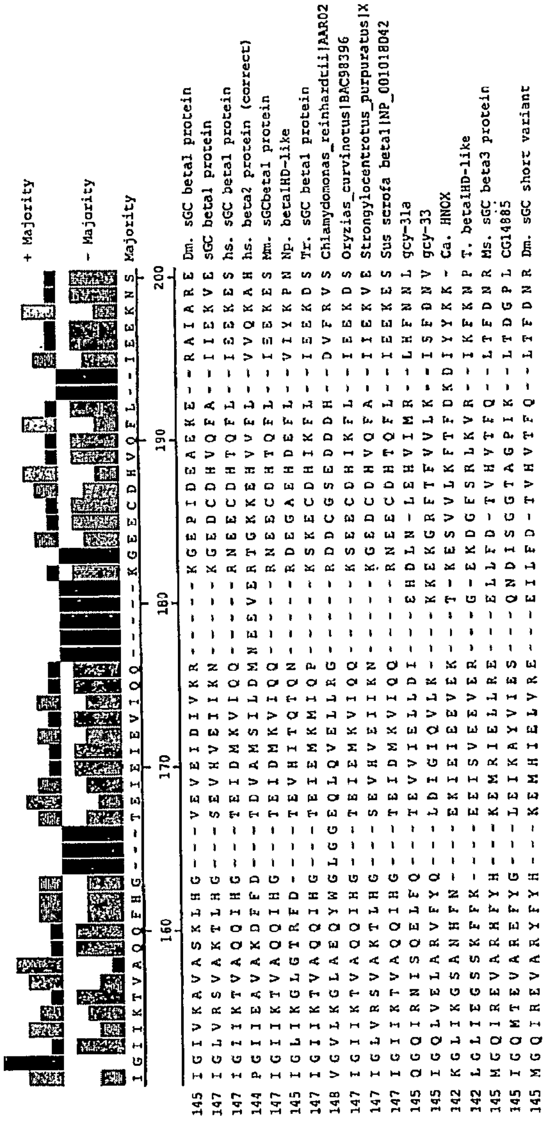
Figure 5B:
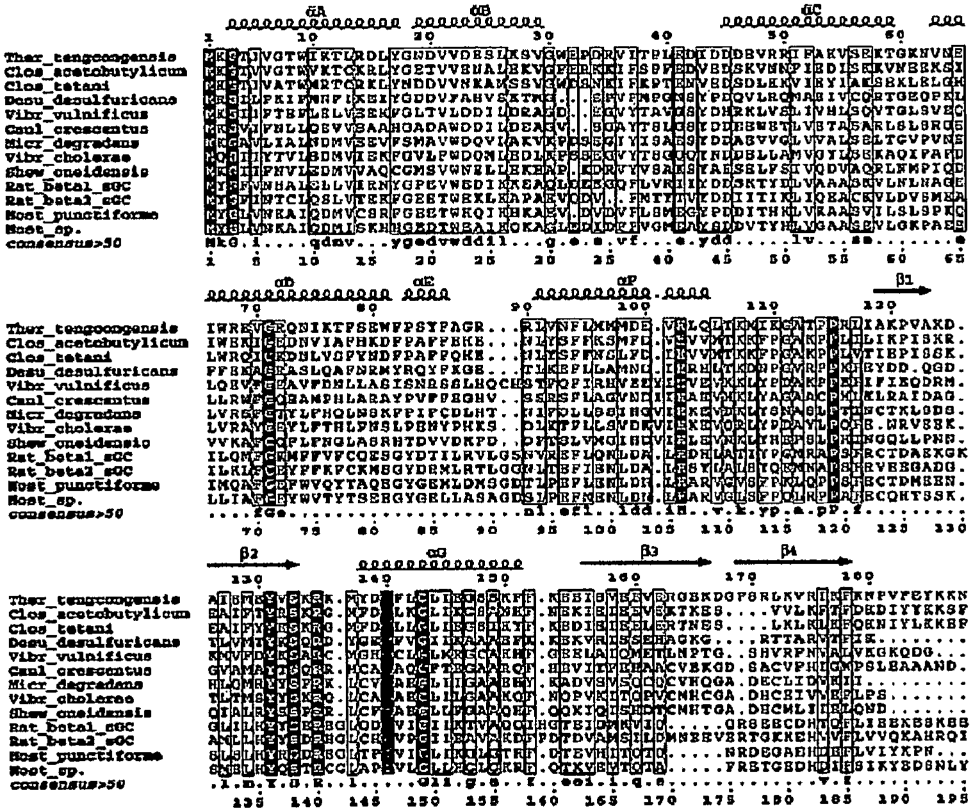
FIG. 5B is a sequence alignment of exemplary H-NOX domains. The secondary structure annotations and the numbering on top of the alignment correspond to the H-NOX domain from *T. tengcongensis*. α-helices are represented by spirals, and β-strands by arrows. The distal pocket is defined by α-helices αA, αD, αE, and αG. Pubmed/NCBI accession numbers are as follows: Ther_tengcongensis gi 120807169| (SEQ ID NO:39), Clos_acetobutylicum gi |15896488| (SEQ ID NO:40), Clos_tetani GI:75543266 (SEQ ID NO:41), Desu_desulfuricans gi |23475919| (SEQ ID NO:42), Vibr- _vulnificus gi |27361734| (SEQ ID NO:43), Caul_crescentus gi |16127222| (SEQ ID NO:44), Micr_degradans gi |23027521| (SEQ ID NO:45), Vibr_cholerae gi |15601476| (SEQ ID NO:46), Shew_oneidensis gi |24373702| (SEQ ID NO:47), Rat_beta1_sGC gi |27127318| (SEQ ID NO:48), Rat_beta2 sGC gi |21956635| (SEQ ID NO:49), Nost_punctiforme gi |23129606| (SEQ ID NO:50), and Nost_sp. gi |17229770| (SEQ ID NO:51). The consensus sequence is shown a the bottom of FIG. 5B (SEQ ID NO:52). The alignments were generated using the program MULTALIN (Corpet, F. (1988) *Nucleic Acids Res.* 16:10881-10890), and FIG. 5B was prepared using the program ESPRIPT (Gouet, P. et al. (1999) *Bioinformatics* 15: 305-308.).

The present invention is based in part on the surprising discovery that H-NOX proteins have a much lower NO reactivity than hemoglobin. This intrinsic low NO reactivity (and high NO stability) makes wild-type and mutant H-NOX proteins desirable blood substitutes because of the lower probability of inactivation of H-NOX proteins by endogenous NO and the lower probability of scavenging of endogenous NO by H-NOX proteins. Importantly, the presence of a distal pocket tyrosine in some H-NOX proteins (Pellicena, P. et al. (Aug. 31, 2004). "Crystal Structure of An Oxygen-Binding Heme Domain Related to Soluble Guanylate Cyclases," *Proc Natl. Acad Sci USA* 101(35):12854-12859) is suggestive of undesirable, high NO reactivity, contraindicating use as a blood substitute. For example, by analogy, a *Mycobacterium tuberculosis* hemoglobin protein, with a structurally analogous distal pocket tyrosine, reacts extremely rapidly with NO, and is used by the *Mycobacterium* to effectively scavenge and avoid defensive NO produced by an infected host (Ouellet, H. et al. (Apr. 30, 2002). "Truncated Hemoglobin HbN Protects *Mycobacterium Bovis* From Nitric Oxide," *Proc. Natl. Acad. Sci. USA* 99(9):5902-5907). However, we surprisingly discovered that H-NOX proteins actually have a much lower NO reactivity than that of hemoglobin making their use as blood substitutes possible.

Additionally, it was surprising discovered that H-NOX proteins that bind NO but not $O_2$ can be converted to H-NOX proteins that bind both NO and $O_2$ by the introduction of a single amino acid mutation. Thus, the affinity of H-NOX proteins for $O_2$ and NO and the ability of H-NOX proteins to discriminate between $O_2$ and NO ligands can be altered by the introduction of one or more amino acid mutations, allowing H-NOX proteins to be tailored to bind $O_2$ or NO with desired affinities. Additional mutations can be introduced to further alter the affinity for $O_2$ and/or NO. The H-NOX protein family can therefore be manipulated to exhibit improved or optimal kinetic and thermodynamic properties for $O_2$ delivery. For example, mutant H-NOX proteins have been generated with altered dissociation constants and/or off rates for $O_2$ binding that improve the usefulness of H-NOX proteins for a variety of clinical and industrial applications. The ability to tune H-NOX proteins to bind and deliver $O_2$ is a therapeutic avenue that addresses and overcomes the central shortcomings of current $O_2$ carriers. Accordingly, the present invention provides proteins, compositions, kits, and methods for the delivery of oxygen.

There are numerous benefits of using H-NOX proteins for $O_2$ delivery. The principle role of blood transfusion following trauma and surgery is to deliver $O_2$. An ideal blood substitute avoids the challenges of conventional blood: viral contamination, typing requirements, limited shelf-life, and limited availability. The major limitations of hemoglobin-based blood substitutes are their high affinity for $O_2$ and their propensity to react with NO. As mentioned above, destruction of even low levels of NO can have serious effects on the tonic resting state of the vasculature and organs and leads to hypertension and gastrointestinal distress. Additionally, in the process of reacting with NO, the hemoglobin loses it ability to deliver $O_2$ on a clinically relevant timeframe. Numerous attempts have been made to minimize the toxicity of first generation hemoglobin-based oxygen carriers (HBOCs), including intra- and inter-molecular cross-linking ("Blood Substitutes," R. Winslow ed. Academic Press, 2006). While these modifications overcame some of the severe toxicity issues related to extravasation of hemoglobin, the destruction of oxygen binding due to high NO reactivity remained. These second generation HBOCs exhibit reduced oxygen affinity, with p50 values close to the p50 value of erythrocytes, yet they have failed in clinical trials. An alternate hypothesis as been proposed by Winslow and colleagues: a low p50 HBOC with an appropriate viscosity and colloidal osmotic pressure is more appropriate for cell-free oxygen delivery than a high p50 HBOC (Tsai, A. G. et al. (2003). "Targeted $O_2$ Delivery by low-$P_{50}$ hemoglobin: A New Basis for $O_2$ Therapeutics," *Am. J. Physiol. Heart Circ. Physiol.* 285:H1411-H1419; Winslow (2007). "Red Cell Substitutes," *Seminars in Hematology*

44:51-59). Whether the NO reactivity of such an HBOC becomes an issue in clinical trials remains to be seen. Engineering H-NOX proteins to bind and deliver $O_2$ with minimal NO reactivity provides a new blood gas $O_2$ carrier for use in blood substitutes where the H-NOX proteins deliver $O_2$ without scavenging NO or being inactivated as $O_2$ carriers by NO. These H-NOX proteins, compositions, kits, and methods are described further herein.

H-NOX Proteins

Overview of H-NOX Protein Family

Unless otherwise indicated, any wild-type or mutant H-NOX protein can be used in the compositions, kits, and methods as described herein. As used herein, an "H-NOX protein" means a protein that has an H-NOX domain (named for Heme-Nitric oxide and OXygen binding domain). An H-NOX protein may or may not contain one or more other domains in addition to the H-NOX domain. H-NOX proteins are members of a highly-conserved, well-characterized family of hemoproteins (Iyer, L. M. et al. (Feb. 3, 2003). "Ancient Conserved Domains Shared by Animal Soluble Guanylyl Cyclases And Bacterial Signaling Proteins," *BMC Genomics* 4(1):5; Karow, D. S. et al. (Aug. 10, 2004). "Spectroscopic Characterization of the Soluble Guanylate Cyclase-Like Heme Domains From *Vibrio Cholerae* And *Thermoanaerobacter Tengcongensis," Biochemistry* 43(31): 10203-10211; Boon, E. M. et at (2005). "Molecular Basis For NO Selectivity in Soluble Guanylate Cyclase," *Nature Chem. Biol.* 1:53-59; Boon, E. M. et al. (October 2005). "Ligand Discrimination in Soluble Guanylate Cyclase and the H-NOX Family of Heme Sensor Proteins," *Curr. Opin. Chem. Biol.* 9(5):441-446; Boon, E. M. et al. (2005). "Ligand Specificity of H-NOX Domains: From sGC to Bacterial NO Sensors," *J. Inorg. Biochem.* 99(4):892-902). H-NOX proteins are also referred to as Pfam 07700 proteins or HNOB proteins (Pfam—A database of protein domain family alignments and Hidden Markov Models, Copyright (C) 1996-2006 The Pfam Consortium; GNU LGPL Free Software Foundation, Inc., 59 Temple Place—Suite 330, Boston, Mass. 02111-1307, USA). In some embodiments, an H-NOX protein has, or is predicted to have, a secondary structure that includes six alpha-helices, followed by two beta-strands, followed by one alpha-helix, followed by two beta-strands. An H-NOX protein can be an apoprotein that is capable of binding heme or a holoprotein with heme bound. An H-NOX protein can covalently or non-covalently bind a heme group. Some H-NOX proteins bind NO but not $O_2$, and others bind both NO and $O_2$. H-NOX domains from facultative aerobes that have been isolated bind NO but not $O_2$. H-NOX proteins from obligate aerobic prokaryotes, *C. elegans*, and *D. melanogaster* bind NO and $O_2$. Mammals have two H-NOX proteins: β1 and β2. An alignment of mouse, rat, cow, and human H-NOX sequences shows that these species share >99% identity. In some embodiments, the H-NOX domain of an H-NOX protein or the entire H-NOX protein is at least about any of 10, 15, 20, 25, 30, 40, 50, 60, 70, 80, 90, 95, 97, 98, 99, or 99.5% identical to that of the corresponding region of a naturally-occurring *Thermoanaerobacter tengcongensis* H-NOX protein or a naturally-occurring sGC protein (e.g., a naturally-occurring sGC β1 protein). As discussed further herein, an H-NOX protein may optionally contain one or more mutations relative to the corresponding naturally-occurring H-NOX protein. In some embodiments, the H-NOX protein includes one or more domains in addition to the H-NOX domain. In particular embodiments, the H-NOX protein includes one or more domains or the entire sequence from another protein. For example, the H-NOX protein may be a fusion protein that includes an H-NOX domain and part or all of another protein, such as albumin (e.g., human serum albumin). In some embodiments, only the H-NOX domain is present.

A crystal structure of a prokaryotic $O_2$-binding H-NOX from *Thermoanaerobacter tengcongensis* (Nioche, P. et al. (Nov. 26, 2004). "Femtomolar Sensitivity of a NO Sensor From *Clostridium Botulinum*," Science 306(5701):1550-1551; Pellicena, P. et al. (Aug. 31, 2004). "Crystal Structure of An Oxygen-Binding Heme Domain Related to Soluble Guanylate Cyclases," *Proc Natl. Acad Sci USA* 101(35): 12854-12859) shows that a tyrosine side chain hydroxyl group makes a critical H-bond to the $Fe^{II}$—$O_2$ moiety. This distal pocket hydrogen-bonding network, involving principally Y140, stabilizes an $Fe^{II}$—$O_2$ complex (FIG. 6B). This tyrosine is not present in H-NOX proteins that discriminate against $O_2$ and only bind NO. For example, this hydrogen-bonding network is predicted to be absent in the H-NOX proteins from sGCs and aerobic prokaryotes, suggesting this as a key molecular factor in the remarkable ligand selectivity against $O_2$ displayed by these heme proteins. FIGS. 7A-7G clearly demonstrate that the addition of a tyrosine in the distal pocket of a wild-type H-NOX protein that binds NO but not $O_2$ can enable the mutant H-NOX protein to bind $O_2$. Thus, a tyrosine in the distal heme pocket of the H-NOX heme fold acts like a switch to turn on or off $O_2$ binding.

Figure 6A:
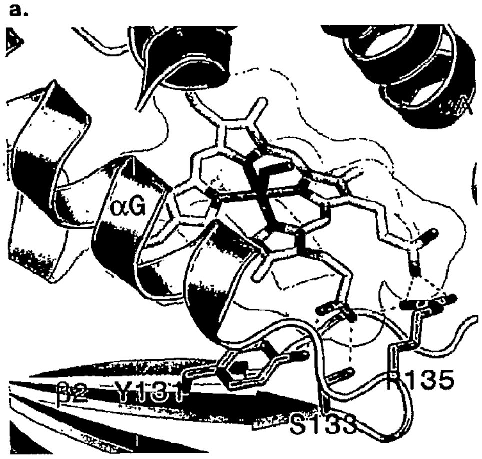
FIGS. 6A and 6B are pictures of the three dimensional structure of the heme environment of the *T. tengcongensis* H-NOX domain.
Figure 6B:
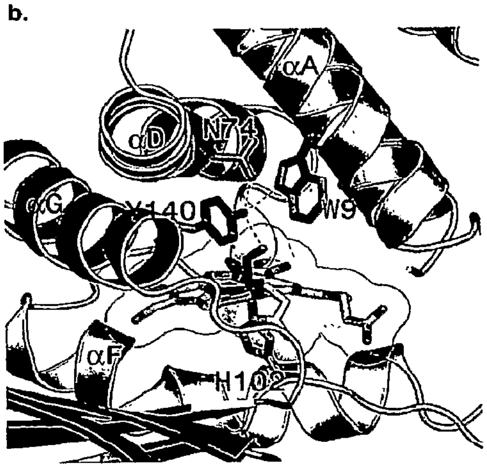
Figures 7A, 7B, 7C, 7D, 7E, 7F:
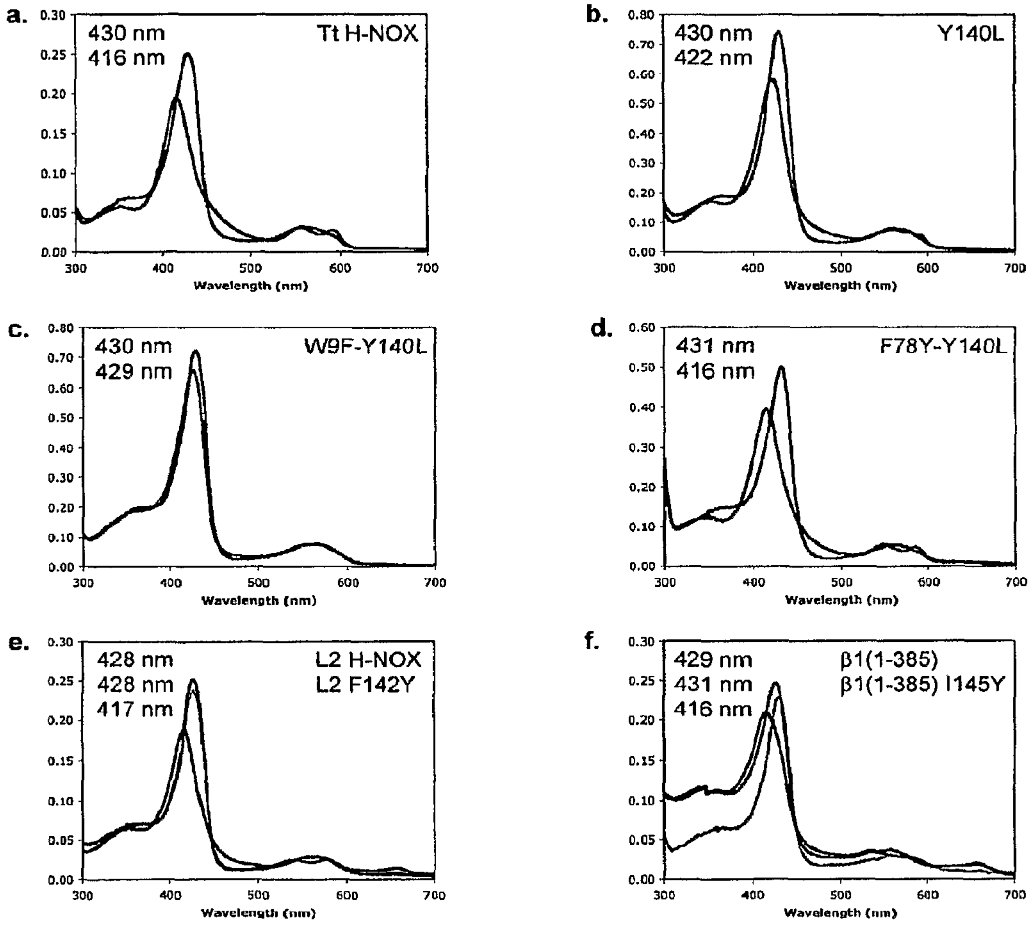
FIGS. 7A-7F are graphs of the UV-visible spectroscopy of H-NOX proteins after anaerobic reduction ($Fe^{II}$ unligated complexes; top line in each graph) before and after being exposed to air ($Fe^{II}$—$O_2$ complexes; bottom line in each graph) for Tt H-NOX (FIG. 7A), Tt Y140L (FIG. 7B), Tt W9F-Y140L (FIG. 7C), Tt F78Y-Y140L (FIG. 7D), L2 H-NOX and L2 F142Y (FIG. 7E), and β1(1-385) and β1(1-385) I145Y (FIG. 7F). In addition to the $Fe^{II}$ and $Fe^{II}$—$O_2$ complexes of L2 F142Y and β1(1-385) I145Y, the spectrum of wild-type L2 H-NOX and β1-(1-385) H-NOX after reduction and exposure to air are shown in the middle line in FIGS. 7E and 7F, respectively, to demonstrate that these proteins do not bind $O_2$ before the addition of a distal pocket tyrosine. The two or three numbers written in the upper left corner of each panel represent the wavelength for the peak of the lines in the graph. The numbers are written vertically in the order in which the corresponding lines appear vertically in the graph. For example, the 430 nm value in FIG. 7A denotes the peak of the wavelength for the top line in the graph (which represents a $Fe^{II}$ unligated complex), and the 416 nm value in FIG. 7A denotes the peak of the wavelength for the bottom line in the graph (which represents a $Fe^{II}$—$O_2$ complex). A shift in the wavelength in the presence of air indicates that the protein binds $O_2$. The formation of a double peak between 500 and 600 nm in the presence of air is also indicative of $O_2$ binding.

As illustrated in FIGS. 6A and 6B, the structure of the porphyrin is highly distorted. As illustrated in FIG. 6A, the conserved Y-S-R motif makes hydrogen-bonding interactions with the propionic acid side chains of the heme group. FIG. 6B, the conserved H102 is the proximal ligand to the heme (FIG. 6B).

As used herein, a "protein" includes proteins and fragments of proteins whether isolated from natural sources, produced by recombinant techniques, or chemically synthesized. A protein may have one or more modifications, such as a post-translational modification (e.g., glycosylation, etc) or any other modification (e.g., PEGylation, etc). The protein may contain one or more non-naturally-occurring amino acids (e.g., such as an amino acid with a side chain modification). In various embodiments, the H-NOX protein has at least about 50, 100, 150, 181, 200, 250, 300, 350, 400, or more amino acids. In some embodiments, the H-NOX proteins may include from about 50 to about 600 amino acids, such as about 100 to about 500 amino acids, about 150 to about 400 amino acids, about 150 to about 300 amino acids, or about 175 to about 200 amino acids.

Sources of H-NOX Proteins

H-NOX proteins from any genus or species can be used in the compositions, kits, and methods described herein. In various embodiments, the H-NOX protein is a protein from a mammal (e.g., a primate (e.g., human, monkey, gorilla, ape, lemur, etc), a bovine, an equine, a porcine, a canine, or a feline), an insect, a yeast, or a bacteria or is derived from such a protein. Exemplary mammalian H-NOX proteins include wild-type human and rat soluble guanylate cyclase (such as the β1 subunit). Examples of H-NOX proteins include wild-type mammalian H-NOX proteins, e.g. *H. sapiens, M. musculus, C. familiaris, B. taurus* and *R. norvegicus*; and wild-type non-mammalian vertebrate H-NOX proteins, e.g., *X. laevis, O. latipes, O. curivatus*, and *F. rubripes*. Examples of non-mammalian wild-type NO-binding H-NOX proteins include wild-type H-NOX proteins of *D. melanogaster, A. gambiae*, and *M. sexta*; examples of non-mammalian wild-type $O_2$-binding H-NOX proteins include wild-type H-NOX proteins of *C. elegans* gcy-31, gcy-32, gcy-33, gcy-34, gcy-35, gcy-36, and gcy-37; *D. melanogaster* CG14885, CG14886, and CG4154; and *M.*

*sexta* beta-3; examples of prokaryotic wild-type H-NOX proteins include *T. tengcongensis, V. cholera, V. Jischerii, N. punctiforme, D. desulfuricans, L. pneumophila* 1, *L. pneumophila* 2, and *C. acetobutylicum*.

NCBI Accession numbers for exemplary H-NOX proteins include the following: *Homo sapiens* β1 [gi:2746083], *Rattus norvegicus* [gi:27127318], *Drosophila melangaster* β1 [gi:861203], *Drosophila melangaster* CG14885-PA [gi:23171476], *Caenorhabditis elegans* GCY-35 [gi:52782806], *Nostoc punctiforme* [gi:23129606], *Caulobacter crescentus* [gi:16127222], *Shewanella oneidensis* [gi:24373702], *Legionella pneumophila* (ORF 2) [CUCGC_272624], *Clostridium acetobutylicum* [gi:15896488], and *Thermoanaerobacter tengcongensis* [gi:20807169].

Exemplary H-NOX protein also include the following H-NOX proteins that are listed by their gene name, followed by their species abbreviation and Genbank Identifiers (such as the following protein sequences available as of May 21, 2006; May 22, 2006; May 21, 2007; or May 22, 2007, which are each hereby incorporated by reference in their entireties): Npun5905 Npu_23129606, alr2278_Ana_17229770, SO2144_Sone_24373702, Mdeg1343_Mde_23027521, VCA0720_Vch_15601476, CC2992_Ccr_16127222, Rsph2043_Rhsp_22958463 (gi:46192757), Mmc10739_Mcsp_22999020, Tar4_Tte_20807169, Ddes2822_Dde_23475919, CAC3243_Cac_15896488, gcy-31_Ce_17568389, CG14885_Dm_24647455, GUCY1B3_Hs_4504215, HpGCS-beta1_Hpul_14245738, Gycbeta100B_Dm_24651577, CG4154_Dm_24646993 (gi: NP_650424.2, gi:62484298), gcy-32_Ce_13539160, gcy-36_Ce_17568391 (gi:32566352, gi:86564713), gcy-35_Ce-17507861 (gi:71990146), gcy-37_Ce_17540904 (gi: 71985505), GCY1a3_Hs_20535603, GCY1a2-Hs_899477, or GYCa-99B_Dm_729270 (gi:68067738) (Lakshminarayan et al. (2003). "Ancient conserved domains shared by animal soluble guanylyl cyclases and bacterial signaling proteins," *BMG Genomics* 4:5-13). The species abbreviations used in these names include Ana—*Anabaena* Sp; Ccr—*Caulobacter crescentus*; Cac—*Clostridium acetobutylicum*; Dde—*Desulfovibrio desulfuricans*; Mcsp—*Magnetococcus* sp.; Mde—*Microbulbifer degradans*; Npu—*Nostoc punctiforme*; Rhsp—*Rhodobacter sphaeroides*; Sone—*Shewanella oneidensis*; Tte—*Thermoanaerobacter tengcongensis*; Vch—*Vibrio cholerae*; Ce—*Caenorhabditis elegans*; Dm—*Drosophila melanogaster*; Hpul—*Hemicentrotus pulcherrimus*; Hs—*Homo sapiens*.

Other exemplary H-NOX proteins include the following H-NOX proteins that are listed by their organism name and Pfam database accession number (such as the following protein sequences available as of May 21, 2006; May 22, 2006; May 17, 2007; May 21, 2007; or May 22, 2007, which are each hereby incorporated by reference in their entireties): *Caenorhabditis briggsae* Q622M5_CAEBR, *Caenorhabditis briggsae* Q61P44_CAEBR, *Caenorhabditis briggsae* Q61R54_CAEBR, *Caenorhabditis briggsae* Q61V90_CAEBR, *Caenorhabditis briggsae* Q61A94_CAEBR, *Caenorhabditis briggsae* Q60TP4_CAEBR, *Caenorhabditis briggsae* Q60M10_CAEBR, *Caenorhabditis elegans* GCY37_CAEEL, *Caenorhabditis elegans* GCY31_CAEEL, *Caenorhabditis elegans* GCY36_CAEEL, *Caenorhabditis elegans* GCY32_CAEEL, *Caenorhabditis elegans* GCY35_CAEEL, *Caenorhabditis elegans* GCY34CAEEL, *Caenorhabditis elegans* GCY33_CAEEL, *Oryzias curvinotus* Q7T040_ORYCU, *Oryzias curvinotus* Q75WF0_ORYCU, *Oryzias latipes* P79998_ORYLA, *Oryzias latipes* Q7ZSZ5_ORYLA, *Tetraodon nigroviridis* Q4SW38_TETNG, *Tetraodon nigroviridis* Q4RZ94_TETNG, *Tetraodon nigroviridis* Q4S6K5_TETNG, *Fugu rubripes* Q9OVY5_FUGRU, *Xenopus laevis* Q6INK9_XENLA, *Homo sapiens* Q5T8J7_HUMAN, *Homo sapiens* GCYA2 HUMAN, *Homo sapiens* GCYB2_HUMAN, *Homo sapiens* GCYB1_HUMAN, *Gorilla gorilla* Q9N193_9 PRIM, *Pongo pygmaeus* Q5RAN8_PONPY, *Pan troglodytes* Q9N192PANTR, *Macaca mulatta* Q9N194_MACMU, *Hylobates lar* Q9N191_HYLLA, *Mus musculus* Q8BXH3_MOUSE, *Mus musculus* GCYB1_MOUSE, *Mus musculus* Q3UTI4_MOUSE, *Mus musculus* Q3UH83_MOUSE, *Mus musculus* Q6XE41_MOUSE, *Mus musculus* Q80YP4_MOUSE, *Rattus norvegicus* Q8OWX7_RAT, *Rattus norvegicus* Q8OWX8_RAT, *Rattus norvegicus* Q920Q1_RAT, *Rattus norvegicus* Q54A43_RAT, *Rattus norvegicus* Q80WY0_RAT, *Rattus norvegicus* Q80WY4_RAT, *Rattus norvegicus* Q8CH85_RAT, *Rattus norvegicus* Q80WY5_RAT, *Rattus norvegicus* GCYB1_RAT, *Rattus norvegicus* Q8CH90 RAT, *Rattus norvegicus* Q91XJ7_RAT, *Rattus norvegicus* Q8OWX9_RAT, *Rattus norvegicus* GCYB2_RAT, *Rattus norvegicus* GCYA2_RAT, *Canis familiaris* Q4ZHR9 CANFA, *Bos taurus* GCYB1_BOVIN, *Sus scrofa* Q4ZHR7_PIG, *Gryllus bimaculatus* Q59HN5_GRYBI, *Manduca sexta* O77106 MANSE, *Manduca sexta* O76340_MANSE, *Apis mellifera* Q5UAFO_APIME, *Apis mellifera* Q5FAN0_APIME, *Apis mellifera* Q6L5L6_APIME, *Anopheles gambiae* str PEST Q7PYK9_ANOGA, *Anopheles gambiae* str PEST Q7Q9W6_ANOGA, *Anopheles gambiae* str PEST Q7QF31_ANOGA, *Anopheles gambiae* str PEST Q7PS01_ANOGA, *Anopheles gambiae* str PEST Q7PFY2_ANOGA, *Anopheles gambiae* Q7KQ93_ANOGA, *Drosophila melanogaster* Q24086_DROME, *Drosophila melanogaster* GCYH_DROME, *Drosophila melanogaster* GCY8E_DROME, *Drosophila melanogaster* GCYDA_DROME, *Drosophila melanogaster* GCYDB_DROME, *Drosophila melanogaster* Q9VA09_DROME, *Drosophila pseudoobscura* Q29CE1_DROPS, *Drosophila pseudoobscura* Q296C7_DROPS, *Drosophila pseudoobscura* Q296C8_DROPS, *Drosophila pseudoobscura* Q29BU7_DROPS, *Aplysia californica* Q7YWK7_APLCA, *Hemicentrotus pulcherrimus* Q95NK5_HEMPU, *Chlamydomonas reinhardtii*, Q5YLC2_CHLRE, *Anabaena* sp Q8YUQ7_ANASP, *Flavobacteria bacterium* BBFL7 Q26GR8_9 BACT, *Psychroflexus torquis* ATCC 700755 Q1VQE5_9 FLAO, marine gamma proteobacterium HTCC2207 Q1YPJ5_9 GAMM, marine gamma proteobacterium HTCC2207 QlYTK4_9 GAMM, *Caulobacter crescentus* Q9A451_CAUCR, *Acidiphilium cryptum* JF-5 Q2DG60_ACICY, *Rhodobacter sphaeroides* Q3J0U9_RHOS4, *Silicibacter pomeroyi* Q5LPV1_SILPO, *Paracoccus denitrificans* PD1222, Q3PC67_PARDE, *Silicibacter* sp TM1040 Q3QNY2_9 RHOB, *Jannaschia* sp Q28ML8 JANSC, *Magnetococcus* sp MC-1 Q3XT27_9 PROT, *Legionella pneumophila* Q5WXPO_LEGPL, *Legionella pneumophila* Q5WTZ5_LEGPL, *Legionella pneumophila* Q5X268_LEGPA, *Legionella pneumophila* Q5X2R2_LEGPA, *Legionella pneumophila* subsp *pneumophila* Q5ZWM9_LEGPH, *Legionella pneumophila* subsp *pneumophila* Q5ZSQ8_LEGPH, *Colwellia psychrerythraea* Q47Y43_COLP3, *Pseudoalteromonas atlantica* T6c Q3CSZ5_ALTAT, *Shewanella oneidensis* Q8EF49_SHEON, *Saccharophagus degradans*

Q21E20_SACD2, *Saccharophagus degradans* Q21ER7_SACD2, *Vibrio angustum* S14 Q1ZWE5_9 VIBR, *Vibrio vulnificus* Q8DAE2_VIBVU, *Vibrio alginolyticus* 12G01 Q1VCP6_VIBAL, *Vibrio* sp DAT722 Q2FA22_9VIBR, *Vibrio parahaemolyticus* Q87NJ1_VIBPA, *Vibrio fischeri* Q5E1F5_VIBF1, *Vibrio vulnificus* Q7MJS8_VIBVY, *Photobacterium* sp SKA34 Q2C6Z5_9 GAMM, *Hahella chejuensis* Q2SFY7_HAHCH, *Oceanospirillum* sp MED92 Q2BKV0_9 GAMM, *Oceanobacter* sp RED65 Q1N035_9 GAMM, *Desulfovibrio desulfuricans* Q310U7_DESDG, *Halothermothrix orenii* H 168 Q2AIW5_9 FIRM, *Thermoanaerobacter tengcongensis* Q8RBX6_THETN, *Caldicellulosiruptor saccharolyticus* DSM 8903 Q2ZH17_CALSA, *Clostridium acetobutylicum* Q97E73_CLOAB, *Alkaliphilus metalliredigenes* QYMF Q3C763_9 CLOT, *Clostridium tetani* Q899J9_CLOTE, and *Clostridium beijerincki* NCIMB 8052 Q2WVN0_CLOBE. These sequences are predicted to encode H-NOX proteins based on the identification of these proteins as belonging to the H-NOX protein family using the Pfam database as described herein.

Additional H-NOX proteins and nucleic acids, which may be suitable for use in the pharmaceutical compositions and methods described herein, can be identified using standard methods. For example, standard sequence alignment and/or structure prediction programs can be used to identify additional H-NOX proteins and nucleic acids based on the similarity of their primary and/or predicted protein secondary structure with that of known H-NOX proteins and nucleic acids. For example, the Pfam database uses defined alignment algorithms and Hidden Markov Models (such as Pfam 21.0) to categorize proteins into families, such as the H-NOX protein family (Pfam—A database of protein domain family alignments and Hidden Markov Models, Copyright (C) 1996-2006 The Pfam Consortium; GNU LGPL Free Software Foundation, Inc., 59 Temple Place—Suite 330, Boston, Mass. 02111-1307, USA). Standard databases such as the swissprot-trembl database (world-wide web at "expasy.org", Swiss Institute of Bioinformatics Swiss-Prot group CMU—1 rue Michel Servet CH-1211 Geneva 4, Switzerland) can also be used to identify members of the H-NOX protein family. The secondary and/or tertiary structure of an H-NOX protein can be predicted using the default settings of standard structure prediction programs, such as PredictProtein (630 West, 168 Street, BB217, New York, N.Y. 10032, USA). Alternatively, the actual secondary and/or tertiary structure of an H-NOX protein can be determined using standard methods.

In some embodiments, the H-NOX protein has the same amino acid in the corresponding position as any of following distal pocket residues in *T. tengcongensis* H-NOX: Thr4, Ile5, Thr8, Trp9, Trp67, Asn74, Ile75, Phe78, Phe82, Tyr140, Leu144, or any combination of two or more of the foregoing. In some embodiments, the H-NOX protein has a proline or an arginine in a position corresponding to that of Pro115 or Arg135 of *T. tengcongensis* H-NOX, respectively, based on sequence alignment of their amino acid sequences. In some embodiments, the H-NOX protein has a histidine that corresponds to His105 of *R. norvegicus* β1 H-NOX. In some embodiments, the H-NOX protein has or is predicted to have a secondary structure that includes six alpha-helices, followed by two beta-strands, followed by one alpha-helix, followed by two beta-strands. This secondary structure has been reported for H-NOX proteins.

If desired, a newly identified H-NOX protein can be tested to determine whether it binds heme using standard methods. The ability of an H-NOX protein to function as an $O_2$ carrier can be tested by determining whether the H-NOX protein binds $O_2$ using standard methods, such as those described herein. If desired, one or more of the mutations described herein can be introduced into the H-NOX protein to optimize its characteristics as an $O_2$ carrier. For example, one or more mutations can be introduced to alter its $O_2$ dissociation constant, $k_{off}$ for oxygen, rate of heme autoxidation, NO reactivity, NO stability or any combination of two or more of the foregoing. Standard techniques such as those described herein can be used to measure these parameters.

As discussed herein, mutant H-NOX proteins (e.g., class I and class II mutants discussed below) may be derived by mutagenesis from these or other natural wild-type source sequences (e.g., the sequences listed in FIG. 2-4D or 8A-8DD or any other sequence described herein). As used herein, "derived from" refers to the source of the protein into which one or more mutations is introduced. For example, a protein that is "derived from a mammalian protein" refers to protein of interest that results from introducing one or more mutations into the sequence of a wild-type (i.e., a sequence occurring in nature) mammalian protein.

Mutant H-NOX Proteins

As discussed further herein, an H-NOX protein may contain one or more mutations, such as a mutation that alters the $O_2$ dissociation constant, the $k_{off}$ for oxygen, the rate of heme autoxidation, the NO reactivity, the NO stability, or any combination of two or more of the foregoing compared to that of the corresponding wild-type protein. Panels of engineered H-NOX proteins may be generated by random mutagenesis followed by empirical screening for requisite or desired dissociation constants, dissociation rates, NO-reactivity, stability, physio-compatibility, or any combination of two or more of the foregoing in view of the teaching provided herein using techniques as described herein and, additionally, as known by the skilled artisan. Alternatively, mutagenesis can be selectively targeted to particular regions or residues such as distal pocket residues apparent from the experimentally determined or predicted three-dimensional structure of an H-NOX protein (FIG. 1A herein; and see, for example, Boon, E. M. et al. (2005). "Molecular Basis For NO Selectivity in Soluble Guanylate Cyclase," *Nature Chemical Biology* 1:53-59, which is hereby incorporated by reference in its entirety, particularly with respect to the sequences of wild-type and mutant H-NOX proteins) or evolutionarily conserved residues identified from sequence alignments (FIGS. 2-4 herein; and see, for example, Boon E. M. et al. (2005). "Molecular Basis For NO Selectivity in Soluble Guanylate Cyclase," *Nature Chemical Biology* 1:53-59, which is hereby incorporated by reference in its entirety, particularly with respect to the sequences of wild-type and mutant H-NOX proteins).

As used herein, a "mutant protein" means a protein with one or more mutations compared to a protein occurring in nature. In one embodiment, the mutant protein has a sequence that differs from that of all proteins occurring in nature. In various embodiments, the amino acid sequence of the mutant protein is at least about any of 10, 15, 20, 25, 30, 40, 50, 60, 70, 80, 90, 95, 97, 98, 99, or 99.5% identical to that of the corresponding region of a protein occurring in nature. In some embodiments, the mutant protein is a protein fragment that contains at least about any of 25, 50, 75, 100, 150, 200, 300, or 400 contiguous amino acids from a full-length protein. Sequence identity can be measured, for example, using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various. amino acids replacements, deletions, and other modifications.

As used herein, a "mutation" means an alteration in a reference nucleic acid or amino acid sequence occurring in nature. Exemplary nucleic acid mutations include an insertion, deletion, frameshift mutation, silent mutation, nonsense mutation, or missense mutation. In some embodiments, the nucleic acid mutation is not a silent mutation. Exemplary protein mutations include the insertion of one or more amino acids (e.g., the insertion of 2, 3, 4, 5, 6, 7, 8, 9, or 10 amino acids), the deletion of one or more amino acids (e.g., a deletion of N-terminal, C-terminal, and/or internal residues, such as the deletion of at least about any of 5, 10, 15, 25, 50, 75, 100, 150, 200, 300, or more amino acids or a deletion of about any of 5, 10, 15, 25, 50, 75, 100, 150, 200, 300, or 400 amino acids), the replacement of one or more amino acids (e.g., the replacement of 2, 3, 4, 5, 6, 7, 8, 9, or 10 amino acids), or combinations of two or more of the foregoing. An exemplary functional truncation of an H-NOX protein includes residues 1-385 of the 131 sequence. In some embodiments, a mutant protein has at least one amino acid alteration compared to a protein occurring in nature. In some embodiments, a mutant nucleic acid sequence encodes a protein that has at least one amino acid alteration compared to a protein occurring in nature. In some embodiments, the nucleic acid is not a degenerate version of a nucleic acid occurring in nature that encodes a protein with an amino acid sequence identical to a protein occurring in nature. The nomenclature used in referring to a particular amino acid mutation first identifies the wild-type amino acid, followed by the residue number and finally the substitute amino acid. For example, Y140L means that tyrosine has been replaced by a leucine at residue number 140.

An "evolutionary conserved mutation" is the replacement of an amino acid in one protein by an amino acid in the corresponding position of another protein in the same protein family. Exemplary evolutionary conserved mutations (also denoted class I mutations) are listed in Table 1A. In Table 1A, mutations are numbered/annotated according to the sequence of human β1 H-NOX, but are analogous for all H-NOX sequences. Thus, the corresponding position in any other H-NOX protein can be mutated to the indicated residue. For example, Phe4 of human β1 H-NOX can be mutated to a tyrosine since other H-NOX proteins have, a tyrosine in this position. The corresponding phenylalanine residue can be mutated to a tyrosine in any other H-NOX protein. In particular embodiments, the one or more mutations are confined to evolutionarily conserved residues. in some embodiments, the one or more mutations may include at least one evolutionarily conserved mutation and at least one non-evolutionarily conserved mutation. If desired, these mutant H-NOX proteins are subjected to empirical screening for NO/$O_2$ dissociation constants, NO-reactivity, stability, and physio-compatibility in view of the teaching provided herein.

TABLE 1A

| Exemplary Class I H-NOX mutations targeting evolutionary conserved residues | | |
|---|---|---|
| F4Y | Q30G | I145Y |
| F4L | E33P | I145H |
| H7G | N61G | K151E |
| A8E | C78H | I157F |
| L9W | A109F | E183F |

In some embodiments, the mutation is a distal pocket mutation, such as mutation of a residue in alpha-helix A, D, E, or G (Pellicena, P. et al. (Aug. 31, 2004). "Crystal Structure of An Oxygen-Binding Heme Domain Related to Soluble Guanylate Cyclases," *Proc Natl. Acad Sci USA* 101(35):12854-12859). Exemplary distal pocket mutations (also denoted class II mutations) are listed in Table 1B. In Table 1B, mutations are numbered/annotated according to the sequence of human β1 H-NOX, but are analogous for all H-NOX sequences. Because several substitutions provide viable mutations at each recited residue, the residue at each indicated position can be changed to any other naturally or non-naturally-occurring amino acid (denoted "X"). Such mutations can produce H-NOX proteins with a variety of desired affinity, stability, and reactivity characteristics.

TABLE 1B

| Exemplary Class II H-NOX mutations targeting distal pocket residues | | |
|---|---|---|
| V8X | M73X | I145X |
| L9X | F77X | I149X |
| F70X | C78X | |

In particular embodiments, the mutation is a heme distal pocket mutation. As described herein, a crucial molecular determinant that prevents $O_2$ binding in NO-binding members of the H-NOX family is the lack of a H-bond donor in the distal pocket of the heme. Accordingly, in some embodiments, the mutation alters H-bonding between the H-NOX domain and the ligand within the distal pocket. In some embodiments, the mutation disrupts an H-bond donor of the distal pocket and/or imparts reduced $O_2$ ligand-binding relative to the corresponding wild-type H-NOX domain. Exemplary distal pocket residues include hr4, Ile5, Thr8, Trp9, Trp67, Asn74, Ile75, Phe78, Phe82, Tyr140, and Leu144 of *T. tengcongensis* H-NOX and the corresponding residues in any other H-NOX protein.

Residues that are not in the distal pocket can also affect the three-dimensional structure of the heme group; this structure in turn affects the binding of $O_2$ and NO to iron in the heme group. Accordingly, in some embodiments, the H-NOX protein has one or more mutations outside of the distal pocket. Examples of residues that can be mutated but are not in the distal pocket include Pro115 and Arg135 of *T. tengcongensis* H-NOX. In some embodiments, the mutation is in the proximal pocket which includes His105 as a residue that ligates to the heme iron.

In some embodiments when two or more mutations are present; at least one mutation is in the distal pocket, and at least one mutation is outside of the distal pocket (e.g., a mutation in the proximal pocket). In some embodiments, all the mutations are in the distal pocket.

In some embodiments, the amino acid sequence of the H-NOX protein is not identical to the sequence of a protein that is produced by an organism in nature. In some embodiments, the amino acid sequence of the H-NOX protein is not identical to a sequence found in any database on May 21, 2006 or May 22, 2006 (such as all known sequences predicted or known to be an H-NOX nucleic acid or amino acid sequence). In some embodiments, the amino acid sequence of the H-NOX protein is not identical to a sequence found in any database on May 21, 2007 or May 22, 2007 (such as all known sequences predicted or known to be an H-NOX nucleic acid or amino acid sequence).

To reduce the immunogenicity of H-NOX proteins derived from sources other than humans, amino acids in an H-NOX protein can be mutated to the corresponding amino acids in a human H-NOX. For example, one or more amino acids on the surface of the tertiary structure of a non-human H-NOX protein can be mutated to the corresponding amino acid in a human H-NOX proteins. In some variations, mutation of one or more surface amino acids may be combined with mutation of two or more distal pocket residues, mutation of one or more residues outside of the distal pocket (e.g., a mutation in the proximal pocket), or combinations of two or more of the foregoing.

Exemplary mutations are shown in Table 2. In addition, any of the residues listed in Table 2 can be mutated to any other amino acid. The invention also relates to any combination of mutation described herein, such as double, triple, or higher multiple mutations. For example, combinations of any of the mutations described herein can be made in the same H-NOX protein. Note that mutations in equivalent positions in other mammalian or non-mammalian H-NOX proteins are also encompassed by this invention. If desired, residues other than the ones mentioned in Table 2 can also be mutated. Exemplary mutant H-NOX proteins comprise one or more mutations that impart altered $O_2$ or NO ligand-binding relative to the corresponding wild-type H-NOX domain and are operative as a physiologically compatible mammalian $O_2$ blood gas carrier.

In Table 2 and all subsequent tables, the residue number for a mutation indicates the position in the sequence of the particular H-NOX protein being described. For example, *T. tengcongensis* 15A refers to the replacement of isoleucine by alanine at the fifth position in *T. tengcongensis* H-NOX. The same isoleucine to alanine mutation can be made in the corresponding residue in any other H-NOX protein (this residue may or may not be the fifth residue in the sequence of other H-NOX proteins). Since the amino acid sequences of mammalian β1 H-NOX domains differ by at most two amino acids, mutations that produce desirable mutant H-NOX proteins when introduced into wild-type rat β1 H-NOX proteins are also expected to produce desirable mutant H-NOX proteins when introduced into wild-type β1 H-NOX proteins from other mammals, such as humans.

TABLE 2

Exemplary H—NOX mutants from *T. tengcongensis* (*Tt*), *L. pneumophila* (*Lp*), *D. desulfuricans* (*Dd*), *V. cholera* (*Vc*), *N. punctiforme* (*Np*), *C. botulinium* (*Cb*), *C. acetobutylicum*, (*Ca*), rat, human, *C. elegans* (*Ce*).

| *Tt* | *Lp* | *Dd* | Other Bacteria | Rat | Human | Worm |
|---|---|---|---|---|---|---|
| *Tt* H—NOX | L2 H—NOX | *Dd* H—NOX (728-899) | *Vc* H—NOX | β1(1-385) | β1(1-385) | *Ce* GCY-35(1-252) |
| *Tt* H—NOX His6 | L2 F142Y | *Dd* Y139L | *Np* H—NOX | β1(1-385) I145Y | β1(1-385) I145Y | |
| *Tt* I5A | L2 F9W-F142Y | | *Cb* H—NOX (1-175) | β1(1-385) I145H | β1(1-385) I145H | |
| *Tt* I5L | L1 H—NOX | | *Cb* H—NOX (1-186) | β1(1-385) C78Y | β1(1-385) C78Y | |
| *Tt* I5L-P115A | L1 F142Y | | *Ca* H—NOX (1-197) | β1(1-194) | β1(1-194) | |
| *Tt* W9F | | | *Ca* H—NOX (1-183) | β1 H105F | β1 H105F | |
| *Tt* W9F-Y140L | | | | β1 H105G | β1 H105G | |
| *Tt* W9F-Y140H | | | | β1(1-194) I145Y | β1(1-194) I145Y | |
| *Tt* W9F-N74A | | | | β1(1-194) L9W-I145Y | β1(1-194) L9W-I145Y | |
| *Tt* W9Y | | | | β2(1-217) | β2(1-217) | |
| *Tt* W9N | | | | β2(1-217) I142Y | β2(1-217) I142Y | |
| *Tt* W9H | | | | | | |
| *Tt* N74E | | | | | | |
| *Tt* N74A | | | | | | |
| *Tt* N74H | | | | | | |
| *Tt* N74A-Y140H | | | | | | |
| *Tt* I75F His6 | | | | | | |
| *Tt* F78Y-Y140L | | | | | | |
| *Tt* F78Y-Y140F | | | | | | |
| *Tt* P115A | | | | | | |
| *Tt* R135Q | | | | | | |

TABLE 2-continued

Exemplary H—NOX mutants from *T. tengcongensis* (*Tt*), *L. pneumophila* (*Lp*), *D. desulfuricans* (*Dd*), *V. cholera* (*Vc*), *N. punctiforme* (*Np*), *C. botulinium* (*Cb*), *C. acetobutylicum*, (*Ca*), rat, human, *C. elegans* (*Ce*).

| *Tt* | *Lp* | *Dd* | Other Bacteria | Rat | Human | Worm |
|---|---|---|---|---|---|---|
| His6 | | | | | | |
| *Tt* Y140F | | | | | | |
| *Tt* Y140L | | | | | | |
| *Tt* Y140H | | | | | | |
| *Tt* Y140A | | | | | | |
| *Tt* L144F | | | | | | |
| His6 | | | | | | |

Modifications to H-NOX Proteins

Any of the wild-type or mutant H-NOX proteins can be modified and/or formulated using standard methods to enhance therapeutic or industrial applications. For example, and particularly as applied to heterologous engineered H-NOX proteins, a variety of methods are known in the art for insulating such agents from immune surveillance, including crosslinking, PEGylation, carbohydrate decoration, etc. (e.g., Rohlfs, R. J. et al. (May 15, 1998). "Arterial Blood Pressure Responses to Cell-Free Hemoglobin Solutions And The Reaction With Nitric Oxide," *J. Biol. Chem.* 273(20):12128-12134; Migita, R. et al. (June 1997). "Blood Volume And Cardiac Index in Rats After Exchange Transfusion With Hemoglobin-Based Oxygen Carriers," *J. Appl. Physiol.* 82(6):1995-2002; Vandegriff, K. D. et al. (Aug. 15, 2004). "Kinetics of NO and $O_2$ Binding to a Maleimide Poly(ethylene glycol)-Conjugated Human Haemoglobin," *Biochem* 382(Pt 1):183-189, which are each hereby incorporated by reference in their entireties, particularly with respect to the modification of proteins) as well as other techniques known to the skilled artisan. Fusing an H-NOX protein with a human protein such as human serum albumin can increase the serum half-life, viscosity, and colloidal oncotic pressure. In some embodiments, an H-NOX protein is modified during or after its synthesis to decrease its immunogenicity and/or to increase its plasma retention time. H-NOX proteins can also be encapsulated (such as encapsulation within liposomes or nanoparticles).

Characteristics of Wild-type and Mutant H-NOX Proteins

As described herein, a large number of diverse H-NOX mutant proteins providing ranges of NO and $O_2$ dissociation constants, $O_2$ $k_{off}$, NO reactivity, and stability have been generated. To provide operative blood gas carriers, the H-NOX proteins may be used to functionally replace or supplement endogenous $O_2$ carriers, such as hemoglobin. Accordingly, in some embodiments, an H-NOX protein has a similar or improved $O_2$ association rate, $O_2$ dissociation rate, dissociation constant for $O_2$ binding, NO stability, NO reactivity, autoxidation rate, plasma retention time, or any combination of two or more of the foregoing compared to an endogenous $O_2$ carrier, such as hemoglobin.

As used herein, "hemoglobin" means a protein or a mutant thereof from the well-characterized family of hemoglobins, which are iron-containing $O_2$-transport metalloproteins in red blood cells. Purified, stroma-free, human hemoglobin has a kinetic $K_D$ for $O_2$ of about 200-500 nM. This value is subunit dependent.

As used herein, a "$k_{off}$" means a dissociation rate, such as the rate of release of $O_2$ or NO from a protein. A lower numerical lower $k_{off}$ indicates a slower rate of dissociation. In various embodiments, the $k_{off}$ for $O_2$ for an H-NOX protein is between about 0.01 to about 200 $s^{-1}$ at 20° C., such as about 0.1 to about 200 $s^{-1}$, about 0.1 to 100 $s^{-1}$, about 1.0 to about 16.0 $s^{-1}$, about 1.35 to about 23.4 $s^{-1}$, about 1.34 to about 18 $s^{-1}$, about 1.35 to about 14.5 $s^{-1}$, about 0.21 to about 23.4 $s^{-1}$, about 1.35 to about 2.9 $s^{-1}$, about 2 to about 3 $s^{-1}$, about 5 to about 15 $s^{-1}$, or about 0.1 to about 1 $s^{-1}$. In some embodiments, the H-NOX protein has a $k_{off}$ for oxygen that is less than or equal to about 0.65 $s^{-1}$ at 20° C. (such as between about 0.21 $s^{-1}$ to about 0.65 $s^{-1}$ at 20° C.).

By a "$k_{on}$" is meant an association rate, such as the rate of binding of $O_2$ or NO to a protein. A lower numerical lower $k_{on}$ indicates a slower rate of association. In various embodiments, the $k_{on}$ for $O_2$ for an H-NOX protein is between about 0.14 to about 60 $\mu M^{-1}$ $s^{-1}$ at 20° C., such as about 6 to about 60 $\mu M^{-1}$ $s^{-1}$, about 6 to 12 $\mu M^{-1}$ $s^{-1}$, about 15 to about 60 $\mu M^{-1}$ $s^{-1}$, about 5 to about 18 $\mu M^{-}s^{-1}$, or about 6 to about 15 $\mu M^{-1}$ $s^{-1}$.

By "dissociation constant" is meant a "kinetic dissociation constant" or a "calculated dissociation constant." A "kinetic dissociation constant" or "$K_D$" means a ratio of kinetic off-rate ($k_{off}$) to kinetic on-rate ($k_{on}$), such as a $K_D$ value determined as an absolute value using standard methods (e.g., standard spectroscopic, stopped-flow, or flash-photolysis methods) including methods known to the skilled artisan and/or described herein. "Calculated dissociation constant" or "calculated $K_D$" refers to an approximation of the kinetic dissociation constant based on a measured $k_{off}$. A value for the $k_{on}$ is derived via the correlation between kinetic $K_D$ and $k_{off}$ as described herein.

In various embodiments, the kinetic or calculated $K_D$ for $O_2$ binding by an H-NOX protein is between about 1 nM to 1 mM, such as about 2 nM to about 2 µM, about 2 µM to about 1 mM, about 100 nM to about 1 µM, about 9 µM to about 50 µM, about 100 µM to about 1 mM, about 50 nM to about 10 µM, about 2 nM to about 50 µM, about 100 nM to about 1.9 µM, about 150 nM to about 1 µM, or about 100 nM to about 255 nM, about 20 nM to about 2 µM, 20 nM to about 75 nM, about 1 µM to about 2 µM, about 2 µM to about 10 µM, about 2 µM to about 9 µM, or about 100 nM to 500 nM at 20° C. In some embodiments, the kinetic or calculated $K_D$ for $O_2$ binding is less than about any of 100 nM, 80 nM, 50 nM, 30 nM, 25 nM, 20 nM, or 10 nM at 20° C.

In various embodiments, the kinetic or calculated $K_D$ for $O_2$ binding by an H-NOX protein is within about 0.01 to about 100-fold of that of hemoglobin under the same conditions (such as at 20° C.), such as between about 0.1 to about 10-fold or between about 0.5 to about 2-fold of that of hemoglobin under the same conditions (such as at 20° C.). In various embodiments, the kinetic or calculated $K_D$ for NO binding by an H-NOX protein is within about 0.01 to about 100-fold of that of hemoglobin under the same conditions (such as at 20° C.), such as between about 0.1 to about 10-fold or between about 0.5 to about 2-fold of that of hemoglobin under the same conditions (such as at 20° C.).

As used herein, "oxygen affinity" is a qualitative term that refers to the strength of oxygen binding to the heme moiety of a protein. This affinity is affected by both the $k_{off}$ and $k_{on}$ for oxygen. A numerically lower oxygen $K_D$ value means a higher affinity. "NO affinity" is a qualitative term that refers to the strength of NO binding to a protein (such as binding to a heme group or to an oxygen bound to a heme group associated with a protein). This affinity is affected by both the $k_{off}$ and $k_{on}$ for NO. A numerically lower NO $K_D$ value means a higher affinity.

As used herein, "NO stability" refers to the stability or resistance of a protein to oxidation by NO in the presence of oxygen. For example, the ability of the protein to not be oxidized when bound to NO in the presence of oxygen is indicative of the protein's NO stability. In some embodiments, less than about any of 50, 40, 30, 10, or 5% of an H-NOX protein is oxidized after incubation for about any of 1, 2, 4, 6, 8, 10, 15, or 20 hours at 20° C.

As used herein, "NO reactivity" refers to the rate at which iron in the heme of a heme-binding protein is oxidized by NO in the presence of oxygen at a concentration of 2 μM protein. A lower numerical value for NO reactivity in units of $s^{-1}$ indicates a lower NO reactivity. In various embodiments, the NO reactivity of an H-NOX protein is less than about 700 $s^{-1}$ at 20° C., such as less than about 600 $s^{-1}$, 500 $s^{-1}$, 400 $s^{-1}$, 300 $s^{-1}$, 200 $s^{-1}$, 100 $s^{-1}$, 75 $s^{-1}$, 50 $s^{-1}$, 25 $s^{-1}$, 20 $s^{-1}$, 10 $s^{-1}$, 50 $s^{-1}$, 3 $s^{-1}$, 2 $s^{-1}$, 1.8 $s^{-1}$, 1.5 $s^{-1}$, 1.2 $s^{-1}$, 1.0 $s^{-1}$, 0.8 $s^{-1}$, 0.7 $s^{-1}$, or 0.6 $s^{-1}$ at 20° C. In various embodiments, the NO reactivity of an H-NOX protein is between about 0.1 to about 600 $s^{-1}$ at 20° C., such as between about 0.5 to about 400 $s^{-1}$, about 0.5 to about 100 $s^{-1}$, about 0.5 to about 50 $s^{-1}$, about 0.5 to about 10 $s^{-1}$, about 1 to about 5 $s^{-1}$, or about 0.5 to about 2.1 $s^{-1}$ at 20° C. In various embodiments, the reactivity of an H-NOX protein is at least about 10, 100, 1,000, or 10,000 fold lower than that of hemoglobin under the same conditions, such as at 20° C.

As used herein, an "autoxidation rate" refers to the rate at which iron in the heme of a heme-binding protein is autoxidized. A lower numerical autoxidation rate in units of indicates a lower autoxidation rate. In various embodiments, the rate of heme autoxidation of an H-NOX protein is less than about 1.0 $h^{-1}$ at 37° C., such as less than about any of 0.9 $h^{-1}$, 0.8 $h^{-1}$, 0.7 $h^{-1}$, 0.6 $h^{-1}$, 0.5 $h^{-1}$, 0.4 $h^{-1}$, 0.3 $h^{-1}$, 0.2 $h^{-1}$, 0.1 $h^{-1}$, or 0.05 $h^{-1}$ at 37° C. In various embodiments, the rate of heme autoxidation of an H-NOX protein is between about 0.006 to about 5.0 $h^{-1}$ at 37° C., such as about 0.006 to about 1.0 $h^{-1}$, 0.006 to about 0.9 $h^{-1}$, or about 0.06 to about 0.5 $h^{-1}$ at 37° C.

In various embodiments, a mutant H-NOX protein has (a) an $O_2$ or NO dissociation constant, association rate ($k_{on}$ for $O_2$ or NO), or dissociation rate ($k_{off}$ for $O_2$ or NO) within 2 orders of magnitude of that of hemoglobin, (b) has an NO affinity weaker (e.g., at least about 10-fold, 100-fold, or 1000-fold weaker) than that of sGC β1, respectively, (c) an NO reactivity with bound $O_2$ at least 1000-fold less than hemoglobin, (d) an in vivo plasma retention time at least 2, 10, 100, or 1000-fold higher than that of hemoglobin, or (e) any combination of two or more of the foregoing.

Exemplary suitable $O_2$ carriers provide dissociation constants within two orders of magnitude of that of hemoglobin, i.e. between about 0.01 and 100-fold, such as between about 0.1 and 10-fold, or between about 0.5 and 2-fold of that of hemoglobin. A variety of established techniques may be used to quantify dissociation constants, such as the techniques described herein (Boon, E. M. et al. (2005). "Molecular Basis For NO Selectivity in Soluble Guanylate Cyclase," *Nature Chem. Biol.* 1:53-59; Boon, E. M. et al. (October 2005). "Ligand Discrimination in Soluble Guanylate Cyclase and the H-NOX Family of Heme Sensor Proteins," *Curr. Opin. Chem. Biol.* 9(5):441-446; Boon, E. M. et al. (2005). "Ligand Specificity of H-NOX Domains: From sGC to Bacterial NO Sensors," *J. Inorg. Biochem.* 99(4):892-902), Vandegriff, K. D. et al. (Aug. 15, 2004). "Kinetics of NO and $O_2$ Binding to a Maleimide Poly(ethylene glycol)-Conjugated Human Haemoglobin," *Biochem J.* 382(Pt 1):183-189, which are each hereby incorporated by reference in their entireties, particularly with respect to the measurement of dissociation constants), as well as those known to the skilled artisan. Exemplary $O_2$ carriers provide low or minimized NO reactivity of the H-NOX protein with bound $O_2$, such as an NO reactivity lower than that of hemoglobin. In some embodiments, the NO reactivity is much lower, such as at least about 10, 100, 1,000, or 10,000-fold lower than that of hemoglobin. A variety of established techniques may be used to quantify NO reactivity (Boon, E. M. et al. (2005). "Molecular Basis For NO Selectivity in Soluble Guanylate Cyclase," *Nature Chem. Biol.* 1:53-59; Boon, E. M. et al. (October 2005). "Ligand Discrimination in Soluble Guanylate Cyclase and the H-NOX Family of Heme Sensor Proteins," *Curr. Opin. Chem. Biol.* 9(5):441-446; Boon, E. M. et al. (2005). "Ligand Specificity of H-NOX Domains: From sGC to Bacterial NO Sensors," *J. Inorg. Biochem.* 99(4):892-902), Vandegriff, K. D. et al. (Aug. 15, 2004). "Kinetics of NO and $O_2$ Binding to a Maleimide Poly(ethylene glycol)-Conjugated Human Haemoglobin,". *Biochem J.* 382(Pt 1):183-189, which are each hereby incorporated by reference in their entireties, particularly with respect to the measurement of NO reactivity) as well as those known to the skilled artisan. Because wild-type *T. tengcongensis* H-NOX has such a low NO reactivity, other wild-type H-NOX proteins and mutant H-NOX proteins may have a similar low NO reactivity. For example, *T. tengcongensis* H-NOX Y140H has an NO reactivity similar to that of wild-type *T. tengcongensis* H-NOX.

In addition, suitable $O_2$ carriers provide high or maximized stability, particularly in vivo stability. A variety of stability metrics may be used, such as oxidative stability (e.g., stability to autoxidation or oxidation by NO), temperature stability, and in vivo stability. A variety of established techniques may be used to quantify stability, such as the techniques described herein (Boon, E. M. et al. (2005). "Molecular Basis For NO Selectivity in Soluble Guanylate Cyclase," *Nature Chem. Biol.* 1:53-59; Boon, E. M. et al. (October 2005). "Ligand Discrimination in Soluble Guanylate Cyclase and the H-NOX Family of Heme Sensor Proteins," *Curr. Opin. Chem. Biol.* 9(5):441-446; Boon, E. M. et al. (2005). "Ligand Specificity of H-NOX Domains: From sGC to Bacterial NO Sensors," *J. Inorg. Biochem.* 99(4):892-902), as well as those known to the skilled artisan. For in vivo stability in plasma, blood, or tissue, exemplary metrics of stability include retention time, rate of clearance, and half-life. H-NOX proteins from thermophilic organisms are expected to be stable at high temperatures. In various embodiments, the plasma retention times are at least about 2-, 10-, 100-, or 1000-fold greater than that of hemoglobin (e.g. Bobofchak, K. M. et al. (August 2003). "A Recombinant Polymeric Hemoglobin With Conformational, Functional, And Physiological characteristics of an in vivo $O_2$ transporter," *Am. J. Physiol. Heart Circ. Physiol.* 285(2): H549-H561). As will be appreciated by the skilled artisan, hemoglobin-based blood substitutes are limited by the rapid clearance of cell-free hemoglobin from plasma due the presence of receptors for hemoglobin that remove cell-free hemoglobin from plasma. Since there are no receptors for H-NOX proteins in plasma, wild-type and mutant H-NOX proteins are expected to have a longer plasma retention time than that of hemoglobin. If desired, the plasma retention time can be increased by PEGylating or crosslinking an H-NOX protein or fusing an H-NOX protein with another protein using standard methods (such as those described herein and those known to the skilled artisan).

In various embodiments, the H-NOX protein has an $O_2$ dissociation constant between about 1 nM to about 1 mM at 20° C. and a NO reactivity at least about 10-fold lower than that of hemoglobin under the same conditions, such as at 20° C. In some embodiments, the H-NOX protein has an $O_2$ dissociation constant between about 1 nM to about 1 mM at 20° C. and a NO reactivity less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.). In some embodiments, the H-NOX protein has an $O_2$ dissociation constant within 2 orders of magnitude of that of hemoglobin and a NO reactivity at least about 10-fold lower than that of hemoglobin under the same conditions, such as at 20° C. In some embodiments, the H-NOX protein has a $k_{off}$ for oxygen between about 0.01 to about 200 $s^{-1}$ at 20° C. and an NO reactivity at least about 10-fold lower than that of hemoglobin under the same conditions, such as at 20° C. In some embodiments, the H-NOX protein has a $k_{off}$ for oxygen that is less than about 0.65 $s^{-1}$ at 20° C. (such as between about 0.21 $s^{-1}$ to about 0.64 $s^{-1}$ at 20° C.) and a NO reactivity at least about 10-fold lower than that of hemoglobin under the same conditions, such as at 20° C. In particular embodiments, the $O_2$ dissociation constant of the H-NOX protein is between about 2 nM to about 50 μM, about 50 nM to about 10 μM, about 100 nM to about 1.9 μM, about 150 nM to about 1 μM, or about 100 nM to about 255 nM at 20° C. In various embodiments, the $O_2$ dissociation constant of the H-NOX protein is less than about 80 nM at 20° C., such as between about 20 nM to about 75 nM at 20° C. In some embodiments, the NO reactivity of the H-NOX protein is at least about 100-fold lower or about 1,000 fold lower than that of hemoglobin, under the same conditions, such as at 20° C. In some embodiments, the NO reactivity of the H-NOX protein is less than about 700 $s^{-1}$ at 20° C., such as Less than about 600 $s^{-1}$, 500 $s^{-1}$, 400 $s^{-1}$, 300 $s^{-1}$, 200 $s^{-1}$, 100 $s^{-1}$, 75 $s^{-1}$, 50 $s^{-1}$, 25 $s^{-1}$, 20 $s^{-1}$, 10 $s^{-1}$, 50 $s^{-1}$, 3 $s^{-1}$, 2 $s^{-1}$, 1.8 $s^{-1}$, 1.5 $s^{-1}$, 1.2 $s^{-1}$, 1.0 $s^{-1}$, 0.8 $s^{-1}$, 0.7 $s^{-1}$, or 0.6 $s^{-1}$ at 20° C. In some embodiments, the $k_{off}$ for oxygen of the H-NOX protein is between 0.01 to 200 $s^{-1}$ at 20° C., such as about 0.1 to about 200 $s^{-1}$, about 0.1 to 100 $s^{-1}$, about 1.35 to about 23.4 $s^{-1}$, about 134 to about 18 $s^{-1}$, about 1.35 to about 14.5 $s^{-1}$, about 0.21 to about 23.4 $s^{-1}$, about 2 to about 3 $s^{-1}$, about 5 to about 15 $s^{-1}$, or about 0.1 to about 1 $s^{-1}$. In some embodiments, the $O_2$ dissociation constant of the H-NOX protein is between about 100 nM to about 1.9 μM at 20° C., and the $k_{off}$ for oxygen of the H-NOX protein is between about 1.35 $s^{-1}$ to about 14.5 $s^{-1}$ at 20° C. In some embodiments, the rate of heme autoxidation of the H-NOX protein is less than about 1 $h^{-1}$ at 37° C., such as less than about any of 0.9 $h^{-1}$, 0.8 $s^{-1}$,0.7 $h^{-1}$, 0.6 $h^{-1}$, 0.5 $h^{-1}$, 0.4 $h^{-1}$, 0.3 $h^{-1}$, 0.2 $h^{-1}$, or 0.1 $s^{-1}$. In some embodiments, the $k_{off}$ for oxygen of the H-NOX protein is between about 1.35 $s^{-1}$ to about 14.5 $s^{-1}$ at 20° C., and the rate of heme autoxidation of the H-NOX protein is less than about 1 $h^{-1}$ at 37° C. In some embodiments, the $k_{off}$ for oxygen of the H-NOX protein is between about 1.35 $s^{-1}$ to about 14.5 $s^{-1}$ at 20° C., and the NO reactivity of the H-NOX protein is less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.). In some embodiments, the rate of heme autoxidation of the H-NOX protein is less than about 1 $h^{-1}$ at 37° C., and the NO reactivity of the H-NOX protein is less than about 700 $s^{-1}$ at 20° C. (e.g., less than about 600 $s^{-1}$, 500 $s^{-1}$, 100 $s^{-1}$, 20 or 1.8 $s^{-1}$ at 20° C.).

In some embodiments, the viscosity of the H-NOX protein solution is between 1 and 4 centipoise (cP). In some embodiments, the colloid oncotic pressure of the H-NOX protein solution is between 20 and 50 mm Hg.

Table 3 lists exemplary sizes, oxygen affinities, autoxidation stabilities, NO reactivity rates, and modifications for wild-type and mutant H-NOX proteins. In Table 3, the vehicle size refers to the molecular weight of a modified (e.g., PEGylated) or unmodified H-NOX protein.

TABLE 3

Exemplary Embodiments for H—NOX proteins

| Vehicle size | Oxygen Affinity | Stability (autoxidation) | NO reactivity ($s^{-1}$) | Particle decoration |
|---|---|---|---|---|
| >1 MD | <1 nM | 1 hour | 0.01 to 0.1 | Cross-liking |
| 0.5 kD to 1 MD | 1 nM to 100 nM | 1 h to 12 h | 0.1 to 1 | PEGylation |
| 0.1 kD to 0.5 kD | 100 nM to 1 uM | 12 h to 48 h | 1 to 10 | Encapsulation |
| 0.01 kD to 0.1 kD | 1 uM to 10 uM | 48 h to 2 weeks | 10 to 100 | |

Exemplary data for particular mutants are reported in Tables 4-12. In Tables 4-12, β1 and B2 refer to proteins derived from rat H-NOX proteins. Since the amino acid sequences of mammalian β1 H-NOX domains differ by at most two amino acids, similar results are expected for the corresponding mutations in other mammalian β1 H-NOX proteins, such as human β1. As shown in Table 4, introducing one or more mutations into wild-type H-NOX proteins allows the autoxidation rate and $O_2$ dissociation rate to be altered. If desired, the autoxidation rate or $O_2$ dissociation rate can be further altered by combining any of the single or double mutations listed in Table 4 or by introducing one or more additional mutations into an H-NOX protein, as described herein.

TABLE 4

Stability to autoxidation, $O_2$-binding properties (such as rate of $O_2$ dissociation) and distal pocket H-bonding residues are listed for wild-type and class II mutant H—NOX proteins

| Protein | Stability | $O_2$-binding activity[b] | Distal pocket residues |
|---|---|---|---|
| *Tt* H—NOX, a prokaryotic H—NOX and a strong $O_2$ binder | | | |
| *Tt* H—NOX | $k_{ox}$ ~0[c] | $k_{off}$ = 1.22 | Trp9, Phe78, Tyr140 |
| *Tt* Y140F | $k_{ox}$ = 0.05 | $k_{off}$ = 15.7[d] | Trp9, Phe78, Phe140 |
| *Tt* Y140L | $k_{ox}$ = 0.19 | $k_{off}$ = 20.[d] | Trp9, Phe78, Leu140 |
| *Tt* Y140H | $k_{ox}$ = 0.87 | $k_{off}$ = 5.03 | Trp9, Phe78, His140 |
| *Tt* Y140A | Stable[a] | Partial complex[d,e] | Trp9, Phe78, Ala140 |
| *Tt* W9F | $k_{ox}$ ~0[c] | $k_{off}$ = 1.84 | Phe9, Phe78, Tyr140 |
| *Tt* W9F-Y140L | $k_{ox}$ = 0.12 | No complex formed | Phe9, Phe78, Leu140 |
| *Tt* W9F-Y140H | $k_{ox}$ = 0.11 | $k_{off}$ = 23.4 | Phe9, Phe78, His140 |
| *Tt* F78Y-Y140L | $k_{ox}$ ~0[c] | $k_{off}$ = 0.83 | Trp9, Tyr78, Leu140 |
| *Tt* F78Y-Y140F | $k_{ox}$ ~0[c] | $k_{off}$ = 1.48 | Trp9, Tyr78, Phe140 |
| Prokaryotic H—NOX proteins for which the wild-type protein does not bind $O_2$ | | | |
| L2 H—NOX | Stable[a] | No complex formed | Phe9, Phe78, Phe142 |
| L2 F142Y | Stable[f] | $k_{off}$ = 3.68 | Phe9, Phe78, Tyr142 |
| L2 F9W-F142Y | Stable[f] | Binds $O_2$[e] | Trp9, Phe78, Tyr142 |
| L1 H—NOX | $k_{ox}$ = 0.31 | No complex formed | Leu9, Leu78, Phe142 |
| L1 F142Y | $k_{ox}$ = 1.8 | $k_{off}$ = 1.73[d] | Leu9, Leu78, Tyr142 |
| Eukaryotic H—NOX for which the wild-type protein does not bind $O_2$ | | | |
| β2(1-217) | $k_{ox}$ = 0.18 | No complex formed | Leu9, Cys76, Ile142 |
| β2(1-217) I142Y | | g | Leu9, Cys76, Tyr142 |
| β1(1-194) | $k_{ox}$ = 4.3 | No complex formed | Leu9, Cys78, Ile145 |
| β1(1-194) I145Y | $k_{ox}$ = 2.8 | g | Leu9, Cys78, Tyr145 |
| β1(1-194) L9W-I145Y | $k_{ox}$ ~10 | g | Trp9, Cys78, Tyr145 |
| β1(1-385) | Stable[e] | No complex found | Leu9, Cys78, Ile145 |
| β1(1-385) I145Y | $k_{ox}$ = 0.72 | $k_{off}$ = 2.69 | Leu9, Cys78, Tyr145 |
| β1(1-385) I145H | | | Leu9, Cys78, His145 |
| β1(1-385) C78Y | | | Leu9, Tyr78, Ile145 |
| Other H—NOX predicted to bind $O_2$ as the wild-type construct | | | |
| *Dd* H—NOX(728-899) | $k_{ox}$ = 0.98 | $k_{off}$ = 5.80 | Phe9, Phe75, Tyr139 |
| *Dd* Y139L | | | Phe9, Phe75, Leu139 |
| *Cb* H—NOX(1-175) | Not stable construct[h] | g | Trp9, Phe78, Tyr140 |
| *Cb* H—NOX(1-186) | Slightly more stable[i] | g | Trp9, Phe78, Tyr140 |
| *Ca* H—NOX(1-197) | Not stable construct[h] | g | Trp9, Phe78, Tyr140 |
| *Ca* H—NOX(1-183) | Slightly more stable[i] | g | Trp9, Phe78, Tyr140 |
| *Ce* GCY-35(1-252) | Stable | Binds $O_2$[e] | Phe9, Thr78, Tyr144 |

[a]The construct is stable to oxidation (evaluated by the rate of autoxidation, $k_{ox}$ [$h^{-1}$] at 37° C.) and/or heme loss.

[b]$O_2$-binding activity was evaluated by the rate of $O_2$ dissociation from the heme at 20° C. ($s^{-1}$).

[c]After 24 hours at 37° C., there is still no indication of autoxidation.

[d]Only a small portion of the protein forms a complex with $O_2$, the rate reported represents the kinetics for this population.

[e]The protein binds $O_2$ but the $k_{off}$ was not determined.

[f]Although relatively stable, this protein precipitated as it oxidized, making it difficult to measure $k_{ox}$.

[g]Not applicable due to instability or rapid oxidation.

[h]"Not stable construct" means the protein oxidizes immediately under the conditions tested.

[i]"Slightly more stable" means the protein oxidizes over a period of minutes to hours, but does not remain stable beyond 24 hours under the conditions tested.

Table 5 illustrates the alteration of the $O_2$ association rate ($k_{on}$), $O_2$ dissociation rate ($k_{off}$), $O_2$ dissociation constant ($K_D$), and autoxidation rate ($k_{ox}$) in fl-NOX proteins by the introduction of one or more mutations. In some embodiments, any of the single or double mutations listed in Table 5 are combined with another mutation (such as another mutation in Table 5 or any other mutation described herein) to further alter the $O_2$ association rate, $O_2$ dissociation rate, $O_2$ dissociation constant, autoxidation rate, or combinations of two or more of the foregoing.

TABLE 5

$O_2$-binding kinetic constants for histidyl-ligated $Fe^{II}$ heme proteins

| Protein | $K_D$[a] | $k_{on}$[b] | $k_{off}$[c] | $k_{ox}$[d] | Ref. |
|---|---|---|---|---|---|
| *Tt* H—NOX | 89.7 ± 6.2 | 13.6 ± 1.0 | 1.22 ± 0.09 | e | i |
| *Tt* P115A | 21.2 ± 2.1 | 10.4 ± 1.1 | 0.22 ± 0.01 | e | j |
| *Tt* I5A | ~80 | | 0.82 ± 0.03 | 0.7 | j |
| *Tt* I5L | ~1000 | | 9.50 ± 0.64 | 0.6 | j |
| *Tt* I5L- | ~30 | | 0.28 ± 0.01 | 0.6 | j |

TABLE 5-continued $O_2$-binding kinetic constants for histidyl-ligated $Fe^{II}$ heme proteins

| Protein | $K_D{}^a$ | $k_{on}{}^b$ | $k_{off}{}^c$ | $k_{ox}{}^d$ | Ref. |
|---|---|---|---|---|---|
| P115A | | | | | |
| *Tt* W9F | 305 ± 31 | 6.02 ± 0.62 | 1.84 ± 0.17 | e | i |
| *Tt* Y140F | f | 15.7 ± 1.4 | 15.7 ± 9.8 | 0.05 | j |
| *Tt* Y140L | ~2000 | Geminal | 20.1 ± 2.0 | 0.19 | i |
| *Tt* Y140H | ~500 | | 5.03 ± 0.69 | 0.87 | j |
| *Tt* W9F-Y140H | ~2500 | | 23.4 ± 3.7 | 0.11 | j |
| *Tt* W9F-Y140L | No complex with $O_2$ observed | | | 0.12 | i |
| *Tt* F78Y-Y140F | ~150 | | 1.48 ± 0.33 | e | j |
| *Tt* F78Y-Y140L | ~80 | | 0.83 ± 0.17 | e | i |
| *Tt* W9F-N74A | Millimolar | very slow | | | j |
| *Dd* H—NOX | Millimolar | very slow | 7.13 ± 0.45 | 0.14 | j |
| *Dd* Y139L | No complex with $O_2$ observed | | | | j |
| β1(1-385) I145Y | 70,000,00 | 0.00004 | 2.69 ± 0.61 | 0.72 | i |
| L2 F142Y | 9200 ± 3000 | 0.40 ± 0.14 | 3.68 ± 0.71 | | i |
| Hs Hb beta | 267 | 60 | 16 | | n |
| Hs Hb alpha | 560 | 50 | 28 | | k |
| Sw Mb | 880 | 17 | 15 | 0.006 | k |
| Bj FixL | 140,000 | 0.14 | 20 | 2.7 | l |
| HemAT-B | 720 | 32 | 23 | 0.06 | m |

[a]dissociation constant at 20° C. (nM);
[b]rate of $O_2$ association to the heme at 20° C. ($\mu M^{-1}s^{-1}$);
[c]rate of $O_2$ dissociation from the heme at 20° C. ($s^{-1}$);
[d]rate of heme autoxidation ($h^{-1}$) at 37° C.;
[e]after 24 hours at 37° C., still no indication of autoxidation;
[f]only a small portion of the protein forms a complex with $O_2$, although the kinetics for this population could be measured;
[i]Boon, E. M. et al. (June 2005). "Molecular Basis For NO Selectivity in Soluble Guanylate Cyclase," *Nature Chemical Biology* 1(1): 53-59,
[j]unpublished data;
[k]Springer, B. A. et al. (1994) "Family Physicians Key Partners in Preventing Suicide Among Youth," *Chem. Rev.* 94: 699-714;
[l]Gilles-Gonzalez et al. (1994) "Heme-Based Sensors, Exemplified by the Kinase FixL, are a New Class of Heme Protein with Distinctive Ligand Binding and Autoxidation," *Biochemistry* 33: 8067-8073.
[m]Aono, S. et al. (2002) "Resonance Raman and Ligand Binding Studies of the Oxygen-Sensing Signal Transducer Protein HemAT from *Bacillus Subtilis*," *J. Biol. Chem.* 277: 13528-13538.
[n]Antonini, E. et al. (1971). "Hemoglobin and Myoglobin in Their Reactions with Ligands," North-Holland Publ., Amsterdam.

Table 6 illustrates that the $O_2$ association rate, $O_2$ dissociation rate, $O_2$, autoxidation rate, NO reactivity, and stability of $Fe^{II}$—$O_2$ complexes in H-NOX proteins may be altered by the introduction of one or more mutations. In some embodiments, any of the single or double mutations listed in Table 6 are combined with another mutation (such as another mutation in Table 6 or any other mutation described herein) to further alter the $O_2$ association rate, $O_2$ dissociation rate, $O_2$, autoxidation rate, NO reactivity, or stability of $Fe^{II}$—$O_2$ complexes in an H-NOX protein. As will be appreciated by the skilled artisan, introduction of one or more additional mutations, such as those described herein, may be used to further alter these values.

TABLE 6

$O_2$ association rate, $O_2$ dissociation rate, $O_2$, autoxidation rate, NO reactivity, and stability of $Fe^{II}$—$O_2$ complexes in H—NOX proteins.

| Protein | $k_{on}{}^a$ | $K_{off}{}^b$ | $k_{ox}{}^c$ | NO reactivity[d] | stability of FeII—$O_2$ complex |
|---|---|---|---|---|---|
| Hs Hb | 23 | 11 | 0.006 | <0.001 s (~7,000 $s^{-1}$)[e] | oxidizes o/n in air at RT, stable at 4° C. in air, stable anaerobic |
| *Tt* H—NOX | 13.6 | 1.22 | Very slow | 0.54 ± 0.07 $s^{-1}$ | Always stable |
| *Tt* Y140H | ~10 | 5.03 | 0.87 | 1.7 ± 0.4 $s^{-1}$ | oxidizes o/n in air at RT, stable at 4° C. in air, stable anaerobic |
| β1(1-385) I145Y | ~105 | 2.69 | 0.72 | slow to $Fe^{III}$—NO | oxidizes o/n in air at RT, stable at 4° C. in air, stable anaerobic |

[a]rate of $O_2$ association to the heme at 20° C. (μM−1s−1);
[b]rate of $O_2$ dissociation from the heme at 20° C. (s−1);
[c]rate of heme autoxidation (h−1) at 37° C.;
[d]For determination of NO reactivities: purified proteins (Tt WT HNOX, Tt Y140H HNOX, *Homo sapiens* hemoglobin (Hs Hb)) were prepared at 2 μM in buffer A and nitric oxide (NO) was prepared at 200 μM in Buffer A (Buffer A: 50 mM Hepes, pH 7.5, 50 mM NaCl) at 20° C. Using stopped flow spectroscopy, the protein was rapidly mixed with NO in a 1:1 ratio with an integration time of 0.00125 seconds. The wavelengths of maximum change were fit to a single exponential, essentially measuring the rate-limiting step of oxidation by NO. The end products of the reaction were ferric-NO for the HNOX proteins and ferric-aquo for Hs Hb.
[e]For Hs Hb, the reaction of the protein with NO was so fast that the reaction was completed within the dead time of the experiment (0.001 seconds). The NO reactivity for hemoglobin is approximately 7,000 $s^{-1}$ at 20° C. based on Eich, R. F. et al. (1996) "Mechanism of NO-Induced Oxidation of Myoglobin and Hemoglobin," *Biochemistry* 35: 6976-6983.

Table 7 demonstrates that the dissociation constant for $O_2$ binding can be significantly changed by mutating one or more residues in H-NOX proteins. The kinetic $K_D$ values for these exemplary H-NOX proteins range from 21.20 nM to 1000000.00 nM at 20° C. If desired, the dissociation constant for $O_2$ binding can be further altered by combining any of the single or double mutations listed in Table 7 or by introducing one or more additional mutations into an H-NOX protein, as described herein.

TABLE 7

Wild-type and mutant H—NOX proteins and reference proteins arranged by the value of the dissociation constant for $O_2$ binding

| Protein | Kinetic $K_D$ (nM) | ± | Calculated $K_D$ (nM) |
|---|---|---|---|
| *Tt* P115A | 21.2 | 2.1 | |
| *Tt* N74H | | | 27 |
| *Tt* I5L-P115A | | | 30 |
| *Tt* N74A | | | 32 |
| *Tt* I5A | | | 80 |
| *Tt* F78Y-Y140L | | | 80 |
| *Tt* H—NOX His6 | | | 89 |
| *Tt* H—NOX | 89.7 | 6.2 | |
| *Tt* wt | | | 90 |
| *Tt* F78Y-Y140F | | | 150 |
| *Tt* W9Y | | | 218 |
| *Tt* R135Q His6 | | | 252 |
| Hs Hb beta | | | 267 |
| *Tt* W9F | 305 | 31 | |
| *Tt* W9H | | | 456 |
| *Tt* Y140H | | | 500 |
| Hs Hb alpha | | | 560 |
| *Tt* W9N | | | 573 |
| *Tt* I75F-His6 | | | 713-773 |
| HemAT-B | | | 720 |
| Sw Mb | | | 880 |
| *Tt* I5L | | | 1000 |
| *Tt* L144F-His6 | | | 1092-1185 |
| *Tt* Y140L | | | 2000 |
| *Tt* W9F-Y140H | | | 2500 |
| L2 F142Y | 9200 | 3000 | |
| Bj FixL | | | 140000 |
| *Tt* W9F-N74A | | | 1000000 |
| *Dd* H—NOX | | | 1000000 |
| β1(1-385) I145Y | | | 1000000 |

Table 8 demonstrates that the dissociation rates for $O_2$ binding can be significantly changed by mutating one or more residues in H-NOX proteins. The dissociation rates for these exemplary H-NOX proteins range from 0.21 $s^{-1}$ to 23.4 $s^{-1}$ at 20° C. If desired, the dissociation rate for $O_2$ binding can be further altered by combining any of the single or double mutations listed in Table 8 or by introducing one or more additional mutations into an H-NOX protein, as described herein.

TABLE 8

Wild-type and mutant H—NOX proteins and reference proteins arranged by the value of the dissociation rate for $O_2$ binding

| Protein | $k_{off}$ ($s^{-1}$) | ± |
|---|---|---|
| *Tt* N74A | 0.21 | 0.004 |
| *Tt* P115A | 0.22 | 0.01 |
| *Tt* I5L-P115A | 0.28 | 0.03 |
| *Tt* N74E | 0.38 | 0.01 |
| *Tt* N74H | 0.44 | 0.01 |
| *Tt* I5A | 0.82 | 0.03 |
| *Tt* F78Y-Y140L | 0.83 | 0.17 |
| *Tt* H—NOX His6 | 1.2 | 0.02 |
| *Tt* H—NOX | 1.22 | 0.09 |
| *Tt* F78Y-Y140F | 1.48 | 0.33 |
| L1 F142Y | 1.73 | |
| *Tt* W9F | 1.84 | 0.17 |
| β1(1-385) I145Y | 2.69 | 0.61 |
| *Tt* W9Y | 3.07 | 0.1 |
| *Tt* R135Q His6 | 3.56 | 0.08 |
| L2 F142Y | 3.68 | 0.71 |
| *Tt* Y140H | 5.03 | 0.69 |
| *Tt* W9H | 6.42 | 0.11 |
| *Dd* H—NOX | 7.13 | 0.45 |
| *Tt* W9N | 8.09 | 0.14 |
| *Tt* I5L | 9.5 | 0.64 |
| *Tt* I75F-His6 | 10.48 | 0.12 |
| Sw Mb | 15 | |
| *Tt* Y140F | 15.7 | 9.8 |
| Hs Hb beta | 16 | |
| *Tt* L144F-His6 | 16.06 | 0.21 |
| Bj FixL | 20 | |
| *Tt* Y140L | 20.1 | 2 |
| HemAT-B | 23 | |
| *Tt* W9F-Y140H | 23.4 | 3.7 |
| Hs Hb alpha | 28 | |

Table 9 demonstrates that the association rates for $O_2$ binding can be significantly changed by mutating one or more residues in H-NOX proteins. The association rates for these exemplary H-NOX proteins range from 60 $\mu M^{-1} s^{-1}$ to 0.14 $\mu M^{-1} s^{-1}$ at 20° C. If desired, the association rate for $O_2$ binding can be further altered by combining any of the single or double mutations listed in Table 9 or by introducing one or more additional mutations into an H-NOX protein, as described herein.

TABLE 9

Wild-type and mutant H—NOX proteins and reference proteins arranged by the value of the association rate for $O_2$ binding

| Protein | $k_{on}$ ($\mu M^{-1}s^{-1}$) | ± |
|---|---|---|
| Hs Hb beta | 60 | |
| Hs Hb alpha | 50 | |
| HemAT-B | 32 | |
| Sw Mb | 17 | |
| *Tt* Y140F | 15.7 | 1.4 |
| *Tt* H—NOX | 13.6 | 1 |
| *Tt* P115A | 10.4 | 1.1 |
| *Tt* W9F | 6.02 | 0.62 |
| L2 F142Y | 0.4 | 0.14 |
| Bj FixL | 0.14 | |
| *Tt* W9F-N74A | very slow[a] | |
| *Dd* H—NOX | very slow[a] | |
| β1(1-385) I145Y | very slow[a] | |

[a]By "very slow" is meant slower than hemoglobin, such as approximately one to two orders of magnitude slower than hemoglobin.

Table 10 illustrates the effect of exemplary H-NOX mutations on $O_2$ and NO-binding. Each number listed in Table 10 for the Fe-unligated form is for a single peak (which is listed in between the p and a columns). When $O_2$ or NO binds, this single peak splits into two peaks, β and α (which are listed below the β and a columns, respectively). If desired, $O_2$ or NO-binding can be further altered by combining any of the single or double mutations listed in Table 10 or by introducing one or more additional mutations into an H-NOX protein, as described herein.

TABLE 10

UV-visible peak positions[a] for some histidyl-ligated $Fe^{II}$ heme protein complexes

| Protein | Soret | β | α |
|---|---|---|---|
| $Fe^{II}$ unligated complex | | | |
| sGC | 431 | 555 | |
| β1(1-385) I145Y | 429 | 549 | |
| *Tt* H—NOX | 431 | 565 | |
| *Tt* W9F-Y140L | 430 | 560 | |
| *Vc* H—NOX | 429 | 568 | |
| *Np* H—NOX | 430 | 555 | |
| L2 H—NOX | 428 | 557 | |
| L2 F142Y | 428 | 557 | |
| *Tt* I75F-His6 | 431 | 569 | |
| *Tt* L144F-His6 | 433 | 564 | |
| Hb | 430 | 555 | |
| $Fe^{II}$—NO complex | | | |
| sGC | 398 | 537 | 572 |
| β1(1-385) I145Y | 399/416 | 542 | 574 |
| *Tt* H—NOX | 420 | 547 | 575 |
| *Tt* W9F-Y140L | 423 | 540 | 573 |
| *Vc* H—NOX | 398 | 540 | 573 |
| *Np* H—NOX | 416/400 | 543 | 576 |
| L2 H—NOX | 399/416 | 544 | 575 |
| L2 F142Y | 417 | 544 | 578 |
| *Tt* I75F-His6 | 418 | 545 | 574 |
| *Tt* L144F-His6 | 416 | 544 | 574 |
| Hb | 418 | 545 | 575 |
| $Fe^{II}$—$O_2$ complex | | | |
| sGC | No complex observed | | |
| β1(1-385) I145Y | 416 | 541 | 575 |
| *Tt* H—NOX | 416 | 556 | 591 |
| *Tt* W9F-Y140L | No complex observed | | |
| *Vc* H—NOX | No complex observed | | |
| *Np* H—NOX | No complex observed | | |
| L2 H—NOX | No complex observed | | |
| L2 F142Y | 417 | 542 | 577 |
| *Tt* I75F-His6 | 416 | 552 | 589 |
| *Tt* L144F-His6 | 416 | 544 | 574 |
| Hb | 415 | 541 | 577 |

[a]nm (at 20° C.)

Table 11 contains UV-visible peak positions for some Fe(II), Fe(III), Fe(II)-NO, and Fe(II)-$O_2$ complexes. When a hemoglobin or H-NOX protein is anaerobic, it has a Soret peak at 431 nm, and it is in an unligated state. If the H-NOX protein does not bind $O_2$, then the Soret peak will not change when $O_2$ is added. If the H-NOX protein does bind $O_2$, then its Soret peak will shift to between 414 nm and 418 nm when $O_2$ is added, which is the same shift that occurs in hemoglobin, indicative of $O_2$ bound to the heme. Soret peaks for oxidized H-NOX (Fe(III)) or H-NOX bound to NO in a 6 coordinate state may be relevant to the state of the H-NOX protein after storage or use. If the H-NOX protein does not bind NO, then the Soret peak will not change when NO is added. If the H-NOX protein binds NO and forms a 6-coordinate ferrous-nitrosyl complex, then its Soret peak will shift to between 420 nm and 424 nm when NO is added. If the H-NOX protein binds NO and forms a 5-coordinate ferrous-nitrosyl complex, the Soret peak will shift to 399 nm. If desired, $O_2$ or NO-binding can be further altered by combining any of the single or double mutations listed in Table 11 or by introducing one or more additional mutations into an H-NOX protein, as described herein.

TABLE 11

UV-visible peak positions for some Fe (II), Fe (III), Fe(II)—NO, and Fe(II)—$O_2$ complexes.

| Complex | Protein | Soret | | α |
|---|---|---|---|---|
| | | | β | |
| Fe (II) | *Tt* wt | 430 | 563 | |
| | *Tt* W9Y | 430 | 569 | |
| | *Tt* N74A | 433 | 558 | |
| | *Tt* N74H | 431 | 561 | |
| | *Tt* N74A-Y140H | 430 | 567 | |
| | *Tt* W9H | 431 | 563 | |
| | *Tt* N74E | 433 | 559 | |
| | *Tt* W9N | 431 | 569 | |
| | *Tt* wt $His_6$ | 430 | 565 | |
| | | | β[a] | |
| Fe (III) | *Tt* wt | 413 | 550 | 585 |
| | *Tt* W9Y | 409 | N.A. | |
| | *Tt* N74A | 416 | 554 | 586 |
| | *Tt* N74H | 408 | N.A. | |
| | *Tt* N74A-Y140H | 407 | N.A. | |
| | *Tt* W9H | 407 | N.A. | |
| | *Tt* N74E | 408 | N.A. | |
| | *Tt* W9N | 408 | N.A. | |
| | *Tt* wt $His_6$ | 413 | 550 | 586 |
| | | | β | |
| Fe(II)—NO | *Tt* wt | 420 | 550 | 578 |
| | *Tt* W9Y | 420 | 552 | 576 |
| | *Tt* N74A | 421 | 572 | |
| | *Tt* N74H | 424 | 562 | |
| | *Tt* N74A-Y140H | 421 | 549 | 576 |
| | *Tt* W9H | 420 | 548 | 575 |
| | *Tt* N74E | 422 | 544 | 571 |
| | *Tt* W9N | 421 | 541 | 576 |
| | *Tt* wt $His_6$ | 420 | 547 | 576 |
| Fe(II)—$O_2$ | *Tt* wt | 416 | 556 | 591 |
| | *Tt* W9Y | 416 | 555 | 590 |
| | *Tt* N74A | 418 | 553 | 589 |
| | *Tt* N74H | 418 | 553 | 589 |
| | *Tt* N74A-Y140H | 414 | 555 | 584 |
| | *Tt* W9H | 418 | 556 | 589 |
| | *Tt* N74E | 417 | 555 | 587 |
| | *Tt* W9N | 416 | 588 | 553 |
| | *Tt* wt $His_6$ | 416 | 556 | 591 |

[a]"N.A." denotes nonassignable α and β bands due to low signal at longer wavelengths.

Table 12 contains autoxidation rates for exemplary *T. tengcongensis* H-NOX proteins. If desired, the autoxidation rate can be further altered by combining any the mutations listed in Table 12 or by introducing one or more additional mutations into an H-NOX protein, as described herein. The 2 nm and 3 nm values mean in Table 12 refer to a shift in the UV-V is Soret peak by 2 to 3 nm over the time period of the observation; this extremely small change may be due to autoxidation.

TABLE 12

Autoxidation rates for *T. tengcongensis* (*Tt*) H—NOX proteins

| Protein | Autoxidation Rate (25° C., $hr^{-1}$)[a] |
|---|---|
| *Tt* wt | Stable |
| *Tt* W9Y | Stable |
| *Tt* N74A | Stable |
| *Tt* N74H | stable at 4° C., very slow at RT (2 nm) |
| *Tt* W9H | Stable |
| *Tt* N74E | very slow at 4° C. (2 nm), slow at RT |
| *Tt* W9N | stable at 4° C., very slow at RT (3 nm) |
| *Tt* wt $His_6$ | Stable |

TABLE 12-continued

| Autoxidation rates for *T. tengcongensis* (*Tt*) H—NOX proteins | |
|---|---|
| Protein | Autoxidation Rate (25° C., $hr^{-1}$)[a] |
| *Tt* I75F-His6 | Stable |
| *Tt* L144F-His6 | Stable |

[a]"Stable" denotes lack of heme oxidation after at least 24 hours.
"RT" denotes room temperature.

H-NOX Nucleic Acids

The invention also features nucleic acids encoding any of the mutant H-NOX proteins described herein. As used herein, a "nucleic acid" refers to two or more deoxyribonucleotides and/or ribonucleotides in either single or double-stranded form, and unless otherwise limited, encompasses known analogs of naturally-occurring nucleotides that hybridize to nucleic acids in a manner similar to nucleotides occurring in nature. In some embodiments, the nucleic acid is a recombinant nucleic acid. By "recombinant nucleic acid" means a nucleic acid of interest that is free of one or more nucleic acids (e.g., genes) which, in the genome occurring in nature of the organism from which the nucleic acid of interest is derived, flank the nucleic acid of interest. In some embodiments, an H-NOX nucleic acid is operably linked to another nucleic acid encoding all or a portion of another protein such that the recombinant nucleic acid encodes a fusion protein that includes an H-NOX protein (e.g., an H-NOX domain with or without another domain from an H-NOX protein) and all or part of another protein, such as human serum albumin. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences.

The invention also features vectors with one more nucleic acids encoding any of the mutant H-NOX proteins that are described herein. As used herein, a "vector" means a construct that is capable of delivering, and optionally expressing one or more nucleic acids of interest in a host cell. Examples of vectors include, but are not limited to, plasmids, viral vectors, DNA or RNA expression vectors, cosmids, and phage vectors. In some embodiments, the vector contains a nucleic acid under the control of an expression control sequence. An "expression control sequence" means a nucleic acid sequence that directs transcription of a nucleic acid of interest. An expression control sequence can be a promoter, such as a constitutive or an inducible promoter, or an enhancer. The expression control sequence is operably linked to the nucleic acid segment to be transcribed.

In particular embodiments, the nucleic acid includes a segment of or the entire nucleic acid sequence of any of the nucleic acids shown in FIGS. 2-4D or 8A-8DD. In some embodiments, the nucleic acid includes at least about 50, 100, 150, 200, 300, 400, 500, 600, 700, 800, or more contiguous nucleotides from a H-NOX nucleic acid and contains one or more mutations (e.g., 1, 2, 3, 4, 5, 6, 7, 8, 9, or 10 mutations) compared to the H-NOX nucleic acid from which it was derived. In various embodiments, a mutant H-NOX nucleic acid contains less than about 20, 15, 12, 10, 9, 8, 7, 6, 5, 4, 3, or 2 mutations compared to the H-NOX nucleic acid from which it was derived. The invention also features degenerate variants of any nucleic acid encoding a mutant H-NOX protein.

The invention also includes a cell or population of cells containing at least one nucleic acid encoding a mutant H-NOX protein described herein. Exemplary cells include insect, plant, yeast, bacterial, and mammalian cells. These cells are useful for the production of mutant H-NOX proteins using standard methods, such as those described herein.

Formulations of H-NOX Proteins

Any wild-type or mutant H-NOX protein described herein may be used for the formulation of pharmaceutical or non-pharmaceutical compositions. As discussed further below, these formulations are useful in a variety of therapeutic and industrial applications.

In some embodiments, the pharmaceutical composition includes one or more wild-type or mutant H-NOX proteins (such as any of the H-NOX wild-type or mutant proteins described herein) and a pharmaceutically acceptable carrier. In various embodiments, the H-NOX protein is an isolated or purified protein. By "pharmaceutically acceptable carrier" is meant any material which, when combined with an active ingredient, allows the ingredient to retain biological activity and does not provoke an unacceptable immune response (e.g., a severe allergy or anaphylactic shock) based on the knowledge of a skilled practitioner. Examples include, but are not limited to, any of the standard pharmaceutical carriers such as phosphate buffered saline solutions, water, emulsions such as oil/water emulsion, and various types of wetting agents. Exemplary diluents for aerosol or parenteral administration are phosphate buffered saline or normal (0.9%) saline. Compositions comprising such carriers are formulated by well known conventional methods (see, for example, *Remington's Pharmaceutical Sciences*, 18th edition, A. Gennaro, ed., Mack Publishing Co., Easton, Pa., 1990; and *Remington, The Science and Practice of Pharmacy* 20th Ed. Mack Publishing, 2000, which are each hereby incorporated by reference in their entireties, particularly with respect to formulations).

While any suitable carrier known to those of ordinary skill in the art may be employed in the pharmaceutical compositions of this invention, the type of carrier will vary depending on the mode of administration. Compositions can be formulated for any appropriate manner of administration, including, for example, intravenous, intra-arterial, intravesicular, inhalation, intraperitoneal, intrapulmonary, intramuscular, subcutaneous, intra-tracheal, transmucosal, intraocular, intrathecal, or transdermal administration. For parenteral administration, such as subcutaneous injection, the carrier may include, e.g., water, saline, alcohol, a fat, a wax, or a buffer. For oral administration, any of the above carriers or a solid carrier, such as mannitol, lactose, starch, magnesium stearate, sodium saccharine, talcum, cellulose, glucose, sucrose, or magnesium carbonate, may be employed. Biodegradable microspheres (e.g., polylactate polyglycolate) may also be used as carriers.

In some embodiments, the pharmaceutical or non-pharmaceutical compositions include a buffer (e.g., neutral buffered saline, phosphate buffered saline, etc), a carbohydrate (e.g., glucose, mannose, sucrose, dextran, etc), an antioxidant, a chelating agent (e.g., EDTA, glutathione, etc.), a preservative, another compound useful for binding and/or transporting oxygen, an inactive ingredient (e.g., a stabilizer, filler, etc), or combinations of two or more of the foregoing. In some embodiments, the composition is formulated as a lyophilizate. H-NOX proteins may also be encapsulated within liposomes or nanoparticles using well known technology. Other exemplary formulations that can be used for H-NOX proteins are described by, e.g., U.S. Pat. Nos. 6,974,795, and 6,432,918, which are each hereby incorporated by reference in their entireties, particularly with respect to formulations of proteins.

The compositions described herein may be administered as part of a sustained release formulation (e.g., a formulation such as a capsule or sponge that produces a slow release of compound following administration). Such formulations may generally be prepared using well known technology and administered by, for example, oral, rectal or subcutaneous implantation, or by implantation at the desired target site. Sustained-release formulations may contain an H-NOX protein dispersed in a carrier matrix and/or contained within a reservoir surrounded by a rate controlling membrane. Carriers for use within such formulations are biocompatible, and may also be biodegradable. In some embodiments, the formulation provides a relatively constant level of H-NOX protein release. The amount of H-NOX protein contained within a sustained release formulation depends upon the site of implantation, the rate and expected duration of release, and the nature of the condition to be treated or prevented.

In some embodiments, the pharmaceutical composition contains an effective amount of a wild-type or mutant H-NOX protein. The term "effective amount" intends such amount of one or more proteins described herein which in combination with its parameters of efficacy and toxicity should be effective in a given therapeutic form based on the knowledge of the practicing specialist. As is understood in the art, an effective amount can be in one or more doses. As is understood in the clinical context, an effective dosage of a pharmaceutical composition may or may not be achieved in conjunction with another drug, compound, or pharmaceutical composition. Thus, an effective amount can be considered in the context of administering one or more therapeutic agents, and a single agent can be considered to be given in an effective amount if, in conjunction with one or more other agents, a desirable or beneficial result can be or is achieved.

An exemplary dose of hemoglobin as a blood substitute is from about 10 mg to about 5 grams or more of extracellular hemoglobin per kilogram of patient body weight. Thus, in some embodiments, an effective amount of an H-NOX protein for administration to a human is between a few grams to over about 350 grams. Other exemplary doses of an H-NOX protein include about any of 4.4, 5, 10, or 13 G/DL (where G/DL is the concentration of the H-NOX protein solution prior to infusion into the circulation) at an appropriate infusion rate, such as about 0.5 ml/min (see, for example, Winslow, R. Chapter 12 In *Blood Substitutes*). It will be appreciated that the unit content of active ingredients contained in an individual dose of each dosage form need not in itself constitute an effective amount since the necessary effective amount could be reached by the combined effect of a plurality of administrations. The selection of the amount of an H-NOX protein to include in a pharmaceutical composition depends upon the dosage form utilized, the condition being treated, and the particular purpose to be achieved according to the determination of the ordinarily skilled artisan in the field.

Exemplary compositions include genetically engineered, recombinant H-NOX proteins, which may be isolated or purified, comprising one or more mutations that collectively impart altered $O_2$ or NO ligand-binding relative to the corresponding wild-type H-NOX protein, and operative as a physiologically compatible mammalian blood gas carrier. For example, mutant H-NOX proteins as described herein.

The invention also provides blood substitutes comprising or consisting essentially of one or more wild-type or mutant H-NOX proteins. Suitable buffers and other ingredients for formulating blood substitutes are known in the art.

To reduce or prevent an immune response in human subjects who are administered a pharmaceutical composition, human H-NOX proteins (either wild-type human proteins or human proteins into which one or more mutations have been introduced) or other non-antigenic H-NOX proteins (e. g., mammalian H-NOX proteins) can be used. To reduce or eliminate the immunogenicity of H-NOX proteins derived from sources other than humans, amino acids in an H-NOX protein can be mutated to the corresponding amino acids in a human H-NOX. For example, one or more amino acids on the surface of the tertiary structure of a non-human H-NOX protein can be mutated to the corresponding amino acid in a human H-NOX protein.

Therapeutic Applications of H-NOX Proteins

Any of the wild-type or mutant H-NOX proteins (e.g., isolated or purified H-NOX proteins) or pharmaceutical compositions described herein may be used in therapeutic applications. Particular H-NOX proteins can be selected for such applications based on the desired $O_2$ association rate, $O_2$ dissociation rate, dissociation constant for $O_2$ binding, NO stability, NO reactivity, autoxidation rate, plasma retention time, or any combination of two or more of the foregoing for the particular indication being treated. H-NOX proteins can be used to treat cardiovascular disease, neurological disease, tumor hypoxia, loss of blood, or wounds. For example, an $O_2$-binding H-NOX protein can be used in most situations where red blood cells or plasma expanders are currently utilized. Specifically, H-NOX protein can be used as red blood cell substitutes for the treatment of trauma (e.g., battlefield, disaster relief, or accidents), hemorrhages, hemorrhagic shock, surgery (e.g., abdominal aneurysm-surgery, orthopedic surgery such as hip replacement surgery, or any other surgery that produces high blood loss), hemodilution, blood extension uses (e.g., supplementing auto-donation), and any other situation where blood volume is lost or $O_2$ carrying capacity is reduced. Examples of wound repair applications include post-radiation wound repair (e.g., hyperbaric oxygen effect), post-surgical repair, diabetic ulcer repair, and burn wounds.

An oxygen-binging H-NOX-can also be used to temporarily augment $O_2$ delivery during or after pre-donation of autologous blood prior to the return of the autologous blood to the individual (such as a replacement for blood that is removed during surgical procedures where the individual's blood is removed and saved for reinfusion at the end of surgery or during recovery). In some embodiments, the H-NOX proteins also function as simple volume expanders that provide oncotic pressure due to the presence of the large H-NOX protein molecule.

Because the distribution in the vasculature of extracelluar H-NOX proteins is not limited by the size of the red blood cells, H-NOX proteins of the present invention can be used to deliver $O_2$ to areas that red blood cells cannot penetrate. These areas can include any tissue areas that are located downstream of obstructions to red blood cell flow, such as areas downstream of one or more thrombi, sickle cell occlusions, arterial occlusions, peripheral vascular occlusions, angioplasty balloons, surgical instruments, tissues that are suffering from oxygen starvation or are hypoxic, and the like. Additionally, all types of tissue ischemia can be treated using H-NOX proteins. Such tissue ischemias include, for example, perioperative ischemia, stroke, emerging stroke, transient ischemic attacks, myocardial stunning and hibernation, acute or unstable angina, emerging angina, and myocardial infarction (e.g., ST-segment elevation myocardial infarction). Other exemplary cardiovascular indications that can be treated using H-NOX proteins include cardioplegia and sickle cell anemia. Exemplary target indications include conditions of functional hemoglobin deficiency, such as where a blood substitute or $O_2$ carrier is indicated, including blood loss, hypoxia, etc.

H-NOX proteins can also be used as an adjunct with radiation or chemotherapy for the treatment of cancer. In some embodiments, an H-NOX protein is used as a radiation therapy adjuvant in solid tumors (e.g., individuals with poor pre-metastatic prognoses) or as a PDT therapy adjuvant in surface tumors (e.g., colon, lung, or skin cancer, or cancer in another accessible surface or location). H-NOX proteins can be used to treat anemia by providing additional oxygen-carrying capacity in a patient who is suffering from anemia. Exemplary neurological indications include ischemic stroke, traumatic brain injury, and spinal cord injury. The methods and compositions are applicable to both acute (providing rapid oxygen to tissues or a specific site, e.g. acute myocardial infarction, acute local or systemic tissue oxygenation, or blood transfusion), and chronic situations (e.g. post-acute recovery from cardiac infarction).

In various embodiments, the invention features a method of delivering $O_2$ to an individual (e.g., a mammal, such as a primate (e.g., a human, a monkey, a gorilla, an ape, a lemur, etc), a bovine, an equine, a porcine, a canine, or a feline) by administering to an individual in need thereof a wild-type or mutant H-NOX protein in an amount sufficient to deliver $O_2$ to the individual. In some embodiments, the invention provides methods of carrying or delivering blood gas to an individual such as a mammal, comprising the step of delivering (e.g., transfusing, etc) to the blood of the individual (e.g., a mammal) one or more of H-NOX compositions. Methods for delivering $O_2$ carriers to blood or tissues (e.g., mammalian blood or tissues) are known in the art. In various embodiments, the H-NOX protein is an apoprotein that is capable of binding heme or is a holoprotein with heme bound. The H-NOX protein may or may not have heme bound prior to the administration of the H-NOX protein to the individual. In some embodiments, $O_2$ is bound to the H-NOX protein before it is delivered to the individual. In other embodiments, $O_2$ is not bound to the H-NOX protein prior to the administration of the protein to the individual, and the H-NOX protein transports $O_2$ from one location in the individual to another location in the individual.

The methods of the present invention can be used to treat any individual. For use herein, unless clearly indicated otherwise, "an individual" as used herein intends a mammal, including but not limited to, a primate (e.g., a human, monkey, gorilla, ape, lemur, etc.), a bovine, an equine, a porcine, a canine, and a feline. Thus, the invention finds use in both human medicine and in the veterinary context, including use in agricultural animals and domestic pets. The individual may have been diagnosed with, is suspected of having, or is at risk of developing an indication, such as a cardiovascular disease, a neurological disease, hypoxia (e.g., tumor hypoxia), a loss of blood, or a wound. The individual may exhibit one or more symptoms associated with the indication. The individual can be genetically or otherwise predisposed to developing such a condition.

As used herein, "in need thereof" includes individuals who have a condition or disease (such as a cardiovascular disease, a neurological disease, hypoxia such as tumor hypoxia, a loss of blood, or a wound) or are "at risk" for the condition or disease. As used herein, an "at risk" individual is an individual who is at risk of development of a condition, such as a cardiovascular disease, a neurological disease, hypoxia (e.g., tumor hypoxia), a loss of blood, or a wound. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). These risk factors include, but are not limited to, age, sex, race, diet, history of previous disease, presence of precursor disease, genetic (i.e., hereditary) considerations, and environmental exposure. Surgery, presence in or near a military or war zone, or conditions that predispose an individual to blood loss (such as hemophilia) are exemplary risk factors for blood loss.

These methods can be used to treat or delay any condition for which delivery of $O_2$ is beneficial. By "treatment" or "treating" is meant an approach for obtaining a beneficial or desired result, including clinical results. For purposes of this invention, beneficial or desired results include, but are not limited to, alleviation of symptoms associated with a condition (such as, but not limited to, a cardiovascular disease, a neurological disease, hypoxia such as tumor hypoxia, a loss of blood, or a wound), diminishment of the extent of the symptoms associated with a condition, or prevention of a worsening of the symptoms associated with a condition. In some embodiments, treatment with a one or more proteins disclosed herein is accompanied by no or fewer side effects than are associated with currently available therapies.

As used herein, "delaying" development of a disease or condition means to defer, hinder, slow, retard, stabilize and/or postpone development of the disease or condition, such as a cardiovascular disease, a neurological disease, hypoxia (e.g., tumor hypoxia), a loss of blood, or a wound. This delay can be of varying lengths of time, depending on the history of the disease and/or individual being treated. As is evident to one skilled in the art, a sufficient or significant delay can, in effect, encompass prevention, in that the individual does not develop the disease or condition. For example, the method may reduce the probability of disease development in a given time frame and/or reduce the extent of the disease in a given time frame, when compared to not using the method. In some embodiments, such comparisons are based on clinical studies using a. statistically significant number of subjects. Disease development can be detectable using standard clinical techniques. Development may also refer to disease progression that can be initially undetectable and includes occurrence, recurrence, and onset.

Wild-type and mutant H-NOX proteins with a relatively low $K_D$ for $O_2$ (such as less than about 80 nM or less than about 50 nM) are expected to be particularly useful to treat tissues with low oxygen tension (such as tumors, some wounds, or other areas where the oxygen tension is very low, such as a p50 below 1 mm Hg). The high affinity of such H-NOX proteins for $O_2$ may increase the length of time the $O_2$ remains bound to the H-NOX protein, thereby reducing the amount of $O_2$ that is released before the H-NOX protein reaches the tissue to be treated.

While not intending to be bound by a particular theory, the utility of a cell-free red cell substitute as a resuscitation fluid is believed to be influenced by the p50 of the $O_2$ carrier. For example, a PEGylated hemoglobin-based $O_2$ carrier called MP4 appears to deliver $O_2$ more effectively to the microvasculature than some lower affinity hemoglobin-based $O_2$ carriers. MP4 is reported to have a p50 of ~5 mmHg, (perhaps 100 to 200 nm $K_D$), and the p50 of stroma-free hemoglobin is 14 mm Hg (~400 nm $K_r$)). Since MP4 is capable of oxygen delivery in tissues ($PO_2$ ~5 to 10 mm Hg), it is likely that the appropriate $O_2$ affinity for vehicles to deliver $O_2$ to hypoxic tissues is less than about 5 mm Hg, and perhaps less than about 2 mm Hg, which roughly corresponds to a $K_D$ less than about 80 nm. These values indicate that MP4 has been engineered with a higher $O_2$ affinity (lower p50) than native hemoglobin. From an equilibrium perspective, this suggests that high-affinity $O_2$-binding proteins may be more successful in delivering $O_2$ to areas of low $O_2$ tension, such as the peripheral vasculature.

In some embodiments for the direct delivery of an H-NOX protein with bound $O_2$ to a particular site in the body (such as a tissue, organ, wound, or tumor), the $k_{off}$ for $O_2$ is more important than the $K_D$ value because $O_2$ is already bound to the protein (making the $k_{on}$ less important) and oxygen needs to be released at or near a particular site in the body (at a rate influenced by the $k_{off}$). In some embodiments, the $k_{off}$ may also be important when H-NOX proteins are in the presence of red cells in the circulation, where they facilitate diffusion of $O_2$ from red cells, and perhaps prolonging the ability of diluted red cells to transport $O_2$ to further points in the vasculature.

In some embodiments for the delivery of an H-NOX protein that circulates in the bloodstream of an individual, the H-NOX protein binds $O_2$ in the lungs and releases $O_2$ at one or more other sites in the body. For some of these applications, the $K_D$ value is more important than the $k_{off}$ since $O_2$ binding is at or near equilibrium. In some embodiments for extreme hemodilution, the $K_D$ more important than the $k_{off}$ when the H-NOX protein is the primary $O_2$ carrier because the H-NOX protein will bind and release $O_2$ continually as it travels through the circulation. Since hemoglobin has a p50 of 14 mm Hg, red cells (which act like capacitors) have a p50 of 30 mm Hg, and HBOCs have been developed with ranges between 5 mm Hg and 90 mm Hg, the optimal $K_D$ range for H-NOX proteins may therefore be between 2 mm Hg to 100 mm Hg for some applications.

H-NOX proteins can also be used for imaging. In particular, light imaging (e.g., optical coherence tomography; see, for example, Villard, J. W. (2002). "Use of a Blood Substitute to Determine Instantaneous Murine Right Ventricular Thickening with Optical Coherence Tomography," *Circulation* 105:1843-1849, which is incorporated by reference in its entirety particularly with respect to optical coherence tomography) is obfuscated by erythrocytes. Perfusion with an H-NOX solution allows for clearer images of the circulation and vessel walls because the H-NOX protein is much smaller than erythrocytes.

H-NOX proteins and pharmaceutical compositions of the invention can be administered to an individual by any conventional means such as by oral, topical, intraocular, intrathecal, intrapulmonary, intra-tracheal, or aerosol administration; by transdermal or mucus membrane adsorption; or by injection (e.g., subcutaneous, intravenous, intra-arterial, intravesicular, or intramuscular injection). H-NOX proteins may also be included in large volume parenteral solutions for use as blood substitutes. In exemplary embodiments, the H-NOX protein is administered to the blood (e.g., administration to a blood vessel such as a vein, artery, or capillary), a wound, a tumor, a hypoxic tissue, or a hypoxic organ of the individual.

In some embodiments, a sustained continuous release formulation of the composition is used. Administration of an H-NOX protein can occur, e.g., for a period of seconds to hours depending on the purpose of the administration. For example, as a blood delivery vehicle, an exemplary time course of administration is as rapid as possible. Other exemplary time courses include about any of 10, 20, 30, 40, 60, 90, or 120 minutes. Exemplary infusion rates for H-NOX solutions as blood replacements are from about 30 mL/hour to about 13,260 mL/hour, such as about 100 mL/hour to about 3,000 mL/hour. An exemplary total dose of*H-NOX protein is about 900 mg/kg administered over 20 minutes at 13,260 mL/hour. An exemplary total dose of H-NOX protein for a swine is about 18.9 grams.

Exemplary dosing frequencies include, but are not limited to, at least 1, 2, 3, 4, 5, 6, or 7 times (i.e., daily) a week. In some embodiments, an H-NOX protein is administered at least 2, 3, 4, or 6 times a day. The H-NOX protein can be administered, e.g., over a period of a few days or weeks. In some embodiments, the H-NOX protein is administrated for a longer period, such as a few months or years. The dosing frequency of the composition may be adjusted over the course of the treatment based on the judgment of the administering physician.

As noted above, the selection of dosage amounts for H-NOX proteins depends upon the dosage form utilized, the frequency and number of administrations, the condition being treated, and the particular purpose to be achieved according to the determination of the ordinarily skilled artisan in the field. In some embodiments, an effective amount of an H-NOX protein for administration to human is between a few grams to over 350 grams.

In some embodiments, two or more different H-NOX proteins are administered simultaneously, sequentially, or concurrently. In some embodiments, another compound or therapy useful for the delivery of $O_2$ is administered simultaneously, sequentially, or concurrently with the administration of one or more H-NOX proteins.

Other exemplary therapeutic applications for which H-NOX proteins can be used are described by, e.g., U.S. Pat. Nos. 6,974,795, and 6,432,918, which are each hereby incorporated by reference in their entireties, particularly with respect to therapeutic applications for $O_2$ carriers.

Industrial Applications of H-NOX Proteins

The H-NOX proteins and composition described herein can also be used for a number of in vitro or industrial applications (see, e.g., U.S. Pat. No. 6,455,676, which is hereby incorporated by reference in its entirety, particularly with respect to in vitro or industrial applications). Particular H-NOX proteins can be selected for such applications based on the desired $O_2$ association rate, $O_2$ dissociation rate, dissociation constant for $O_2$ binding, NO stability, NO reactivity, autoxidation rate, half-life, or any combination of two or more of the foregoing for the particular application. In various embodiments of industrial applications, the H-NOX protein is an apoprotein that is capable of binding heme or is a holoprotein with heme bound.

H-NOX proteins can be used, for example, as reference standards for analytical instrumentation needing such reference standards. The delivery of $O_2$ by H-NOX proteins can be used for the enhancement of cell growth in cell culture by maintaining or increasing $O_2$ levels in vitro. For these applications, H-NOX proteins can be added to a cell culture medium to deliver $O_2$ to the medium (and to cells in the medium). In some embodiments, $O_2$ is bound to the H-NOX protein before it is added to the cell culture medium. In other embodiments, $O_2$ is not bound to the H-NOX protein prior to its addition to the cell culture medium, and the H-NOX protein transports $O_2$ from one location in the medium to another location in the medium.

Alternatively, cells can be genetically modified to encode an H-NOX protein to increase the amount of $O_2$ obtained by the cells. For example, cells that express a compound of interest (such as a small molecule or protein useful in pharmaceutical applications) can be genetically modified to also produce a H-NOX protein that facilitates growth of the cells, especially under low $O_2$ conditions (Sullivan et al. (2006). "Targeted Oxygen Delivery within Hepatic Hollow Fiber Bioreactors via Supplementation of Hemoglobin-Based Oxygen Carriers," *Biotechnol. Prog.* 22:1374-87; Frey et al. (2001). "Dissection of Central Carbon Metabolism of Hemoglobin-Expressing *Escherichia Coli* by 13C Nuclear Magnetic Resonance Flux distribution Analysis in Microaerobic Bioprocesses," *Applied and Environmental Biology* 67(2):680-687). Moreover, the H-NOX proteins can be used to remove $O_2$ from solutions requiring the removal of $O_2$.

Kits with H-NOX Proteins

Also provided are articles of manufacture and kits that include any of the H-NOX proteins described herein and suitable packaging. In some embodiments, the invention includes a kit with (i) an H-NOX protein (such as a wild-type or mutant H-NOX protein described herein or formulations thereof as described herein) and (ii) instructions for using the kit to deliver $O_2$ to an individual. In various embodiments, the invention features a kit with (i) an H-NOX protein (such as a wild-type or mutant H-NOX protein described herein or formulations thereof as described herein) and (ii) instructions for using the kit for any of the industrial uses described herein (e.g., use of an H-NOX protein as a reference standard for analytical instrumentation needing such a reference standard, enhancement of cell growth in cell culture by maintaining or increasing $O_2$ levels in vitro, addition of $O_2$ to a solution, or removal of $O_2$ from a solution).

Suitable packaging for compositions described herein are known in the art, and include, for example, vials (e.g., sealed vials), vessels, ampules, bottles, jars, flexible packaging (e.g., sealed Mylar or plastic bags), and the like. These articles of manufacture may further be sterilized and/or sealed. Also provided are unit dosage forms comprising the compositions described herein. These unit dosage forms can be stored in a suitable packaging in single or multiple unit dosages and may also be further sterilized and sealed. Instructions supplied in the kits of the invention are typically written instructions on a label or package insert (e.g., a paper sheet included in the kit), but machine-readable instructions (e.g., instructions carried on a magnetic or optical storage disk) are also acceptable. The instructions relating to the use of H-NOX proteins generally include information as to dosage, dosing schedule, and route of administration for the intended treatment or industrial use. The kit may further comprise a description of selecting an individual suitable or treatment.

The containers may be unit doses, bulk packages (e.g., multi-dose packages) or sub-unit doses. For example, kits may also be provided that contain sufficient dosages of H-NOX proteins disclosed herein to provide effective treatment for an individual for an extended period, such as about any of a week, 2 weeks, 3 weeks, 4 weeks, 6 weeks, 8 weeks, 3 months, 4 months, 5 months, 6 months, 7 months, 8 months, 9 months, or more. Kits may also include multiple unit doses of H-NOX proteins and instructions for use and packaged in quantities sufficient for storage and use in pharmacies, for example, hospital pharmacies and compounding pharmacies. In some embodiments, the kit includes a dry (e.g., lyophilized) composition that can be reconstituted, resuspended, or rehydrated to form generally a stable aqueous suspension of H-NOX protein.

Exemplary Methods for Production of H-NOX Proteins

The present invention also provides methods for the production of any of the mutant H-NOX proteins described herein. In some embodiments, the method involves culturing a cell that has a nucleic acid encoding a mutant H-NOX protein under conditions suitable for production of the mutant H-NOX protein. In various embodiments, the mutant H-NOX is also purified (such as purification of the H-NOX protein from the cells or the culture medium).

As noted above, the sequences of several wild-type H-NOX proteins and nucleic acids are known and can be use to generate mutant H-NOX proteins and nucleic acids of the present invention. Techniques for the mutation, expression, and purification of recombinant H-NOX proteins have been described by, e.g., Boon, E. M. et al. (2005). "Molecular Basis For NO Selectivity in Soluble Guanylate Cyclase," *Nature Chemical Biology* 1:53-59 and Karow, D. S. et al. (Aug. 10, 2004). "Spectroscopic Characterization of The Soluble Guanylate Cyclase-Like Heme Domains From *Vibrio Cholerae* And *Thermoanaerobacter Tengcongensis,*" *Biochemistry* 43(31):10203-10211, which is hereby incorporated by reference in its entirety, particularly with respect to the mutation, expression, and purification of recombinant H-NOX proteins. These techniques or other standard techniques can be used to generate any mutant H-NOX protein.

In particular, mutant H-NOX proteins described herein can be generated a number of methods that are known in the art. Mutation can occur at either the amino acid level by chemical modification of an amino acid or at the codon level by alteration of the nucleotide sequence that codes for a given amino acid. Substitution of an amino acid at any given position in a protein can be achieved by altering the codon that codes for that amino acid. This can be accomplished by site-directed mutagenesis using, for example: (i) the Amersham technique (Amersham mutagenesis kit, Amersham, Inc., Cleveland, Ohio) based on the methods of Taylor, J. W. et al. (Dec. 20, 1985). "The Use of Phosphorothioate-Modified DNA in Restriction Enzyme Reactions to Prepare Nicked DNA," *Nucleic Acids Res.* 13(24):8749-8764; Taylor, J. W. et al. (Dec. 20, 1985). "The Rapid Generation of Oligonucleotide-Directed Mutations at High Frequency Using Phosphorothioate-Modified DNA," *Nucleic Acids Res.* 13(24):8765-8785; Nakamaye, K. L. et al. (Dec. 22, 1986). "Inhibition of Restriction Endonuclease Nci I Cleavage by Phosphorothioate Groups and its Application to Oligonucleotide-Directed Mutagenesis," *Nucleic Acids Res.* 14(24):9679-9698; and Dente et al. (1985). in DNA Cloning, Glover, Ed., IRL Press, pages 791-802, (ii) the Promega kit (Promega Inc., Madison, Wis.), or (iii) the Biorad kit (Biorad Inc., Richmond, Calif.), based on the methods of Kunkel, T. A. (January 1985). "Rapid And Efficient Site-Specific Mutagenesis Without Phenotypic Selection," *Proc. Natl. Acad. Sci. USA* 82(2):488-492; Kunkel, T. A. (1987). "Rapid And Efficient Site-Specific Mutagenesis Without Phenotypic, Selection," *Methods Enzymol.* 154:367-382; Kunkel, U.S. Pat. No. 4,873,192, which are each hereby incorporated by reference in their entireties, particularly with respect to the mutagenesis of proteins. Mutagenesis can also be accomplished by other commercially available or non-commercial means, such as those that utilize site-directed mutagenesis with mutant oligonucleotides.

Site-directed mutagenesis can also be accomplished using PCR-based mutagenesis such as that described in Zhengbin et al. (1992). pages 205-207 in PCR Methods and Applications, Cold Spring Harbor Laboratory Press, New York; Jones, D. H. et al. (February 1990). "A Rapid Method For Site-Specific Mutagenesis And Directional Subcloning by Using the Polymerase Chain Reaction to Generate Recombinant Circles," *Biotechniques* 8(2):178-183; Jones, D. H. et al. (January 1991). "A Rapid Method For Recombination And Site-Specific Mutagenesis by Placing Homologous Ends on DNA Using Polymerase Chain Reaction," *Biotechniques* 10(1):62-66, which are each hereby incorporated by reference in their entireties, particularly with respect to the mutagenesis of proteins. Site-directed mutagenesis can also be accomplished using cassette mutagenesis with techniques that are known to those of skill in the art.

A mutant H-NOX nucleic acid can be incorporated into a vector, such as an expression vector, using standard techniques. For example, restriction enzymes can be used to cleave the mutant H-NOX nucleic acid and the vector. Then, the compatible ends of the cleaved mutant H-NOX nucleic acid and the cleaved vector can be ligated. The resulting vector can be inserted into a cell (e.g., an insect cell, a plant cell, a yeast cell, or a bacterial cell) using standard techniques (e.g., electroporation) for expression of the encoded H-NOX protein.

In particular, heterologous proteins have been expressed in a number of biological expression systems, such as insect cells, plant cells, yeast cells, and bacterial cells. Thus, any suitable biological protein expression system can be utilized to produce large quantities of recombinant H-NOX protein. In some embodiments, the H-NOX protein (e.g., a mutant or wild-type H-NOX protein) is an isolated protein. As used herein, an "isolated protein" means a protein separated from one or more components with which the protein is naturally associated in nature, including, for example, nucleic acids, lipids, and other proteins. An isolated protein also does not occur in a library of proteins, such as a library of 2, 5, 10, 20, 50 or more different proteins. An isolated protein can be obtained, for example, by expression of a recombinant nucleic acid encoding the protein or by chemical synthesis of the protein.

If desired, H-NOX proteins can be purified using standard techniques. As used herein, a "purified protein" means a protein (e.g., a mutant or wild-type H-NOX protein) that has been separated from one or more components that are present when the protein is produced. In some embodiments, the protein is at least about 60%, by weight, free from other components that are present when the protein is produced. In various embodiments, the protein is at least about 75%, 90%, or 99%, by weight, pure. A purified protein can be obtained, for example, by purification (e.g., extraction) from a natural source, a recombinant expression system, or a reaction mixture for chemical synthesis. Exemplary methods of purification include immunoprecipitation, column chromatography such as immunoaffinity chromatography, magnetic bead immunoaffinity purification, and panning with a plate-bound antibody, as well as other techniques known to the skilled artisan. Purity can be assayed by any appropriate method, e.g., by column chromatography, polyacrylamide gel electrophoresis, or HPLC analysis. In some embodiments, the purified protein is incorporated into a pharmaceutical composition of the invention or used in a method of the invention. The pharmaceutical composition of the invention may have additives, carriers, or other components in addition to the purified protein.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed. Unless indicated otherwise, temperature is in degrees Centigrade and pressure is at or near atmospheric.

Example 1

Production of Wild-Type and Mutant H-NOX Proteins

Wild-type and mutant H-NOX proteins were produced, expressed, and purified using standard methods, essentially as described by Boon, E. M. et al. (2005). "Molecular Basis For NO Selectivity in Soluble Guanylate Cyclase," *Nature Chemical Biology* 1:53-59 and Karow, D. S. et al. (Aug. 10, 2004). "Spectroscopic Characterization of The Soluble Guanylate Cyclase-Like Herne Domains From *Vibrio Cholerae* And *Thermoanaerobacter Tengcongensis," Biochemistry* 43(31):10203-10211, which are both hereby incorporated by reference in their entireties, particularly with respect to the mutagenesis, expression, and purification of H-NOX proteins. Mutagenesis was performed using the QuickChange® protocol from Strategene (La Jolla, Calif.). Expression of the proteins in cell culture and subsequent purification of the proteins was performed as described by Karow, D. S. et al. (Aug. 10, 2004). "Spectroscopic Characterization of The Soluble Guanylate Cyclase-Like Heme Domains From *Vibrio Cholerae* And *Thermoanaerobacter Tengcongensis," Biochemistry* 43(31):10203-10211.

Example 2

Characterization of Mutant H-NOX Proteins as Oxygen Delivery Vehicles

Kinetic $K_D$: Ratio of $k_{off}$ to $k_{on}$

The kinetic $K_D$ value was determined for wild-type and mutant H-NOX proteins essentially as described by Boon, E. M. et al. (2005). "Molecular Basis For NO Selectivity in Soluble Guanylate Cyclase," *Nature Chemical Biology* 1:53-59, which is hereby incorporated by reference in its entirety, particularly with respect to the measurement of $O_2$ association rates, $O_2$ dissociation rates, dissociation constants for $O_2$ binding, autoxidation rates, and NO dissociation rates.

$k_{on}$ ($O_2$ Association Rate)

$O_2$ association to the heme was measured using flash photolysis at 20° C. It was not possible to flash off the $Fe^{II}$—$O_2$ complex as a result of the very fast geminate recombination kinetics; thus, the $Fe^{II}$—CO complex was subjected to flash photolysis with laser light at 560 nm (Hewlett-Packard, Palo Alto, Calif.), producing the 5-coordinate $Fe^{II}$ intermediate, to which the binding of molecular $O_2$ was followed at various wavelengths. Protein samples were made by anaerobic reduction with 10 mM dithionite, followed by desalting on a PD-10 column (Millipore, Inc., Billerica, Mass.). The samples were then diluted to 20 μM heme in 50 mM TEA, 50 mM NaCl, pH 7.5 buffer in a controlled-atmosphere quartz cuvette, with a size of 100 μL to 1 mL and a path-length of 1-cm. CO gas was flowed over the headspace of this cuvette for 10 minutes to form the $Fe^{II}$—CO complex, the formation of which was verified by UV-visible spectroscopy (Soret maximum 423 nm). This sample was then either used to measure CO-rebinding kinetics after flash photolysis while still under 1 atmosphere of CO gas, or it was opened and stirred in air for 30 minutes to fully oxygenate the buffer before flash photolysis to watch $O_2$-rebinding events. $O_2$ association to the heme was monitored at multiple wavelengths versus time. These traces were fit with a single exponential using Igor Pro software (Wavemetrics, Inc., Oswego, Oreg.; latest 2005 version). This rate was independent of observation wavelength but dependent on $O_2$ concentration. UV-visible spectroscopy was used throughout to confirm all the complexes and intermediates (Cary 3K, Varian, Inc. Palo Alto, Calif.). Transient absorption data were collected using instruments described in Dmochowski, I. J. et al. (Aug. 31, 2000). "Enantiomeric Discrimination of Ru-Substrates by Cytochrome P450cam," *Inorg Biochem.* 81(3):221-228, which is hereby incorporated by reference in its entirety, particularly with respect to instrumentation. The instrument has a response time of 20 ns, and the data are digitized at 200 megasamples $s^{-1}$.

$k_{off}$ ($O_2$ Dissociation Rate)

To measure the $k_{off}$, $Fe^{II}$—$O_2$ complexes of protein (5 μM heme), diluted in anaerobic 50 mM TEA, 50 mM NaCl, pH 7.5 buffer, were rapidly mixed with an equal volume of the same buffer (anaerobic) containing various concentrations of dithionite and/or saturating CO gas. Data were acquired on a HI-TECH Scientific SF-61 stopped-flow spectrophotometer equipped with a Neslab RTE-100 constant-temperature bath set to 20° C. (TGK Scientific LTD., Bradford On Avon, United Kingdom). The dissociation of $O_2$ from the heme was monitored as an increase in the absorbance at 437 nm, a maximum in the $Fe^{II}$—$Fe^{II}$—$O_2$ difference spectrum, or 425 nm, a maximum in the $Fe^{II}$—$Fe^{II}$—CO difference spectrum. The final traces were fit to a single exponential using the software that is part of the instrument. Each experiment was done a minimum of six times, and the resulting rates were averaged. The dissociation rates measured are independent of dithionite concentration (100, 50, 25, 10, 5 and 2.5 mM dithionite were tested) and independent of saturating CO as a trap for the reduced species, both with and without 10 mM dithionite present.

Kinetic $K_D$

The kinetic $K_D$ is determined by calculating the ratio of $k_{off}$ to $k_{on}$ using the measurements of $k_{off}$ and $k_{on}$ described above.

Calculated $K_D$

To measure the calculated $K_D$, the values for the $k_{off}$ and kinetic $K_D$ that were obtained as described above were graphed. A linear relationship between $k_{off}$ and kinetic $K_D$ was defined by the equation (y=mx+b). $k_{off}$ values were then interpolated along the line to derive the calculated $K_D$ using Excel: MAC 2004 (Microsoft, Redmond, Wash.). In the absence of a measured $k_{on}$, this interpolation provides a way to relate $k_{off}$ to $IC_D$.

Rate of Autoxidation

To measure the rate of autoxidation, the protein samples were anaerobically reduced, then diluted to 5 μM heme in aerobic 50 mM TEA, 50 mM NaCl, pH 7.5 buffer. These samples were then incubated in a Cary 3E spectrophotometer equipped with a Neslab RTE-100 constant-temperature bath set to 37° C. and scanned periodically (Cary 3E, Varian, Inc., Palo Alto, Calif.). The rate of autoxidation was determined from the difference between the maximum and minimum in the $Fe^{III}$—$Fe^{II}$ difference spectrum plotted versus time and fit with a single exponential using Excel: MAC 2004 (Microsoft, Redmond, Wash.).

Rate of Reaction with NO

NO reactivity was measured using purified proteins (Tt WT HNOX, Tt Y140H HNOX, and *Homo sapiens* hemoglobin (Hs Hb)) prepared at 2 μM in buffer A and NO prepared at 200 μM in Buffer A (Buffer A: 50 mM Hepes, pH 7.5, 50 mM NaCl). Data were acquired on a HI-TECH Scientific SF-61 stopped-flow spectrophotometer equipped with a Neslab RTE-100 constant-temperature bath set to 20° C. (TGK Scientific LTD., Bradford On Avon, United Kingdom). The protein was rapidly mixed with NO in a 1:1 ratio with an integration time of 0.00125 sec. The wavelengths of maximum change were fit to a single exponential using the software that is part of the spectrometer, essentially measuring the rate-limiting step of oxidation by NO. The end products of the reaction were ferric-NO for the HNOX proteins and ferric-aquo for Hs Hb.

p50 Measurements

If desired, the p50 value for mutant or wild-type H-NOX proteins can be measured as described by Guarnone, R. et al. (September/October 1995). "Performance Characteristics of Hemox-Analyzer For Assessment of The Hemoglobin Dissociation Curve," *Haematologica* 80(5):426-430, which is hereby incorporated by reference in its entirety, particularly with respect to the measurement of p50 values. The p50 value is determined using a HemOx analyzer. The measurement chamber starts at 0% oxygen and slowly is raised, incrementally, towards 100% oxygen. An oxygen probe in the chamber measures the oxygen saturation %. A second probe (UV-V is light) measures two wavelengths of absorption, tuned to the alpha and beta peaks of the hemoprotein's (e.g., a protein such as H-NOX complexed with heme) UV-V is spectra. These absorption peaks increase linearly as hemoprotein binds oxygen. The percent change from unbound to 100% bound is then plotted against the % oxygen values to generate a curve. The p50 is the point on the curve where 50% of the hemoprotein is bound to oxygen.

Specifically, the Hemox-Analyzer (TCS Scientific Corporation, New Hope, Pa.) determines the oxyhemoprotein dissociation curve (ODC) by exposing 50 μL of blood or hemoprotein to an increasing partial pressure of oxygen and deoxygenating it with nitrogen gas. A Clark oxygen electrode detects the change in oxygen tension, which is recorded on the x-axis of an x-y recorder. The resulting increase in oxyhemoprotein fraction is simultaneously monitored by dual-wavelength spectrophotometry at 560 nm and 576 nm and displayed on the y-axis. Blood samples are taken from the antemedial vein, anticoagulated with heparin, and kept at 4° C. on wet ice until the assay. Fifty μL of whole blood are diluted in 5 μL of Hemox-solution, a manufacturer-provided buffer that keeps the pH of the solution at a value of 7.4±0.01. The sample-buffer is drawn into a cuvette that is part of the Hemox-Analyzer and the temperature of the mixture is equilibrated and brought to 37° C.; the sample is then oxygenated to 100% with air. After adjustment of the $pO_2$ value the sample is deoxygenated with nitrogen; during the deoxygenation process the curve is recorded on graph paper. The P50 value is extrapolated on the x-axis as the point at which $O_2$ saturation is 50% using the software that is part of the Hemox-Analyzer. The time required for a complete recording is approximately 30 minutes.

The p50 values for any of the H-NOX proteins can be compared to that of hemoglobin as an indication of the relative affinity of the H-NOX protein for $O_2$ compared to that of hemoglobin. Table 13 lists previously reported p50 values for hemoglobin.

TABLE 13

Hemoglobin variants and their reported oxygen affinities

| Name | Modification | $K_D$ (nM) | p50 (mmHg) | Reference/ Manufacturer |
|---|---|---|---|---|
| Hemoglobin (stroma-free) | | ~400 | 14 | |
| Hemoglobin (RBC's) | | | 27 | |
| Hemopure (HBOC-201) | Bovine polymerized | | 36 | Biopure |
| Oxyglobin (HBOC-301 | Bovine polymerized | | 54 | Biopure |
| Hemospan (MP4) | Maleimide-PEG | | 5 | Sangart |
| Polyheme | Pyridoxal | | 28-30 | Northfield Labs |
| Hemolink | 0-raffinose | | 40 | Hemosol |
| Hemassist | Diaspirin | | 32 | Baxter |

Viscosity Measurements

If desired, the viscosity of the H-NOX solutions can be measured using a cone/plate rheometer (model DV-III, Brookfield; Middleboro, Mass.) with the CPE-40 cone spindle at a shear rate of 200/s. Solutions with viscosities between 1 and 4 centipoise (cP) administered in hemodilution oxygen delivery experiments are reported as safe (Winslow, R. M. et al. (October 2004). "Comparison of PEG-Modified Albumin And Hemoglobin in Extreme Hemodilution in the Rat," *J Appl Physiol.* 97(4):1527-1534, U.S. Pat. Nos. 6,974,795, and 6,432,918, which are each hereby incorporated by reference in their entireties, particularly with respect to the measurement of viscosity). Accordingly, in some embodiments, the viscosity of the H-NOX protein solution is between 1 and 4 cP.

Colloid Oncotic Pressure Measurements

If desired, the colloid oncotic pressure can be measured using a colloid osmometer according to the manufacturer's instructions (model 4420, Wescor; Logan, Utah). Exemplary methods to measure colloid oncotic pressure are described in Vandegriff, K. D. et al. (November 1997). "Colloid Osmotic Properties of Modified Hemoglobins: Chemically Cross-Linked Versus Polyethylene Glycol Surface-Conjugated," *Biophys. Chem.* 69(1):23-30, in the world-wide web at "anaesthesiamcq.com/FluidBook/f12_4.php;" U.S. Pat. Nos. 6,974,795, and 6,432,918, which are each hereby incorporated by reference in their entireties, particularly with respect to measuring colloid oncotic pressure. Solutions with colloid oncotic pressure between 20 and 50 mm Hg administered in hemodilution oxygen delivery experiments are reported as safe (Winslow, R. M. et al. (October 2004). "Comparison of PEG-Modified Albumin And Hemoglobin in Extreme Hemodilution in the Rat," *J. Appl. Physiol.* 97(4):1527-1534). Accordingly, in some embodiments, the colloid oncotic pressure of the H-NOX protein solution is between 20 and 50 mm Hg.

Example 3

Surgery Model for $O_2$ Carrier H-NOX Mutants: Comparison of a Panel of $O_2$ Carrier H-NOX Mutants and H-NOX in Extreme Hemodilution in the Rat To evaluate the ability of H-NOX mutants to transport $O_2$ in a surgery model, an adaptation of an established protocol (Winslow, R. M. et al. (October 2004). "Comparison of PEG-Modified Albumin And Hemoglobin in Extreme Hemodilution in the Rat," *J. Appl. Physiol.* 97(4):1527-1534, which is hereby incorporated by reference in its entirety, particularly with respect to surgery models) can be performed using continuous exchange transfusion in the rat.

Acclimated male Sprague-Dawley rats are anesthetized by intramuscular injection of a rodent cocktail containing a mixture of ketamine (40 mg/kg), acepromazine (0.75 mg/kg), and xylazine (3 mg/kg). Catheters made of polyetheylene tubing (Clay Adams PE-50 and PE-10) are implanted into both femoral arteries and one femoral vein. The catheters are externalized at the base of the tail and covered by a tail sheath for protection and future access. After closure of the surgical wounds, animals are returned to their cages and allowed to wake up and recover for 24 h before initiation of the experiment. Animals are given free access to food and water during recovery. For the hemodynamic measurements, the femoral artery catheter is connected through a stopcock and a 23-gauge needle to a pressure transducer, and the arterial pressure is sampled continuously at 100 Hz.

Arterial pH, $PCO_2$, and $PO_2$ are measured in a Bayer model 248 blood-gas analyzer using 100-μl heparinized samples of blood. Lactic acid is measured in femoral artery blood using a YSI lactate analyzer (Yellow Springs Institute, Yellow Springs, Ohio). Total $CO_2$, standard bicarbonate (HCO), and base excess (BE) are calculated from $PCO_2$, pH, and Hb concentration.

Fully conscious animals (n=5 for each treatment group) are placed in Plexiglas restrainers. The arterial and venous cannulae are flushed with 200 and 100 respectively, of heparinized saline (100 U/ml). The arterial and venous catheters are connected to an infusion pump (Labconco model 4262000, Kansas City, Mo.), and exchange-transfusion carried out at a rate of 0.5 ml/min for 100 minutes. Thus the total volume of solution exchanged is 50 ml or 2.5 blood volumes. The peristaltic pump is operated so that blood is removed at exactly the same rate as test material is infused. Test solutions are warmed to 37° C. in a water bath before infusion and kept warm during infusion by a heating pad. At the end of the 100-minute exchange period, animals that survive are monitored for an additional 70 minutes before euthanasia. Blood samples (0.3 ml) are taken every 10 minutes for hematologic and blood-gas analysis.

The treatment groups include animals that are administered one or more H-NOX proteins that have been previously tested for NO or $O_2$ dissociation constants, NO-reactivity, stability, physio-compatibility, or combinations of two or more of the foregoing. Red blood cell H-NOX and pentastarch treated groups provide positive and negative controls, respectively.

Objective end points include survival and the onset of anaerobic metabolism, signaled by acid-base derangement and accumulation of lactic acid. H-NOX proteins that increase the survival rate (such as producing a statistically significant increase in survival rate) compared to that of the control group are useful for oxygenating tissues in extreme hemodilution. Such H-NOX proteins are expected to also be useful to treat other indications for which delivery of $O_2$ is beneficial.

Example 4

Trauma Model for $O_2$ Carrier H-NOX Mutants: Comparing the Effects of $O_2$ Carrier H-NOX Mutants and Recombinant-Hemoglobin Solutions on Blood Pressure, Intestinal Blood Flow, and Gut Oxygenation in a Rat Model of Hemorrhagic Shock To evaluate the ability of H-NOX proteins to transport $O_2$ in a trauma model, an adaptation of an established protocol (Raat, N. J. et al. (January 2005). "Effects of Recombinant-Hemoglobin Solutions rHb2.0 and rHb1.1 on Blood Pressure, Intestinal Blood Flow, And Gut Oxygenation in a Rat Model of Hemorrhagic Shock," *J Lab Clin Med.* 145(1):21-32, which is hereby incorporated by reference in its entirety, particularly with respect to animal models of trauma) can be performed in a fixed-pressure (40 mm Hg) rat model of hemorrhagic shock and resuscitation.

Wistar rats are anesthetized with an intraperitoneal injection of a mixture of 90 mg/kg ketamine, O_5 mg/kg medetomidine, and 0.005 mg/kg atropine sulfate. The body temperature of each rat is kept between 36.5° C. and 37.5° C. with the use of a heating pad thermocontrolled by a temperature probe placed in the rat's rectum. In addition, heat loss is compensated for with the use of a ceramic heating lamp positioned 40 to 50 cm above the rat. For mechanical ventilation, a tracheotomy is performed and a 3.5-cm length of 6F polyvinyl chloride tubing placed 0.5 cm into the trachea and secured with a suture. A modified infant ventilator is used to ventilate the animal. To minimize ventilatory fluid loss, a humidity filter is placed before the ventilation tube. A side port of this filter is used to monitor end-tidal $CO_2$ with the use of a capnograph. Ventilation parameters such as inspiratory phase (0.25-0.35) and respiration rate (50-75 breaths/min) are adjusted to keep arterial $PCO_2$ values between 35 and 45 mm Hg during surgery as checked by taking a baseline blood sample. No further adjustments are made till the end of the experiment.

Vessels are cannulated using 0.5×0.9-mm polyethylene vein catheter. The catheters are filled with 0.9% NaCl solution with 25 IU of heparin. The right carotid artery catheter is shortened to 20 cm and fitted to a pressure transducer for continuous monitoring of mean arterial pressure (MAP) and heart rate. MAP is calculated with the use of this formula: (Systolic blood pressure−Diastolic blood pressure)/3+Diastolic blood pressure. In addition, the jugular vein is cannulated for fluid support with 15 mL/kg/hr Ringer's lactate and 5 mL/kg/hr maintenance anesthesia (ketamine 50 mg/kg/hr in Ringer's lactate). The femoral artery is cannulated for blood withdrawal and arterial blood-gas sampling. The femoral vein is cannulated for infusion of the resuscitation fluids and venous blood-gas sampling.

A midline laparotomy is performed on each rat: the abdomen is covered with Saran wrap to prevent evaporation of body fluids. A small hole is pierced in the Saran wrap to permit access of the optical fiber for microcirculatory $PO_2$ measurements. An ileocecal vein is also cannulated with a 0.8-mm polyethylene catheter for mesenteric venous blood sampling.

Intestinal microvascular $PO_2$ is measured using the previously described technique of oxygen-dependent quenching of palladium-porphyrin phosphorence. After 2.5 to 3 hours of surgery, palladium (II) meso-tetra(4-carboxy-phenyl) porphine coupled to HSA solution (50 mg in 10 mL of 4% albumin solution, 4 mmol/L palladium-porphyrin solution, pH adjusted to 7.4 with HCl) is infused at a dose of 12 mg/kg body wt at a rate of 9.6 mL/kg/hr for 15 minutes.

Excitation of palladium-porphyrin with a pulse of light causes emission of phosphorescence with a decay in time, which is quantitatively related to the oxygen concentration (Vanderkooi, J. M. et al. (Apr. 25, 1987). "An Optical Method for Measurement of Dioxygen Concentration Based Upon Quenching of Phosphorescence," *J. Biol. Chem.* 262 (12):5476-5482). Microvascular $PO_2$ measurements are made with an optical fiber positioned above the proximal part of the ileum. The flash lamp is recorded before infusing the palladium-porphyrin and a deconvolution algorithm is used to calculate oxygen concentrations. After the infusion of palladium-porphyrin solution and 45 minutes' stabilization, baseline blood samples (0.2 mL/sample) are taken from the femoral artery, femoral vein, and mesenteric vein for blood-gas determination. Blood samples are analyzed in a blood-gas analyzer and a hemoximeter.

Hemorrhagic shock is induced by withdrawing blood from the femoral artery in 3-mL syringes with heparin (25 IU/mL blood) at a rate of approximately 1 mL/min for several minutes until the MAP is approximately 40 mm Hg. MAP is maintained at this level with the use of further blood withdrawals or blood infusions for 45 minutes. Just before resuscitation, blood samples (0.2 mL/sample) are withdrawn from the femoral artery, femoral vein, and mesenteric vein for blood-gas determination, and a similar amount of rat blood (collected during hemorrhagic shock) is reinfused. After this shock period, animals are randomly assigned to 1 of 8 different resuscitation groups. Resuscitation is carried out with wild-type or mutant H-NOX proteins or with another $O_2$ carrier, such as recombinant hemoglobin solution rHb1.1 (Baxter), rHb2.0 (Baxter), serum free hemoglobin (standard solution), MP4 (Sangart), hemopure (Biopure), or polyheme (Northfield Labs) (Raat, N. J. et ed. (January 2005). *J Lab Clin Med.* 145(1):21-32; stock concentration 100 mg/mL), all at a dose of 20 mL/kg (2 g/kg) infused at a rate of 60 mL/kg/hr. HSA (13.4% albumin solution) infused at the same dosage (20 mL/kg) and rate is used as a control for the volume effect on pressure and flow during resuscitation. When resuscitation is complete, 0.2-mL blood samples are taken from the femoral artery, femoral vein, and mesenteric vein after 30, 60, 90, and 120 minutes, and a similar amount of rat blood is given back each time.

H-NOX that cause the same or less (such as substantially or significantly less) systemic vasoconstriction, the same or less of an increase in MAP, or the same or less of an increase in mesenteric vascular resistance (MVR) after resuscitation compared with that caused by another $O_2$ carrier (such as rHb1.1, rHb2.0, serum free hemoglobin, MP4, hemospan, or polyheme) or by oncotically matched HAS are useful to treat hemorrhagic shock. Such H-NOX proteins are expected to also be useful to treat other indications for which delivery of $O_2$ is beneficial.

The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. Although the foregoing invention has been described in some detail byway of illustration and example for purposes of clarity of understanding, it will be readily apparent to those of ordinary skill in the art in light of the teachings of this invention that certain changes and modifications may be made thereto without departing from the spirit or scope of the appended claims.

Unless defined otherwise, the meanings of all technical and scientific terms used herein are those commonly understood by one of skill in the art to which this invention belongs. One of skill in the art will also appreciate that any methods and materials similar or equivalent to those described herein can also be used to practice or test the invention.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X."

It is understood that aspect and embodiments of the invention described herein include "comprising," "consisting," and "consisting essentially of" aspects and embodiments.

What is claimed as new and desired to be protected by Letters Patent of the United States is:

1. An isolated H-NOX protein comprising at least one distal pocket mutation that alters the $O_2$ dissociation constant or NO reactivity compared to that of a corresponding wild-type H-NOX protein, wherein the $O_2$ dissociation constant of the mutant H-NOX protein is within 2 orders of magnitude of that of hemoglobin, wherein the NO reactivity of the mutant H-NOX protein is at least 10-fold lower than that of hemoglobin, wherein the H-NOX protein does not comprise a guanylyl cyclase catalytic domain, wherein the distal pocket mutation comprises a substitution at a residue that corresponds to at least one of Thr4, Ile5, Thr8, Trp9, Trp67, Asn74, Ile75, Phe78, Phe82, Tyr140, and Leu144 of a T. tengcongensis H-NOX of SEQ ID NO: 54, and wherein the mutant H-NOX protein is not T. tengcongensis H-NOX Y140L, T. tengcongensis H-NOX F78Y/Y140L, T. tengcongensis H-NOX W9F, T. tengcongensis H-NOX W9F/Y140L, H. sapiens β1 H-NOX (1-385) I145Y, or L. pneumophilia 2 H-NOX F142Y.

2. The isolated H-NOX protein of claim 1, wherein the $O_2$ dissociation constant of the mutant H-NOX protein is between 1 nM and 1 mM at 20° C., and the NO reactivity of the mutant H-NOX protein is less than 700 $s^{-1}$ at 20° C.

3. The isolated H-NOX protein of claim 1, wherein the $O_2$ dissociation constant of the H-NOX protein is between 2 nM and 50 μM at 20° C.

4. The isolated H-NOX protein of claim 1, wherein the NO reactivity of the H-NOX protein is less than 1 $s^{-1}$ at 20° C.

5. The isolated H-NOX protein of claim 1, wherein the NO reactivity of the H-NOX protein is at least 100-fold lower than that of human hemoglobin alpha.

6. The isolated H-NOX protein of claim 1, wherein the $k_{off}$ for oxygen of the H-NOX protein is between 0.01 $s^{-1}$ and 200 $s^{-1}$ at 20° C.

7. The isolated H-NOX protein of claim 1, wherein the rate of heme autoxidation of the H-NOX protein is less than 1 $h^{-1}$ at 37° C.

8. The isolated H-NOX protein of claim 1, wherein the distal pocket mutation is a L144F mutation.

9. The isolated H-NOX protein of claim 1, wherein the H-NOX protein is a T. tengcongensis H-NOX protein comprising a L144F mutation in SEQ ID NO: 54.

10. The isolated H-NOX protein of claim 1, wherein the H-NOX protein is a fusion protein that includes an H-NOX domain and part or all of another protein.

11. The isolated H-NOX protein of claim 1, wherein the H-NOX protein is covalently bound to polyethylene glycol.

12. An isolated H-NOX protein comprising a distal pocket mutation wherein the $O_2$ dissociation constant of the H-NOX protein is within 2 orders of magnitude of that of hemoglobin, wherein the NO reactivity of the mutant H-NOX protein is at least 10-fold lower than that of hemoglobin, and wherein the distal pocket mutation is at an amino acid position corresponding to position L144 of T. tengcongensis H-NOX of SEQ ID NO: 54, wherein the H-NOX protein does not comprise a guanylyl cyclase catalytic domain.

13. The isolated H-NOX protein of claim 12, wherein the H-NOX protein is a fusion protein that includes an H-NOX domain and part or all of another protein.

14. The isolated H-HOX protein of claim 12, wherein the H-NOX protein is covalently bound to polyethylene glycol.

15. The isolated H-NOX protein of claim 13, wherein the H-NOX protein is covalently bound to polyethylene glycol.

16. An isolated H-NOX protein comprising a distal pocket mutation, wherein the $O_2$ dissociation constant of the mutant H-NOX protein is within 2 orders of magnitude of that of hemoglobin, wherein the NO reactivity of the mutant H-NOX protein is at least 10-fold lower than that of hemoglobin, wherein the H-NOX protein is a T. tengcongensis H-NOX protein comprising a L144F mutation in SEQ ID NO: 54 and does not comprise a guanylyl cyclase catalytic domain, wherein the H-NOX protein is a fusion protein that includes an H-NOX domain and part or all of another protein, and wherein the H-NOX protein is covalently bound to polyethylene glycol.

* * * * *

UNITED STATES PATENT AND TRADEMARK OFFICE

CERTIFICATE OF CORRECTION

PATENT NO. : 9,493,526 B2
APPLICATION NO. : 14/489395
DATED : November 15, 2016
INVENTOR(S) : Stephen P. L. Cary et al.

It is certified that error appears in the above-identified patent and that said Letters Patent is hereby corrected as shown below:

In the Specification

At Column 1, Line 34, under STATEMENT REGARDING FEDERALLY SPONSORED RESEARCH OR DEVELOPMENT,
please delete "This work was supported by Grant No. DE-AC03-76SF. The U.S. government may have rights in any patent issuing on this application."
and insert --This invention was made with government support under DE-AC02-05CH11231 and DE-AC03-76SF00098 awarded by the Department of Energy. The government has certain rights in the invention.--

Signed and Sealed this
Fourth Day of April, 2017

Michelle K. Lee
*Director of the United States Patent and Trademark Office*